(12) United States Patent
Quattropani et al.

(10) Patent No.: US 8,802,663 B2
(45) Date of Patent: Aug. 12, 2014

(54) PYRAZOLE OXADIAZOLE DERIVATIVES AS S1P$_1$ AGONISTS

(75) Inventors: Anna Quattropani, Geneva (CH); Charles Baker-Glenn, Essex (GB); Wesley Blackaby, Essex (GB); Chris Knight, Essex (GB)

(73) Assignee: Merck Serono SA, Coinsins, Vaud (CH)

( * ) Notice: Subject to any disclaimer, the term of this patent is extended or adjusted under 35 U.S.C. 154(b) by 3 days.

(21) Appl. No.: 13/322,939

(22) PCT Filed: Jun. 7, 2010

(86) PCT No.: PCT/EP2010/057893
§ 371 (c)(1),
(2), (4) Date: Nov. 29, 2011

(87) PCT Pub. No.: WO2010/142628
PCT Pub. Date: Dec. 16, 2010

(65) Prior Publication Data
US 2012/0071460 A1 Mar. 22, 2012

Related U.S. Application Data

(60) Provisional application No. 61/218,477, filed on Jun. 19, 2009.

(30) Foreign Application Priority Data

Jun. 8, 2009 (EP) .................. 09162206

(51) Int. Cl.
| A61K 31/4245 | (2006.01) |
| A61K 31/4155 | (2006.01) |
| C07D 231/10 | (2006.01) |
| C07D 271/06 | (2006.01) |

(52) U.S. Cl.
CPC ............ *C07D 231/10* (2013.01); *C07D 271/06* (2013.01)
USPC ...... 514/210.18; 514/364; 514/406; 514/326; 514/307; 514/121; 546/209; 546/269.1; 546/121; 546/148; 548/364.1; 548/131

(58) Field of Classification Search
USPC ........ 514/364, 406; 548/364, 406, 364.1, 131
See application file for complete search history.

(56) References Cited

U.S. PATENT DOCUMENTS 8,389,509 B2 * 3/2013 Dyckman et al. ........ 514/210.18

FOREIGN PATENT DOCUMENTS

| WO | WO 2004/037248 | 5/2004 |
| WO | WO 2004037248 A2 * | 5/2004 |
| WO | WO 2004/091502 | 10/2004 |
| WO | WO 2006/131336 | 12/2006 |
| WO | WO 2008/074820 | 6/2008 |
| WO | WO 2008/076356 | 6/2008 |
| WO | WO 2009/003998 | 1/2009 |
| WO | WO 2010085584 A1 * | 7/2010 |
| WO | WO 01/02385 | 1/2011 |

OTHER PUBLICATIONS

CAS RN 957332-28-4, entered STN ChemBank database on Dec. 11, 2007.*
CAS RN 676437-62-0, entered STN Chemical Library database on Apr. 22, 2004 by Maybridge plc.*
CAS RN 676437-36-8, entered STN Chemical Library database on Apr. 22, 2004 by Maybridge plc.*
Press, J. et al. "Aryl Coupling Reactions of Pyrazolo[3,4-d]pyrimidin-4-yl Radicals" *Journal of Organic Chemistry*, 1983, pp. 4605-4611, vol. 48, No. 24.
Rice, K. et al. "An Improved Synthesis of 1,2,4-Oxadiazoles on Solid Support" *Bioorganic & Medicinal Chemistry Letters*, 2001, pp. 753-755, vol. 11, No. 6.
Written Opinion in International Application No. PCT/EP2010/057893, Sep. 3, 2010, pp. 1-8.
Yoshida, M. et al. "Study of biodegradable copoly(L-lactic acid/glycolic acid) formulations with controlled release of Z-100 for application in radiation therapy" *International Journal of Pharmaceutics*, 1995, pp. 61-67, vol. 115.
Kappos, L. et al. "Oral Fingolimod (FTY720) for Relapsing Multiple Sclerosis" *The New England Journal of Medicine*, Sep. 14, 2006, pp. 1124-1140, vol. 355.
Massberg, S. et al. "Fingolimond and Sphingosine-1-Phosphate-Modifiers of Lymphocyte Migration" *The New England Journal of Medicine*, Sep. 14, 2006, pp. 1088-1091, vol. 355.
Yopp, A. etal. "Sphingosine 1-phosphate receptor modulators: a new class of immunosuppressants" *Clinical Transplatation*, 2006, pp. 788-795, vol. 20.
Rosen, H. et al. "Sphingosine 1-phosphate and its Receptors: An Autocrine and Paracrine Network" *Nature*, Jul. 2005, pp. 560-570, vol. 5.
Rosen, H. et al. "Tipping the gatekeeper: S1P regulation of endothelial barrier function" *TRENDS in Immunology*, 2007, pp. 102-107, vol. 28, No. 3.
Menozzi, G. etal. "1-Phenyl-1H-Pyrazole Derivatives With Antiinflammatory, Analgesic and Antipiretic Activities" *Il Farmaco*, 1990, pp. 167-186, vol. 45, No. 2.
Cyster, J. "Chemokines, Sphingosine-1-Phosphate, and Cell Migration in Secondary Lymphoid Organs" *Annual Review of Immunology*, 2005, pp. 127-159, vol. 23.
Database Registry [Online] Chemical Abstracts Service, Accession No. 1152513-78-4, Chemcats, "Phenol, 3-[5-(1,5-dimethyl-1H-pyrazol-4-yl)-1,2,4-oxadiazol-3-yl]-" Jun. 5, 2009, p. 1, XP-002537331.
Database Registry [Online] Chemical Abstracts Service, Accession No. 1152499-15-4, Chemcats, "Phenol, 4-(5-(1,5-dimethyl-1H-pyrazol-4-yl)-1,2,4-oxadiazol-3-yl)-" Jun. 5, 2009, p. 1, XP-0002537332.

(Continued)

*Primary Examiner* — Yong Chu
(74) *Attorney, Agent, or Firm* — Saliwanchik, Lloyd & Eisenschenk

(57) ABSTRACT

The present invention relates to pyrazole oxadiazoles derivatives of Formula (I), and their use for treating multiple sclerosis and other diseases, wherein $R^1$, $R^2$ and $R^3$ are as defined in the description.

8 Claims, No Drawings

(56) References Cited

OTHER PUBLICATIONS

Database Registry [Online] Chemical Abstracts Service, Accession No. 1024529-37-0, ChemDB, "1,2,4-Oxadiazole, 3-(4-(1,1-dimethylethyl)phenyl)-5-(1-methyl-5-propyl-1H-pyrazol-4-yl)-" Jun. 1, 2008, p. 1, XP-0002537333.

Database Registry [Online] Chemical Abstracts Service, Accession No. 1023516-08-6, ChemDB, "1,2,4-Oxadiazole, 5-[1-(4-chlorophenyl)-5-propyl-1H-pyrazol-4-yl)-3-[4-(1,1-dimethylethyl)phenyl]" May 29, 2008, p. 1, XP-0002537334.

Database Registry [Online] Chemical Abstracts Service, Accession No. 1023515-92-5, ChemDB, "1,2,4-Oxadiazole, 5-[1-(4-chlorophenyl)-5-propyl-1H-pyrazol-4-yl)-3-[4-(trifluoromethyl)phenyl]" May 29, 2008, p. 1, XP-0002537335.

Database Registry [Online] Chemical Abstracts Service, Accession No. 959579-18-1, Chemcats, "1,2,4-Oxadiazole, 5-(2,4-dichlorophenyl)-3-[3-(methylthio)-1-phenyl-1H-pyrazol-4-yl]" Dec. 26, 2007, p. 1, XP-0002537336.

Database Registry [Online] Chemical Abstracts Service, Accession No. 959574-89-1, Chemcats, "1,2,4-Oxadiazole, 3[3-(methylthio)-1-phenyl-1H-pyrazol-4-yl]-5-[4-(trifluoromethyl)phenyl]-" Dec. 26, 2007, p. 1, XP-0002537337.

Database Registry [Online] Chemical Abstracts Service, Accession No. 957947-36-3, Chemcats, "1,2,4-Oxadiazole, 3-[3-(methylthio)-1-phenyl-1H-pyrazol-4-yl]-5-(2-thienyl)-" Dec. 13, 2007, p. 1, XP-0002537338.

Database Registry [Online] Chemical Abstracts Service, Accession No. 957332-28-4, Chemcats, "1,2,4-Oxadiazole, 5-(4-chlorophenyl)-3-[3-(methylthio)-1-phenyl-1H-pyrazol-4yl]-" Dec. 11, 2007, p. 1, XP-0002537339.

Database Registry [Online] Chemical Abstracts Service, Accession No. 676438-70-3, Chemcats, "1,2,4-Oxadiazole, 3-[3-(trifluoromethyl)phenyl)-5-[1-(4-chlorophenyl)-5-propyl-1H-pyrazol-4-yl]-" Apr. 22, 2004, p. 1, XP-0002537340.

Database Registry [Online] Chemical Abstracts Service, Accession No. 676437-65-3, Chemcats, "1,2,4-Oxadiazole, 3-[4-(1,1-dimethylethyl)phenyl]-5-(1-phenyl-5-propyl-1H-pyrazol-4-yl)-" Apr. 22, 2004, p. 1, XP-0002537341.

Database Registry [Online] Chemical Abstracts Service, Accession No. 676437-64-2, Chemcats, "1,2,4-Oxadiazole, 5-(1-phenyl-5-propyl-1H-pyrazol-4-yl)-3-[4-(trifluoromethyl)phenyl]-" Apr. 22, 2004, p. 1, XP-0002537342.

Database Registry [Online] Chemical Abstracts Service, Accession No. 676437-63-1, Chemcats, "1,2,4-Oxadiazole, 3-[3,5-bis(trifluoromethyl)phenyl]-5-(1-phenyl-5-propyl-1H-pyrazol-4-yl)-" Apr. 22, 2004, p. 1, XP-0002537343.

Database Registry [Online] Chemical Abstracts Service, Accession No. 676437-62-0, Chemcats, "1,2,4-Oxadiazole, 3-(4-chlorophenyl)-5-(1-phenyl-5-propyl-1H-pyrazol-4-yl)-" Apr. 22, 2004, p. 1, XP-0002537344.

Database Registry [Online] Chemical Abstracts Service, Accession No. 676229-95-1, Chemcats, "1,2,4-Oxadiazole, 5-(1-methyl-5-propyl-1H-pyrazol-4-yl)-3-[4-(trifluoromethyl)phenyl]-" Apr. 20, 2004, p. 1, XP-0002537345.

Database Registry [Online] Chemical Abstracts Service, Accession No. 442870-44-2, Interchim, "1,2,5-Oxadiazol-3-amine, 4-[5-(1-ethyl-3-methyl-1H-pyrazol-4yl)-1,2,4-oxadiazol-3-yl]" Aug. 7, 2002, p. 1, XP-0002537346.

* cited by examiner

PYRAZOLE OXADIAZOLE DERIVATIVES AS S1P₁ AGONISTS

CROSS-REFERENCE TO RELATED APPLICATIONS

This application is the U.S. national stage application of International Patent Application No. PCT/EP2010/057893, filed Jun. 7, 2010, which claims the benefit of U.S. Provisional Patent Application No. 61/218,477, filed Jun. 19, 2009.

The present invention relates to pyrazole oxadiazoles derivatives, their use as medicament and their use for treating multiple sclerosis and other diseases.

In particular, the invention relates to compounds of formula (I):

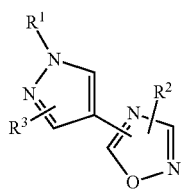

(I)

wherein $R^1$ denotes $Ar^1$, $Het^1$, Cyc, A, $(C_1-C_6)$alkyl, $(C_2-C_6)$alkyl, $-(CH_2)_nAr^1$, $(CH_2)_nHet^1$, $(CH_2)_nHet^2$.

$R^2$ is $Ar^2$, $Het^1$;

$R^3$ denotes $Ar^1$, $Ar^2$, $Het^1$, $Het^2$, Cyc or A, or if $R^1$ is $Het^1$, Cyc, A, $-(CH_2)_nAr^1$, $(CH_2)_nHet^1$, $(CH_2)_nHet^2$, $(C_2-C_6)$alkyl, or if $R^1$ denotes $Ar^1$ or $R^2$ is $Ar^2$, $Het^1$ or $Het^2$ wherein $Ar^1$ and $Ar^2$ are mono, di- or trisubstituted by the substituents hereby mentioned, $R^3$ also denotes $CH_3$, or if $R^1$ denotes $Het^1$, Cyc, A, $(C_1-C_6)$alkyl, $(C_2-C_6)$alkyl, $-(CH_2)_nAr^1$, $(CH_2)_nHet^1$, $(CH_2)_nHet^1$, $R^3$ also denotes $S-(C_1-C_6$-alkyl), A is a branched or linear alkyl having 2 to 12 C-atoms, wherein one or more, preferably 1 to 7 H-atoms may be replaced by Hal, $OR^4$, CN, $CO_2R^4$, $CF_3$, cycloalkyl having 3 to 7 ring carbon atoms, $Ar^1$, $Ar^2$, or $N(R^4)_2$ and wherein one or more, preferably 1 to 7 non-adjacent $CH_2$-groups may be replaced by O, $NR^4$, $-CO-$, $NR^4CO_2-$, $-CO_2-$, $-NR^4CONR^4-$, $-CH=CH-$, $-C\equiv C-$, or denotes cycloalkyl or cycloalkylalkylen having 3-7 ring C atoms, or denotes $Het^1$ or $Het^2$;

Z is a branched or linear alkyl having 2 to 12 C-atoms, wherein one or more, preferably 1 to 7 H-atoms are replaced by Hal, $OR^4$, CN, $CO_2R^4$, $CF_3$, cycloalkyl having 3 to 7 ring carbon atoms, $Ar^1$, $Ar^2$, $N(R^4)_2$ and/or wherein one or more, preferably 1 to 7 $CH_2$-groups are replaced by O, $NR^4$, S, $-CO-$, $NR^4CO_2-$, $-NR^4CONR^4-$, $-CH=CH-$, $-C\equiv C-$, or denotes cycloalkyl or cycloalkylalkylen having 3-7 ring C atoms;

Hal is F, Cl, Br or I;

$Ar^1$ denotes a monocyclic or bicyclic, unsaturated or aromatic carbocyclic ring having 6 to 14 carbon atoms which may be unsubstituted, monosubstituted, disubstituted or trisubstituted by substituents selected from A, Hal, $-OR^4$, $-SO_2R^4$, $-CN$, $-NO_2$, $-N(R^3)_2$, $-CO(NR^4)_2$, $-OR^4$, $(NR^4)COR^4$, $-CO_2R^4$, $-COR^4$, $-SO_2N(R^4)_2$, $-SO_2$alkyl, $NR^4SO_2$alkyl, $NR^4SO_2$alkyl, or $C_1-C_6$ alkyl;

$Ar^2$ denotes a monocyclic or bicyclic, unsaturated or aromatic carbocyclic ring having 6 to 14 carbon atoms which may be unsubstituted, monosubstituted, disubstituted or trisubstituted by substituents selected from Z, F, Br, I, $-OR^4$, $-(CH_2)OR^4$, $-(CH_2)N(R^4)_2$, Perfluoro-alkoxy, $-SO_2R^4$, $-CN$, $-NO_2$, $-N(R^4)_2$, $-CO(NR^4)_2$, $(NR^4)COR^4$, $-CO_2R^4$, $-COR^4$, $-SO_2N(R^4)_2$, $-SO_2(C_1-C_6)$alkyl, $NR^4SO_2(C_1-C_6)$alkyl, $-(CH_2)_nHet^1$, $-OHet^1$, $-(CH_2)_nHet^2$, $-OHet^2$, or if $R^3$ is $Het^1$, $Het^2$, $Ar^1$, $Ar^2$ or Cyc, or if $R^1$ is $Het^1$, Cyc, A, $(C_1-C_6)$alkyl, $(C_2-C_6)$alkyl, $-(CH_2)_nAr^1$, $(CH_2)_nHet^1$, $(CH_2)_nHet^1$, $Ar^2$ also denotes a monocyclic or bicyclic, unsaturated or aromatic carbocyclic ring having 6 to 14 carbon atoms which may be unsubstituted, monosubstituted, disubstituted or trisubstituted by $CF_3$, $Het^1$ denotes a monocyclic saturated, unsaturated or aromatic heterocyclic ring or a bicyclic, saturated, or unsaturated heterocyclic ring having 1 to 4 N, and/or O atoms which may be unsubstituted, monosubstituted, disubstituted or trisubstituted by substituents selected from A, Hal, $-OR^4$, $-(CH_2)OR^4$, Perfluoro-alkyl, Perfluoro-alkoxy, $-SO_2(R^4)_2$, CN, $NO_2$, $-N(R^4)_2$, $-CO(NR^4)_2$, $(NR^4)COR^4$, $-CO_2R^4$, $-COR^4$, $-SO_2N(R^4)_2$, $-SO_2$alkyl, $NR^4SO_2$alkyl, $NR^4SO_2$alkyl, or $C_1-C_6$ alkyl, $Het^2$ denotes a monocyclic or bicyclic, saturated, unsaturated or aromatic heterocyclic ring having 1 to 4 N, O and/or S atoms which may be unsubstituted, monosubstituted, disubstituted or trisubstituted by substituents selected from A, F, Br, I, $-OR^4$, $-(CH_2)OR^4$, Perfluoro-alkyl, Perfluoro-alkoxy, $-SO_2(R^4)_2$, CN, $NO_2$, $-N(R^4)_2$, $-CO(NR^4)_2$, $(NR^4)COR^4$, $-CO_2R^4$, $-COR^4$, $-SO_2N(R^4)_2$, $-SO_2$alkyl, $NR^4SO_2$alkyl, $NR^4SO_2$alkyl, or $C_1-C_6$ alkyl;

Cyc denotes a saturated or unsaturated carbocyclic ring containing 3 to 7 carbon atoms which may be substituted by Hal, A, $(C_1-C_6)$alkyl, $-[C(R^4)_2]_n-Ar$, $-[C(R^4)_2]_n-$cycloalkyl, $OR^4$, $CF_3$, $OCF_3$, $N(R^4)_2$, $NR^4CON(R^4)_2$, $NO_2$, CN, $-[C(R^4)_2]_n-COOR^4$, $-[C(R^4)_2]_n-CON(R^4)_2$, $NR^4COA$, $NR^4SO_2A$, $COR^4$, $CO_2R^4$, $SO_2N(R^4)_2$, SOA, and/or $SO_2A$, $R^4$ is H, A, Cyc or $(C_1-C_6)$alkyl, preferably H or $(C_1-C_6)$alkyl;

n is 1, 2, 3 or 4 and pharmaceutically acceptable derivatives, solvates, tautomers, salts and stereo-isomers thereof, including mixtures thereof in all ratios as a medicament, especially for treating multiple sclerosis and other diseases.

The compounds of formula (I) and related formulae are preferably binding on receptors for sphingosine 1-phosphate (S1P). S1P is a bioactive sphingolipid metabolite that is secreted by hematopoietic cells and stored and released from activated platelets. It acts as an agonist on a family of G protein-coupled receptors (GPCR). Five sphingosine 1-phosphate receptors have been identified (S1P₁, S1P₂, S1P₃, S1P₄, and S1P₅, also known as endothelial differentiation genes, which are Edg1, Edg5, Edg3, Edg6 and Edg8 respectively), that have widespread cellular and tissue distribution and are well conserved in human and rodent species.

S1P is involved in a number of cellular functions such as survival, proliferation and immunological responses. The compounds of the present invention are preferably acting as S1P₁/Edg1 receptor agonists and thus have immunosuppressive activities by modulating leukocyte trafficking, sequestering lymphocytes in secondary lymphoid tissues, and interfering with cell-cell interactions required for an efficient immune response. The invention is also directed to pharmaceutical compositions containing such compounds and methods of treatment or prevention.

FTY720 or fingolimod, a non selective S1P₁ agonist, exerts immunosuppressive activity and shows therapeutic effects in the treatment of relapsing-remitting multiple sclerosis.

Numerous publications have been already published using this compound: Oyster JG Annu Rev Immunol 23:127-59, 2005, Rosen H Nat Rev Immunol 5:560-570, 2005, Rosen H Trends Immunol 28:102-107, 2007, Yopp AC Clin Transplant 20:788-795, 2006, Kappos L N Engl J Med 355:1124-1140, 2006, Massberg S N Engl J Med 355:1088-1089, 2006.

The patent applications WO 2006/131336 and WO 2004/091502 disclose other compounds active against immunological diseases and rheumatoid arthritis.

Immunosuppressive agents are further useful in a wide variety of autoimmune and chronic inflammatory diseases, including systemic lupus erythematosus, chronic rheumatoid arthritis, type I diabetes mellitus, inflammatory bowel diseases, biliary cirrhosis, uveitis and other disorders such as Crohn's diseases, ulcerative colitis, bullous pemphigoid, sarcoidosis, psoriasis, autoimmune myositis, Wegener's granulomatosis, ichthyosis, Graves ophthalmopathy, atopic dermatitis and asthma. They are also useful as part of chemotherapeutic regimens for the treatment of cancers, lymphomas and leukemias.

It has been found that the compounds of the present invention are selective $S1P_1$ agonists.

Thus, the present invention preferably comprises compounds which are agonists of the $S1P_1$/Edg1 receptor, especially having selectivity over the $S1P_3$/Edg3 receptor. An $S1P_1$/Edg1 receptor selective agonist has advantages over current therapies and extends the therapeutic window of lymphocyte sequestration agents, allowing better tolerability with higher dosing and thus improving efficacy.

The invention further relates to the manufacture of a medicament for the improvement of vascular function, either alone or in combination with other active compounds or therapies.

According to another aspect of the invention is provided a kit or a set comprising at least one compound of Formula (I), preferably in combination with immunomodulating agents.

Alternatively, the kit consists of separate packs of:

(a) an effective amount of a compound of the formula (I) and/or pharmaceutically usable derivatives, solvates and stereoisomers thereof, including mixtures thereof in all ratios, and (b) an effective amount of a further medicament active ingredient.

The pyrazole oxadiazole derivatives according to formula I and related formulae may be prepared from readily available starting materials using the following general methods and procedures. It will be appreciated that where typical or preferred experimental conditions (i.e. reaction temperatures, time, moles of reagents, solvents etc.) are given, other experimental conditions can also be used unless otherwise stated. Optimum reaction conditions may vary with the particular reactants or solvents used, but such conditions can be determined by the person skilled in the art, using routine optimisation procedures.

The following abbreviations refer respectively to the definitions below:

aq (aqueous), h (hour), g (gram), L (liter), mg (milligram), MHz (Megahertz), μM (micromolar) min. (minute), mm (millimeter), mmol (millimole), mM (millimolar), m.p. (melting point), eq (equivalent), mL (milliliter), μL (microliter), ACN (acetonitrile), BINAP (2,2'-bis(disphenylphosphino)-1,1'-binaphthalene, BOC (tert-butoxy-carbonyl), CBZ (carbobenzoxy), CDCl₃ (deuterated chloroform), CD₃OD (deuterated methanol), CH₃CN (acetonitrile), c-hex (cyclohexane), DCC (dicyclohexyl carbodiimide), DCM (dichloromethane), DIC (diisopropyl carbodiimide), DIEA (diisopropylethyl-amine), DMF (N,N-dimethylformamide), DMF.DMA (N,N-dimethylformamide dimethylacetal), DMSO (dimethylsulfoxide), DMSO-$d_6$ (deuterated dimethylsulfoxide), EDC (1-(3-dimethyl-aminopropyl)-3-ethylcarbodiimide), ESI (Electro-spray ionization), EtOAc (ethyl acetate), Et₂O (diethyl ether), EtOH (ethanol), FMOC (fluorenylmethyloxycarbonyl), HATU (dimethylamino-([[1,2,3]triazolo[4,5-b]pyridin-3-yloxy)-methylene]-dimethyl-ammonium hexafluorophosphate), HPLC (High Performance Liquid Chromatography), i-PrOH (2-propanol), K₂CO₃ (potassium carbonate), LC (Liquid Chromatography), MeCN (Acetonitrile), MeOH (methanol), MgSO₄ (magnesium sulfate), MS (mass spectrometry), MTBE (Methyl tert-butyl ether), Mtr. (4-Methoxy-2,3,6-trimethylbenzensulfonyl), MW (microwave), NaHCO₃ (sodium bicarbonate), NaBH₄ (sodium borohydride), NMM (N-methyl morpholine), NMR (Nuclear Magnetic Resonance), POA (phenoxyacetate), PPTS (pyridinium p-toluenesulfonate), PyBOP® (benzotriazole-1-yl-oxy-tris-pyrrolidino-phosphonium hexafluorophosphate), RT (room temperature), Rt (retention time), SPE (solid phase extraction), TBTU (2-(1-H-benzotriazole-1-yl)-1,1,3,3-tetramethyluromium tetrafluoro borate), TEA (triethylamine), TFA (trifluoroacetic acid), THF (tetrahydrofuran), TLC (Thin Layer Chromatography), UV (Ultraviolet).

Depending on the nature of $R^1$, $R^2$ and $R^3$, different synthetic strategies may be selected for the synthesis of compounds of Formula (I) and related formulae. In the process illustrated in the following schemes, $R^1$, $R^2$ and $R^3$ are as above defined in the description. In general, the pyrazole derivatives according to Formula (I) and related formulae of this invention may be prepared from readily available starting materials. If such starting materials are not commercially available they may be prepared by standard synthetic techniques. The following general methods and procedures described hereinafter in the examples may be employed to prepare compounds of Formula (I) and related formulae.

The processes for the preparation of compounds of Formula (I) and related formulae, wherein $R^1$, $R^2$ and $R^3$ are defined as above, and as outlined in Schemes 1-12, are also objects of the invention.

Compounds of Formula (If), where $R^1$ is alkyl and related formulae, belonging to the Formula (I), may be prepared from compounds of Formula (II) as outlined in Scheme 1. Typically compounds of Formula (If) can be prepared by treatment of vinylogous amide of Formula (II) with a hydrazine (III), or a salt of a hydrazine, in the presence of a base, preferably sodium carbonate, in a suitable solvent or mixture of solvents, preferably a mixture of ethanol and water, at a temperature rising from RT to about 90° C., typically 80° C., for a few hours, e.g. one hour to eighteen hours.

Scheme 1

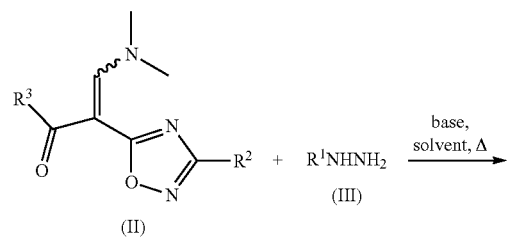

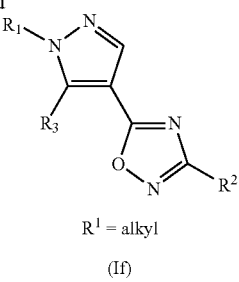

(If)

Alternatively, compounds of Formula (If) where $R^1$ is aromatic or Formula (Ig) where $R^1$ is alkyl and related formulae, belonging both to the Formula (I), can be prepared from compounds of Formula (II) as outlined in Scheme 2.

Typically, treatment of vinylogous amides of Formula (II) with a hydrazine (III), or a salt of a hydrazine, where $R^1$ is aromatic, in the presence of an acid, preferably acetic acid, in a suitable solvent or mixture of solvents, preferably ethanol, at a temperature rising from RT to about 90° C., typically 80° C., for a few hours, e.g., one hour to eighteen hours, will yield preferably compounds of Formula (If). Moreover, treatment of vinylogous amides of Formula (II) with a hydrazine (III), or a salt of a hydrazine, where $R^1$ is alkyl, under these same reaction conditions, will yield preferably compounds of Formula (Ig).

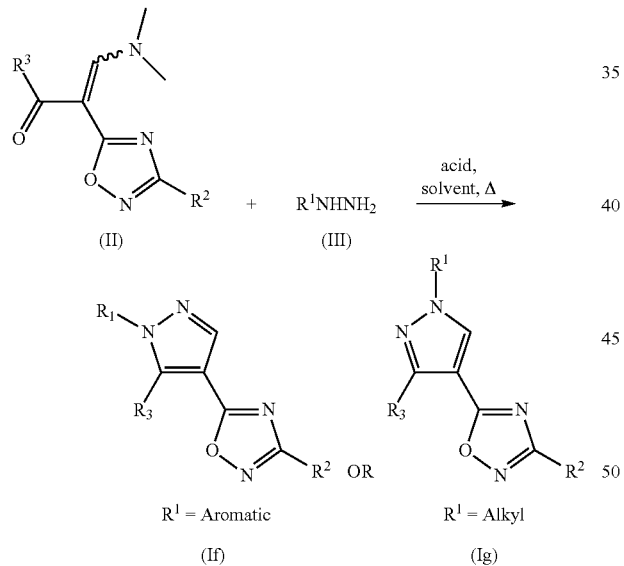

Compounds of Formula (III), wherein $R^1$ is defined as above, are either commercially available or may be prepared by standard synthetic techniques well known to those skilled in the art. Typically, the reductive amination of an aldehyde of a ketone with tert-butyl carbazate, using $NaBH_3CN$ or $NaBH(OAc)_3$ as reductive agents, followed by the acidic cleavage of the Boc protecting group would yield the salt of hydrazine of Formula (III). The method for preparing hydrazine or a salt of hydrazine of Formula (III) selected below:
tetrahydro-2H-pyran-4-ylhydrazine, trifluoroacetate
(2-methylcyclohexyl)hydrazine, hydrochloride
is more particularly described in the examples.

Alternatively, esters of Formula (IV) and Formula (VI), wherein $R^1$, $R^3$ and $R^4$ are as above defined in the description, can be directly transformed into compounds of Formula (If), Formula (Ig) and related formulae by thermolysis at a temperature rising from RT to about 180° C., typically 180° C., using possibly a microwave reactor, for a time comprised between about 15 minutes and about 24 hours, preferably for 30 min in a microwave, in a suitable solvent such as ACN, THF, toluene, Pyridine, DMF or a mixture of two solvents such as Toluene/DMF or Toluene/ACN, in the presence of a base, such as but not limited to $K_2CO_3$ or NaH (Scheme 3).

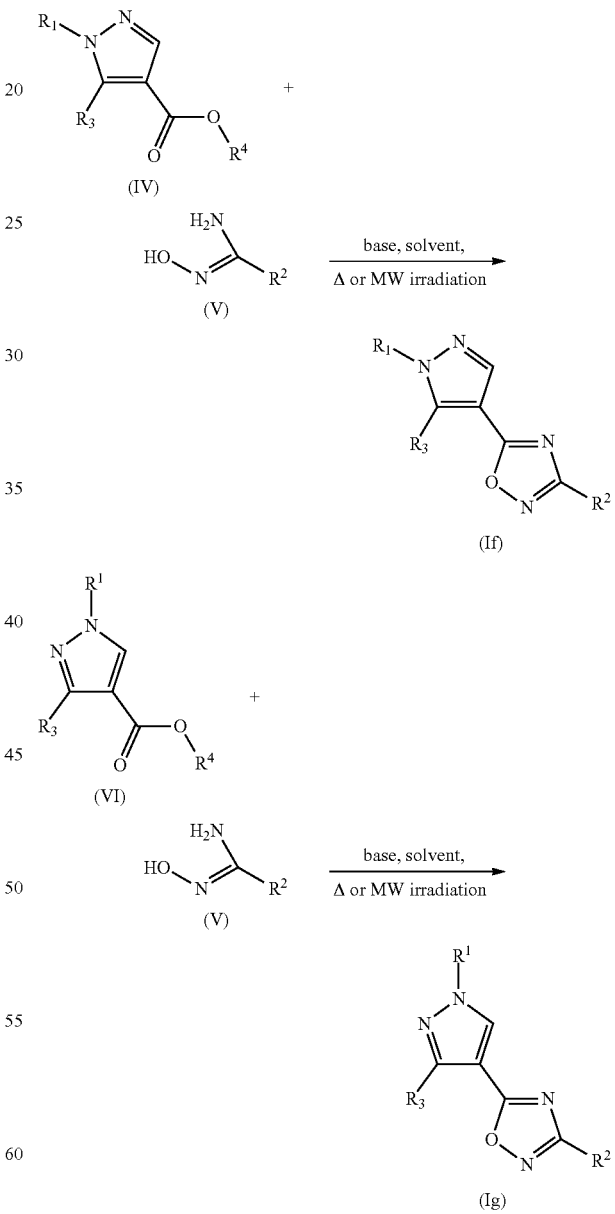

Alternatively, compounds of Formula (If), Formula (Ig) and related formulae can be obtained in a 2-step protocol as outlined in Scheme 4.

Scheme 4

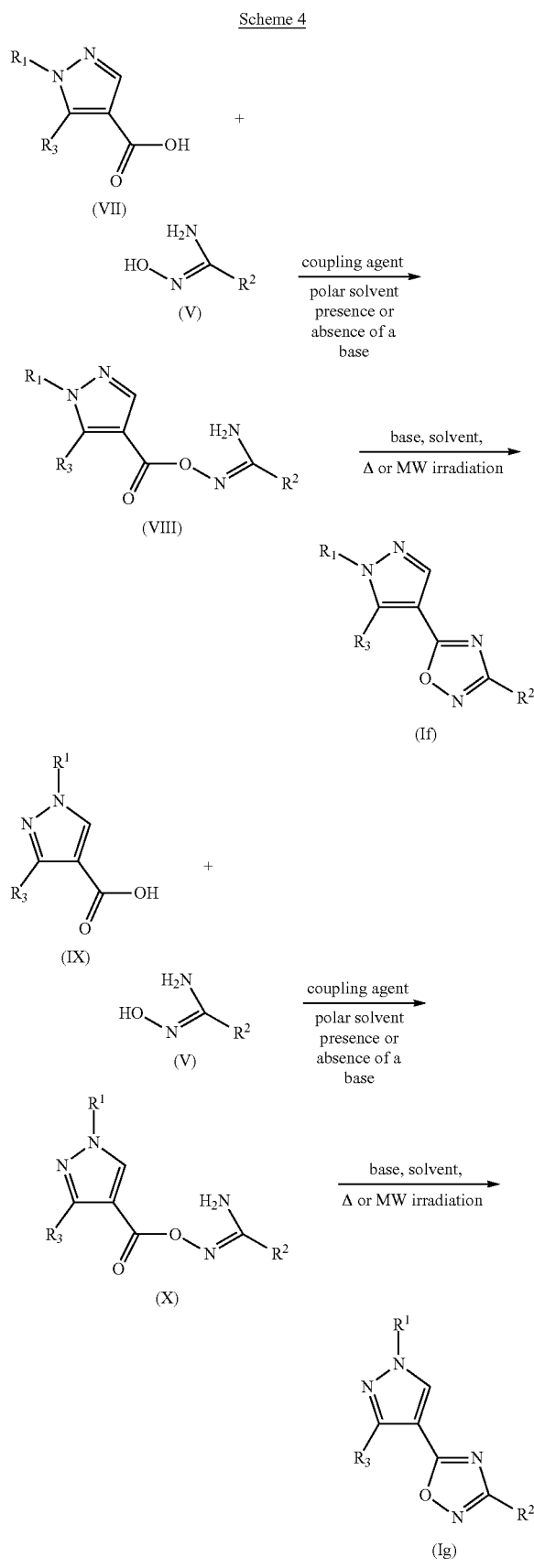

The first step consists in the coupling of an amidoxime of Formula (V) with a carboxylic acid of Formula (VII) or Formula (IX), wherein $R^1$, $R^2$ and $R^3$ are defined as above. General protocols for such coupling are given below in the Examples, using conditions and methods well known to those skilled in the art to prepare O-substituted amidoximes (VIII) or (X). Standard coupling agents, such as but not limited to EDC, HATU, TBTU, can be used or condensation agents, in the presence or not of bases such as TEA, DIEA, NMM in a suitable solvent such as DCM, ACN, THF or DMF, at a temperature rising from about 20° C. to about 50° C., preferably at room temperature, for a few hours, e.g. one hour to 24 h.

The second step consists of the cyclization and dehydration of the O-substituted amidoximes (VIII) or (X) to form pyrazole oxadiazole derivatives of Formula (If), Formula (Ig) and related formulae. Protocols are given below in the Examples, using conditions and methods well known to those skilled in the art to prepare oxadiazoles, such as thermolysis at temperature rising from RT to about 150° C., typically 150° C., using possibly a microwave reactor, for a time comprised between 15 minutes and 24 hours, preferably for 30 min, in a suitable solvent such as ACN, THF, Pyridine, DMF, or a mixture of two solvents such as Pyridine/ACN, in the presence or not of a base such as DIEA, TEA, or tetrabutyl ammonium fluoride.

Compounds of Formula (Ih), which belong to Formula (I), may be prepared from amidoximes of Formula (XI) by thermolysis at temperature rising from RT to about 180° C., typically 180° C., using possibly a microwave reactor, for a time comprised between 15 minutes and 24 hours, preferably for 2 hours in a microwave, in a suitable solvent such as ACN, THF, toluene, Pyridine, DMF or a mixture of two solvents such as Toluene/DMF or Toluene/ACN, in the presence of a base, such as but not limited to $K_2CO_3$ or NaH (Scheme 5).

Scheme 5

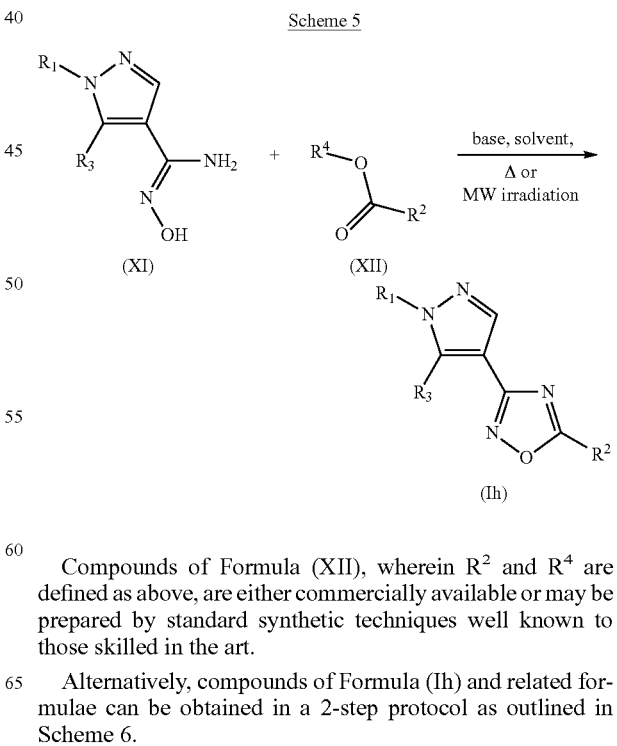

Compounds of Formula (XII), wherein $R^2$ and $R^4$ are defined as above, are either commercially available or may be prepared by standard synthetic techniques well known to those skilled in the art.

Alternatively, compounds of Formula (Ih) and related formulae can be obtained in a 2-step protocol as outlined in Scheme 6.

Scheme 6

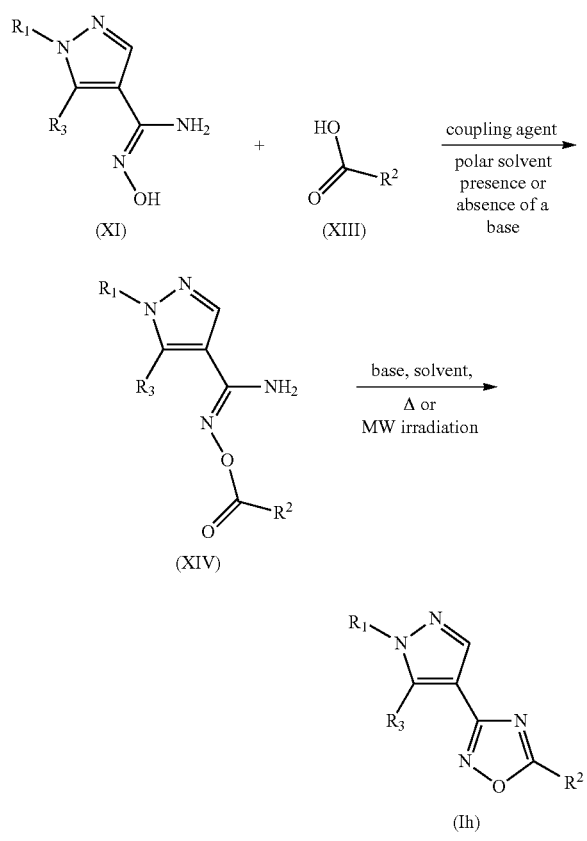

The first step consists in the coupling of an amidoxime of Formula (XI) with a carboxylic acid of Formula (XIII), wherein $R^1$, $R^2$ and $R^3$ are defined as above. General protocols for such coupling are given below in the Examples, using conditions and methods well known to those skilled in the art to prepare O-substituted amidoximes (XIV). Standard coupling agents, such as but not limited to EDC, HATU, TBTU, can be used in the presence or not of bases such as TEA, DIEA, NMM in a suitable solvent such as DCM, ACN, THF or DMF, at a temperature rising from about 20° C. to about 50° C., preferably at room temperature, for a few hours, e.g. one hour to 24 h.

The second step consists of the cyclization and dehydration of the O-substituted amidoximes (XIV) to form pyrazole oxadiazole derivatives of Formula (Ih) and related formulae. Protocols are given below in the Examples, using conditions and methods well known to those skilled in the art to prepare oxadiazole, such as thermolysis at temperature rising from RT to 150° C., typically 150° C., using possibly a microwave reactor, for a time comprised between 15 minutes and 24 hours, preferably for 30 min, in a suitable solvent such as ACN, THF, Pyridine, DMF, or a mixture of two solvents such as Pyridine/ACN, in the presence or not of a base such as DIEA, TEA, or tetrabutyl ammonium fluoride.

Compounds of Formula (XIII), wherein $R^2$ is defined as above, are either commercially available or may be prepared by standard synthetic techniques well known to those skilled in the art.

Compounds of Formula (I) and related formulae, wherein $R^1$, $R^2$ and $R^3$ are defined as above, can be converted to alternative compounds of Formula (I) and related formulae, wherein $R^1$, $R^2$ and $R^3$ are defined as above, employing suitable interconversion techniques well known by a person skilled in the art. Typically, when $R^2$ is a benzyl alcohol, compound of Formula (Ii) can be further modified into compound of Formula (Ij), as illustrated in Scheme 7. Compounds of Formula (Ii) can be first be transformed into the corresponding mesyl or tosyl groups (Ik), which can then reacted with an amine $HN(R^4)_2$, affording compounds of Formula (Ij) wherein $R^1$, $R^3$ and $R^4$ are defined as above (Scheme 7). Alcohol (Ii) can be oxidized into the corresponding aldehyde (Im), using conditions well known to those skilled in the art, such as but not limited to Swern oxidation conditions, or the use of $MnO_2$ as oxidative agent, as illustrated on Scheme 7. Then a reductive amination of the compounds of Formula (Im) with a suitable amine $HN(R^4)_2$, would afford compounds of Formula (Ij), wherein $R^1$, $R^3$ and $R^4$ are defined as above.

Scheme 7

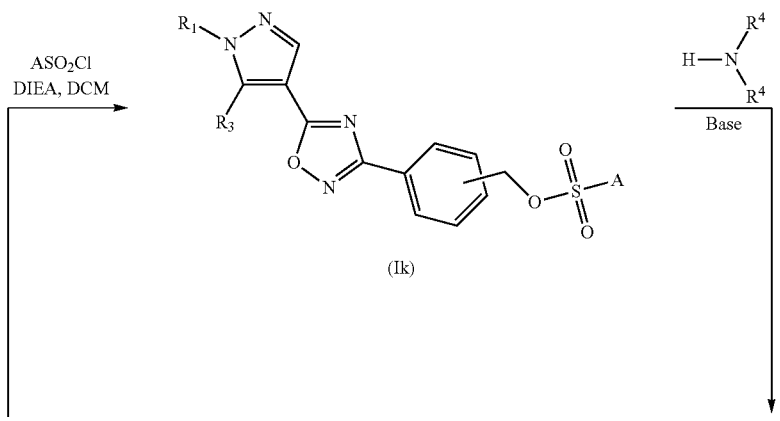

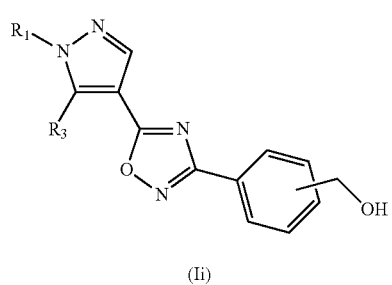

(Ii)

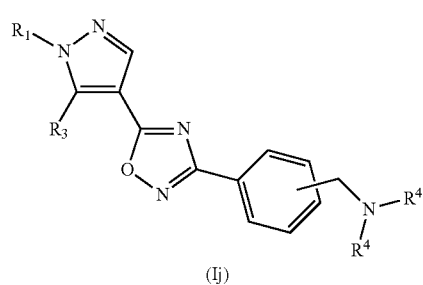

(Ij)

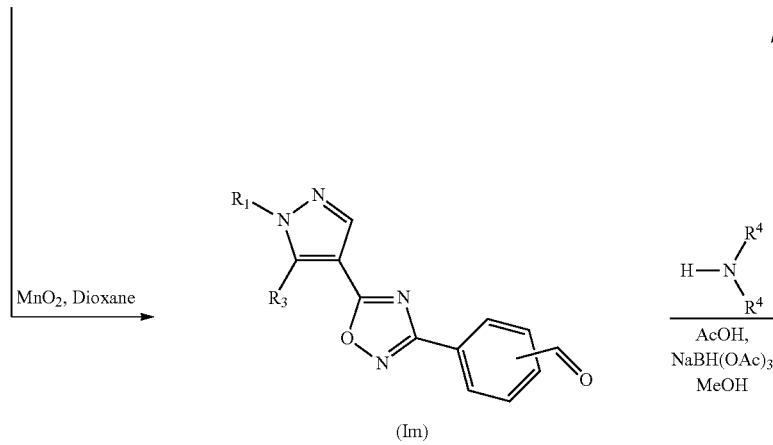

(Im)

Compounds of Formula (II), wherein $R^2$ and $R^3$ are defined as above, may be prepared by standard synthetic techniques well known to those skilled in the art. The first step consists of the transformation of ester (XV) into compound of structure (XVI) and related formulae by reacting with compound (V) wherein $R^2$ is as defined above, at temperature rising from about 20° C. to about 180° C., using possibly a microwave reactor, for a time between 15 minutes and 24 hours, in a suitable solvent, such as toluene (Scheme 8). The second step consists of treatment of the ketone (XVI) with DMF.DMA and PPTS in a suitable solvent, such as toluene, to form vinylogous amides of Formula (II) and related formulae.

Scheme 8

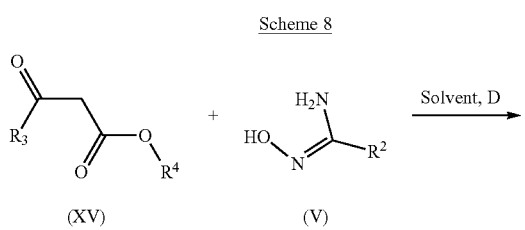

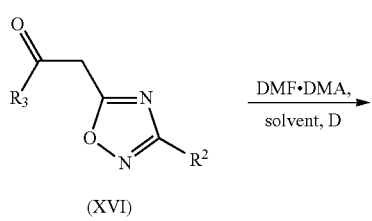

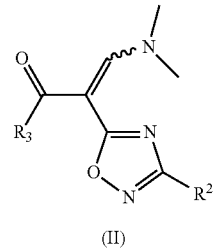

(II)

The method for preparing ketone of Formula (XVI) selected below:
2-[3-(2,5-difluorophenyl)-1,2,4-oxadiazol-5-yl]-1-phenylethanone
2-[3-(2,5-difluorophenyl)-1,2,4-oxadiazol-5-yl]-1-pyridin-4-ylethanone
2-{3-[3-(methylsulfonyl)phenyl]-1,2,4-oxadiazol-5-yl}-1-pyridin-4-ylethanone
1-[3-(2,5-difluorophenyl)-1,2,4-oxadiazol-5-yl]-3-methoxyacetone
1-[3-(2,5-difluorophenyl)-1,2,4-oxadiazol-5-yl]butan-2-one
2-[3-(2,5-difluorophenyl)-1,2,4-oxadiazol-5-yl]-1-(tetrahydro-2H-pyran-4-yl)ethanone
is more particularly described in the examples.

Compounds of Formula (V), wherein $R^2$ is defined as above, are either commercially available or may be prepared by standard synthetic techniques well known to those skilled in the art. Typically, compounds of Formula (V) can be prepared according to Scheme 9 by addition of hydroxylamine to a solution of the corresponding substituted benzonitrile of Formula (XVII) in a solvent or a mixture of solvents, such as EtOH, water, at a temperature rising from 20° C. to 80° C., preferably at 74° C., for a few hours, e.g. one hour to 24 h.

Scheme 9

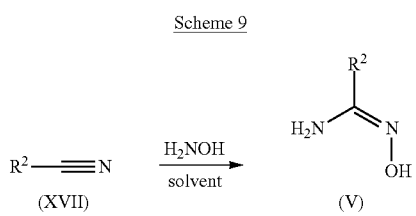

The method for preparing compounds of formula (V) selected below:
N'-hydroxy-3-(methylsulfonyl)benzenecarboximidamide
N'-hydroxy-4-(hydroxymethyl)benzenecarboximidamide
N'-hydroxy-1H-indazole-5-carboximidamide
N'-hydroxy-1,2,3,4-tetrahydroisoquinoline-7-carboximidamide
N'-hydroxy-4-(1H-imidazol-1-ylmethyl)benzenecarboximidamide
N'-hydroxy-4-(1H-pyrazol-1-ylmethyl)benzenecarboximidamide
N',3-dihydroxybenzenecarboximidamide
N'-hydroxy-4-(2-hydroxyethyl)benzenecarboximidamide
6-amino-N'-hydroxypyridine-3-carboximidamide
is more particularly described in the examples.

Compounds of Formula (XVII), wherein $R^2$ is defined as above, are either commercially available or may be prepared by standard synthetic techniques well known to those skilled in the art.

Compounds of Formula (IV), wherein $R^1$, $R^3$ and $R^4$ are defined as above, may be prepared by standard synthetic techniques well known to those skilled in the art. Typically, compounds of Formula (IV) can be prepared according to Scheme 10. The first step consists of treatment of the ketone (XV) with DMF.DMA and PPTS in a suitable solvent, such as toluene, to form vinylogous amides of Formula (XVIII) and related formulae. The second step consists of treatment of vinylogous amide of Formula (XVIII) with a hydrazine, or salt of a hydrazine, in the presence of either a base, when $R^1$ is alkyl and related formulae, preferably sodium carbonate, in a suitable solvent or mixture of solvents, preferably a mixture of ethanol and water, at a temperature rising from RT to 90° C., typically 80° C., for a few hours, e.g., one hour to eighteen hours, or in the presence of an acid, when $R^1$ is aromatic, preferably acetic acid, in a suitable solvent or mixture of solvents, preferably ethanol, at a temperature rising from RT to 90° C., typically 80° C., for a few hours, e.g., one hour to eighteen hours.

Scheme 10

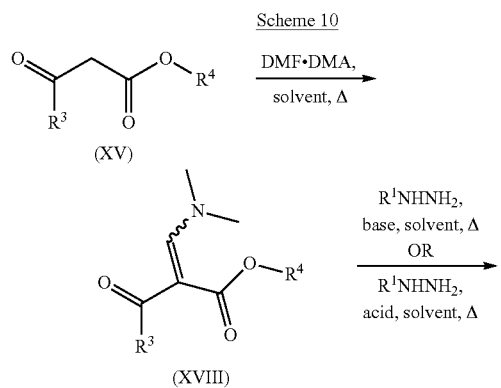

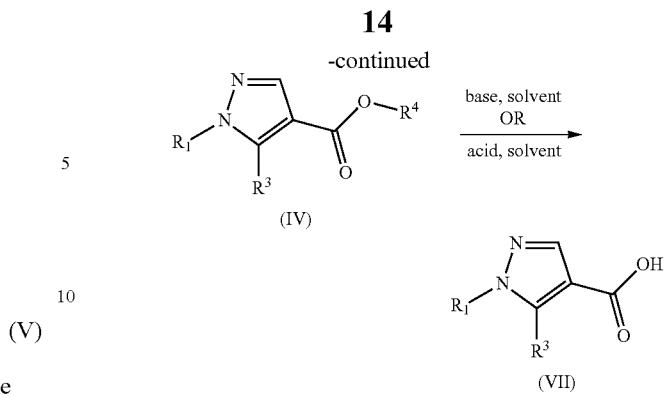

The method for preparing compounds of formula (IV) selected below:
ethyl 1-cyclohexyl-5-pyridin-4-yl-1H-pyrazole-4-carboxylate
methyl 1-(2-fluorophenyl)-5-methyl-1H-pyrazole-4-carboxylate
ethyl 1-isobutyl-5-pyridin-4-yl-1H-pyrazole-4-carboxylate
ethyl 1-(2-methylcyclohexyl)-5-phenyl-1H-pyrazole-4-carboxylate
methyl 1-cyclohexyl-5-(methoxymethyl)-1H-pyrazole-4-carboxylate
ethyl 1-isobutyl-5-(tetrahydro-2H-pyran-4-yl)-1H-pyrazole-4-carboxylate
ethyl 1-cyclohexyl-5-(tetrahydro-2H-pyran-4-yl)-1H-pyrazole-4-carboxylate
methyl 1-isobutyl-5-(methoxymethyl)-1H-pyrazole-4-carboxylate
methyl 1-cyclohexyl-5-(2-methoxyethyl)-1H-pyrazole-4-carboxylate
ethyl 1-cyclohexyl-5-(tetrahydrofuran-2-yl)-1H-pyrazole-4-carboxylate
methyl 1-isobutyl-5-(methoxymethyl)-1H-pyrazole-4-carboxylate
ethyl 1-(2-phenylethyl)-5-pyridin-4-yl-1H-pyrazole-4-carboxylate
ethyl 1-(cyclopropylmethyl)-5-pyridin-4-yl-1H-pyrazole-4-carboxylate
ethyl 1-(2,2-dimethylpropyl)-5-pyridin-4-yl-1H-pyrazole-4-carboxylate
is more particularly described in the examples.

Compounds of Formula (IV) can be further transformed into compounds of Formula (VII), using conditions well known to those skilled in the art. Typically, compounds of Formula (VII), wherein $R^1$ and $R^3$ are defined as above, can be prepared by hydrolysis of the ester of Formula (IV), wherein $R^4$ is as above defined and more preferably $R^4$ is methyl, ethyl or tert-butyl group, using conditions, such as a metal hydroxide, e.g. lithium hydroxide, sodium hydroxide or potassium hydroxide, in a suitable solvent such as THF, methanol, ethanol or water or mixtures thereof, or using an acid, e.g. HCl or TFA, in a suitable solvent such as dioxane, DCM, at a temperature between about 20° C. to about 50° C., preferably at RT, for a few hours, e.g. one hour to 24 h (Scheme 10).

The method for preparing compounds of formula (VII) selected below:
1-cyclohexyl-5-(2-methoxyethyl)-1H-pyrazole-4-carboxylic acid
1-cyclohexyl-5-(methoxymethyl)-1H-pyrazole-4-carboxylic acid
is more particularly described in the examples.

Alternatively, when $R^1$ is alkyl and related formulae, compounds of Formula (VI) can be prepared from the vinylogous amide of Formula (XVIII) with a hydrazine, or salt of a hydrazine, in the presence of an acid, preferably acetic acid, in a suitable solvent or mixture of solvents, preferably ethanol, at a temperature rising from RT to 90° C., typically 80° C., for a few hours, e.g., one hour to eighteen hours (Scheme 11).

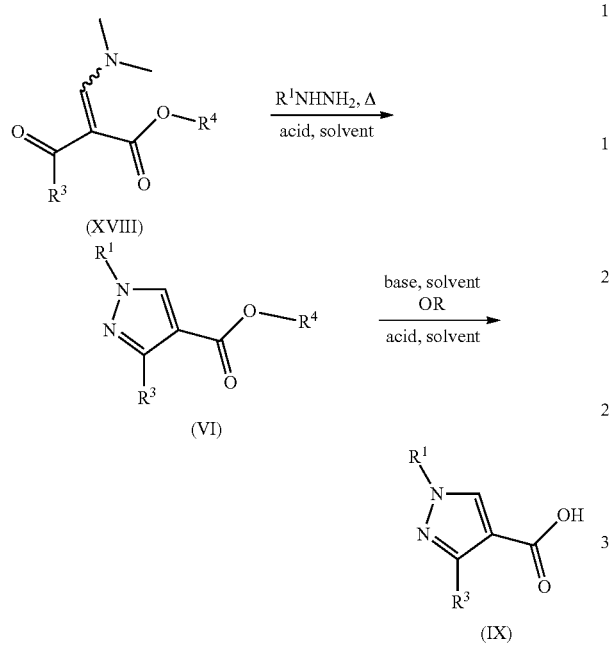

Compounds of Formula (VI) can be further transformed into compounds of Formula (IX), using conditions well known to those skilled in the art. Typically, compounds of Formula (IX), wherein $R^1$ and $R^3$ are defined as above, can be prepared by hydrolysis of the ester of Formula (VI), wherein $R^4$ is as above defined and more preferably $R^4$ is methyl, ethyl or tert-butyl group, using conditions, such as a metal hydroxide, e.g. lithium hydroxide, sodium hydroxide or potassium hydroxide, in a suitable solvent such as THF, methanol, ethanol or water or mixtures thereof, or using an acid, e.g. HCl or TFA, in a suitable solvent such as dioxane, DCM, at a temperature between about 20° C. to about 50° C., preferably at RT, for a few hours, e.g. one hour to 24 h (Scheme 11).

Compounds of Formula (XV), wherein $R^3$ and $R^4$ are defined as above, are either commercially available or may be prepared by standard synthetic techniques well known to those skilled in the art.

Compounds of Formula (XI), wherein $R^1$ and $R^3$ are defined as above, may be prepared by standard synthetic techniques well known to those skilled in the art. Typically, compounds of Formula (XI) can be prepared according to Scheme 12. The first step consists of treatment of the cyano ketone (XIX) with DMF.DMA and PPTS in a suitable solvent, such as toluene, to form vinylogous amides of Formula (XX) and related formulae. The second step consists of treatment of vinylogous amide of Formula (XX) with a hydrazine, or salt of a hydrazine, in the presence of either a base, preferably sodium carbonate, in a suitable solvent or mixture of solvents, preferably a mixture of ethanol and water, at a temperature rising from RT to 90° C., typically 80° C., for a few hours, e.g., one hour to eighteen hours, or in the presence of an acid, preferably acetic acid, in a suitable solvent or mixture of solvents, preferably ethanol, at a temperature rising from RT to 90° C., typically 80° C., for a few hours, e.g., one hour to eighteen hours. The resulting pyrazole-4-carbonitrile of Formula (XXI) can be transformed into the amidoxime of Formula (XI), by addition of hydroxylamine in a solvent or a mixture of solvents, such as EtOH, water, at a temperature rising from 20° C. to 80° C., preferably at 74° C., for a few hours, e.g. one hour to 24 h.

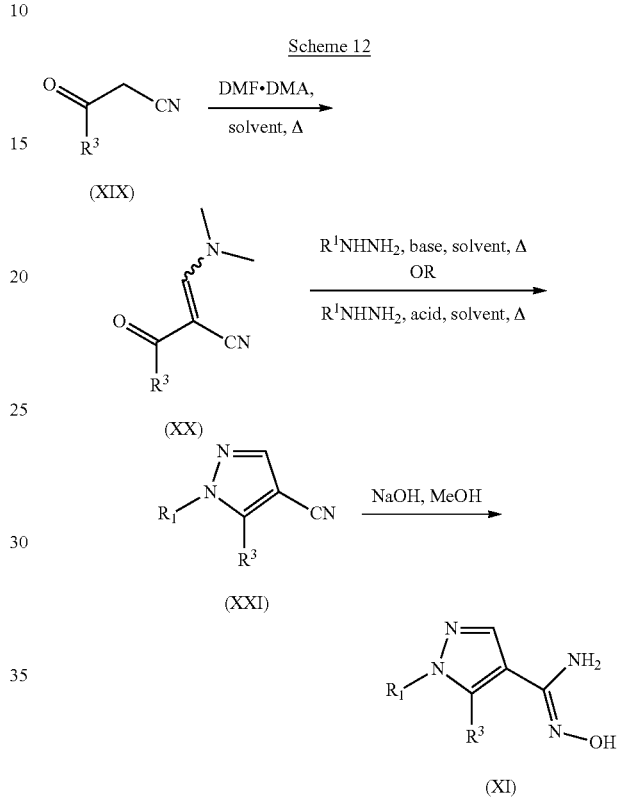

The method for preparing compounds of formula (XI) selected below:
1-cyclohexyl-N'-hydroxy-5-phenyl-1H-pyrazole-4-carboximidamide
is more particularly described in the examples.

Compounds of Formula (XIX), wherein $R^3$ is defined as above, are either commercially available or may be prepared by standard synthetic techniques well known to those skilled in the art.

If the above set of general synthetic methods are not applicable for the obtention of compounds of Formula I, and related formulae, and/or necessary intermediates for the synthesis of compounds of Formula (I), suitable methods of preparation known by a person skilled in the art should be used.

According to a further general process, compounds of Formula (I) and related formulae, such as but not exclusively, Formulae (IV), (VI), (VII), (IX), (XII), (XIII), (XV), (XVI), (XVII), (XIX) and (XXI), wherein $R^1$, $R^2$, $R^3$ and $R^4$ are defined as above, can be converted to alternative compounds of Formula (I) and related formulae, such as but not exclusively, Formulae (IV), (VI), (VII), (IX), (XII), (XIII), (XV), (XVI), (XVII), (XIX) and (XXI), wherein $R^1$, $R^2$, $R^3$ and $R^4$ are defined as above, employing suitable interconversion techniques well known by a person skilled in the art.

Compounds of this invention can be isolated in association with solvent molecules by crystallization from an appropriate solvent or by evaporation of an appropriate solvent.

The pharmaceutically acceptable anionic salts of the compounds of Formula (I), which contain a basic center, may be prepared in a conventional manner. For example, a solution of the free base may be treated with a suitable acid, either neat or in a suitable solution, and the resulting salt isolated either by filtration or by evaporation under vacuum of the reaction solvent.

The pharmaceutically acceptable cationic salts of the compounds of Formula (I), which contain an acidic center, may be prepared in a conventional manner. For example, a solution of the free acid may be treated with a suitable base, either neat or in a suitable solution, and the resulting salt isolated either by filtration or by evaporation under vacuum of the reaction solvent. In some cases, salts can be prepared by mixing a solution of the acid with a solution of the cation (sodium ethylhexanoate, magnesium oleate), employing a solvent in which the desired cationic salt precipitates, or can be otherwise isolated by concentration and addition of a non-solvent.

Both types of salts may be formed or interconverted using ion-exchange resin techniques.

The pharmaceutically acceptable acid addition salts of the compounds of formula (I) and related formulae, which contain a basic center, may be prepared in a conventional manner. For example, a solution of the free base may be treated with a suitable acid, either neat or in a suitable solution, and the resulting salt isolated either by filtration or by evaporation under vacuum of the reaction solvent. Pharmaceutically acceptable base addition salts may be obtained in an analogous manner by treating a solution of compound of formula (I), which contain an acid center, with a suitable base. Both types of salts may be formed or interconverted using ion-exchange resin techniques.

Depending on the nature of $R^1$, $R^2$ and $R^3$, different synthetic strategies may be selected for the synthesis of compounds of formula (I) and related formulae.

In general, the pyrazol oxadiazol derivatives according to formula (I) and related formulae of this invention may be prepared from readily available starting materials. If such starting materials are not commercially available they may be prepared by standard synthetic techniques. The following general methods and procedures described hereinafter in the examples may be employed to prepare compounds of formula I and related formulae.

In general, the synthesis pathways for any individual compound of formula (I) and related formulae will depend on the specific substituents of each molecule and upon the ready availability of intermediates necessary; again such factors being appreciated by those of ordinary skill in the art. For all the protection and deprotection methods, see Philip J. Kocienski, in "*Protecting Groups*", Georg Thieme Verlag Stuttgart, New York, 1994 and, Theodora W. Greene and Peter G. M. Wuts in "*Protective Groups in Organic Synthesis*", Wiley Interscience, 3$^{rd}$ Edition 1999.

Depending on the conditions used, the reaction times are generally between a few minutes and 14 days, and the reaction temperature is between about −30° C. and 140° C., normally between −10° C. and 90° C., in particular between about 0° C. and about 70° C.

Compounds of the formula I and related formulae can furthermore be obtained by liberating compounds of the formula I from one of their functional derivatives by treatment with a solvolysing or hydrogenolysing agent.

Preferred starting materials for the solvolysis or hydrogenolysis are those which conform to the formula (I) and related formulae, but contain corresponding protected amino and/or hydroxyl groups instead of one or more free amino and/or hydroxyl groups, preferably those which carry an amino-protecting group instead of an H atom bonded to an N atom, in particular those which carry an R'—N group, in which R' denotes an amino-protecting group, instead of an HN group, and/or those which carry a hydroxyl-protecting group instead of the H atom of a hydroxyl group, for example those which conform to the formula I, but carry a —COOR" group, in which R" denotes a hydroxyl-protecting group, instead of a —COOH group.

It is also possible for a plurality of—identical or different—protected amino and/or hydroxyl groups to be present in the molecule of the starting material. If the protecting groups present are different from one another, they can in many cases be cleaved off selectively.

The term "amino-protecting group" is known in general terms and relates to groups which are suitable for protecting (blocking) an amino group against chemical reactions, but which are easy to remove after the desired chemical reaction has been carried out elsewhere in the molecule. Typical of such groups are, in particular, unsubstituted or substituted acyl, aryl, aralkoxymethyl or aralkyl groups. Since the amino-protecting groups are removed after the desired reaction (or reaction sequence), their type and size are furthermore not crucial; however, preference is given to those having 1-20, in particular 1-8, carbon atoms. The term "acyl group" is to be understood in the broadest sense in connection with the present process. It includes acyl groups derived from aliphatic, araliphatic, aromatic or heterocyclic carboxylic acids or sulfonic acids, and, in particular, alkoxycarbonyl, aryloxycarbonyl and especially aralkoxycarbonyl groups. Examples of such acyl groups are alkanoyl, such as acetyl, propionyl and butyryl; aralkanoyl, such as phenylacetyl; aroyl, such as benzoyl and tolyl; aryloxyalkanoyl, such as POA; alkoxycarbonyl, such as methoxycarbonyl, ethoxycarbonyl, 2,2,2-trichloroethoxycarbonyl, BOC (tert-butoxycarbonyl) and 2-iodoethoxycarbonyl; aralkoxycarbonyl, such as CBZ ("carbobenzoxy"), 4-methoxybenzyloxycarbonyl and FMOC; and arylsulfonyl, such as Mtr. Preferred amino-protecting groups are BOC and Mtr, furthermore CBZ, Fmoc, benzyl and acetyl.

The term "hydroxyl-protecting group" is likewise known in general terms and relates to groups which are suitable for protecting a hydroxyl group against chemical reactions, but are easy to remove after the desired chemical reaction has been carried out elsewhere in the molecule. Typical of such groups are the above-mentioned unsubstituted or substituted aryl, aralkyl or acyl groups, furthermore also alkyl groups. The nature and size of the hydroxyl-protecting groups are not crucial since they are removed again after the desired chemical reaction or reaction sequence; preference is given to groups having 1-20, in particular 1-10, carbon atoms. Examples of hydroxyl-protecting groups are, inter alia, benzyl, 4-methoxybenzyl, p-nitrobenzoyl, p-toluenesulfonyl, tert-butyl and acetyl, where benzyl and tert-butyl are particularly preferred.

The compounds of the formula (I) and related formulae are liberated from their functional derivatives—depending on the protecting group used—for example using strong acids, advantageously using TFA or perchloric acid, but also using other strong inorganic acids, such as hydrochloric acid or sulfuric acid, strong organic carboxylic acids, such as trichloroacetic acid, or sulfonic acids, such as benzene- or p-toluenesulfonic acid. The presence of an additional inert solvent is possible, but is not always necessary. Suitable inert solvents are preferably organic, for example carboxylic acids, such as acetic acid, ethers, such as tetrahydrofuran or dioxane, amides, such as DMF, halogenated hydrocarbons, such as dichloromethane, furthermore also alcohols, such as methanol, ethanol or isopropanol, and water. Mixtures of the above-mentioned solvents are furthermore suitable. TFA is preferably used in excess without addition of a further solvent, and perchloric acid is preferably used in the form of a mixture of acetic acid and 70% perchloric acid in the ratio 9:1. The reaction temperatures for the cleavage are advantageously between about 0 and about 50° C., preferably between 15 and 30° C. (room temperature).

The BOC, OBut and Mtr groups can, for example, preferably be cleaved off using TFA in dichloromethane or using approximately 3 to 5N HCl in dioxane at 15-30° C., and the FMOC group can be cleaved off using an approximately 5 to 50% solution of dimethylamine, diethylamine or piperidine in DMF at 15-30° C.

Protecting groups which can be removed hydrogenolytically (for example CBZ, benzyl or the liberation of the amidino group from the oxadiazole derivative thereof) can be cleaved off, for example, by treatment with hydrogen in the presence of a catalyst (for example a transition-metal catalyst, such as palladium, advantageously on a support, such as carbon). Suitable solvents here are those indicated above, in particular, for example, alcohols, such as methanol or ethanol, or amides, such as DMF. The hydrogenolysis is generally carried out at temperatures between about 0 and 100° C. and pressures between about 1 and 200 bar, preferably at 20-30° C. and 1-10 bar. Hydrogenolysis of the CBZ group succeeds well, for example, on 5 to 10% Pd/C in methanol or using ammonium formate (instead of hydrogen) on Pd/C in methanol/DMF at 20-30° C.

Examples of suitable inert solvents are hydrocarbons, such as hexane, petroleum ether, benzene, toluene or xylene; chlorinated hydrocarbons, such as trichloroethylene, 1,2-dichloroethane, tetrachloromethane, trifluoromethylbenzene, chloroform or dichloromethane; alcohols, such as methanol, ethanol, isopropanol, n-propanol, n-butanol or tert-butanol; ethers, such as diethyl ether, diisopropyl ether, tetrahydrofuran (THF) or dioxane; glycol ethers, such as ethylene glycol monomethyl or monoethyl ether or ethylene glycol dimethyl ether (diglyme); ketones, such as acetone or butanone; amides, such as acetamide, dimethylacetamide, N-methylpyrrolidone (NMP) or dimethylformamide (DMF); nitriles, such as acetonitrile; sulfoxides, such as dimethyl sulfoxide (DMSO); carbon disulfide; carboxylic acids, such as formic acid or acetic acid; esters, such as ethyl acetate, or mixtures of the said solvents.

Esters can be saponified, for example, using acetic acid or using LiOH, NaOH or KOH in water, water/THF, water/THF/ethanol or water/dioxane, at temperatures between 0 and 100° C.

Free amino groups can furthermore be acylated in a conventional manner using an acid chloride or anhydride or alkylated using an unsubstituted or substituted alkyl halide or reacted with $CH_3$—C(=NH)—OEt, advantageously in an inert solvent, such as dichloromethane or THF and/or in the presence of a base, such as triethylamine or pyridine, at temperatures between −60° C. and +30° C.

Throughout the specification, the term leaving group preferably denotes Cl, Br, I or a reactively modified OH group, such as, for example, an activated ester, an imidazolide or alkylsulfonyloxy having 1-6 carbon atoms (preferably methylsulfonyloxy or trifluoro-methylsulfonyloxy) or arylsulfonyloxy having 6-10 carbon atoms (preferably phenyl- or p-tolylsulfonyloxy).

Radicals of this type for activation of the carboxyl group in typical acylation reactions are described in the literature (for example in the standard works, such as Houben-Weyl, Methoden der organischen Chemie [Methods of Organic Chemistry], Georg-Thieme-Verlag, Stuttgart).

Activated esters are advantageously formed in situ, for example through addition of HOBt or N-hydroxysuccinimide.

The formula (I) and related formulae also encompasses the optically active forms (stereoisomers), the enantiomers, the racemates, the diastereomers and the hydrates and solvates of these compounds.

The term "solvates of the compounds" is taken to mean adductions of inert solvent molecules onto the compounds which form owing to their mutual attractive force. Solvates are, for example, mono- or dihydrates or alcoholates.

The term "pharmaceutically usable derivatives" is taken to mean, for example, the salts of the compounds of the formula I and so-called prodrug compounds.

The term "prodrug derivatives" is taken to mean compounds of the formula I which have been modified with, for example, alkyl or acyl groups, sugars or oligopeptides and which are rapidly cleaved in the organism to form the active compounds.

These also include biodegradable polymer derivatives of the compounds according to the invention, as described, for example, in Int. J. Pharm. 115, 61-67 (1995).

The formula (I) and related formulae also encompasses mixtures of the compounds of the formula (I), for example mixtures of two diastereomers, for example in the ratio 1:1, 1:2, 1:3, 1:4, 1:5, 1:10, 1:100 or 1:1000.

These are particularly preferably mixtures of stereoisomeric compounds.

In a specific embodiment, the present invention provides a compound of Formula (I)

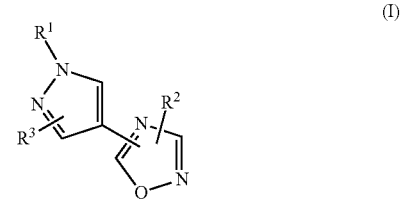

wherein
$R^1$ denotes $Ar^1$, $Het^1$, Cyc, A, $(C_1$-$C_6)$alkyl, $(C_2$-$C_6)$alkyl, —$(CH_2)_n Ar^1$, $(CH_2)_n Het^1$, $(CH_2)_n Het^2$.
$R^2$ is $Ar^2$, $Het^1$;
$R^3$ denotes $Ar^1$, $Ar^2$, $Het^1$, $Het^2$, Cyc or A,
A is a branched or linear alkyl having 2 to 12 C-atoms, wherein one or more, preferably 1 to 7H-atoms may be replaced by Hal, $OR^4$, CN, $CO_2R^4$, $CF_3$, cycloalkyl having 3 to 7 ring carbon atoms, $Ar^1$, $Ar^2$, or $N(R^4)_2$ and wherein one or more, preferably 1 to 7 non-adjacent $CH_2$-groups may be replaced by O, $NR^4$, —CO—, $NR^4CO_2$—, —$CO_2$—, —$NR^4CONR^4$—, —CH=CH—, —C≡C—, or denotes cycloalkyl or cycloalkylalkylen having 3-7 ring C atoms, or denotes $Het^1$ or $Het^2$;
Z is a branched or linear alkyl having 2 to 12 C-atoms, wherein one or more, preferably 1 to 7H-atoms are replaced by Hal, $OR^4$, CN, $CO_2R^4$, $CF_3$, cycloalkyl having 3 to 7 ring carbon atoms, $Ar^1$, $Ar^2$, $N(R^4)_2$ and/or wherein one or more, preferably 1 to 7 $CH_2$-groups are replaced by O, $NR^4$, S, —CO—, $NR^4CO_2$—, —$NR^4CONR^4$—, —CH=CH—, —C≡C—, or denotes cycloalkyl or cycloalkylalkylen having 3-7 ring C atoms;

Hal is F, Cl, Br or I;

Ar$^1$ denotes a monocyclic or bicyclic, unsaturated or aromatic carbocyclic ring having 6 to 14 carbon atoms which may be unsubstituted, monosubstituted, disubstituted or trisubstituted by substituents selected from A, Hal, —OR$^4$, —SO$_2$R$^4$, —CN, —NO$_2$, —N(R$^3$)$_2$, —CO(NR$^4$)$_2$, —OR$^4$, (NR$^4$)COR$^4$, —CO$_2$R$^4$, —COR$^4$, —SO$_2$N(R$^4$)$_2$, —SO$_2$alkyl, NR$^4$SO$_2$alkyl, NR$^4$SO$_2$alkyl, or C$_1$-C$_6$alkyl;

Ar$^2$ denotes a monocyclic or bicyclic, unsaturated or aromatic carbocyclic ring having 6 to 14 carbon atoms which may be unsubstituted, monosubstituted, disubstituted or trisubstituted by substituents selected from Z, F, Br, I, —OR$^4$, —(CH$_2$)OR$^4$, —(CH$_2$)N(R$^4$)$_2$, Perfluoro-alkoxy, —SO$_2$R$^4$, —CN, —NO$_2$, —N(R$^4$)$_2$, —CO$_2$R$^4$, —COR$^4$, —SO$_2$N(R$^4$)$_2$, —SO$_2$(C$_1$-C$_6$)alkyl, NR$^4$SO$_2$(C$_1$-C$_6$)alkyl, —(CH$_2$)$_n$Het$^1$, —OHet$^1$, —(CH$_2$)$_n$Het$^2$, —OHet$^2$, Het$^1$ denotes a monocyclic saturated, unsaturated or aromatic heterocyclic ring having 1 to 4 N, and/or O atoms which may be unsubstituted, monosubstituted, disubstituted or trisubstituted by substituents selected from A, Hal, —OR$^4$, —(CH$_2$)OR$^4$, Perfluoro-alkyl, Perfluoro-alkoxy, —SO$_2$(R$^4$)$_2$, CN, NO$_2$, —N(R$^4$)$_2$, —CO(NR$^4$)$_2$, (NR$^4$)COR$^4$, —CO$_2$R$^4$, —COR$^4$, —SO$_2$N(R$^4$)$_2$, —SO$_2$alkyl, NR$^4$SO$_2$alkyl, NR$^4$SO$_2$alkyl, or C$_1$-C$_6$ alkyl.

Het$^2$ denotes a monocyclic or bicyclic, saturated, unsaturated or aromatic heterocyclic ring having 1 to 4 N, O and/or S atoms which may be unsubstituted, monosubstituted, disubstituted or trisubstituted by substituents selected from A, F, Br, I, —OR$^4$, —(CH$_2$)OR$^4$, Perfluoro-alkyl, Perfluoro-alkoxy, —SO$_2$(R$^4$)$_2$, CN, NO$_2$, —N(R$^4$)$_2$, —CO(NR$^4$)$_2$, (NR$^4$)COR$^4$, —CO$_2$R$^4$, —COR$^4$, —SO$_2$N(R$^4$)$_2$, —SO$_2$alkyl, NR$^4$SO$_2$alkyl, NR$^4$SO$_2$alkyl, or C$_1$-C$_6$ alkyl;

Cyc denotes a saturated or unsaturated carbocyclic ring containing 3 to 7 carbon atoms which may be substituted by Hal, A, (C$_1$-C$_6$)alkyl, —[C(R$^4$)$_2$]$_n$—Ar, —[C(R$^4$)$_2$]$_n$-cycloalkyl, OR$^4$, CF$_3$, OCF$_3$, N(R$^4$)$_2$, NR$^4$CON(R$^4$)$_2$, NO$_2$, CN, —[C(R$^4$)$_2$]$_n$—COOR$^4$, —[C(R$^4$)$_2$]$_n$—CON(R$^4$)$_2$, NR$^4$COA, NR$^4$SO$_2$A, COR$^4$, CO$_2$R$^4$, SO$_2$N(R$^4$)$_2$, SOA, and/or SO$_2$A.

R$^4$ is H, A, Cyc or (C$_1$-C$_6$)alkyl, preferably H or (C$_1$-C$_6$)alkyl;

n is 1, 2, 3 or 4, and pharmaceutically acceptable derivatives, solvates, tautomers, salts and stereo-isomers thereof, including mixtures thereof in all ratios as a medicament, especially for treating multiple sclerosis and other diseases.

In a preferred embodiment, the present invention provides compounds of Formula (IA)

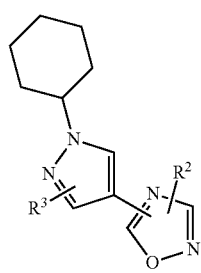

(IA)

and most preferably compounds of Formula (IA')

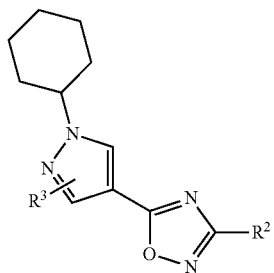

(IA')

Wherein R$^2$ and R$^3$ are as above defined.

In another preferred embodiment, the present invention provides compounds of Formula (IB)

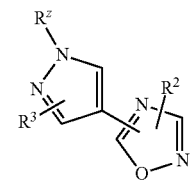

(IB)

And most preferably, compounds of Formula (IB')

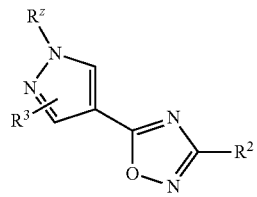

(IB')

Wherein R$^2$ and R$^3$ are as above defined and wherein R$^z$ denotes A, (C$_1$-C$_6$)alkyl, (C$_2$-C$_6$)alkyl, —(CH$_2$)$_n$Ar$^1$, (CH$_2$)$_n$Het$^1$, (CH$_2$)$_n$Het$^2$, whereby n, Ar$^1$, Het$^1$ are as above defined. R$^z$ more preferably denotes A, (C$_1$-C$_6$)alkyl, (C$_2$-C$_6$)alkyl.

In another preferred embodiment, the present invention provides compounds of Formula (IC)

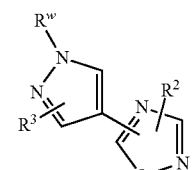

(IC)

more preferably compounds of Formula (IC')

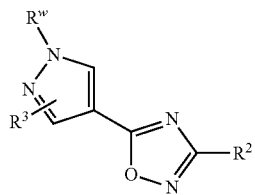
(IC')

Wherein $R^2$ and $R^3$ are as above defined and wherein $R^w$ denotes $Ar^1$, More preferably $R^w$ denotes phenyl.

And most preferably compounds of Formula (IC")

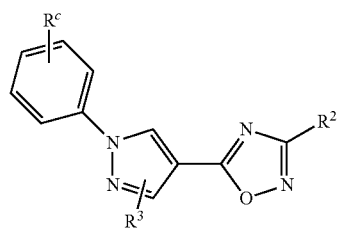
(IC")

Wherein $R^c$ denotes Hal, —$OR^4$, ($C_1$-$C_6$)alkyl, and $R^2$ and $R^3$ are as above defined.

In a preferred embodiment, the present invention also provides compounds of Formulae (ID)

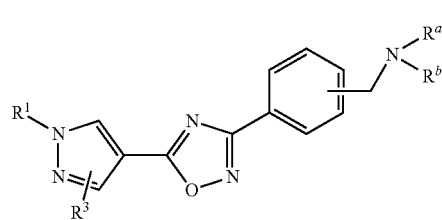
(ID)

Wherein $R^1$ and $R^3$ are as above defined and wherein $R^a$ and $R^b$ independently from one another denotes H, A, ($C_1$-$C_6$)-alkyl or Z, or $R^a$ and $R^b$ together form with the nitrogen atom to which they are bond, an heterocyclic ring optionally substituted by $CO_2R^4$, $OR^4$, or $(CH_2)_nR^4$, whereby n and $R^4$ areas above defined.

In another preferred embodiment, the present invention provides compounds of formula (IE)

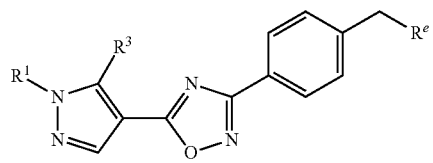
(IE)

Wherein $R^e$ denotes $Het^1$ or $Het^2$, and wherein $R^1$ and $R^3$ are as above defined.

In another preferred embodiment, the present invention provides compounds of Formula (IF)

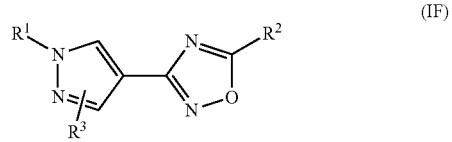
(IF)

Wherein $R^1$, $R^2$, $R^3$ are as above defined and pharmaceutically acceptable derivatives, solvates, tautomers, salts and stereoisomers thereof, including mixtures thereof in all ratios and their use for treating multiple sclerosis and other diseases.

Generally, compounds of formula (I) are the more preferred, the more preferred substituents they carry.

$R^1$ preferably denotes: methyl, cyclohexyl, cyclopentyl, n-propyl, iso-butyl, tert-butyl, phenyl, or one of the following groups:

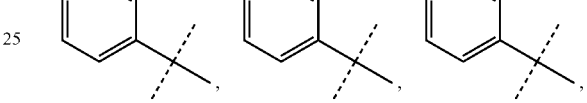

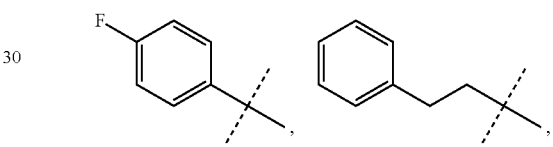

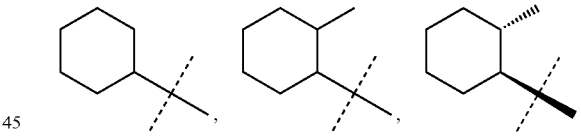

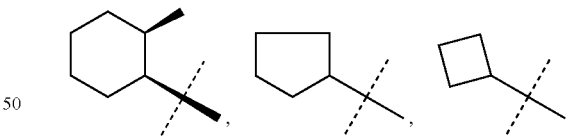

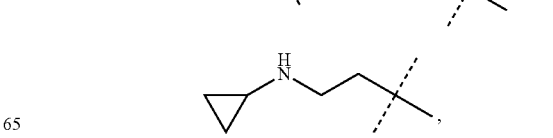

$R^2$ preferably denotes
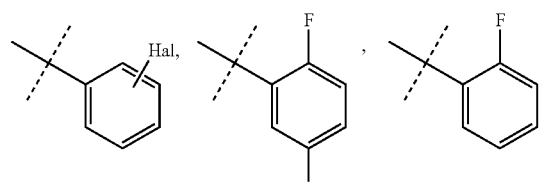
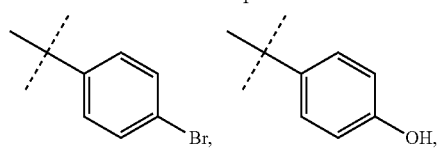
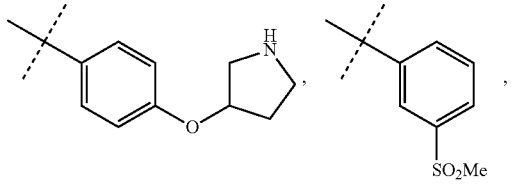
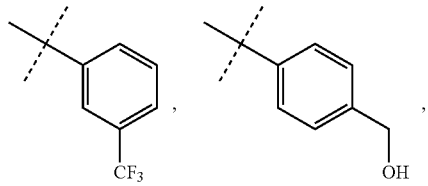
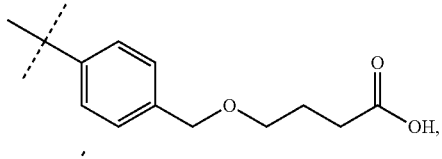
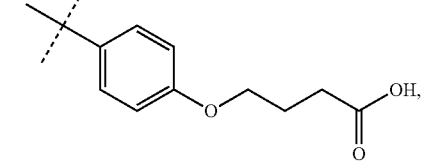
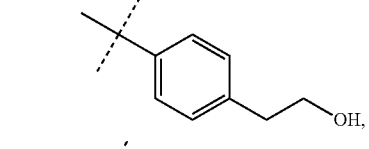
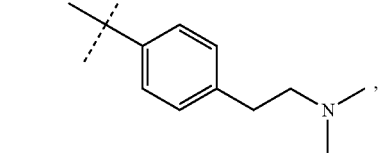
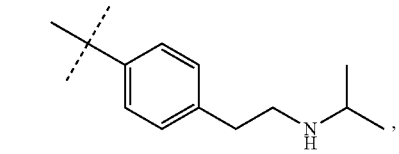
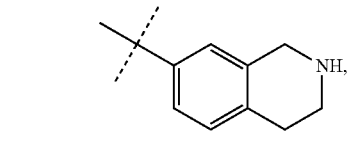
-continued
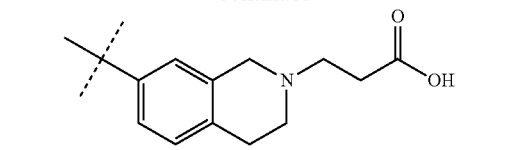
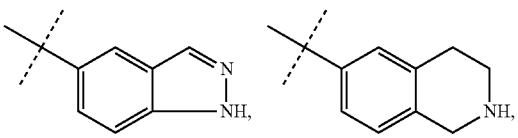
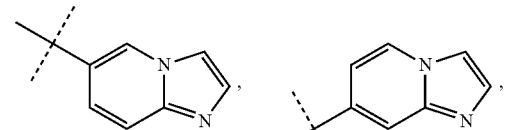
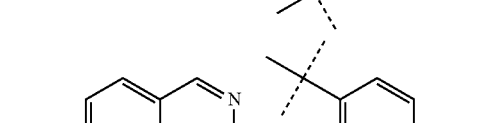
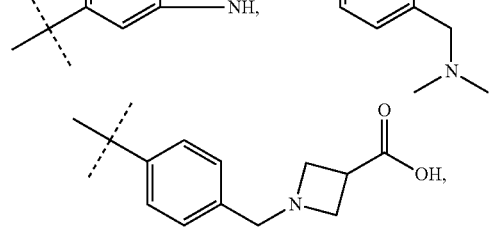
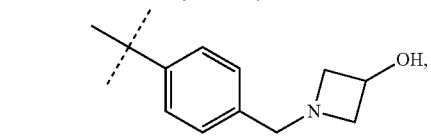
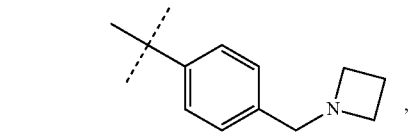
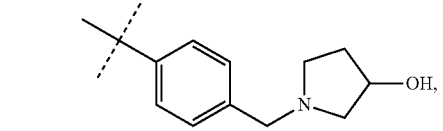
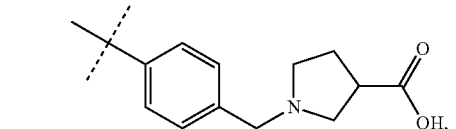
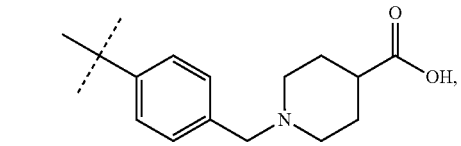
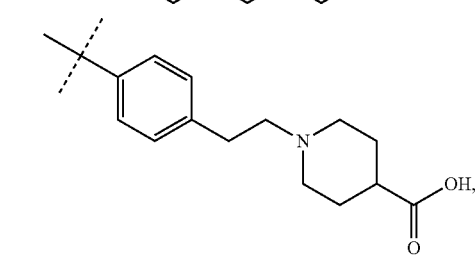

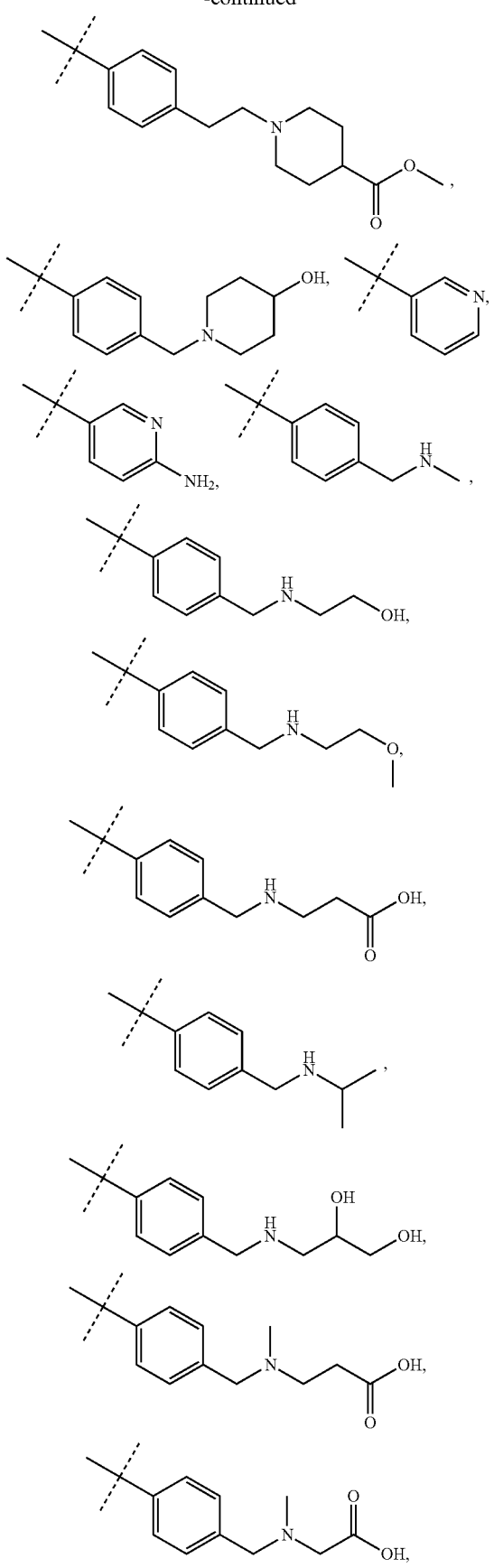
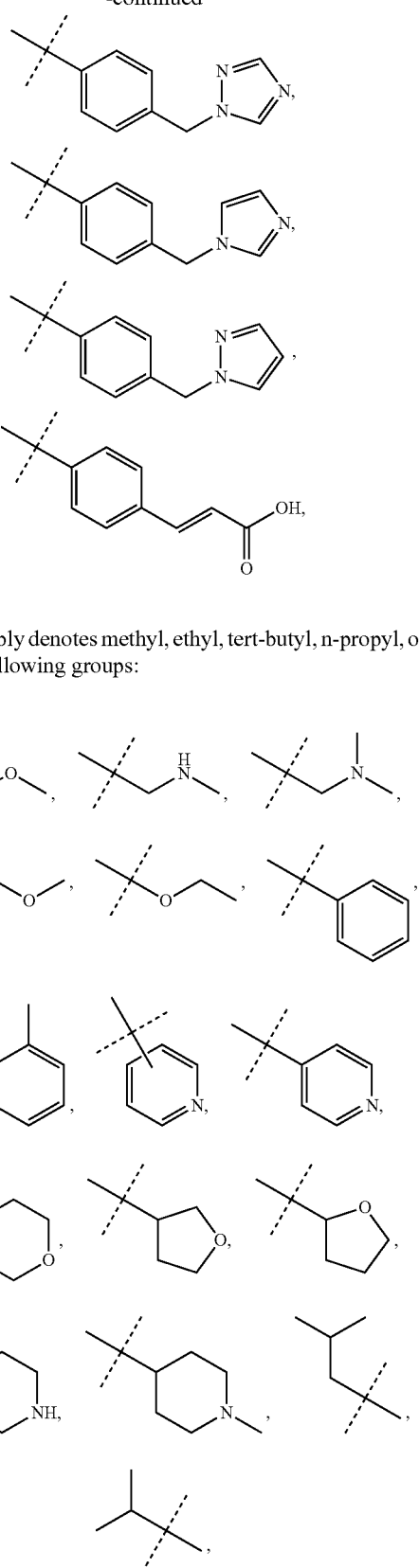
$R^3$ preferably denotes methyl, ethyl, tert-butyl, n-propyl, or one of the following groups:
The most preferred compounds are selected from the following group:

| Example Nb | Formula |
|---|---|
| 1 | 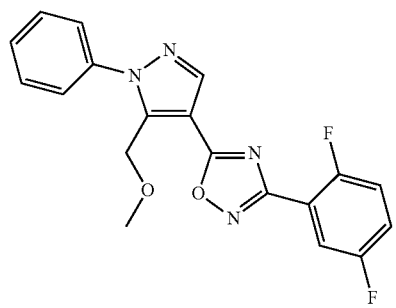 [SMILES: COCc1c(-c2nc(-c3cc(F)ccc3F)no2)cnn1-c1ccccc1] |
| 2 | 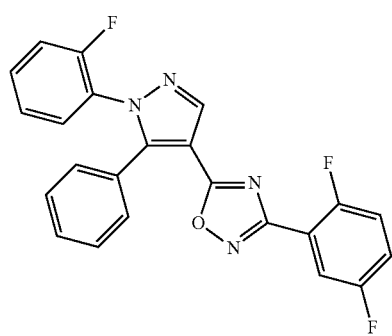 [SMILES: Fc1ccc(F)c(-c2noc(-c3cnn(-c4ccccc4F)c3-c3ccccc3)n2)c1] |
| 3 | 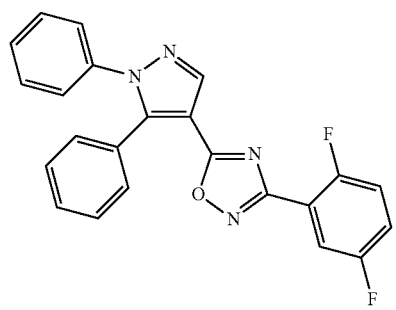 [SMILES: Fc1ccc(F)c(-c2noc(-c3cnn(-c4ccccc4)c3-c3ccccc3)n2)c1] |
| 4 | 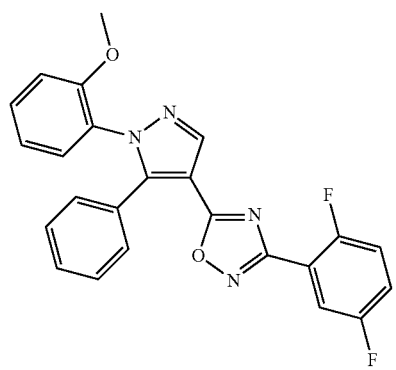 [SMILES: COc1ccccc1-n1ncc(-c2nc(-c3cc(F)ccc3F)no2)c1-c1ccccc1] |

-continued
| Example Nb | Formula |
|---|---|
| 5 | 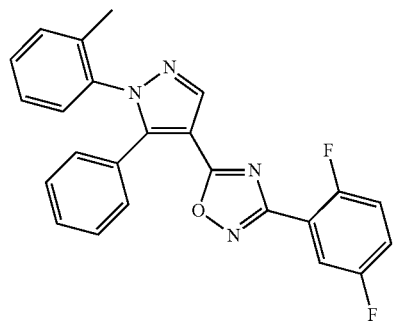 [SMILES: Cc1ccccc1-n1ncc(-c2nc(-c3cc(F)ccc3F)no2)c1-c1ccccc1] |
| 6 | 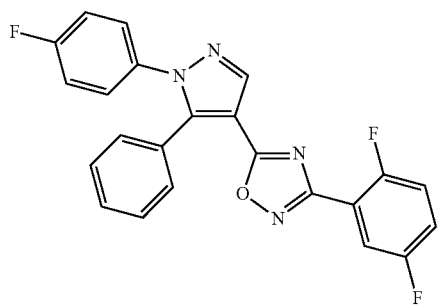 [SMILES: Fc1ccc(-n2ncc(-c3nc(-c4cc(F)ccc4F)no3)c2-c2ccccc2)cc1] |
| 7 | 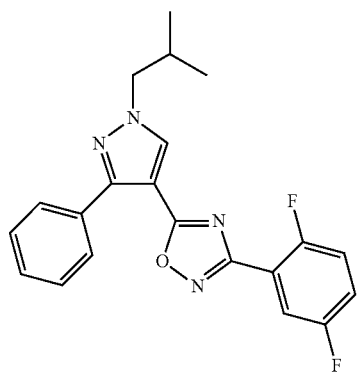 [SMILES: CC(C)Cn1cc(-c2nc(-c3cc(F)ccc3F)no2)c(-c2ccccc2)n1] |
| 8 | 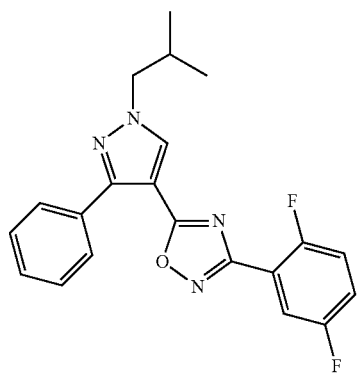 [SMILES: CC(C)Cn1cc(-c2nc(-c3cc(F)ccc3F)no2)c(-c2ccccc2)n1] |

-continued
| Example Nb | Formula |
|---|---|
| 9 | 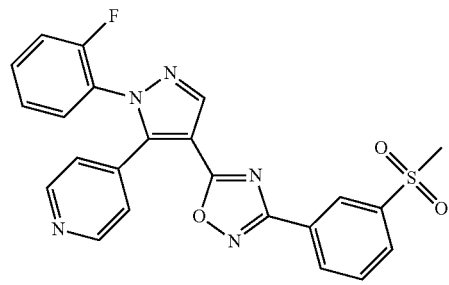 [SMILES: CS(=O)(=O)c1cccc(-c2noc(-c3cnn(-c4ccccc4F)c3-c3ccncc3)n2)c1] |
| 10 | 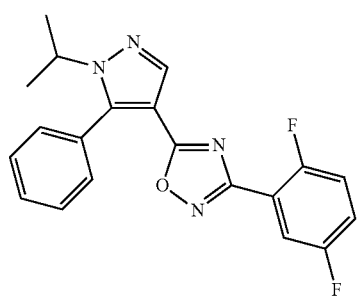 [SMILES: CC(C)n1ncc(-c2nc(-c3cc(F)ccc3F)no2)c1-c1ccccc1] |
| 11 | 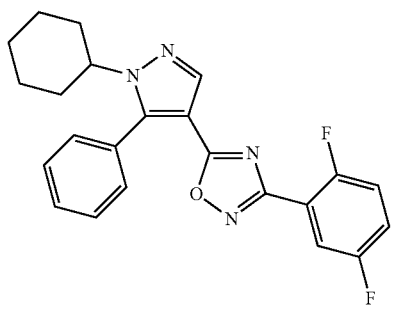 [SMILES: Fc1ccc(F)c(-c2noc(-c3cnn(C4CCCCC4)c3-c3ccccc3)n2)c1] |
| 12 | 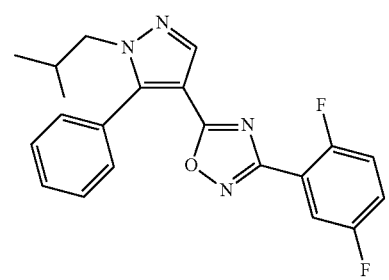 [SMILES: CC(C)Cn1ncc(-c2nc(-c3cc(F)ccc3F)no2)c1-c1ccccc1] |
| 13 | 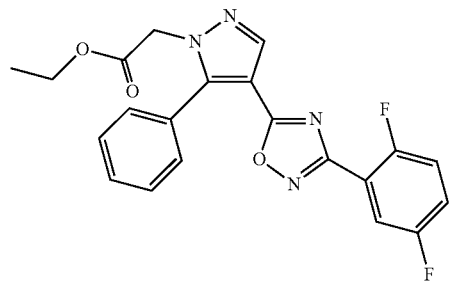 [SMILES: CCOC(=O)Cn1ncc(-c2nc(-c3cc(F)ccc3F)no2)c1-c1ccccc1] |

-continued

| Example Nb | Formula |
|---|---|
| 14 | |
| 15 | |
| 16 | |
| 17 | |
| 18 | |

-continued
| Example Nb | Formula |
|---|---|
| 19 | 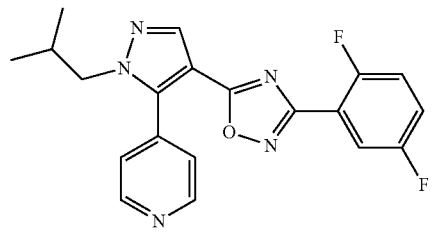 [SMILES: CC(C)Cn1ncc(-c2nc(-c3cc(F)ccc3F)no2)c1-c1ccncc1] |
| 20 | 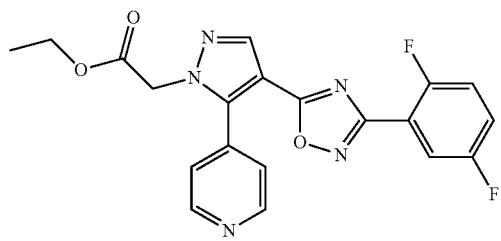 [SMILES: CCOC(=O)Cn1ncc(-c2nc(-c3cc(F)ccc3F)no2)c1-c1ccncc1] |
| 21 | 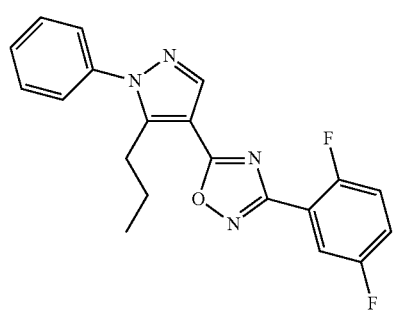 [SMILES: CCCc1c(-c2nc(-c3cc(F)ccc3F)no2)cnn1-c1ccccc1] |
| 22 | 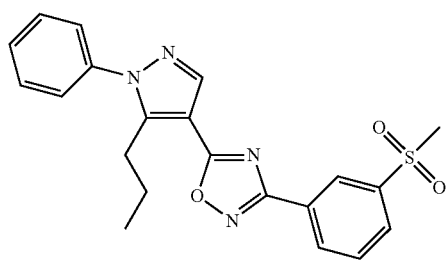 [SMILES: CCCc1c(-c2nc(-c3cccc(S(C)(=O)=O)c3)no2)cnn1-c1ccccc1] |
| 23 | 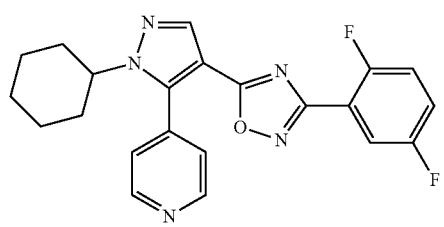 [SMILES: Fc1ccc(F)c(-c2noc(-c3cnn(C4CCCCC4)c3-c3ccncc3)n2)c1] |
| 24 | 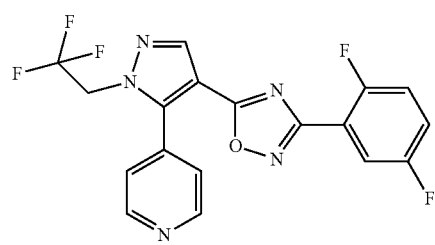 [SMILES: Fc1ccc(F)c(-c2noc(-c3cnn(CC(F)(F)F)c3-c3ccncc3)n2)c1] |

-continued
| Example Nb | Formula |
|---|---|
| 25 | 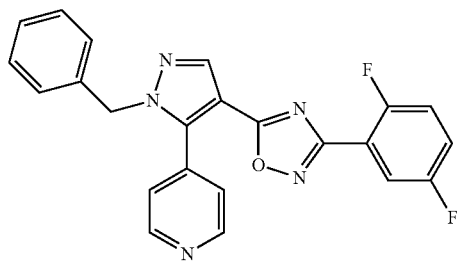 [SMILES: Fc1ccc(F)c(-c2noc(-c3cnn(Cc4ccccc4)c3-c3ccncc3)n2)c1] |
| 26 | 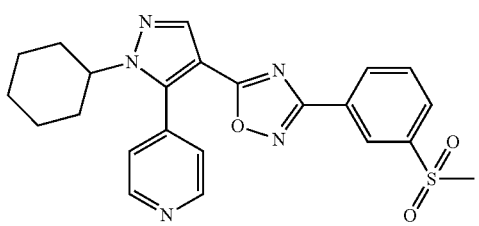 [SMILES: CS(=O)(=O)c1cccc(-c2noc(-c3cnn(C4CCCCC4)c3-c3ccncc3)n2)c1] |
| 27 | 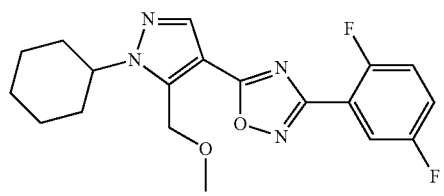 [SMILES: COCc1c(-c2nc(-c3cc(F)ccc3F)no2)cnn1C1CCCCC1] |
| 28 | 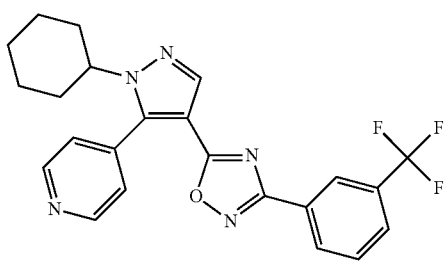 [SMILES: FC(F)(F)c1cccc(-c2noc(-c3cnn(C4CCCCC4)c3-c3ccncc3)n2)c1] |
| 29 | 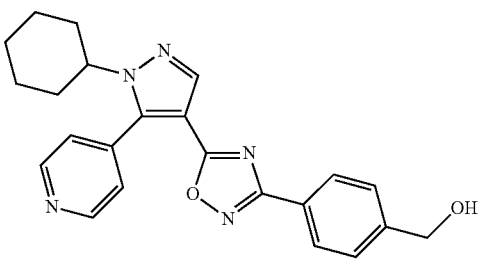 [SMILES: OCc1ccc(-c2noc(-c3cnn(C4CCCCC4)c3-c3ccncc3)n2)cc1] |
| 30 | 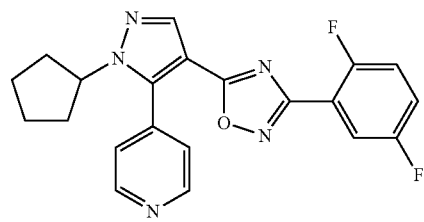 [SMILES: Fc1ccc(F)c(-c2noc(-c3cnn(C4CCCC4)c3-c3ccncc3)n2)c1] |

-continued
| Example Nb | Formula |
|---|---|
| 31 | 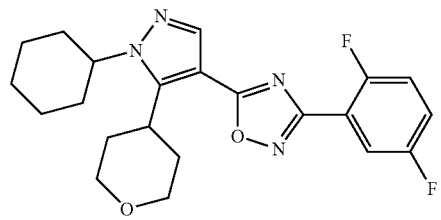 [SMILES: Fc1ccc(F)c(-c2noc(-c3cnn(C4CCCCC4)c3C3CCOCC3)n2)c1] |
| 32 | 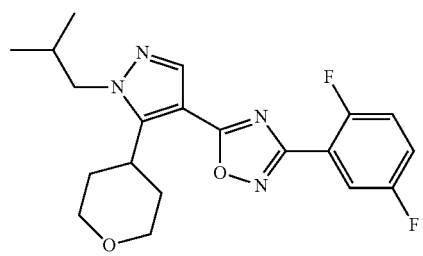 [SMILES: CC(C)Cn1ncc(-c2nc(-c3cc(F)ccc3F)no2)c1C1CCOCC1] |
| 33 | 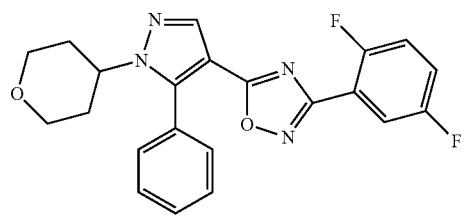 [SMILES: Fc1ccc(F)c(-c2noc(-c3cnn(C4CCOCC4)c3-c3ccccc3)n2)c1] |
| 34 | 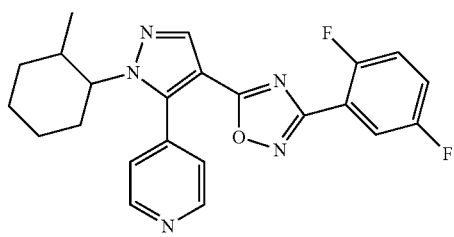 [SMILES: CC1CCCCC1n1ncc(-c2nc(-c3cc(F)ccc3F)no2)c1-c1ccncc1] |
| 35 | 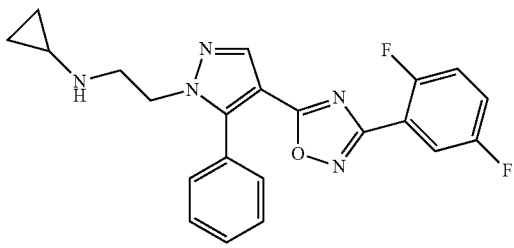 [SMILES: Fc1ccc(F)c(-c2noc(-c3cnn(CCNC4CC4)c3-c3ccccc3)n2)c1] |
| 36 | 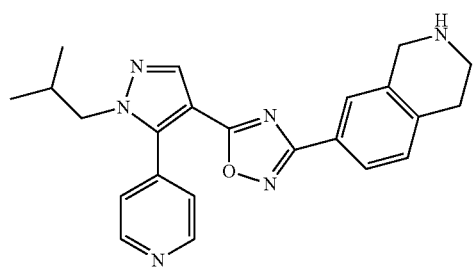 [SMILES: CC(C)Cn1ncc(-c2nc(-c3ccc4c(c3)CNCC4)no2)c1-c1ccncc1] |

-continued

| Example Nb | Formula |
| --- | --- |
| 37 | |
| 38 | |
| 39 | |
| 40 | |
| 41 | |
| 42 | |

-continued
| Example Nb | Formula |
|---|---|
| 43 | 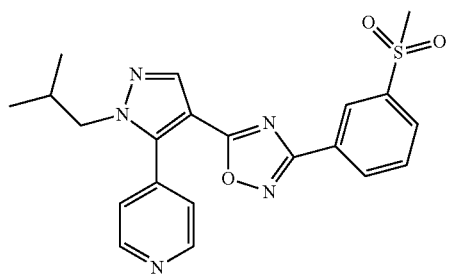 [SMILES: CC(C)Cn1ncc(-c2nc(-c3cccc(S(C)(=O)=O)c3)no2)c1-c1ccncc1] |
| 44 | 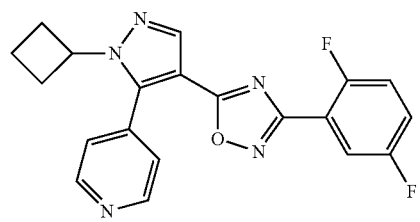 [SMILES: Fc1ccc(F)c(-c2noc(-c3cnn(C4CCC4)c3-c3ccncc3)n2)c1] |
| 45 | 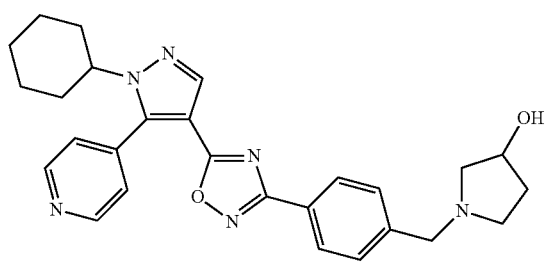 [SMILES: OC1CCN(Cc2ccc(-c3noc(-c4cnn(C5CCCCC5)c4-c4ccncc4)n3)cc2)C1] |
| 46 | 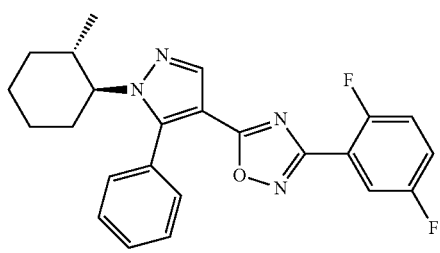 [SMILES: C[C@H]1CCCC[C@@H]1n1ncc(-c2nc(-c3cc(F)ccc3F)no2)c1-c1ccccc1] |
| 47 | 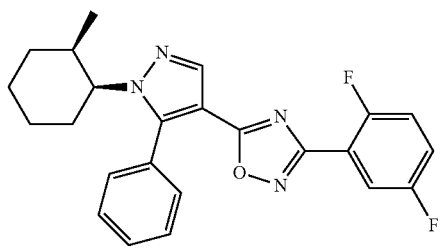 [SMILES: C[C@@H]1CCCC[C@@H]1n1ncc(-c2nc(-c3cc(F)ccc3F)no2)c1-c1ccccc1] |
| 48 | 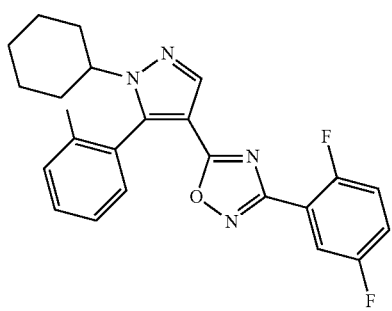 [SMILES: Cc1ccccc1-c1c(-c2nc(-c3cc(F)ccc3F)no2)cnn1C1CCCCC1] |

-continued
| Example Nb | Formula |
|---|---|
| 49 | 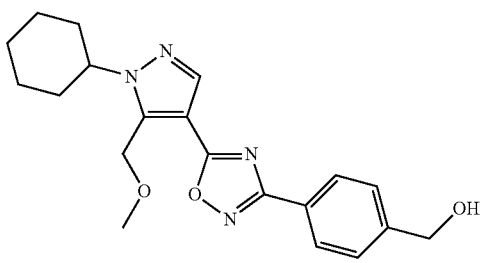 [SMILES: COCc1c(-c2nc(-c3ccc(CO)cc3)no2)cnn1C1CCCCC1] |
| 50 | 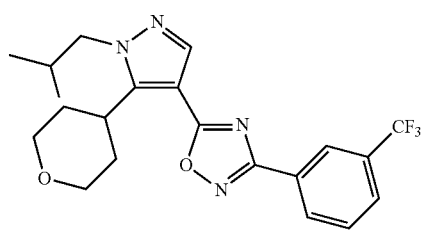 [SMILES: CC(C)Cn1ncc(-c2nc(-c3cccc(C(F)(F)F)c3)no2)c1C1CCOCC1] |
| 51 | 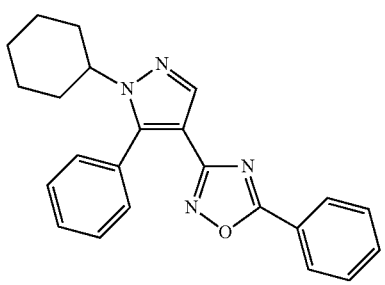 [SMILES: c1ccc(-c2nc(-c3cnn(C4CCCCC4)c3-c3ccccc3)no2)cc1] |
| 52 | 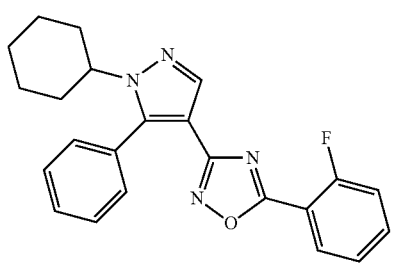 [SMILES: Fc1ccccc1-c1nc(-c2cnn(C3CCCCC3)c2-c2ccccc2)no1] |
| 53 | 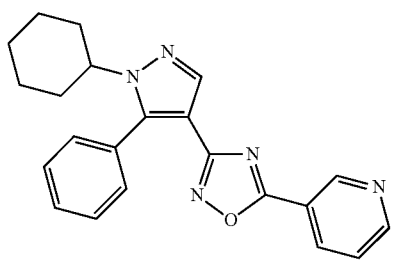 [SMILES: c1ccc(-c2c(-c3noc(-c4cccnc4)n3)cnn2C2CCCCC2)cc1] |
| 54 | 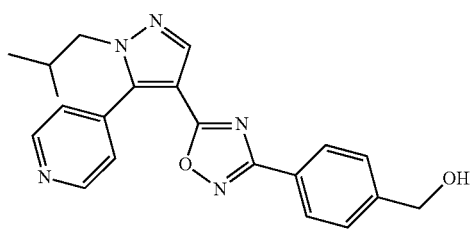 [SMILES: CC(C)Cn1ncc(-c2nc(-c3ccc(CO)cc3)no2)c1-c1ccncc1] |

-continued

| Example Nb | Formula |
|---|---|
| 55 | |
| 56 | |
| 57 | |
| 58 | |
| 59 | |

-continued
| Example Nb | Formula |
|---|---|
| 60 | 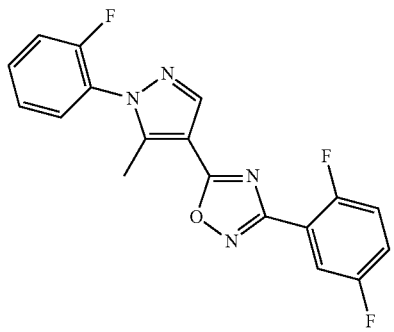 [SMILES: Cc1c(-c2nc(-c3cc(F)ccc3F)no2)cnn1-c1ccccc1F] |
| 61 | 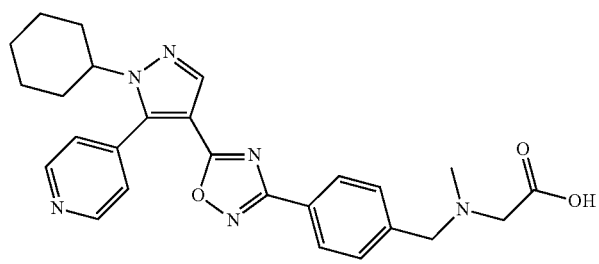 [SMILES: CN(CC(=O)O)Cc1ccc(-c2noc(-c3cnn(C4CCCCC4)c3-c3ccncc3)n2)cc1] |
| 62 | 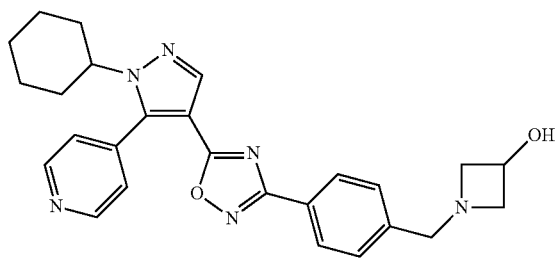 [SMILES: OC1CN(Cc2ccc(-c3noc(-c4cnn(C5CCCCC5)c4-c4ccncc4)n3)cc2)C1] |
| 63 | 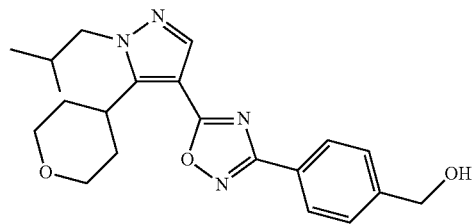 [SMILES: CC(C)Cn1ncc(-c2nc(-c3ccc(CO)cc3)no2)c1C1CCOCC1] |
| 64 | 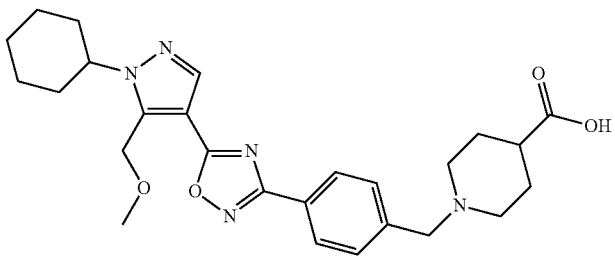 [SMILES: COCc1c(-c2nc(-c3ccc(CN4CCC(C(=O)O)CC4)cc3)no2)cnn1C1CCCCC1] |

-continued
| Example Nb | Formula |
|---|---|
| 65 | 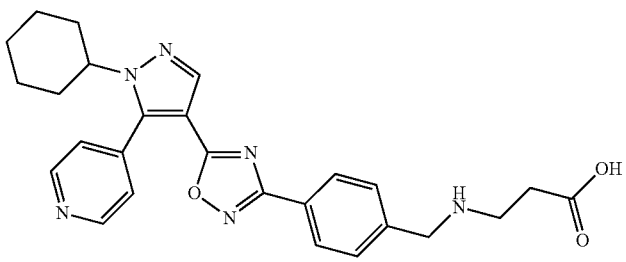 [SMILES: O=C(O)CCNCc1ccc(-c2noc(-c3cnn(C4CCCCC4)c3-c3ccncc3)n2)cc1] |
| 66 | 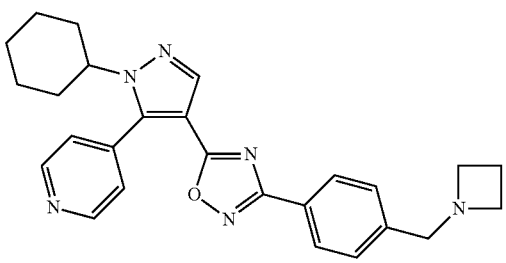 [SMILES: c1cc(-c2c(-c3nc(-c4ccc(CN5CCC5)cc4)no3)cnn2C2CCCCC2)ccn1] |
| 67 | 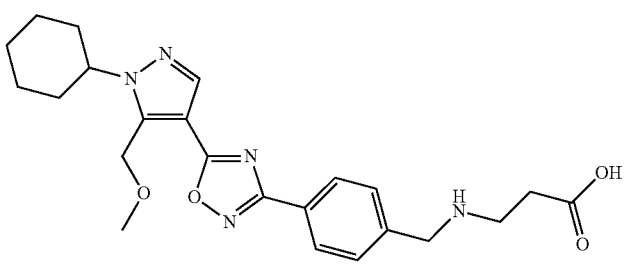 [SMILES: COCc1c(-c2nc(-c3ccc(CNCCC(=O)O)cc3)no2)cnn1C1CCCCC1] |
| 68 | 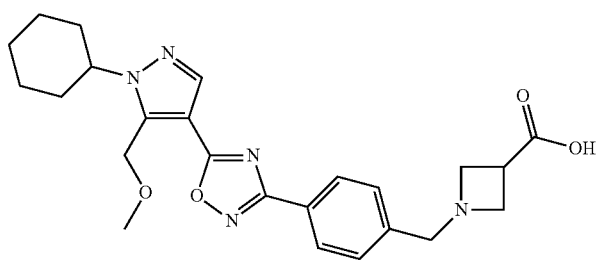 [SMILES: COCc1c(-c2nc(-c3ccc(CN4CC(C(=O)O)C4)cc3)no2)cnn1C1CCCCC1] |
| 69 | 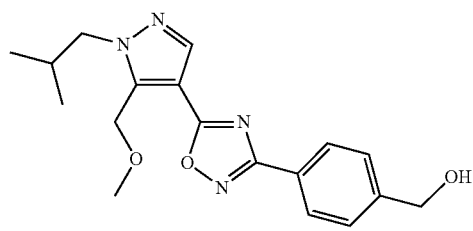 [SMILES: COCc1c(-c2nc(-c3ccc(CO)cc3)no2)cnn1CC(C)C] |
| 70 | 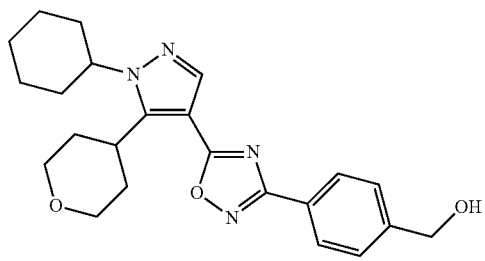 [SMILES: OCc1ccc(-c2noc(-c3cnn(C4CCCCC4)c3C3CCOCC3)n2)cc1] |

-continued
| Example Nb | Formula |
|---|---|
| 71 | 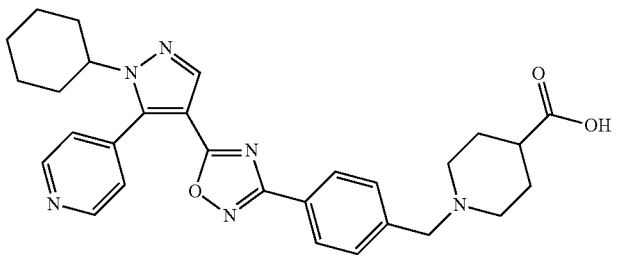 [SMILES: O=C(O)C1CCN(Cc2ccc(-c3noc(-c4cnn(C5CCCCC5)c4-c4ccncc4)n3)cc2)CC1] |
| 72 | 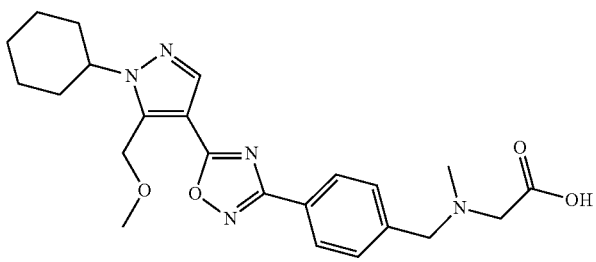 [SMILES: COCc1c(-c2nc(-c3ccc(CN(C)CC(=O)O)cc3)no2)cnn1C1CCCCC1] |
| 73 | 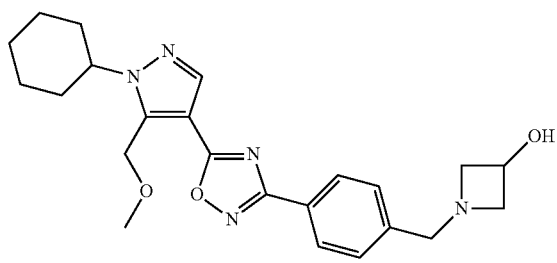 [SMILES: COCc1c(-c2nc(-c3ccc(CN4CC(O)C4)cc3)no2)cnn1C1CCCCC1] |
| 74 | 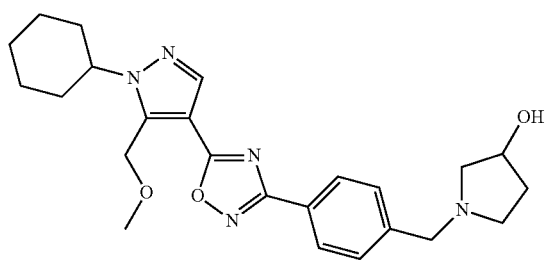 [SMILES: COCc1c(-c2nc(-c3ccc(CN4CCC(O)C4)cc3)no2)cnn1C1CCCCC1] |
| 75 | 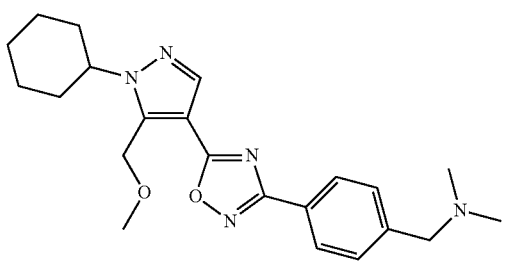 [SMILES: COCc1c(-c2nc(-c3ccc(CN(C)C)cc3)no2)cnn1C1CCCCC1] |
| 76 | 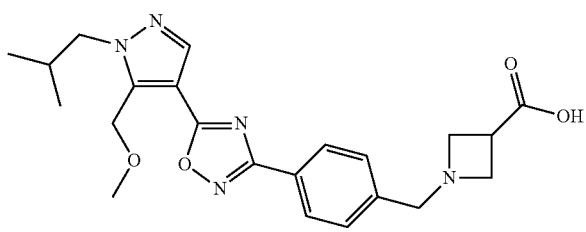 [SMILES: COCc1c(-c2nc(-c3ccc(CN4CC(C(=O)O)C4)cc3)no2)cnn1CC(C)C] |

| Example Nb | Formula |
|---|---|
| 77 | 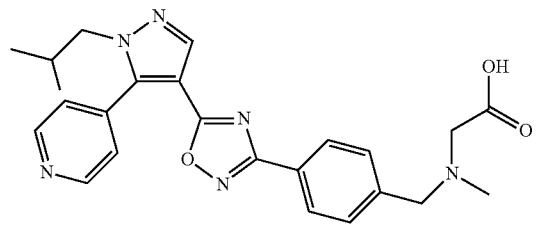 [SMILES: CC(C)Cn1ncc(-c2nc(-c3ccc(CN(C)CC(=O)O)cc3)no2)c1-c1ccncc1] |
| 78 | 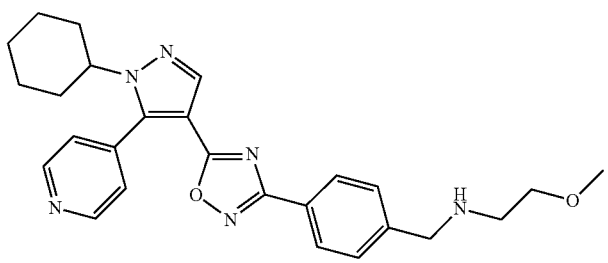 [SMILES: COCCNCc1ccc(-c2noc(-c3cnn(C4CCCCC4)c3-c3ccncc3)n2)cc1] |
| 79 | 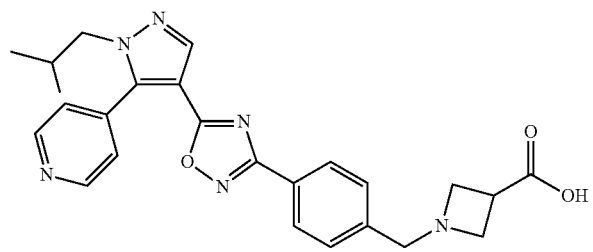 [SMILES: CC(C)Cn1ncc(-c2nc(-c3ccc(CN4CC(C(=O)O)C4)cc3)no2)c1-c1ccncc1] |
| 80 | 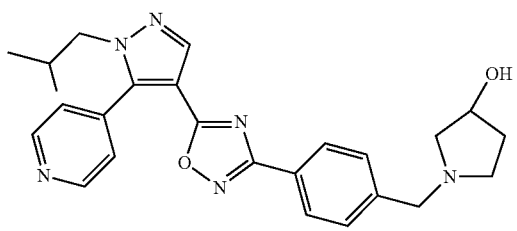 [SMILES: CC(C)Cn1ncc(-c2nc(-c3ccc(CN4CCC(O)C4)cc3)no2)c1-c1ccncc1] |
| 81 | 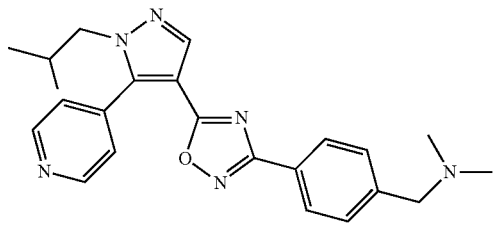 [SMILES: CC(C)Cn1ncc(-c2nc(-c3ccc(CN(C)C)cc3)no2)c1-c1ccncc1] |
| 82 | 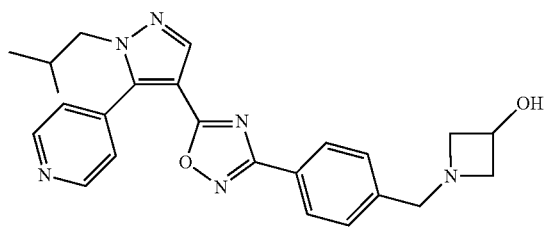 [SMILES: CC(C)Cn1ncc(-c2nc(-c3ccc(CN4CC(O)C4)cc3)no2)c1-c1ccncc1] |

| Example Nb | Formula |
|---|---|
| 83 | 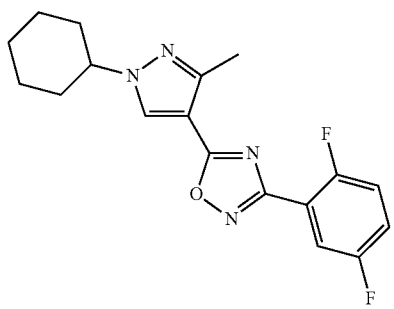 [SMILES: Cc1nn(C2CCCCC2)cc1-c1nc(-c2cc(F)ccc2F)no1] |
| 84 | 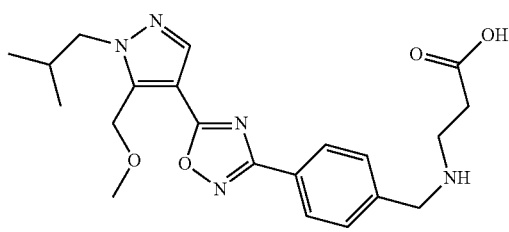 [SMILES: COCc1c(-c2nc(-c3ccc(CNCCC(=O)O)cc3)no2)cnn1CC(C)C] |
| 85 | 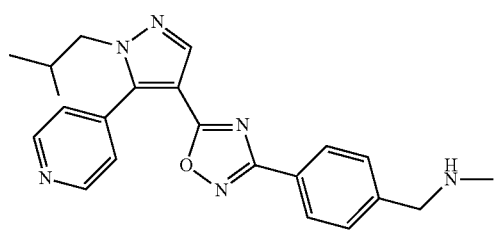 [SMILES: CNCc1ccc(-c2noc(-c3cnn(CC(C)C)c3-c3ccncc3)n2)cc1] |
| 86 | 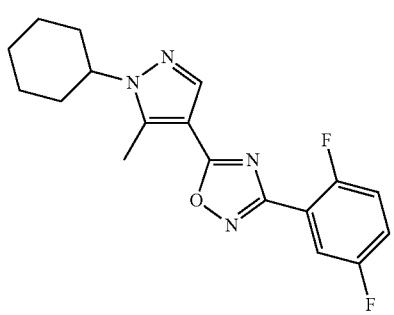 [SMILES: Cc1c(-c2nc(-c3cc(F)ccc3F)no2)cnn1C1CCCCC1] |
| 87 | 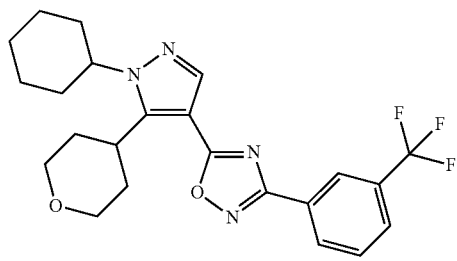 [SMILES: FC(F)(F)c1cccc(-c2noc(-c3cnn(C4CCCCC4)c3C3CCOCC3)n2)c1] |
| 88 | 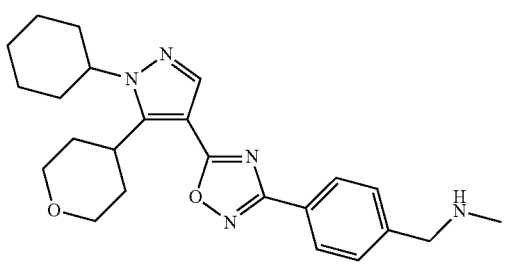 [SMILES: CNCc1ccc(-c2noc(-c3cnn(C4CCCCC4)c3C3CCOCC3)n2)cc1] |

-continued
| Example Nb | Formula |
|---|---|
| 89 | 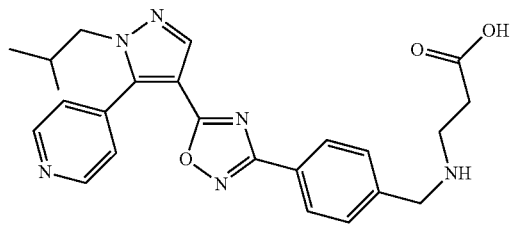 [SMILES: CC(C)Cn1ncc(-c2nc(-c3ccc(CNCCC(=O)O)cc3)no2)c1-c1ccncc1] |
| 90 | 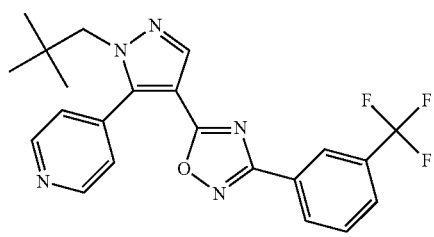 [SMILES: CC(C)(C)Cn1ncc(-c2nc(-c3cccc(C(F)(F)F)c3)no2)c1-c1ccncc1] |
| 91 | 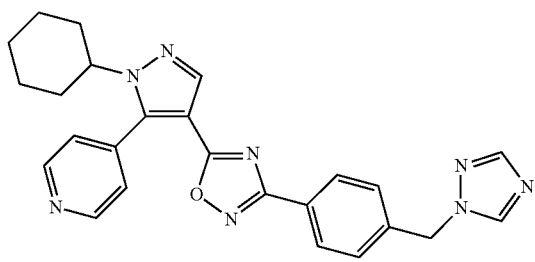 [SMILES: c1cc(-c2c(-c3nc(-c4ccc(Cn5cncn5)cc4)no3)cnn2C2CCCCC2)ccn1] |
| 92 | 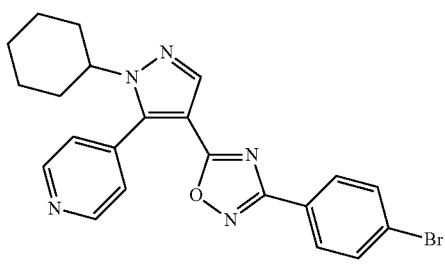 [SMILES: Brc1ccc(-c2noc(-c3cnn(C4CCCCC4)c3-c3ccncc3)n2)cc1] |
| 93 | 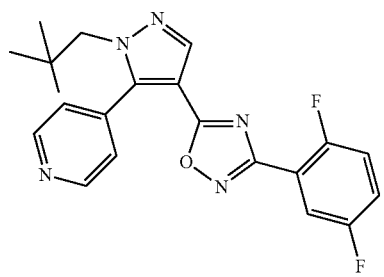 [SMILES: CC(C)(C)Cn1ncc(-c2nc(-c3cc(F)ccc3F)no2)c1-c1ccncc1] |
| 94 | 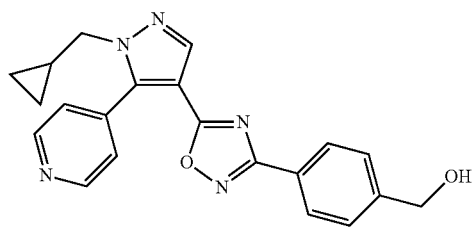 [SMILES: OCc1ccc(-c2noc(-c3cnn(CC4CC4)c3-c3ccncc3)n2)cc1] |

-continued
| Example Nb | Formula |
|---|---|
| 95 | 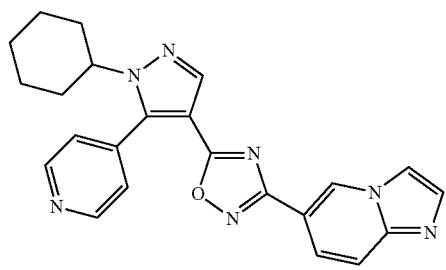 [SMILES: c1cc(-c2c(-c3nc(-c4ccc5nccn5c4)no3)cnn2C2CCCCC2)ccn1] |
| 96 | 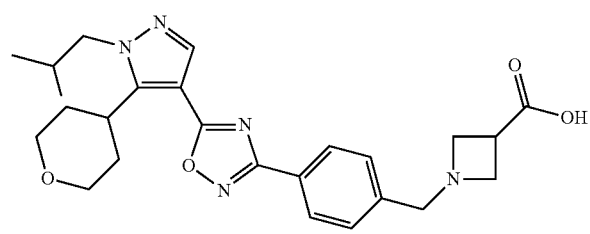 [SMILES: CC(C)Cn1ncc(-c2nc(-c3ccc(CN4CC(C(=O)O)C4)cc3)no2)c1C1CCOCC1] |
| 97 | 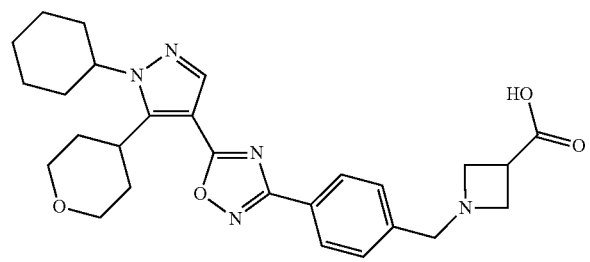 [SMILES: O=C(O)C1CN(Cc2ccc(-c3noc(-c4cnn(C5CCCCC5)c4C4CCOCC4)n3)cc2)C1] |
| 98 | 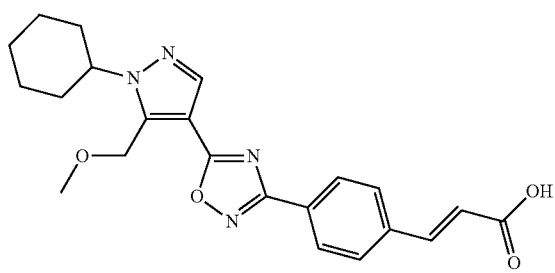 [SMILES: COCc1c(-c2nc(-c3ccc(/C=C/C(=O)O)cc3)no2)cnn1C1CCCCC1] |
| 99 | 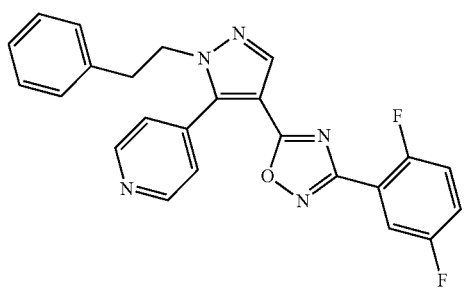 [SMILES: Fc1ccc(F)c(-c2noc(-c3cnn(CCc4ccccc4)c3-c3ccncc3)n2)c1] |
| 100 | 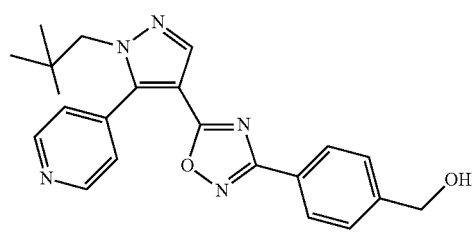 [SMILES: CC(C)(C)Cn1ncc(-c2nc(-c3ccc(CO)cc3)no2)c1-c1ccncc1] |

| Example Nb | Formula |
|---|---|
| 101 | 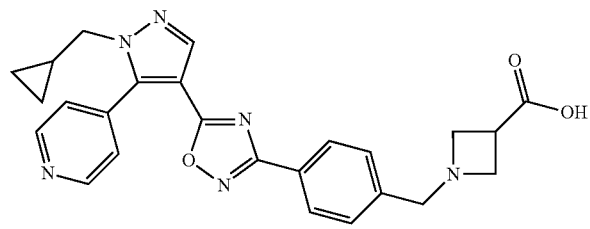 [SMILES: O=C(O)C1CN(Cc2ccc(-c3noc(-c4cnn(CC5CC5)c4-c4ccncc4)n3)cc2)C1] |
| 102 | 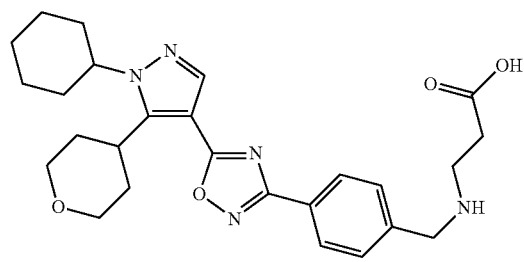 [SMILES: O=C(O)CCNCc1ccc(-c2noc(-c3cnn(C4CCCCC4)c3C3CCOCC3)n2)cc1] |
| 103 | 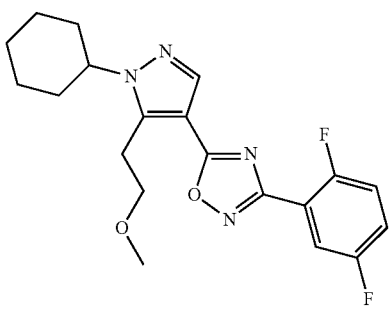 [SMILES: COCCc1c(-c2nc(-c3cc(F)ccc3F)no2)cnn1C1CCCCC1] |
| 104 | 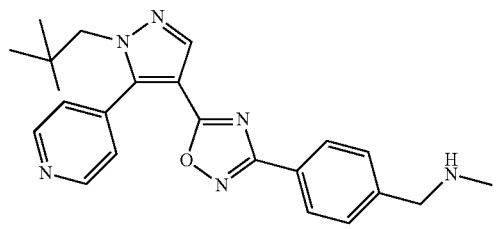 [SMILES: CNCc1ccc(-c2noc(-c3cnn(CC(C)(C)C)c3-c3ccncc3)n2)cc1] |
| 105 | 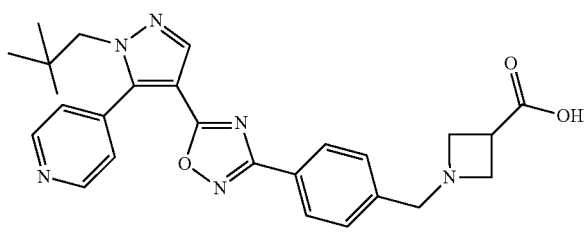 [SMILES: CC(C)(C)Cn1ncc(-c2nc(-c3ccc(CN4CC(C(=O)O)C4)cc3)no2)c1-c1ccncc1] |
| 106 | 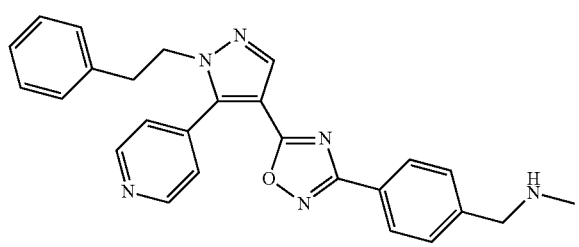 [SMILES: CNCc1ccc(-c2noc(-c3cnn(CCc4ccccc4)c3-c3ccncc3)n2)cc1] |

-continued
| Example Nb | Formula |
|---|---|
| 107 | 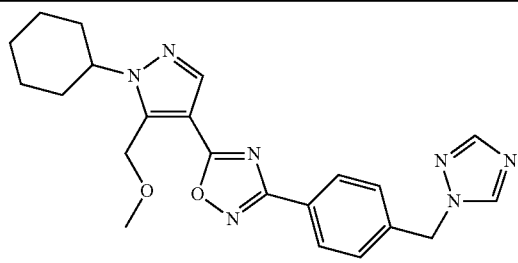 |
| 108 | 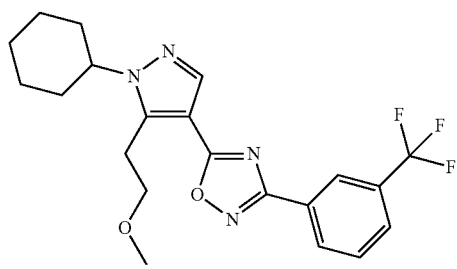 [SMILES: COCCc1c(-c2nc(-c3cccc(C(F)(F)F)c3)no2)cnn1C1CCCCC1] |
| 109 | 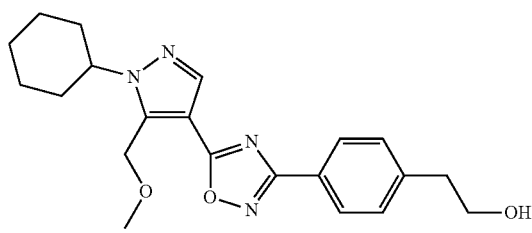 [SMILES: COCc1c(-c2nc(-c3ccc(CCO)cc3)no2)cnn1C1CCCCC1] |
| 110 | 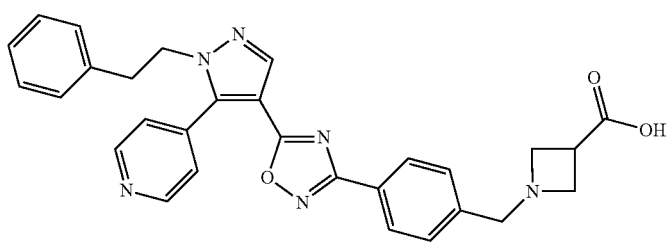 [SMILES: O=C(O)C1CN(Cc2ccc(-c3noc(-c4cnn(CCc5ccccc5)c4-c4ccncc4)n3)cc2)C1] |
| 111 | 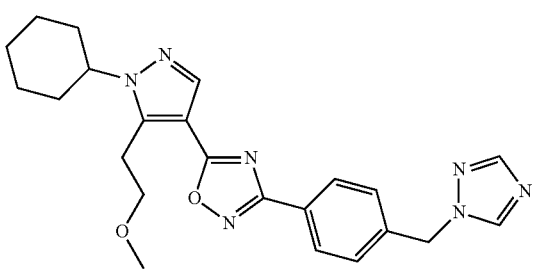 [SMILES: COCCc1c(-c2nc(-c3ccc(Cn4cncn4)cc3)no2)cnn1C1CCCCC1] |
| 112 | 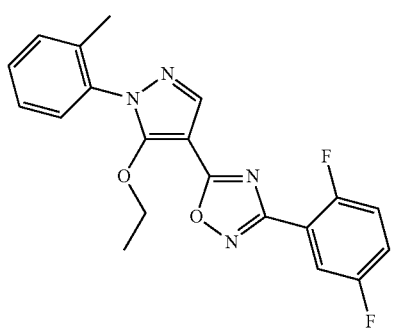 [SMILES: CCOc1c(-c2nc(-c3cc(F)ccc3F)no2)cnn1-c1ccccc1C] |

| Example Nb | Formula |
|---|---|
| 113 | 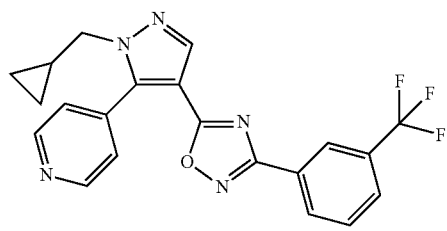 [SMILES: FC(F)(F)c1cccc(-c2noc(-c3cnn(CC4CC4)c3-c3ccncc3)n2)c1] |
| 114 | 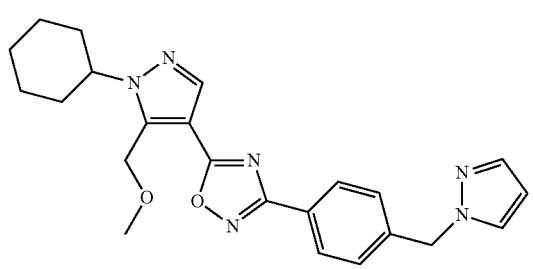 [SMILES: COCc1c(-c2nc(-c3ccc(Cn4cccn4)cc3)no2)cnn1C1CCCCC1] |
| 115 | 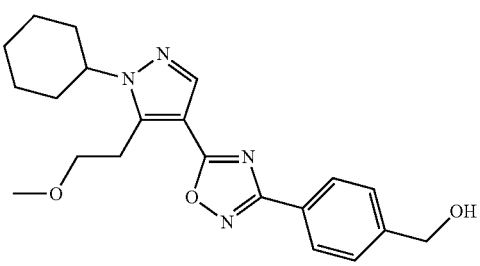 [SMILES: COCCc1c(-c2nc(-c3ccc(CO)cc3)no2)cnn1C1CCCCC1] |
| 116 | 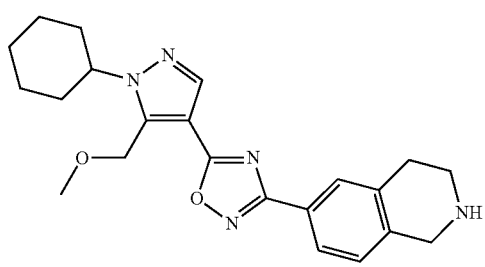 [SMILES: COCc1c(-c2nc(-c3ccc4c(c3)CCNC4)no2)cnn1C1CCCCC1] |
| 117 | 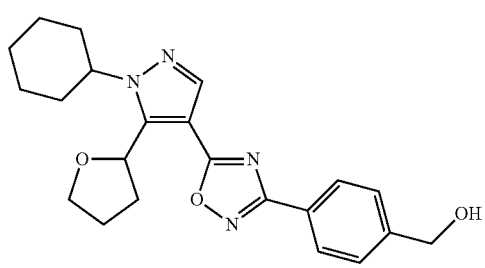 [SMILES: OCc1ccc(-c2noc(-c3cnn(C4CCCCC4)c3C3CCCO3)n2)cc1] |

-continued
| Example Nb | Formula |
|---|---|
| 118 | 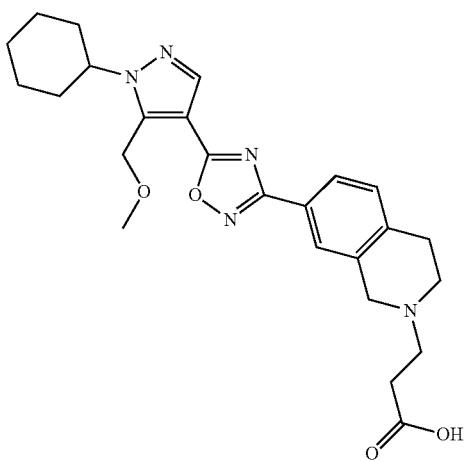 [SMILES: COCc1c(-c2nc(-c3ccc4c(c3)CN(CCC(=O)O)CC4)no2)cnn1C1CCCCC1] |
| 119 | 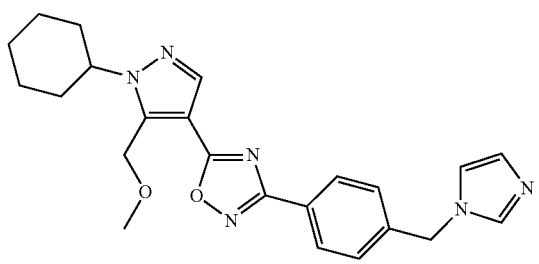 |
| 120 | 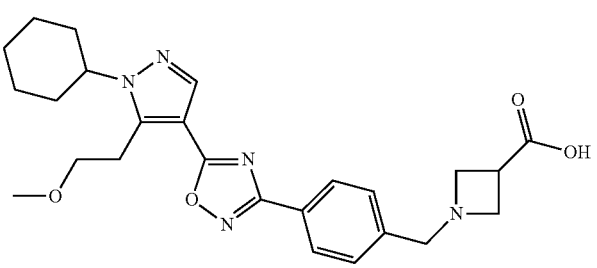 [SMILES: COCCc1c(-c2nc(-c3ccc(CN4CC(C(=O)O)C4)cc3)no2)cnn1C1CCCCC1] |
| 121 | 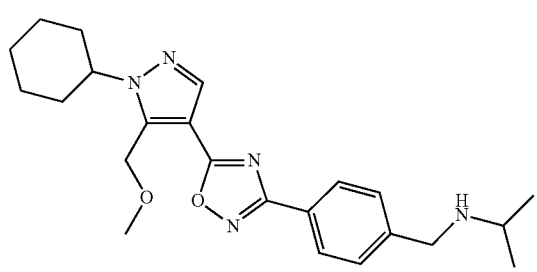 [SMILES: COCc1c(-c2nc(-c3ccc(CNC(C)C)cc3)no2)cnn1C1CCCCC1] |
| 122 | 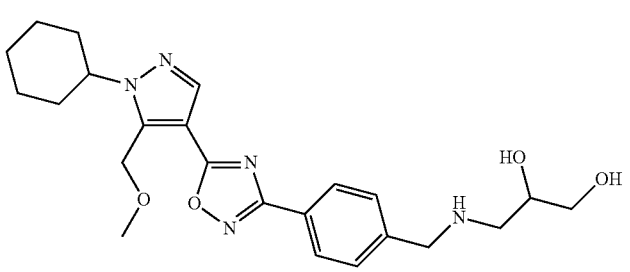 [SMILES: COCc1c(-c2nc(-c3ccc(CNCC(O)CO)cc3)no2)cnn1C1CCCCC1] |

| Example Nb | Formula |
|---|---|
| 123 | 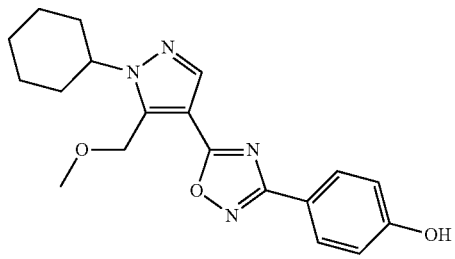 [SMILES: COCc1c(-c2nc(-c3ccc(O)cc3)no2)cnn1C1CCCCC1] |
| 124 | 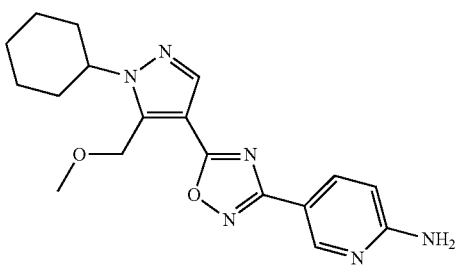 [SMILES: COCc1c(-c2nc(-c3ccc(N)nc3)no2)cnn1C1CCCCC1] |
| 125 | 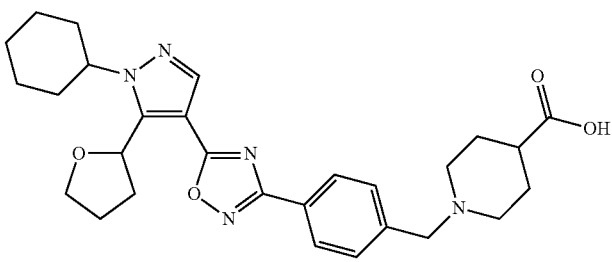 [SMILES: O=C(O)C1CCN(Cc2ccc(-c3noc(-c4cnn(C5CCCCC5)c4C4CCCO4)n3)cc2)CC1] |
| 126 | 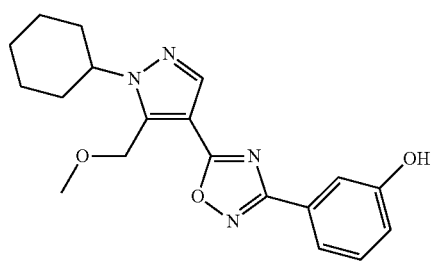 [SMILES: COCc1c(-c2nc(-c3cccc(O)c3)no2)cnn1C1CCCCC1] |
| 127 | 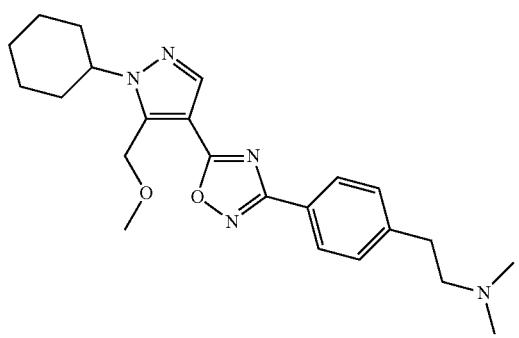 [SMILES: COCc1c(-c2nc(-c3ccc(CCN(C)C)cc3)no2)cnn1C1CCCCC1] |

-continued
| Example Nb | Formula |
|---|---|
| 128 | 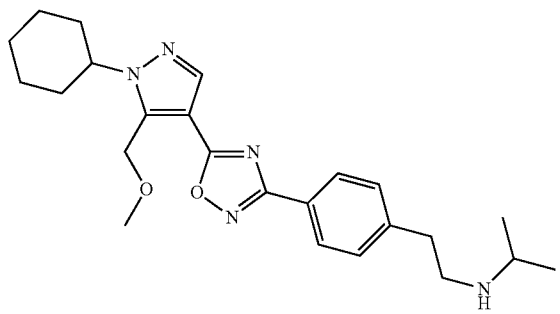 [SMILES: COCc1c(-c2nc(-c3ccc(CCNC(C)C)cc3)no2)cnn1C1CCCCC1] |
| 129 | 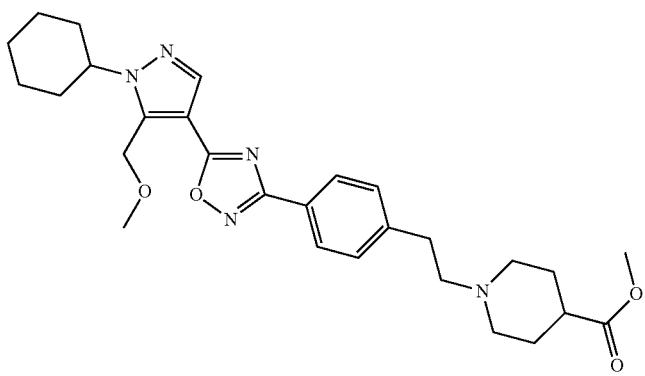 [SMILES: COCc1c(-c2nc(-c3ccc(CCN4CCC(C(=O)OC)CC4)cc3)no2)cnn1C1CCCCC1] |
| 130 | 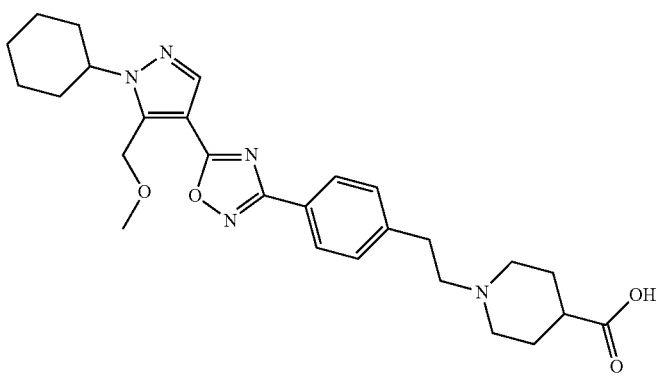 [SMILES: COCc1c(-c2nc(-c3ccc(CCN4CCC(C(=O)O)CC4)cc3)no2)cnn1C1CCCCC1] |
| 131 | 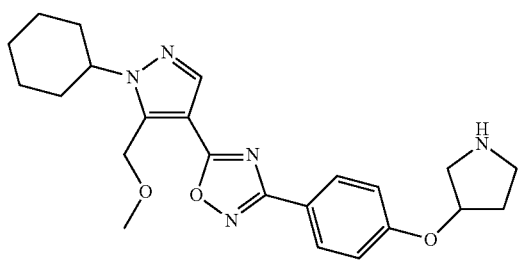 [SMILES: COCc1c(-c2nc(-c3ccc(OC4CCNC4)cc3)no2)cnn1C1CCCCC1] |
| 132 | 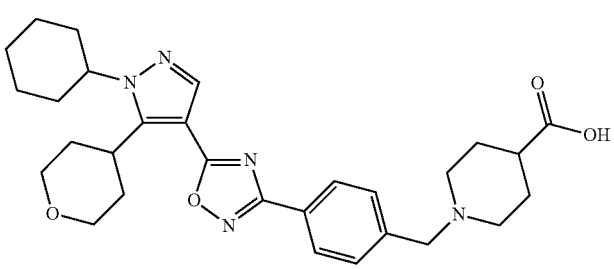 [SMILES: O=C(O)C1CCN(Cc2ccc(-c3noc(-c4cnn(C5CCCCC5)c4C4CCOCC4)n3)cc2)CC1] |

| Example Nb | Formula |
|---|---|
| 133 | 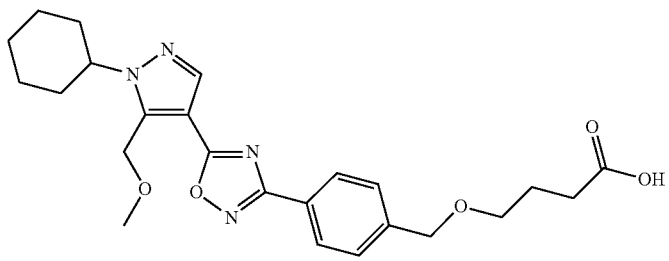 [SMILES: COCc1c(-c2nc(-c3ccc(COCCCC(=O)O)cc3)no2)cnn1C1CCCCC1] |
| 134 | 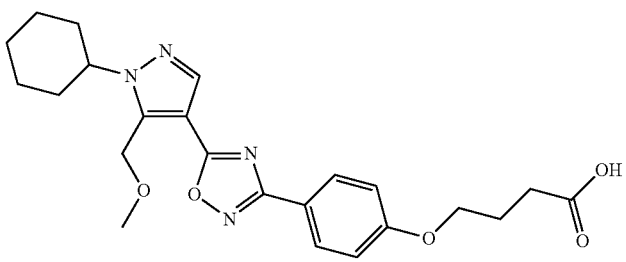 [SMILES: COCc1c(-c2nc(-c3ccc(OCCCC(=O)O)cc3)no2)cnn1C1CCCCC1] |
| 135 | 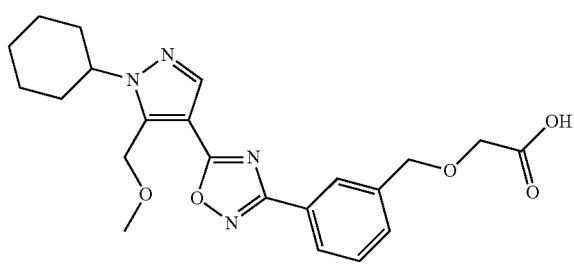 [SMILES: COCc1c(-c2nc(-c3cccc(COCC(=O)O)c3)no2)cnn1C1CCCCC1] |
| 136 | 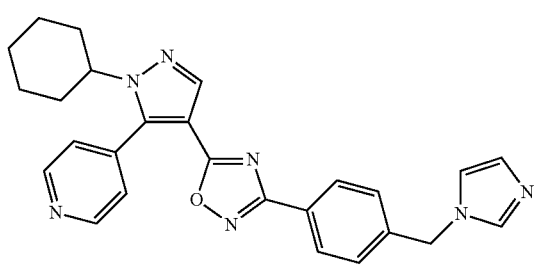 [SMILES: c1cc(-c2c(-c3nc(-c4ccc(Cn5ccnc5)cc4)no3)cnn2C2CCCCC2)ccn1] |
| 137 | 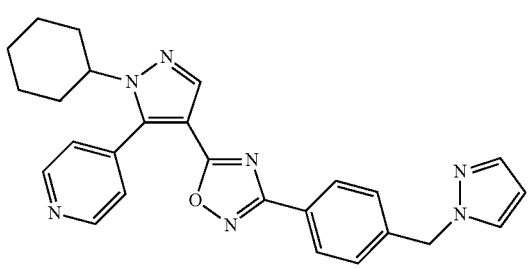 [SMILES: c1cnn(Cc2ccc(-c3noc(-c4cnn(C5CCCCC5)c4-c4ccncc4)n3)cc2)c1] |
| 138 | 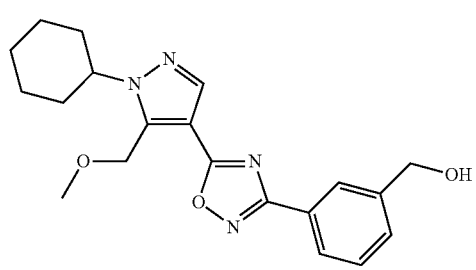 [SMILES: COCc1c(-c2nc(-c3cccc(CO)c3)no2)cnn1C1CCCCC1] |

| Example Nb | Formula |
|---|---|
| 139 | 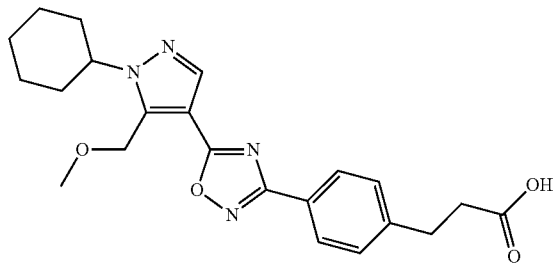 [SMILES: COCc1c(-c2nc(-c3ccc(CCC(=O)O)cc3)no2)cnn1C1CCCCC1] |
| 140 | 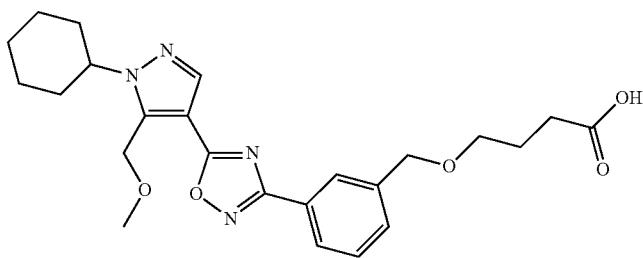 [SMILES: COCc1c(-c2nc(-c3cccc(COCCCC(=O)O)c3)no2)cnn1C1CCCCC1] |
| 141 | 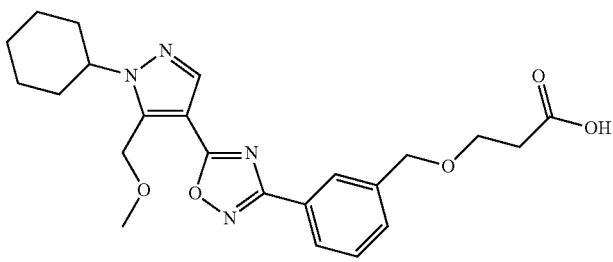 [SMILES: COCc1c(-c2nc(-c3cccc(COCCC(=O)O)c3)no2)cnn1C1CCCCC1] |
| 142 | 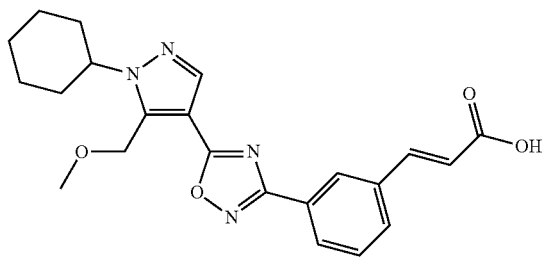 |
| 143 | 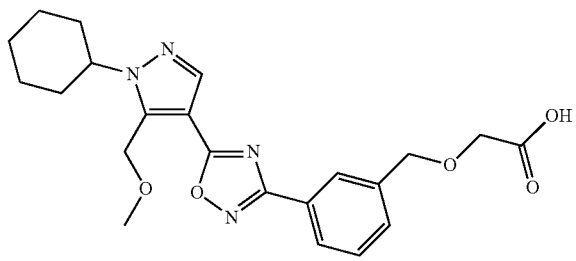 [SMILES: COCc1c(-c2nc(-c3cccc(COCC(=O)O)c3)no2)cnn1C1CCCCC1] |

| Example Nb | Formula |
|---|---|
| 144 | 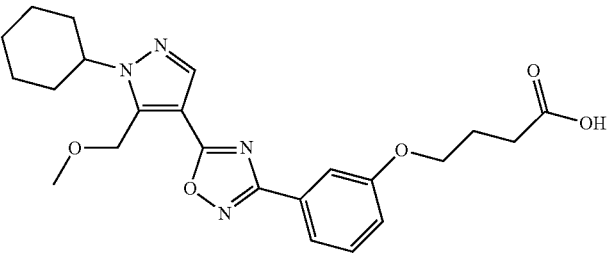 [SMILES: COCc1c(-c2nc(-c3cccc(OCCCC(=O)O)c3)no2)cnn1C1CCCCC1] |
| 145 | 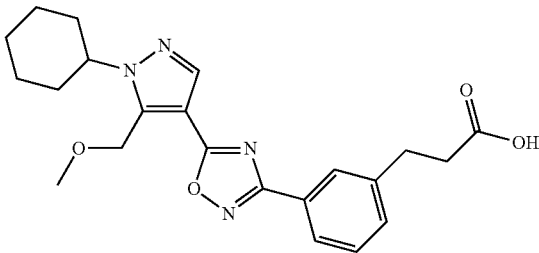 [SMILES: COCc1c(-c2nc(-c3cccc(CCC(=O)O)c3)no2)cnn1C1CCCCC1] |
| 146 | 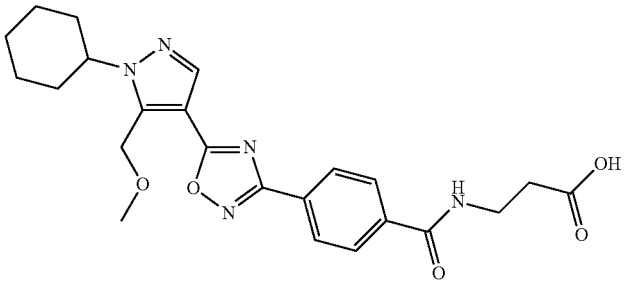 [SMILES: COCc1c(-c2nc(-c3ccc(C(=O)NCCC(=O)O)cc3)no2)cnn1C1CCCCC1] |
| 147 | 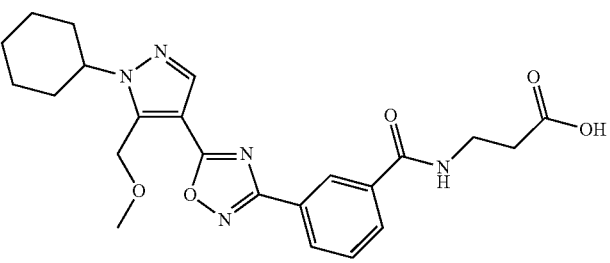 [SMILES: COCc1c(-c2nc(-c3cccc(C(=O)NCCC(=O)O)c3)no2)cnn1C1CCCCC1] |
| 148 | 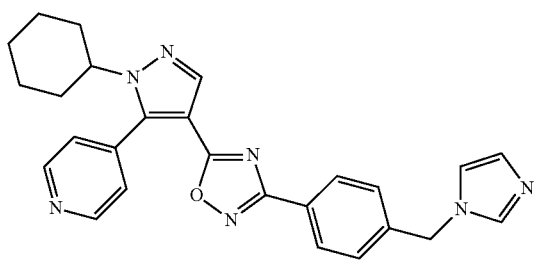 [SMILES: c1cc(-c2c(-c3nc(-c4ccc(Cn5ccnc5)cc4)no3)cnn2C2CCCCC2)ccn1] |
| 149 | 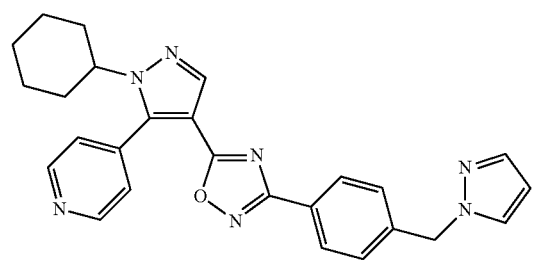 [SMILES: c1cnn(Cc2ccc(-c3noc(-c4cnn(C5CCCCC5)c4-c4ccncc4)n3)cc2)c1] |

| Example Nb | Formula |
|---|---|
| 150 | 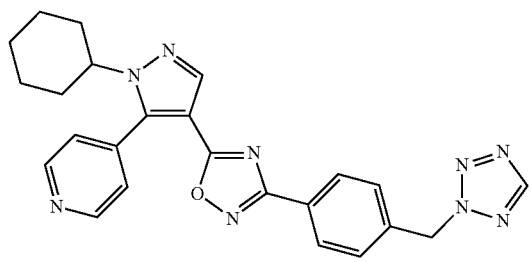 [SMILES: c1cc(-c2c(-c3nc(-c4ccc(Cn5ncnn5)cc4)no3)cnn2C2CCCCC2)ccn1] |
| 151 | 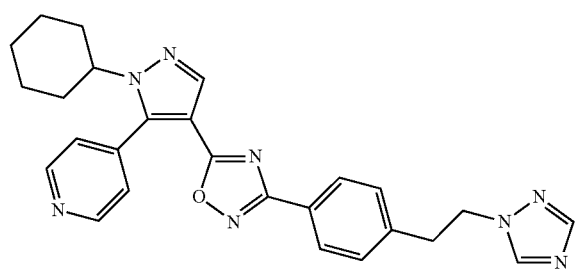 [SMILES: c1cc(-c2c(-c3nc(-c4ccc(CCn5cncn5)cc4)no3)cnn2C2CCCCC2)ccn1] |
| 152 | 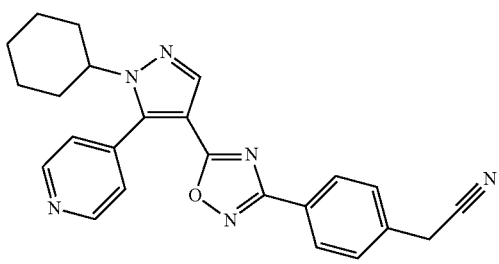 [SMILES: N#CCc1ccc(-c2noc(-c3cnn(C4CCCCC4)c3-c3ccncc3)n2)cc1] |
| 153 | 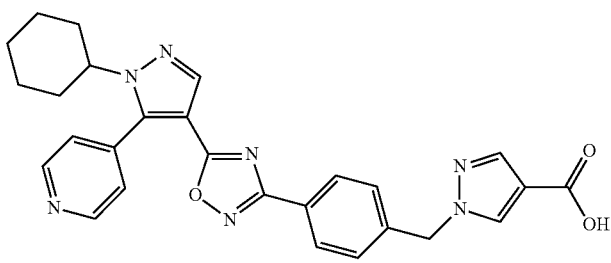 [SMILES: O=C(O)c1cnn(Cc2ccc(-c3noc(-c4cnn(C5CCCCC5)c4-c4ccncc4)n3)cc2)c1] |
| 154 | 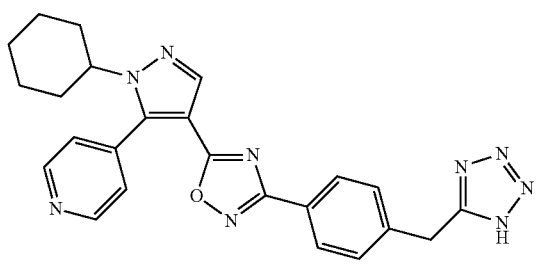 [SMILES: c1cc(-c2c(-c3nc(-c4ccc(Cc5nnn[nH]5)cc4)no3)cnn2C2CCCCC2)ccn1] |

| Example Nb | Formula |
|---|---|
| 155 | |

Alkyl denotes a linear or branched carbon chain having 1 to 12 carbon atoms, preferably 1 to 8 carbon atoms and most preferably 1 to 6 carbon atoms. Alkyl includes ($C_1$-$C_6$)-alkyl, ($C_2$-$C_6$)-alkyl. Alkyl very preferably denotes methyl, furthermore ethyl, propyl, isopropyl, butyl, isobutyl, sec-butyl or tert-butyl, furthermore also pentyl, 1-, 2- or 3-methylbutyl, 1,1-, 1,2- or 2,2-dimethylpropyl, 1-ethylpropyl, hexyl, 1-, 2-, 3- or 4-methylpentyl, 1,1-, 1,2-, 1,3-, 2,2-, 2,3- or 3,3-dimethylbutyl, 1- or 2-ethylbutyl, 1-ethyl-1-methylpropyl, 1-ethyl-2-methylpropyl, 1,1,2- or 1,2,2-trimethylpropyl The group A preferably denotes a branched or linear alkyl having 2 to 12 C-atoms, wherein one or more, preferably 1 to 7H-atoms may be replaced by $OR^4$, $CO_2R^4$, $CF^3$, cycloalkyl having 3 to 7 ring carbon atoms, $Ar^1$, $Ar^2$, or $N(R^4)_2$ and wherein one or more, preferably 1 to 7 non-adjacent $CH_2$-groups may be replaced by O, $NR^4$, —$CO_2$—, or —CH=CH.

The group A most preferably denotes ethyl, propyl, isopropyl, butyl, isobutyl, sec-butyl, or tert-butyl, furthermore also $(CH_2)_nCO_2(CH_2)_nCH_3$, $(CH_2)_pCF_3$, $(CH_2)_n$NHcyclopropyl wherein n is as defined above and p is 1, 2, 3, 4 or 5, Z preferably denotes a branched or linear alkyl having 2 to 12 C-atoms, wherein one or more, preferably 1 to 7H-atoms are replaced by $OR^4$, $CO_2R^4$, and/or wherein one or more, preferably 1 to 7 $CH_2$-groups are replaced by O, $NR^4$, —CO, —CH=CH—, —C≡C—, $R^3$ preferably denotes $Ar^1$, $Ar^2$, $Het^1$, $Het^2$, Cyc or A, ($C_2$-$C_6$-alkyl) or O—($C_1$-$C_6$-alkyl), or if $R^1$ is $Het^1$, Cyc, A, —$(CH_2)_nAr^1$, $(CH_2)_nHet^1$, $(CH_2)_nHet^2$, ($C_2$-$C_6$)alkyl, or if $R^1$ denotes $Ar^1$ or $R^2$ is $Ar^2$, $Het^1$ or $Het^2$ wherein $Ar^1$ and $Ar^2$ are mono di or trisubstituted by the substituents hereby mentioned, $R^3$ also denotes $CH_3$.

or if $R^1$ denotes $Het^1$, Cyc, A, ($C_1$-$C_6$)alkyl, ($C_2$-$C_6$)alkyl, —$(CH_2)_nAr^1$, $(CH_2)_nHet^1$, $(CH_2)_nHet^1$, $R^3$ also denotes S—($C_1$-$C_6$-alkyl)

Cycloalkyl preferably denotes cyclopropyl, cyclobutyl, cyclopentyl, cyclohexyl or cycloheptyl.

Cycloalkylalkylene preferably denotes cyclopropylmethylene, cyclobutylmethylene, cyclopentylmethylene, cyclohexylmethylene or cycloheptylmethylene.

Alkylene is preferably methylene, ethylene, propylene, butylene, pentylene or hexylene, furthermore branched alkylene.

Perfluoroalkyl preferably denotes $CF_3$.
  Perfluoro-alkoxy preferably denotes $OCF_3$.
  Hal denotes Cl, Br, I, F and preferably F, Br or Cl.
  Alkoxy denotes a group —O—$(CH_2)_n$—$CH_3$, wherein n is 0, 1, 2, 3 or 4, preferably Methoxy or Ethoxy.
  Carboxy denotes a group —COOH.

Carboxyalkyl denotes an ester group preferably COOMe or COOEt.

Alkylsulfonyl denotes a group —$S(O)_2$-alkyl preferably Methylsulfonyl or Ethylsulfonyl.

Acyl denotes a group —C(O)R wherein R can be A, Z, $Ar^1$, $Ar^2$, $Het^1$ or $Het^2$ as defined above, preferably Acyl denotes a group Acetyl —$C(O)CH_3$.

Amino denotes the group —NR'R" where each R', R" is independently hydrogen or alkyl having 1 to 6 carbon atoms or $Ar^1$, $Ar^2$, $Het^1$, $Het^2$, A, or Z, and where R' and R", together with the nitrogen atom to which they are attached, can optionally form a 3-8-membered Heterocyclic ring.

Amido refers to the group —C(O)NR'R" where each R', R" is independently hydrogen or alkyl having 1 to 6 carbon atoms or $Ar^1$, $Ar^2$, $Het^1$, $Het^2$, A, or Z, and where R' and R", together with the nitrogen atom to which they are attached, can optionally form a 3-8-membered Heterocyclic ring.

$Ar^1$ preferably denotes phenyl, which may be unsubstituted or monosubstituted, disubstituted or trisubstituted by a substituent selected from $R^5$ and/or $R^6$; wherein $R^5$ and $R^6$ are independently from one another Hal, preferably F, O—($C_1$-$C_6$)-alkyl, ($C_1$-$C_6$)-alkyl, $SO_2$($C_1$-$C_6$)-alkyl, alkoxy, —$(CH_2)_n$OH, $CF_3$, —$(CH_2)_n$N(($C_1$-$C_6$)alkyl)$_2$, —$(CH_2)_n$$Het^1$, —$(CH_2)_n$$Het^2$.

$Ar^2$ preferably denotes phenyl, which may be unsubstituted or monosubstituted, disubstituted or trisubstituted by a substituent selected from $R^5$ and/or $R^6$; wherein $R^5$ and $R^6$ are independently from one another Hal, preferably F, O—($C_1$-$C_6$)-alkyl, ($C_1$-$C_6$)-alkyl, $SO_2$($C_1$-$C_6$)-alkyl, alkoxy, —$(CH_2)_n$OH, $CF_3$, —$(CH_2)_n$N(($C_1$-$C_6$)alkyl)$_2$, —$(CH_2)_n$$Het^1$, —$(CH_2)_n$$Het^2$.

When $Ar^1$ or $Ar^2$ denote a bicyclic system, it may contain 1 or 2 aromatic rings. The eventual non-aromatic ring can be either saturated or unsaturated.

$Ar^1$ or $Ar^2$ very particularly preferably denotes one of the following groups:

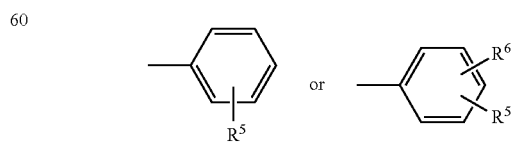

wherein $R^5$ and $R^6$ areas defined above.

More particularly, Ar is one of the following groups:

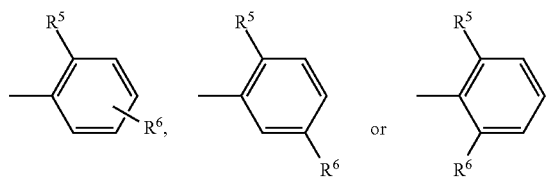

wherein $R^5$, $R^6$ are as defined above and preferably, wherein $R^5$ is Hal and $R^6$ is Hal or H.

Furthermore, $Ar^1$ or $Ar^2$ is preferably unsubstituted or

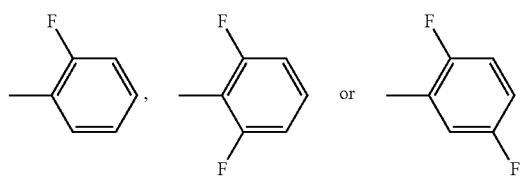

$Het^1$ or $Het^2$ preferably denotes a monocyclic or bicyclic, saturated, unsaturated or aromatic heterocyclic ring having 1 to 3 N atoms which may be unsubstituted or monosubstituted, disubstituted or trisubstituted by a substituent selected from $R^5$ and/or $R^6$; or bicyclic, saturated, unsaturated or aromatic heterocyclic ring having 1 oxygen atom or 2 nitrogen atom or a combination thereof, which may be unsubstituted or monosubstituted, disubstituted or trisubstituted by a substituent selected from $R^4$ and/or $R^5$.

When $Het^1$ denotes a bicyclic system, none of the fused rings is aromatic.

When $Het^2$ denotes a bicyclic system, it may contain 1 or 2 aromatic rings. The eventual non-aromatic ring can be either saturated or unsaturated. The heteroatoms may be either part of the aromatic ring or the non-aromatic ring.

$Het^1$ or $Het^2$ is preferably a 6 to 14 membered ring system and denotes, notwithstanding further substitutions, for example, 2- or 3-furyl, 2- or 3-thienyl, 1-, 2- or 3-pyrrolyl, 1-, 2-, 4- or 5-imidazolyl, 1-, 3-, 4- or 5-pyrazolyl, 2-, 4- or 5-oxazolyl, 3-, 4- or 5-isoxazolyl, 2-, 4- or 5-thiazolyl, 3-, 4- or 5-isothiazolyl, 2-, 3- or 4-pyridyl, 2-, 4-, 5- or 6-pyrimidinyl, furthermore preferably 1,2,3-triazol-1-, -4- or -5-yl, 1,2,4-triazol-1-, -3- or -5-yl, 1- or 5-tetrazolyl, 1,2,3-oxadiazol-4- or -5-yl, 1,2,4-oxadiazol-3- or -5-yl, 1,3,4-thiadiazol-2- or -5-yl, 1,2,4-thiadiazol-3- or -5-yl, 1,2,3-thiadiazol-4- or -5-yl, 3- or 4-pyridazinyl, pyrazinyl, 1-, 2-, 3-, 4-, 5-, 6- or 7-indolyl, indazolyl, 4- or 5-isoindolyl, 1-, 2-, 4- or 5-benzimidazolyl, 1-, 3-, 4-, 5-, 6- or 7-benzopyrazolyl, 2-, 4-, 5-, 6- or 7-benzoxazolyl, 3-, 4-, 5-, 6- or 7-benzisoxazolyl, 2-, 4-, 5-, 6- or 7-benzothiazolyl, 2-, 4-, 5-, 6- or 7-benzisothiazolyl, 4-, 5-, 6- or 7-benz-2,1,3-oxadiazolyl, 2-, 3-, 4-, 5-, 6-, 7- or 8-quinolyl, 1-, 3-, 4-, 5-, 6-, 7- or 8-isoquinolyl, 3-, 4-, 5-, 6-, 7- or 8-cinnolinyl, 2-, 4-, 5-, 6-, 7- or 8-quinazolinyl, 5- or 6-quinoxalinyl, 2-, 3-, 5-, 6-, 7- or 8-2H-benzo-1,4-oxazinyl, furthermore preferably 1,3-benzodioxol-5-yl, 1,4-benzodioxane-6-yl, 2,1,3-benzothiadiazol-4- or -5-yl or 2,1,3-benzoxadiazol-5-yl.

The heterocyclic radicals may also be partially or fully hydrogenated.

Het can thus also denote, for example, 2,3-dihydro-2-, -3-, -4- or -5-furyl, 2,5-dihydro-2-, -3-, -4- or -5-furyl, tetrahydro-2- or -3-furyl, 1,3-dioxolan-4-yl, tetrahydro-2- or -3-thienyl, 2,3-dihydro-1-, -2-, -3-, -4- or -5-pyrrolyl, 2,5-dihydro-1-, -2-, -3-, -4- or -5-pyrrolyl, 1-, 2- or 3-pyrrolidinyl, tetrahydro-1-, -2- or -4-imidazolyl, 2,3-dihydro-1-, -2-, -3-, -4- or -5-pyrazolyl, tetrahydro-1-, -3- or -4-pyrazolyl, 1,4-dihydro-1-, -2-, -3- or -4-pyridyl, 1,2,3,4-tetrahydro-1-, -2-, -3-, -4-, -5- or -6-pyridyl, 1-, 2-, 3- or 4-piperidinyl, 2-, 3- or 4-morpholinyl, tetrahydro-2-, -3- or -4-pyranyl, 1,4-dioxaneyl, 1,3-dioxane-2-, -4- or -5-yl, hexahydro-1-, -3- or -4-pyridazinyl, hexahydro-1-, -2-, -4- or -5-pyrimidinyl, 1-, 2- or 3-piperazinyl, 1,2,3,4-tetrahydro-1-, -2-, -3-, -4-, -5-, -6-, -7- or -8-quinolyl, 1,2,3,4-tetrahydro-1-, -2-, -3-, -4-, -5-, -6-, -7- or -8-isoquinolyl, 2-, 3-, 5-, 6-, 7- or 8-3,4-dihydro-2H-benzo-1,4-oxazinyl, furthermore preferably 2,3-methylenedioxyphenyl, 3,4-methylenedioxyphenyl, 2,3-ethylenedioxyphenyl, 3,4-ethylenedioxyphenyl, 3,4-(difluoromethylenedioxy) phenyl, 2,3-dihydrobenzofuran-5- or -6-yl, 2,3-(2-oxomethylenedioxy)phenyl or also 3,4-dihydro-2H-1,5-benzodioxepin-6- or -7-yl, furthermore preferably 2,3-dihydrobenzofuranyl or 2,3-dihydro-2-oxofuranyl.

$Het^1$ or $Het^2$ very particularly denotes one of the following groups:

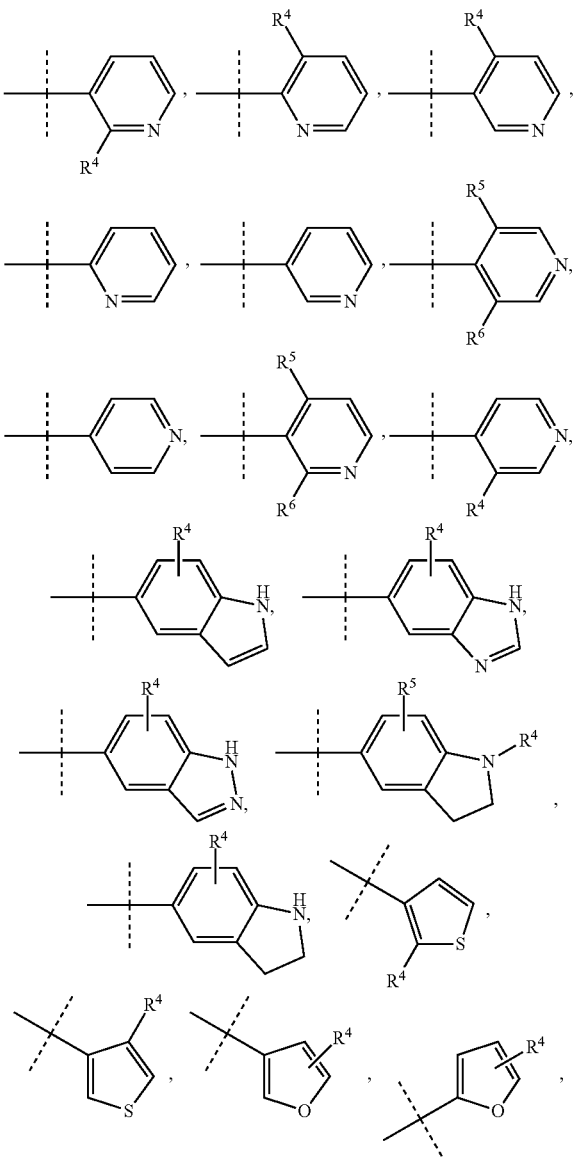

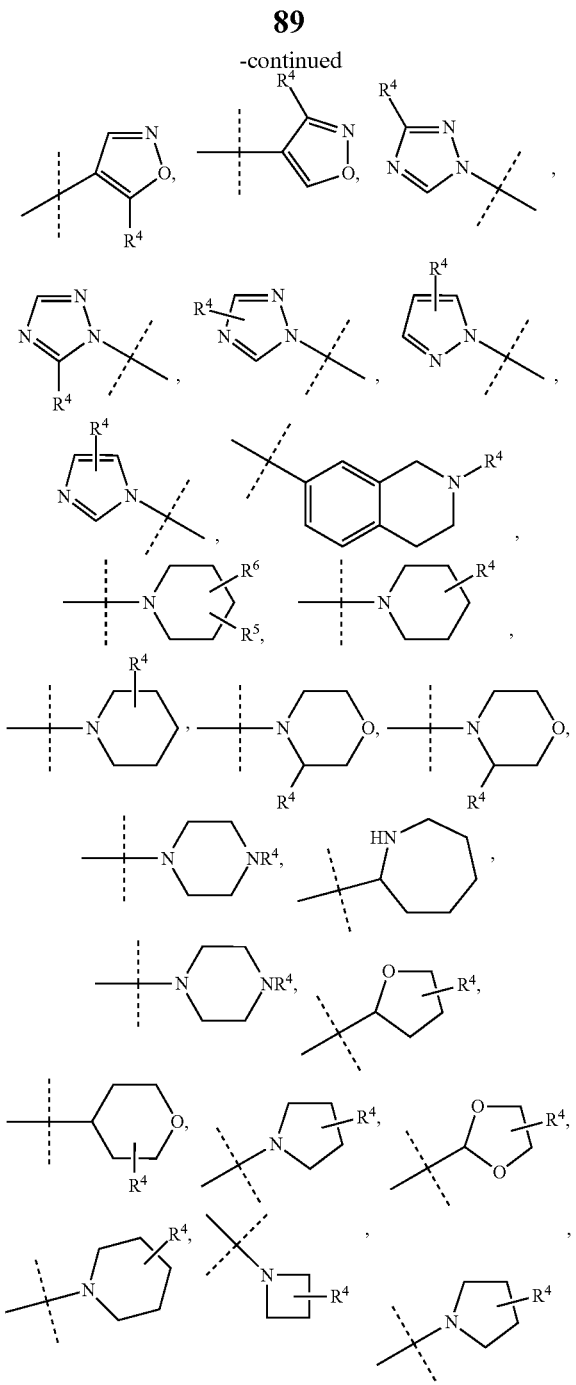

Wherein $R^4$, $R^5$ and $R^6$ are as defined above.

Cyc preferably denotes a saturated carbocyclic ring containing 4 to 6 carbon atoms which may be substituted by Hal, A, or $(C_1-C_6)$alkyl.

More Preferably, Cyc is not substituted.

Most preferably Cyc is selected from the following group:

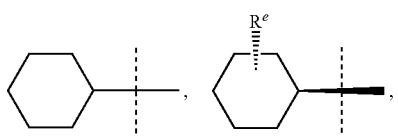

Wherein $R^e$ denotes H or $(C_1-C_6)$-alkyl,

The compounds of the formula I, and related formulae and also the starting materials for the preparation thereof are, in addition, prepared by methods known per se, as described in the literature (for example in the standard works, such as Houben-Weyl, Methoden der organischen Chemie [Methods of Organic Chemistry], Georg-Thieme-Verlag, Stuttgart), under reaction conditions which are known and suitable for the said reactions. For all the protection and deprotection methods, see Philip J. Kocienski, in "*Protecting Groups*", Georg Thieme Verlag Stuttgart, New York, 1994 and, Theodora W. Greene and Peter G. M. Wuts in "*Protective Groups in Organic Synthesis*", Wiley Interscience, $3^{rd}$ Edition 1999.

Use can also be made here of variants which are known per se, but are not mentioned here in greater detail.

If desired, the starting materials can also be formed in situ so that they are not isolated from the reaction mixture, but instead are immediately converted further into the compounds of the formula I.

The starting compounds for the preparation of compounds of formula I are generally known. If they are novel, they can, however, be prepared by methods known per se.

The reactions are preferably carried out in an inert solvent.

Examples of suitable inert solvents are hydrocarbons, such as hexane, petroleum ether, benzene, toluene or xylene; chlorinated hydrocarbons, such as trichloroethylene, 1,2-dichloroethane, tetrachloromethane, chloroform or dichloromethane; alcohols, such as methanol, ethanol, isopropanol, n-propanol, n-butanol or tert-butanol; ethers, such as diethyl ether, diisopropyl ether, tetrahydrofuran (THF) or dioxane; glycol ethers, such as ethylene glycol monomethyl or monoethyl ether or ethylene glycol dimethyl ether (diglyme); ketones, such as acetone or butanone; amides, such as acetamide, dimethylacetamide or dimethylformamide (DMF); nitriles, such as acetonitrile; sulfoxides, such as dimethyl sulfoxide (DMSO); carbon disulfide; carboxylic acids, such as formic acid or acetic acid; nitro compounds, such as nitromethane or nitrobenzene; esters, such as ethyl acetate, or mixtures of the said solvents.

Accordingly, the invention relates, in particular, to the use of compounds of the formula I, and related formulae as defined above, wherein $R^1$, $R^2$, $R^3$, $R^a$ and $R^b$ are as defined above as a medicament.

Accordingly, the invention relates, in particular, to the use of compounds of the formula I, and related formulae as defined above, wherein $R^1$, $R^2$, $R^3$, $R^a$ and $R^b$ are as defined above for the preparation of pharmaceutical formulation for the prevention and/or the treatment of multiple sclerosis and related disorders.

The said compounds of the formula I and related formulae can be used in their final non-salt form. On the other hand, the present invention also relates to the use of these compounds in the form of their pharmaceutically acceptable salts, which can be derived from various organic and inorganic acids and bases by procedures known in the art. Pharmaceutically acceptable salt forms of the compounds of the formula I are for the most part prepared by conventional methods. If the compound of the formula I contains an acidic center, such as a carboxyl group, one of its suitable salts can be formed by reacting the compound with a suitable base to give the corresponding base-addition salt. Such bases are, for example, alkali metal hydroxides, including potassium hydroxide, sodium hydroxide and lithium hydroxide; alkaline earth metal hydroxides, such as barium hydroxide and calcium hydroxide; alkali metal alkoxides, for example sodium- or potassium methoxide and sodium or potassiumpropoxide, alkalihydrides, such as sodium- or potassiumhydride; and various organic bases, such as piperidine, diethanolamine and N-methyl-glutamine, benzathine, choline, diethanolamine, ethylenediamine, meglumine, benethamine, diethylamine, piperazine and tromethamine. The aluminium salts of the compounds of the formula I and related formulae are likewise included. In the case of certain compounds of the formula I and related formulae, which contain a basic center, acid-addition salts can be formed by treating these compounds with pharmaceutically acceptable organic and inorganic acids, for example hydrogen halides, such as hydrogen chloride, hydrogen bromide or hydrogen iodide, other mineral acids and corresponding salts thereof, such as sulfate, nitrate or phosphate and the like, and alkyl- and monoaryl-sulfonates, such as ethanesulfonate, toluenesulfonate and benzene-sulfonate, and other organic acids and corresponding salts thereof, such as acetate, trifluoro-acetate, tartrate, maleate, succinate, citrate, benzoate, salicylate, ascorbate and the like. Accordingly, pharmaceutically acceptable acid-addition salts of the compounds of the formula I and related formulae include the following: acetate, adipate, alginate, arginate, aspartate, benzoate, benzene-sulfonate (besylate), bisulfate, bisulfite, bromide, butyrate, camphorate, camphor-sulfonate, caprylate, chloride, chlorobenzoate, citrate, cyclo-pentane-propionate, digluconate, dihydrogen-phosphate, dinitrobenzoate, dodecyl-sulfate, ethanesulfonate, fumarate, galacterate (from mucic acid), galacturonate, glucoheptanoate, gluco-nate, glutamate, glycerophosphate, hemi-succinate, hemisulfate, heptanoate, hexanoate, hippurate, hydro-chloride, hydrobromide, hydroiodide, 2-hydroxy-ethane-sulfonate, iodide, isethionate, isobutyrate, lactate, lactobionate, malate, maleate, malonate, mandelate, metaphosphate, methanesulfonate, methylbenzoate, mono-hydrogen-phosphate, 2-naphthalenesulfonate, nicotinate, nitrate, oxalate, oleate, palmo-ate, pectinate, persulfate, phenylacetate, 3-phenylpropionate, phosphate, phosphonate, phthalate, but this does not represent a restriction. Both types of salts may be formed or interconverted preferably using ion-exchange resin techniques.

Furthermore, the base salts of the compounds of the formula I and related formulae include aluminium, ammonium, calcium, copper, iron(III), iron(II), lithium, magnesium, manganese(III), manganese(II), potassium, sodium and zinc salts, but this is not intended to represent a restriction. Of the above-mentioned salts, preference is given to ammonium; the alkali metal salts sodium and potassium, and the alkaline earth metal salts calcium and magnesium. Salts of the compounds of the formula I which are derived from pharmaceutically acceptable organic non-toxic bases include salts of primary, secondary and tertiary amines, substituted amines, also including naturally occurring substituted amines, cyclic amines, and basic ion exchanger resins, for example arginine, betaine, caffeine, chloroprocaine, choline, N,N'-dibenzyl-ethylen-ediamine (benzathine), dicyclohexylamine, diethanol-amine, diethyl-amine, 2-diethyl-amino-ethanol, 2-dimethyl-amino-ethanol, ethanolamine, ethylenediamine, N-ethylmorpholine, N-ethyl-piperidine, glucamine, glucosamine, histidine, hydrabamine, isopropyl-amine, lidocaine, lysine, meglumine (N-methyl-D-glucamine), morpholine, piperazine, piperidine, polyamine resins, procaine, purines, theobromine, triethanol-amine, triethylamine, trimethylamine, tripropyl-amine and tris(hydroxy-methyl)-methylamine (tromethamine), but this is not intended to represent a restriction.

Compounds of the formula I and related formulae of the present invention which contain basic nitrogen-containing groups can be quaternised using agents such as $(C_1-C_4)$-alkyl halides, for example methyl, ethyl, isopropyl and tert-butyl chloride, bromide and iodide; di$(C_1-C_4)$alkyl sulfates, for example dimethyl, diethyl and diamyl sulfate; $(C_{10}-C_{18})$alkyl halides, for example decyl, do-decyl, lauryl, myristyl and stearyl chloride, bromide and iodide; and aryl-$(C_1-C_4)$alkyl halides, for example benzyl chloride and phenethyl bromide. Both water- and oil-soluble compounds of the formula I can be prepared using such salts.

The above-mentioned pharmaceutical salts, which are preferred, include acetate, trifluoroacetate, besylate, citrate, fumarate, gluconate, hemisuccinate, hippurate, hydrochloride, hydrobromide, isethionate, mandelate, me-glumine, nitrate, oleate, phosphonate, pivalate, sodium phosphate, stea-rate, sulfate, sulfosalicylate, tartrate, thiomalate, tosylate and tro-meth-amine, but this is not intended to represent a restriction.

The acid-addition salts of basic compounds of the formula I and related formulae are prepared by bringing the free base form into contact with a sufficient amount of the desired acid, causing the formation of the salt in a conventional manner. The free base can be regenerated by bringing the salt form into contact with a base and isolating the free base in a conventional manner. The free base forms differ in a certain respect from the corresponding salt forms thereof with respect to certain physical properties, such as solubility in polar solvents; for the purposes of the invention, however, the salts other-wise correspond to the respective free base forms thereof.

As mentioned, the pharmaceutically acceptable base-addition salts of the compounds of the formula I are formed with metals or amines, such as alkali metals and alkaline earth metals or organic amines. Preferred metals are sodium, potassium, magnesium and calcium.

Preferred organic amines are N,N'-dibenzylethylenediamine, chloroprocaine, choline, diethanol-amine, ethylenediamine, N-methyl-D-glucamine and procaine.

The base-addition salts of acidic compounds of the formula I, and related formulae are prepared by bringing the free acid form into contact with a sufficient amount of the desired base, causing the formation of the salt in a conventional manner. The free acid can be regenerated by bringing the salt form into contact with an acid and isolating the free acid in a conventional manner. The free acid forms differ in a certain respect from the corresponding salt forms thereof with respect to certain physical properties, such as solubility in polar solvents; for the purposes of the invention, however, the salts other-wise correspond to the respective free acid forms thereof.

If a compound of the formula I, and related formulae contains more than one group which is capable of forming pharmaceutically acceptable salts of this type, the formula I also encompasses multiple salts. Typical multiple salt forms include, for example, bitartrate, diacetate, difumarate, dimeglumine, di-phosphate, disodium and trihydrochloride, but this is not intended to represent a restriction.

With regard to that stated above, it can be seen that the term "pharmaceutically acceptable salt" in the present connection is taken to mean an active ingredient which comprises a compound of the formula I, and related formulae in the form of one of its salts, in particular if this salt form imparts improved pharmacokinetic properties on the active ingredient compared with the free form of the active ingredient or any other salt form of the active ingredient used earlier. The pharmaceutically acceptable salt form of the active ingredient can also provide this active ingredient for the first time with a desired pharmacokinetic property which it did not have earlier and can even have a positive influence on the pharmacodynamics of this active ingredient with respect to its therapeutic efficacy in the body.

Owing to their molecular structure, the compounds of the formula I, and related formulae can be chiral and can accordingly occur in various enantiomeric forms. They can therefore exist in racemic or in optically active form.

Since the pharmaceutical activity of the racemates or stereoisomers of the compounds according to the invention may differ, it may be desirable to use the enantiomers. In these cases, the end product or even the intermediates can be separated into enantiomeric compounds by chemical or physical measures known to the person skilled in the art or even employed as such in the synthesis.

In the case of racemic amines, diastereomers are formed from the mixture by reaction with an optically active resolving agent. Examples of suitable resolving agents are optically active acids, such as the R and S forms of tartaric acid, diacetyltartaric acid, dibenzoyltartaric acid, mandelic acid, malic acid, lactic acid, suitable N-protected amino acids (for example N-benzoylproline or N-benzenesulfonylproline), or the various optically active camphorsulfonic acids. Also advantageous is chromatographic enantiomer resolution with the aid of an optically active resolving agent (for example dinitrobenzoylphenylglycine, cellulose triacetate or other derivatives of carbohydrates or chirally derivatised methacrylate polymers immobilised on silica gel). Suitable eluents for this purpose are aqueous or alcoholic solvent mixtures, such as, for example, hexane/isopropanol/acetonitrile, for example in the ratio 82:15:3.

The invention furthermore relates to the use of compounds of formula I, and related formulae in combination with at least one further medicament active ingredient, preferably medicaments used in the treatment of multiple sclerosis such as cladribine or another co-agent, such as interferon, e.g. pegylated or non-pegylated interferons, preferably interferon beta and/or with compounds improving vascular function or in combination with immunomodulating agents for example Fingolimod; cyclosporins, rapamycins or ascomycins, or their immunosuppressive analogs, e.g. cyclosporin A, cyclosporin G, FK-506, ABT-281, ASM981, rapamycin, 40-O-(2-hydroxy)ethyl-rapamycin etc.; corticosteroids; cyclophosphamide; azathioprene; methotrexate; leflunomide; mizoribine; mycophenolic add; mycophenolate mofetil; 15-deoxyspergualine; diflucortolone valerate; diflu-prednate; Alclometasone dipropionate; amcinonide; amsacrine; asparaginase; azathioprine; basiliximab; beclometasone dipropionate; betamethasone; betamethasone acetate; betamethasone dipropionate; betamethasone phosphate sodique; betamethasone valerate; budesonide; captopril; chlormethine chlorhydrate; cladribine; clobetasol propionate; cortisone acetate; cortivazol; cyclophosphamide; cytarabine; daclizumab; dactinomycine; desonide; desoximetasone; dexamethasone; dexamethasone acetate; dexamethasone isonicotinate; dexamethasone metasulfobenzoate sodique; dexamethasone phosphate; dexamethasone tebutate; dichlorisone acetate; doxorubicine chlorhydrate; epirubicine chlorhydrate; fluclorolone acetonide; fludrocortisone acetate; fludroxycortide; flumetasone pivalate; flunisolide; fluocinolone acetonide; fluocinonide; fluocortolone; fluocortolone hexanoate; fluocortolone pivalate; fluorometholone; fluprednidene acetate; fluticasone propionate; gemcitabine chlorhydrate; halcinonide; hydrocortisone, hydrocortisone acetate, hydrocortisone butyrate, hydrocortisone hemisuccinate; melphalan; meprednisone; mercaptopurine; methylprednisolone; methylprednisolone acetate; methylprednisolone hemisuccinate; misoprostol; muromonab-cd3; mycophenolate mofetil; paramethasone acetate; prednazoline, prednisolone; prednisolone acetate; prednisolone caproate; prednisolone metasulfobenzoate sodique; prednisolone phosphate sodique; prednisone; prednylidene; rifampicine; rifampicine sodique; tacrolimus; teriflunomide; thalidomide; thiotepa; tixocortol pivalate; triamcinolone; triamcinolone acetonide hemisuccinate; triamcinolone benetonide; triamcinolone diacetate; triamcinolone hexacetonide; immunosuppressive monoclonal antibodies, e.g., monoclonal antibodies to leukocyte receptors, e.g., MHC, CD2, CD3, CD4, CD7, CD25, CD28, B7, CD40, CD45 or CD58 or their ligands; or other immunomodulatory compounds, e.g. CTLA4Ig, or other adhesion molecule inhibitors, e.g. mAbs or low molecular weight inhibitors including Selectin antagonists and VLA-4 antagonists. A preferred composition is with Cyclosporin A, FK506, rapamycin or 40-(2-hydroxy)ethyl-rapamycin and Fingolimod. These further medicaments, such as interferon beta, may be administered concomitantly or sequentially, e.g. by subcutaneous, intramuscular or oral routes.

These compositions can be used as medicaments in human and veterinary medicine.

In embodiment 1, the present invention provides the use of compounds of formula (I) and pharmaceutically acceptable derivatives, solvates, tautomers, salts and stereoisomers thereof, including mixtures thereof in all ratios as a medicament.

In embodiment 2, the present invention provides the use of compounds according to embodiment 1, and pharmaceutically usable derivatives, salts, tautomers, solvates and stereoisomers thereof, including mixtures thereof in all ratios, for the preparation of a medicament for the treatment and/or prophylaxis of a sphingosine 1-phosphate associated disorder.

In embodiment 3, the present invention provides the use of compounds according to one or more of embodiment 1 to 2, and pharmaceutically usable derivatives, salts, tautomers, solvates and stereoisomers thereof, including mixtures thereof in all ratios, for the preparation of a medicament for the treatment and/or prophylaxis of an immunoregulatory abnormality.

In embodiment 4, the present invention provides the use according to embodiment 3, wherein the immunoregulatory abnormality is an autoimmune or chronic inflammatory disease selected from the group consisting of: systemic lupus erythematosis, chronic rheumatoid arthritis, type I diabetes mellitus, inflammatory bowel disease, biliary cirrhosis, uveitis, multiple sclerosis, amyotrophic lateral sclerosis (ALS), Crohn's disease, ulcerative colitis, bullous pemphigoid, sarcoidosis, psoriasis, autoimmune myositis, Wegener's granulomatosis, ichthyosis, Graves ophthalmopathy, asthma, bone marrow or organ transplant rejection or graft-versus-host disease.

In a further aspect, compounds of the present invention have an EC50 in GTPγS for the binding or modulation to the S1P1 receptor of less than about 5 μM, preferably less than about 1 μM.

In a further aspect, the invention provides the use of compounds of Formula I and related formulae, as well as pharmaceutically usable derivatives, salts, tautomers, solvates and stereoisomers thereof, including mixtures thereof in all ratios, for the preparation of a medicament for the treatment and/or prophylaxis of diseases in which the inhibition, activation, regulation, and/or modulation of S1P$_1$ receptor signal transduction plays a role.

In a further aspect, the invention provides the use of compounds of Formula I and related Formulae for the preparation of a medicament for the treatment and/or prophylaxis of autoimmune disorder or condition associated with an overactive immune response.

Pharmaceutical formulations can be administered in the form of dosage units, which comprise a predetermined amount of active ingredient per dosage unit. Such a unit can comprise, for example, 0.5 mg to 300 mg, preferably 1 mg to 100 mg, particularly preferably 5 mg to 50 mg, of a compound according to the invention, depending on the disease condition treated, the method of administration and the age, weight and condition of the patient, or pharmaceutical formulations can be administered in the form of dosage units which comprise a predetermined amount of active ingredient per dosage unit. Preferred dosage unit formulations are those which comprise a daily dose or part-dose, as indicated above, or a corresponding fraction thereof of an active ingredient. Furthermore, pharmaceutical formulations of this type can be prepared using a process, which is generally known in the pharmaceutical art.

Pharmaceutical formulations can be adapted for administration via any desired suitable method, for example by oral (including buccal or sublingual), rectal, nasal, topical (including buccal, sublingual or transdermal), vaginal or parenteral (including subcutaneous, intramuscular, intravenous or intradermal) methods. Such formulations can be prepared using all processes known in the pharmaceutical art by, for example, combining the active ingredient with the excipient(s) or adjuvant(s).

Pharmaceutical formulations adapted for oral administration can be administered as separate units, such as, for example, capsules or tablets; powders or granules; solutions or suspensions in aqueous or non-aqueous liquids; edible foams or foam foods; or oil-in-water liquid emulsions or water-in-oil liquid emulsions.

Thus, for example, in the case of oral administration in the form of a tablet or capsule, the active-ingredient component can be combined with an oral, non-toxic and pharmaceutically acceptable inert excipient, such as, for example, ethanol, glycerol, water and the like. Powders are prepared by comminuting the compound to a suitable fine size and mixing it with a pharmaceutical excipient comminuted in a similar manner, such as, for example, an edible carbohydrate, such as, for example, starch or mannitol. A flavour, preservative, dispersant and dye may likewise be present.

Capsules are produced by preparing a powder mixture as described above and filling shaped gelatine shells therewith. Glidants and lubricants, such as, for example, highly disperse silicic acid, talc, magnesium stearate, calcium stearate or polyethylene glycol in solid form, can be added to the powder mixture before the filling operation. A disintegrant or solubiliser, such as, for example, agar-agar, calcium carbonate or sodium carbonate, may likewise be added in order to improve the availability of the medica-ment after the capsule has been taken.

In addition, if desired or necessary, suitable binders, lubricants and disintegrants as well as dyes can likewise be incorporated into the mixture. Suitable binders include starch, gelatine, natural sugars, such as, for example, glucose or beta-lactose, sweeteners made from maize, natural and synthetic rubber, such as, for example, acacia, tragacanth or sodium alginate, carboxymethylcellulose, polyethylene glycol, waxes, and the like. The lubricants used in these dosage forms include sodium oleate, sodium stearate, magnesium stearate, sodium benzoate, sodium acetate, sodium chloride and the like. The disintegrants include, without being restricted thereto, starch, methylcellulose, agar, bentonite, xanthan gum and the like. The tablets are formulated by, for example, preparing a powder mixture, granulating or dry-pressing the mixture, adding a lubricant and a disintegrant and pressing the entire mixture to give tablets. A powder mixture is prepared by mixing the compound comminuted in a suitable manner with a diluent or a base, as described above, and optionally with a binder, such as, for example, carboxymethylcellulose, an alginate, gelatine or polyvinyl-pyrrolidone, a dissolution retardant, such as, for example, paraffin, an absorption accelerator, such as, for example, a quaternary salt, and/or an absorbant, such as, for example, bentonite, kaolin or dicalcium phosphate. The powder mixture can be granulated by wetting it with a binder, such as, for example, syrup, starch paste, acadia mucilage or solutions of cellulose or polymer materials and pressing it through a sieve. As an alternative to granulation, the powder mixture can be run through a tableting machine, giving lumps of non-uniform shape which are broken up to form granules. The granules can be lubricated by addition of stearic acid, a stearate salt, talc or mineral oil in order to prevent sticking to the tablet casting moulds. The lubricated mixture is then pressed to give tablets. The active ingredients can also be combined with a free-flowing inert excipient and then pressed directly to give tablets without carrying out the granulation or dry-pressing steps. A transparent or opaque protective layer consisting of a shellac sealing layer, a layer of sugar or polymer material and a gloss layer of wax may be present. Dyes can be added to these coatings in order to be able to differentiate between different dosage units.

Oral liquids, such as, for example, solution, syrups and elixirs, can be prepared in the form of dosage units so that a given quantity comprises a pre-specified amount of the compounds. Syrups can be prepared by dissolving the compounds in an aqueous solution with a suitable flavour, while elixirs are prepared using a non-toxic alcoholic vehicle. Suspensions can be for-mulated by dispersion of the compounds in a non-toxic vehicle. Solubilisers and emulsifiers, such as, for example, ethoxylated isostearyl alcohols and polyoxyethylene sorbitol ethers, preservatives, flavour additives, such as, for example, peppermint oil or natural sweeteners or saccharin, or other artificial sweeteners and the like, can likewise be added.

The dosage unit formulations for oral administration can, if desired, be encapsulated in microcapsules. The formulation can also be prepared in such a way that the release is extended or retarded, such as, for example, by coating or embedding of particulate material in polymers, wax and the like.

The compounds of the formula I and related formulae and salts, solvates and physiologically functional derivatives thereof and the other active ingredients can also be administered in the form of liposome delivery systems, such as, for exam-ple, small unilamellar vesicles, large unilamellar vesicles and multilamellar vesicles. Liposomes can be formed from various phospholipids, such as, for example, cholesterol, stearylamine or phosphatidylcholines.

The compounds of the formula I and related formulae and the salts, solvates and physiologically functional derivatives thereof and the other active ingredients can also be delivered using monoclonal antibodies as individual carriers to which the compound molecules are coupled. The compounds can also be coupled to soluble polymers as targeted medicament carriers. Such polymers may encompass polyvinylpyrrolidone, pyran copolymer, polyhydroxypropyl-methacrylamidophenol, polyhydroxyethylaspartamido-phenol or polyethylene oxide polylysine, substituted by palmitoyl radicals. The compounds may furthermore be coupled to a class of biodegradable polymers which are suitable for achieving controlled release of a medicament, for example polylactic acid, poly-epsilon-caprolactone, polyhydroxybutyric acid, polyorthoesters, polyacetals, polydihydroxypyrans, polycyanoacrylates and crosslinked or amphipathic block copolymers of hydrogels.

Pharmaceutical formulations adapted for transdermal administration can be administered as independent plasters for extended, close contact with the epidermis of the recipient. Thus, for example, the active ingredient can be delivered from the plaster by iontophoresis, as described in general terms in Pharmaceutical Research, 3(6), 318 (1986).

Pharmaceutical compounds adapted for topical administration can be formulated as ointments, creams, suspensions, lotions, powders, solutions, pastes, gels, sprays, aerosols or oils.

For the treatment of the eye or other external tissue, for example mouth and skin, the formulations are preferably applied as topical ointment or cream. In the case of formulation to give an ointment, the active ingredient can be employed either with a paraffinic or a water-miscible cream base. Alternatively, the active ingredient can be formulated to give a cream with an oil-in-water cream base or a water-in-oil base.

Pharmaceutical formulations adapted for topical application to the eye include eye drops, in which the active ingredient is dissolved or sus-pended in a suitable carrier, in particular an aqueous solvent.

Pharmaceutical formulations adapted for topical application in the mouth encompass lozenges, pastilles and mouthwashes.

Pharmaceutical formulations adapted for rectal administration can be administered in the form of suppositories or enemas.

Pharmaceutical formulations adapted for nasal administration in which the carrier substance is a solid comprise a coarse powder having a particle size, for example, in the range 20-500 microns, which is administered in the manner in which snuff is taken, i.e. by rapid inhalation via the nasal passages from a container containing the powder held close to the nose.

Suitable formulations for administration as nasal spray or nose drops with a liquid as carrier substance encompass active-ingredient solutions in water or oil.

Pharmaceutical formulations adapted for administration by inhalation encompass finely particulate dusts or mists, which can be generated by various types of pressurised dispensers with aerosols, nebulisers or insufflators.

Pharmaceutical formulations adapted for vaginal administration can be administered as pessaries, tampons, creams, gels, pastes, foams or spray formulations.

Pharmaceutical formulations adapted for parenteral administration include aqueous and non-aqueous sterile injection solutions comprising antioxidants, buffers, bacteriostatics and solutes, by means of which the formulation is rendered isotonic with the blood of the recipient to be treated; and aqueous and non-aqueous sterile suspensions, which may comprise suspension media and thickeners. The formulations can be administered in single-dose or multidose containers, for example sealed ampoules and vials, and stored in freeze-dried (lyophilised) state, so that only the addition of the sterile carrier liquid, for example water for injection purposes, immediately before use is necessary.

Injection solutions and suspensions prepared in accordance with the recipe can be prepared from sterile powders, granules and tablets.

It goes without saying that, in addition to the above particularly mentioned constituents, the formulations may also comprise other agents usual in the art with respect to the particular type of formulation; thus, for example, formulations which are suitable for oral administration may comprise flavours.

A therapeutically effective amount of a compound of the formula I and related formulae and of the other active ingredient depends on a number of factors, including, for example, the age and weight of the animal, the precise disease condition which requires treatment, and its severity, the nature of the formulation and the method of administration, and is ultimately determined by the treating doctor or vet. However, an effective amount of a compound is generally in the range from 0.1 to 100 mg/kg of body weight of the recipient (mammal) per day and particularly typically in the range from 1 to 10 mg/kg of body weight per day. Thus, the actual amount per day for an adult mammal weighing 70 kg is usually between 70 and 700 mg, where this amount can be administered as an individual dose per day or usually in a series of part-doses (such as, for example, two, three, four, five or six) per day, so that the total daily dose is the same. An effective amount of a salt or solvate or of a physiologically functional derivative thereof can be determined as the fraction of the effective amount of the compound per se.

The present invention furthermore relates to a method for treating a subject suffering from a sphingosine 1-phosphate associated disorder, comprising administering to said subject an effective amount of a compound of formula I. The present invention preferably relates to a method, wherein the sphingosine 1-phosphate-1 associated disorder is an autoimmune disorder or condition associated with an overactive immune response.

The present invention furthermore relates to a method of treating a subject suffering from an immunorgulatory abnormality, comprising administering to said subject a compound of formula I in an amount that is effective for treating said immunoregulatory abnormality. The present invention preferably relates to a method wherein the immunoregulatory abnormality is an autoimmune or chronic inflammatory disease selected from the group consisting of: amyotrophic lateral sclerosis (ALS), systemic lupus erythematosus, chronic rheumatoid arthritis, type I diabetes mellitus, inflammatory bowel disease, biliary cirrhosis, uveitis, multiple sclerosis, Crohn's disease, ulcerative colitis, bullous pemphigoid, sarcoidosis, psoriasis, autoimmune myositis, Wegener's granulomatosis, ichthyosis, Graves ophthalmopathy and asthma. The present invention furthermore relates to a method wherein the immunoregulatory abnormality is bone marrow or organ transplant rejection or graft-versus-host disease. The present invention furthermore relates to a method wherein the immunoregulatory abnormality is selected from the group consisting of: transplantation of organs or tissue, graft-versus-host diseases brought about by transplantation, autoimmune syndromes including rheumatoid arthritis, systemic lupus erythematosus, Hashimoto's thyroiditis, multiple sclerosis, myasthenia gravis, type I diabetes mellitus, uveitis, posterior uveitis, allergic encephalomyelitis, glomerulonephritis, post-infectious autoimmune diseases including rheumatic fever and post-infectious glomerulonephritis, inflammatory and hyperproliferative skin diseases, psoriasis, atopic dermatitis, contact dermatitis, eczematous dermatitis, seborrhoeic dermatitis, lichen planus, pemphigus, bullous pemphigoid, epidermolysis bullosa, urticaria, angioedemas, vasculitis, erythema, cutaneous eosinophilia, lupus erythematosus, acne, alopecia greata, keratoconjunctivitis, vernal conjunctivitis, uveitis associated with Behcet's disease, keratitis, herpetic keratitis, conical cornea, dystrophia epithelialis corneae, corneal leukoma, ocular pemphigus, Mooren's ulcer, scleritis, Graves' ophthalmopathy, Vogt-Koyanagi-Harada syndrome, sarcoidosis, pollen allergies, reversible obstructive airway disease, bronchial asthma, allergic asthma, intrinsic asthma, extrinsic asthma, dust asthma, chronic or inveterate asthma, late asthma and airway hyper-responsiveness, bronchitis, gastric ulcers, vascular damage caused by ischemic diseases and thrombosis, ischemic bowel diseases, inflammatory bowel diseases, necrotizing enterocolitis, intestinal lesions associated with thermal burns, coeliac diseases, proctitis, eosinophilic gastroenteritis, mastocytosis, Crohn's disease, ulcerative colitis, migraine, rhinitis, eczema, interstitial nephritis, Goodpasture's syndrome, hemolytic-uremic syndrome, diabetic nephropathy, multiple myositis, Guillain-Barre syndrome, Meniere's disease, polyneuritis, multiple neuritis, mononeuritis, radiculopathy, hyperthyroidism, Basedow's disease, pure red cell aplasia, aplastic anemia, hypoplastic anemia, idiopathic thrombocytopenic purpura, autoimmune hemolytic anemia, agranulocytosis, pernicious anemia, megaloblastic anemia, anerythroplasia, osteoporosis, sarcoidosis, fibroid lung, idiopathic interstitial pneumonia, dermatomyositis, leukoderma vulgaris, ichthyosis vulgaris, photoallergic sensitivity, cutaneous T cell lymphoma, chronic lymphocytic leukemia, arteriosclerosis, atherosclerosis, aortitis syndrome, polyarteritis nodosa, myocardosis, scleroderma, Wegener's granuloma, Sjogren's syndrome, adiposis, eosinophilic fascitis, lesions of gingiva, periodontium, alveolar bone, substantia ossea dentis, glomerulonephritis, male pattern alopecia or alopecia senilis by preventing epilation or providing hair germination and/or promoting hair generation and hair growth, muscular dystrophy, pyoderma and Sezary's syndrome, Addison's disease, ischemia-reperfusion injury of organs which occurs upon preservation, transplantation or ischemic disease, endotoxin-shock, pseudomembranous colitis, colitis caused by drug or radiation, ischemic acute renal insufficiency, chronic renal insufficiency, toxinosis caused by lung-oxygen or drugs, lung cancer, pulmonary emphysema, cataracta, siderosis, retinitis pigmentosa, senile macular degeneration, vitreal scarring, corneal alkali burn, dermatitis erythema multiforme, linear IgA ballous dermatitis and cement dermatitis, gingivitis, periodontitis, sepsis, pancreatitis, diseases caused by environmental pollution, aging, carcinogenesis, metastasis of carcinoma and hypobaropathy, disease caused by histamine or leukotriene-$C_4$ release, Behcet's disease, autoimmune hepatitis, primary biliary cirrhosis, sclerosing cholangitis, partial liver resection, acute liver necrosis, necrosis caused by toxin, viral hepatitis, shock, or anoxia, B-virus hepatitis, non-A/non-B hepatitis, cirrhosis, alcoholic cirrhosis, hepatic failure, fulminant hepatic failure, late-onset hepatic failure, "acute-on-chronic" liver failure, augmentation of chemotherapeutic effect, cytomegalovirus infection, HCMV infection, AIDS, cancer, senile dementia, trauma, and chronic bacterial infection.

The compounds of invention have been named according the standards used in the program "ACD/Name Batch" from Advanced Chemistry Development Inc., ACD/Labs (7.00 Release). Product version: 7.10, build: 15 Sep. 2003.

EXAMPLES

Methyl 5-(methoxymethyl)-1-phenyl-1H-pyrazole-4-carboxylate (165 mg; 0.67 mmol) was prepared following the procedure described in Menozzi, G et al, Farmaco, 1990, 45, 167-186.

The HPLC data provided in the examples described below were obtained as follows:

Method A: HPLC columns: Phenomenex Luna 5µ C18 (2), 100×4.6 mm. (Plus guard cartridge) at a flow of 2 mL/min; 5 min gradient from 95:5 ([0.1% (V/V) formic acid in $H_2O$]: [0.1% (V/V) formic acid in MeCN]) to 5:95 ([0.1% (V/V) formic acid in $H_2O$]: [0.1% (V/V) formic acid in MeCN]).

Method B: HPLC columns: Waters Xterra MS 5µ C18, 100×4.6 mm. (Plus guard cartridge) at a flow of 2 mL/min; 5 min gradient from 95:5 ([10 mM ammonium bicarbonate in $H_2O$]: MeCN) to 5:95 ([10 mM ammonium bicarbonate in $H_2O$]: MeCN).

Method C: HPLC columns: Waters Sunfire 5µ C18, 150×4.6 mm at a flow of 1 mL/min; 30 min gradient from 95:5 ([0.1% (V/V) formic acid in $H_2O$]: [0.1% (V/V) formic acid in MeCN]) to 0.1% (V/V) formic acid in MeCN.

Method D: HPLC columns: Waters Xterra 5µ C18 (2), 250×4.6 mm at a flow of 1 mL/min; 30 min gradient from 95:5 ([10 mM ammonium bicarbonate in $H_2O$]: MeCN) to MeCN.

Method E: HPLC columns: Waters Sunfire 5µ C18, 150×4.6 mm at a flow of 1 mL/min; 20 min gradient from 98:2 ([0.1% (V/V) formic acid in $H_2O$]: [0.1% (V/V) formic acid in MeCN]) to 0.1% (V/V) formic acid in MeCN.

Method F: HPLC columns: Phenomenex Luna 5µ C18 (2), 100×4.6 mm. (Plus guard cartridge) at a flow of 2 mL/min; 3.5 min gradient from 95:5 ([0.1% (V/V) formic acid in $H_2O$]: [0.1% (V/V) formic acid in MeCN]) to 5:95% ([0.1% (V/V) formic acid in $H_2O$]: [0.1% (V/V) formic acid in MeCN]) then held for 4 minutes at 5:95 ([0.1% (V/V) formic acid in $H_2O$]: [0.1% (V/V) formic acid in MeCN]).

Method G: HPLC columns: Waters Sunfire 5µ C18, 150×4.6 mm at a flow of 2 mL/min; 3.5 min gradient from 95:5 ([0.1% (V/V) formic acid in $H_2O$]: [0.1% (V/V) formic acid in MeCN]) to 5:95 ([0.1% (V/V) formic acid in $H_2O$]: [0.1% (V/V) formic acid in MeCN]) then held for 2 minutes at 5:95 ([0.1% (V/V) formic acid in $H_2O$]: [0.1% (V/V) formic acid in MeCN]).

All Methods Typical Injections 2-7 µl, UV detection via HP or Waters DAD, Start Range (nm); 210, End Range (nm); 400, Range interval (nm); 4.0. Other wavelength traces are extracted from the DAD data.

Optional ELS detection using Polymer Labs ELS-1000. MS detection: MicromassZQ, single quadrapole LC-MS instrument.

Ionisation is either electrospray (ESI) or APCI dependent on compound types.

The NMR data provided in the examples described below were obtained as followed: $^1$H-NMR: Bruker DPX 400 MHz The microwave chemistry was performed on a single mode microwave reactor Smith Creator™ from Personal Chemistry or a single mode microwave reactor Initiator™ Sixty from Biotage.

Intermediate 1

2-[3-(2,5-difluorophenyl)-1,2,4-oxadiazol-5-yl]-1-phenylethanone

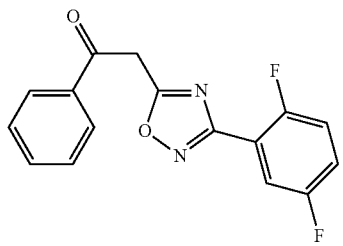 [SMILES: O=C(Cc1nc(-c2cc(F)ccc2F)no1)c1ccccc1]

A solution of ethyl 3-oxo-3-phenylpropanoate (14 mL; 80 mmol) and 2,5-difluoro-N'-hydroxybenzenecarboximidamide (JRD-Fluorochemical, 6.89 g; 40 mmol) in toluene (40 mL) was heated to 120° C. for 18 hours. The solvent was removed in vacuo and the residue triturated with diethyl ether to give Intermediate 1 as a pink solid which was used directly without any further purification. $^1$H NMR: (CDCl$_3$, 400 MHz) δ 11.68$^‡$ (1 H, br s), 8.04-8.00* (2 H, m), 7.91-7.86$^‡$ (2 H, m), 7.80-7.73$^‡$ (1 H, m), 7.69-7.63* (1 H, m), 7.58-7.45 (3 H, m), 7.28-7.16 (2 H, m), 6.32$^‡$ (1 H, s), 4.71* (2 H, s) (compound isolated as a mixture of keto and enol forms, *=keto form, $^‡$=enol form).

Intermediate 2

2-[3-(2,5-difluorophenyl)-1,2,4-oxadiazol-5-yl]-1-pyridin-4-ylethanone

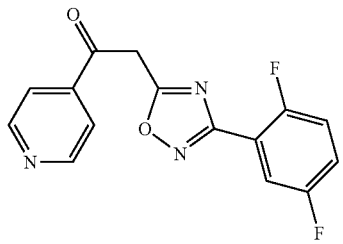 [SMILES: O=C(Cc1nc(-c2cc(F)ccc2F)no1)c1ccncc1]

A solution of ethyl 3-oxo-3-(pyridin-4-yl)propanoate (Apollo; 772 mg; 4 mmol) and 2,5-difluoro-N'-hydroxybenzenecarboximidamide (JRD-Fluorochemical, 344 g; 2 mmol) in toluene (2 mL) and MeCN (2 mL) was heated to 180° C. in a microwave reactor for 15 min. This reaction was performed three times and the reaction mixtures were combined for workup. The solid formed was removed by filtration, washed with water and diethyl ether and dried to give Intermediate 2 as an off-white solid which was used directly without any further purification. $^1$H NMR: (DMSO-d$_6$, 400 MHz) δ 8.94-8.90* (2 H, m), 8.82-8.77$^‡$ (2 H, m), 8.28-8.19* (1 H, m), 7.98-7.90 (2 H, m), 7.85-7.76$^‡$ (1 H, m), 7.63-7.54 (2 H, m), 6.94$^‡$ (1 H, s), 5.28* (2 H, s) (compound isolated as a mixture of keto and enol forms, *=keto form, $^‡$=enol form). LC/MS: 300 (M−H)$^−$. HPLC (Method B) Rt 2.64 min (Purity: 96.5%).

Intermediate 3

N'-hydroxy-3-(methylsulfonyl)benzenecarboximidamide

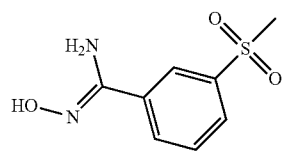

To a solution of 3-(methylsulfonyl)benzonitrile (Apollo; 2.7 g; 15 mmol) in abs. EtOH (20 mL) was added hydroxylamine (5 mL; 75 mmol) (50% in water) and the mixture was heated to 78° C. for 18 hours. Brine (100 mL) was added and the solid formed was removed by filtration, washed with water and dried to give Intermediate 3 as a white solid (2.67 g, 83%). $^1$H NMR: (DMSO-d$_6$, 400 MHz) δ 9.91 (1H, s), 8.25 (1H, t, J=1.8 Hz), 8.04 (1H, dt, J=7.9, 1.4 Hz), 7.96-7.93 (1H, m), 7.70 (1H, t, J=7.9 Hz), 6.06 (2H, s), 3.27 (3H, s). LC/MS: 215 (M+H)$^+$. HPLC (Method B) Rt 1.80 min (Purity: 99.2%).

Intermediate 4

2-{3-[3-(methylsulfonyl)phenyl]-1,2,4-oxadiazol-5-yl}-1-pyridin-4-ylethanone

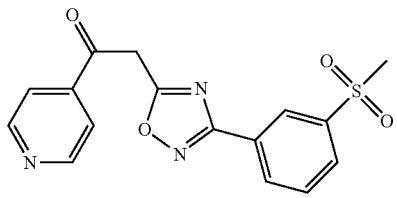 [SMILES: CS(=O)(=O)c1cccc(-c2noc(CC(=O)c3ccncc3)n2)c1]

A solution of ethyl 3-oxo-3-(pyridin-4-yl)propanoate (Apollo; 386 mg; 2 mmol) and Intermediate 3 (214 mg; 1 mmol) in toluene (2 mL) was heated to 180° C. in a microwave reactor for 45 min. The solvent was removed in vacuo and the residue triturated with isopropanol to give Intermediate 4 as an off-white solid, which was used directly without any further purification. $^1$H NMR: (DMSO-d$_6$, 400 MHz) δ 11.58$^‡$ (1 H, br s), 8.93-8.90* (2H, m), 8.82-8.75$^‡$ (2H, m), 8.67 (1 H, s), 8.44-8.38$^‡$ (2 H, m), 8.40-8.35* (2 H, m), 8.18-8.12$^‡$ (2 H, m), 8.13-8.07* (2 H, m), 7.83-7.70 (3 H, m), 6.45$^‡$ (1 H, s), 4.71* (2 H, s), 3.15$^‡$ (3 H, s), 3.11* (3 H, s) (compound isolated as a mixture of keto and enol forms, *=keto form, $^‡$=enol form).

Intermediate 5

1-[3-(2,5-difluorophenyl)-1,2,4-oxadiazol-5-yl]-3-methoxyacetone

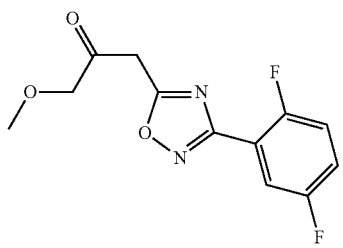 [SMILES: COCC(=O)Cc1nc(-c2cc(F)ccc2F)no1]

A solution of methyl 4-methoxy-3-oxobutanoate (Apollo; 0.26 mL; 2 mmol) and 2,5-difluoro-N'-hydroxybenzenecarboximidamide (JRD-Fluorochemical, 172 mg; 1 mmol) in toluene (2 mL) and MeCN (1 mL) was heated to 180° C. in a microwave reactor for 45 min. DCM (10 mL) and water (10 mL) were added and the mixture filtered through a hydrophobic frit. The solvent was removed in vacuo and the residue purified by flash chromatography on a Biotage 25+S column, eluting with petrol containing increasing amounts of EtOAc. The product was dissolved in DCM (10 mL) and washed with copious amounts of water and the mixture passed through a hydrophobic frit. The solvent was removed in vacuo to give Intermediate 5 as a yellow oil which was used directly without any further purification. $^1$H NMR: (CDCl$_3$, 400 MHz) δ 10.70$^‡$ (1 H, br s), 7.78-7.68 (1 H, m), 7.25-7.16 (2 H, m), 5.96$^‡$ (1 H, s), 4.26* (2 H, s), 4.15 (2 H, s), 3.49$^‡$ (3 H, s), 3.46* (3H, s) (compound isolated as a mixture of keto and enol forms, *=keto form, $^‡$=enol form). LC/MS: 267 (M−H)$^-$. HPLC (Method B) Rt 2.98 min (Purity: 92.9%).

Intermediate 6

1-[3-(2,5-difluorophenyl)-1,2,4-oxadiazol-5-yl]butan-2-one

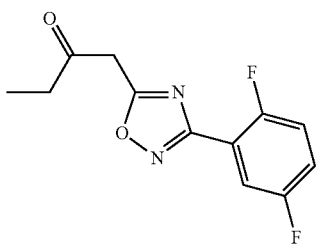 [SMILES: CCC(=O)Cc1nc(-c2cc(F)ccc2F)no1]

A solution of methyl 3-oxopentanoate (Apollo; 0.25 mL; 2 mmol) and 2,5-difluoro-N'-hydroxybenzenecarboximidamide (JRD-Fluorochemical, 172 mg; 1 mmol) in toluene (2 mL) and MeCN (1 mL) was heated to 180° C. in a microwave reactor for 45 min. DCM (10 mL) and water (10 mL) were added and the mixture filtered through a hydrophobic frit. The solvent was removed in vacuo and the residue purified by flash chromatography on a Biotage 25+S column, eluting with petrol containing increasing amounts of EtOAc to give Intermediate 6 as an off-white solid which was used directly without any further purification. $^1$H NMR: (CDCl$_3$, 400 MHz) δ 10.76$^‡$ (1 H, br s), 7.79-7.73 (1H, m, ArH), 7.24-7.16 (2 H, m), 5.63$^‡$ (1 H, s), 4.14* (2 H, s), 2.66* (2 H, q), 2.44$^‡$ (2 H, q), 1.24$^‡$ (3 H, t), 1.14* (3 H, t) (compound isolated as a mixture of keto and enol forms, *=keto form, $^1$=enol form). LC/MS: 251 (M−H)$^-$. HPLC (Method B) Rt 3.37 min (Purity: 98.1%).

Intermediate 7 ethyl 1-cyclohexyl-5-pyridin-4-yl-1H-pyrazole-4-carboxylate

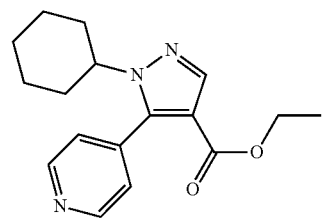 [SMILES: CCOC(=O)c1cnn(C2CCCCC2)c1-c1ccncc1]

To a solution of ethyl 3-oxo-3-(pyridin-4-yl)propanoate (Apollo; 3 g; 15.5 mmol) in toluene (109 mL) was added DMF.DMA (2.7 mL; 20.15 mmol) and PPTS (400 mg). The mixture was heated to 90° C. for 2 hours. The solvent was removed in vacuo and DCM (100 mL) and water (100 mL) were added and the mixture passed through a hydrophobic frit. The solvent was removed in vacuo and the residue redissolved in ethanol (100 mL) and water (10 mL). This solution was added to a mixture of cyclohexylhydrazine hydrochloride (Fluorochem; 2.34 g; 15.5 mmol), and sodium acetate (2.54 g; 31 mmol). The mixture was heated to reflux for 3 hours and the ethanol removed in vacuo. DCM (100 mL) was added and the mixture was filtered through a hydrophobic frit and the solvent removed in vacuo. The residue was purified by flash chromatography on a Biotage 25+M column, eluting with petrol containing increasing amounts of EtOAc. The residue was triturated with diethyl ether to give Intermediate 7 as an off-white solid. $^1$H NMR: (CDCl$_3$, 400 MHz) δ 8.80-8.73 (2H, m), 8.02 (1H, s), 7.30-7.26 (2H, m), 4.14 (2H, q, J=7.0 Hz), 3.84-3.75 (1H, m), 2.08-1.91 (2H, m), 1.90-1.76 (4H, m), 1.70-1.59 (1H, m), 1.30-1.18 (3H, m), 1.16 (3H, t, J=7.0 Hz). LC/MS: 300 (M+H)$^+$. HPLC (Method B) Rt 3.45 min (Purity: 96.3%).

Intermediate 8

N'-hydroxy-4-(hydroxymethyl)benzenecarboximidamide

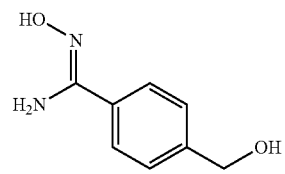 [SMILES: N/C(=N\O)c1ccc(CO)cc1]

To a solution of 4-(hydroxymethyl)benzonitrile (11.05 g; 83.08 mmol) in abs. EtOH (100 mL) was added hydroxylamine (27.4 mL; 415.4 mmol) (50% in water) and the mixture was heated to 74° C. for 16 hours. The mixture was poured into a crystallizing dish and the solvent allowed to evaporate. The residue was washed with copious amounts of EtOAc, dry MeOH and dry MeCN which was filtered through a hydrophobic frit and the solvent removed in vacuo to give Intermediate 8 as a white solid (13.12 g; 95%). $^1$H NMR: (DMSO-d$_6$, 400 MHz) δ 9.58 (1H, s), 7.70-7.62 (2H, m), 7.34 (2H, d, J=8.1 Hz), 5.79 (2H, s), 5.23 (1H, t, J=5.6 Hz), 4.54 (2H, d, J=5.6 Hz).

Intermediate 9

1-cyclohexyl-N'-hydroxy-5-phenyl-1H-pyrazole-4-carboximidamide

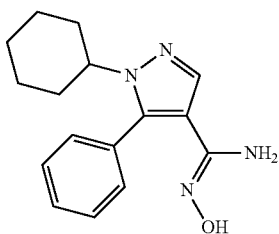 [SMILES: N/C(=N\O)c1cnn(C2CCCCC2)c1-c1ccccc1]

Step 1: 1-cyclohexyl-5-phenyl-1H-pyrazole-4-carbonitrile

To a solution of 3-oxo-3-phenylpropanenitrile (Avocado; 2.2 g; 15 mmol) in toluene (100 mL) was added DMF.DMA (2.7 mL; 20 mmol) and PPTS (375 mg). The mixture was heated to 90° C. for 4 hours. The solvent was removed in vacuo and DCM (100 mL) and water (100 mL) were added and the mixture passed through a hydrophobic frit. The solvent was removed in vacuo and the residue redissolved in ethanol (95 mL) and water (9.5 mL). This solution was added to a mixture of cyclohexylhydrazine hydrochloride (Fluorochem; 2.26 g; 15 mmol), and sodium acetate (2.46 g; 30 mmol). The mixture was heated to reflux for 24 hours and the ethanol removed in vacuo. DCM (100 mL) and water (50 mL) were added and the mixture was filtered through a hydrophobic frit and the solvent removed in vacuo. The residue was purified by flash chromatography on a Biotage 40+M column, eluting with petrol containing increasing amounts of EtOAc. The residue was triturated with diethyl ether to give the title compound as an off-white solid. $^1$H NMR: (CDCl$_3$, 400 MHz) δ 7.85 (1H, s), 7.58-7.50 (3H, m), 7.46-7.37 (2H, m), 4.14-4.04 (1H, m), 2.07-1.95 (2H, m), 1.95-1.78 (4H, m), 1.74-1.59 (1H, m), 1.72-0.81 (3H, m). LC/MS: 252 (M+H)$^+$. HPLC (Method B) Rt 4.30 min (Purity: 96.3%).

Step 2: 1-cyclohexyl-N'-hydroxy-5-phenyl-1H-pyrazole-4-carboximidamide

To a solution of 1-cyclohexyl-5-phenyl-1H-pyrazole-4-carbonitrile (2.37 g; 9.4 mmol), obtained from step 1, in abs. EtOH (12.5 mL) was added hydroxylamine (3 mL; 45 mmol) (50% in water) and the mixture was heated to 78° C. for 18 hours. Brine (5 mL) was added and the EtOH removed in vacuo. DCM (20 mL) was added and the mixture was passed through a hydrophobic frit. The solvent was removed in vacuo and the solid washed with water and diethyl ether and dried to give Intermediate 9 as an off-white solid (2.6 g, 97%). $^1$H NMR: (DMSO-d$_6$, 400 MHz) δ 9.18 (1H, s), 7.73 (1H, s), 7.53-7.44 (3H, m), 7.40 (2H, d, J=6.9 Hz), 5.35 (2H, br s), 3.84-3.74 (1H, m), 1.92-1.73 (6H, m), 1.59 (1H, s), 1.19-1.06 (3H, m). LC/MS: 285 (M+H)$^+$. HPLC (Method B) Rt 3.35 min (Purity: 98.5%).

Intermediate 10 methyl 1-(2-fluorophenyl)-5-methyl-1H-pyrazole-4-carboxylate

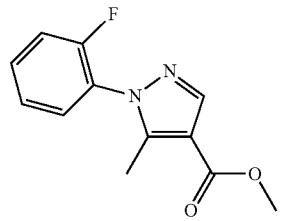 [SMILES: COC(=O)c1cnn(-c2ccccc2F)c1C]

To a solution of methyl 3-oxobutanoate (1.6 mL; 15 mmol) in toluene (100 mL) was added DMF.DMA (2.65 mL; 20 mmol) and PPTS (375 mg). The mixture was heated to 90° C. for 2 hours. The solvent was removed in vacuo and DCM (25 mL) and water (25 mL) were added and the mixture passed through a hydrophobic frit. The solvent was removed in vacuo and the residue redissolved in ethanol (90 mL). This mixture was added to a solution of (2-fluorophenyl)hydrazine hydrochloride (Fluorochem; 2.44 g; 15 mmol) and sodium acetate (2.46 g; 30 mmol) in water (9 mL). The mixture was heated to reflux for 7 hours and the ethanol removed in vacuo. DCM (100 mL) and water (50 mL) were added and the mixture was filtered through a hydrophobic frit and the solvent removed in vacuo. The residue was purified by flash chromatography on a Biotage 40+M column, eluting with petrol containing increasing amounts of EtOAc to give Intermediate 10 as a brown oil (3.1 g; 88%). $^1$H NMR: (CDCl$_3$, 400 MHz) δ 8.06 (1H, s), 7.51-7.42 (2H, m), 7.33-7.22 (2H, m), 3.86 (3H, s), 2.46 (3H, s). LC/MS: 235 (M+H)$^+$. HPLC (Method A) Rt 3.28 min (Purity: 96.2%).

Intermediate 11

2-[3-(2,5-difluorophenyl)-1,2,4-oxadiazol-5-yl]-1-(tetrahydro-2H-pyran-4-yl)ethanone

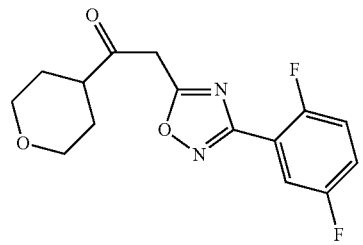 [SMILES: O=C(Cc1nc(-c2cc(F)ccc2F)no1)C1CCOCC1]

A solution of 3-oxo-3-(tetrahydro-pyran-4-yl)-propionic acid ethyl ester (Pharmacore; 200.0 mg; 1.0 mmol) and 2,5-difluoro-N'-hydroxybenzenecarboximidamide (JRD-Fluorochemical, 86.1 mg; 0.50 mmol) in toluene (2 mL) and acetonitrile (2 mL) was heated to 180° C. for 15 minutes in the microwave. The solvent was removed in vacuo and the residue redissolved in DCM (10 mL) and washed with water (3×10 mL). The organic layer was passed through a hydrophobic and the solvent removed in vacuo. The residue was purified by flash chromatography using a Biotage 12+M column, eluting with petrol containing increasing amounts of EtOAc. The product was triturated with 1:1 petrol:diethyl ether and DIPE to give Intermediate 11 as a pale yellow solid. LC/MS: 309 (M+H)$^+$. HPLC (Method B) Rt 3.26 min (Purity: 92.6%).

Intermediate 12 tetrahydro-2H-pyran-4-ylhydrazine, trifluoroacetate

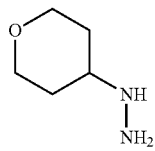

Tetrahydro-4H-pyran-4-one (Apollo; 924 µL; 10.0 mmol) and tert-butyl carbazate (1.39 g; 10.50 mmol) were dissolved in ethanol (10 mL) and stirred at room temperature overnight. The solvent was removed in vacuo and the residue was redissolved in 1:1 water:acetic acid (10 mL) and sodium cyanoborohydride (660 mg; 10.50 mmol) added. The mixture was stirred at room temperature for 3 hours and then 2:1 ethyl acetate:10% aqueous potassium carbonate (50 mL) added. The organic layer was separated, washed with brine, passed through a hydrophobic frit and the solvent removed in vacuo. The residue was redissolved in DCM (10 mL) and trifluoroacetic acid (1 mL) added and the mixture stirred overnight. The solvent was removed in vacuo to yield Intermediate 12 as a semi-solid slurry which was used directly without any purification. $^1$H NMR: (DMSO-d$_6$, 400 MHz) δ 4.08-3.76 (2 H, m), 3.41-3.27 (2 H, m), 3.23-3.14 (1 H, m), 1.99-1.83 (2 H, m), 1.59-1.43 (2 H, m). LC/MS: 117 (M+H)$^+$.

Intermediate 13

(2-methylcyclohexyl)hydrazine, hydrochloride

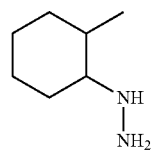

The title compound was prepared following the procedure described for Intermediate 12 but starting from 4-methylcyclohexanone (884 µL; 7.20 mmol) and using 2M HCl in dioxane (10 mL), to give Intermediate 13 as a white solid, which was used directly without any purification. $^1$H NMR: (DMSO-d$_6$, 400 MHz) δ 3.08-3.01 (1 H, m), 2.68-0.88 (9 H, m), 1.04* (3H, d, J=6.6 Hz), 0.97‡ (3 H, d, J=7.1 Hz) (compound isolated as a mixture of diastereomers *=diastereomer 1, ‡=diastereomer 2). LC/MS: 129 (M+H)$^+$.

Intermediate 14 ethyl 1-isobutyl-5-pyridin-4-yl-1H-pyrazole-4-carboxylate

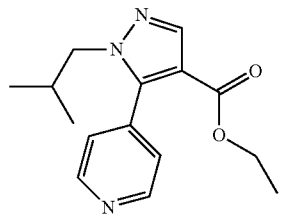 [SMILES: CCOC(=O)c1cnn(CC(C)C)c1-c1ccncc1]

To a solution of ethyl isonicotinoylacetate (Apollo; 1.0 g; 5.35 mmol) in toluene (15 mL) was added DMF.DMA (0.92 mL; 7.0 mmol) and PPTS (14 mg). The mixture was heated at 90° C. for 2 hours. Water (20 mL) was added and the product extracted into DCM (3×20 mL). The combined organic fractions were passed through a hydrophobic frit and the solvent was removed in vacuo and the residue redissolved in ethanol (20 mL). This solution was added to a mixture of 2-methylpropylhydrazine hydrochloride (666.7 mg; 5.35 mmol) and sodium acetate (878 mg; 10.70 mmol) in ethanol (5 mL) and water (2.5 mL). The mixture was heated at 90° C. for 3 hours and the solvent removed in vacuo. The residue was redissolved in DCM (10 mL), washed with water (3×10 mL), passed through a hydrophobic frit and the solvent removed in vacuo. The residue was purified by flash chromatography using a Biotage 25+M column, eluting with petrol containing increasing amounts of EtOAc to give Intermediate 14 as a pale yellow solid (1.25 g; 85%). $^1$H NMR (CDCl$_3$, 400 MHz) δ 8.76 (2 H, dd, J=4.6, 1.5 Hz), 8.03 (1 H, s), 7.31-7.26 (2 H, m), 4.15 (2 H, q, J=7.1 Hz), 3.77 (2 H, d, J=7.5 Hz), 2.23-2.11 (1 H, m), 1.17 (3 H, t, J=7.1 Hz), 0.77 (6 H, d, J=6.7 Hz). LC/MS: 274 (M+H)$^+$. HPLC (Method A) Rt=2.89 min (Purity: 94.3%).

Intermediate 15

N'-hydroxy-1H-indazole-5-carboximidamide

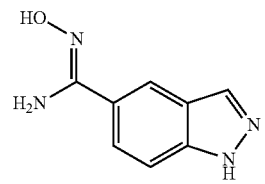 [SMILES: N/C(=N\O)c1ccc2[nH]ncc2c1]

Step 1: 1H-indazole-5-carbonitrile

Three identical reactions were carried out and combined for workup.

5-Bromo-1H-indazole (Fluorochem; 500 mg; 2.54 mmol), S-Phos (93.8 mg; 0.229 mmol), Pd$_2$(dba)$_3$ (93.0 mg; 0.102 mmol) and zinc cyanide (337.0 mg; 2.87 mmol) were suspended in degassed water:DMF (1:99, 11.5 mL) in a microwave vial and further degassed for 10 minutes in a sonicator. The vial was then sealed and heated in the microwave at 150° C. for 45 minutes. The solid material was removed by filtration and the crude material purified by flash chromatography on a Biotage 40+M column, eluting with DCM containing increasing amounts of methanol. The residue was recrystallised from chloroform/petrol to yield the title compound as an off white solid (1.33 g; 91%). $^1$H NMR (CDCl$_3$, 400 MHz) δ 10.46 (1 H, br s), 8.20 (2 H, d, J=8.3 Hz), 7.61 (2 H, s).

Step 2: N'-hydroxy-1H-indazole-5-carboximidamide

Hydroxylamine (1.4 mL; 46.5 mmol) was added to a solution of 1H-indazole-5-carbonitrile (1.33 g; 9.30 mmol), obtained from step 1, in ethanol (15 mL) and the mixture was heated in a sealed tube at 80° C. for 3 hours. The solvent was removed in vacuo and the residue triturated with chloroform to yield Intermediate 15 as a white solid. $^1$H NMR (DMSO-d$_6$) δ 13.15 (1 H, s), 9.57 (1 H, s), 8.1 (1 H, s), 8.1 (1 H, s), 7.75 (1 H, d, J=8.8 Hz), 7.53 (1 H, d, J=8.8 Hz), 5.84 (2 H, s). LC/MS: 177 (M+H)$^+$. HPLC (Method D) Rt=3.24 min (Purity: 90.6%).

Intermediate 16

N'-hydroxy-1,2,3,4-tetrahydroisoquinoline-7-carboximidamide

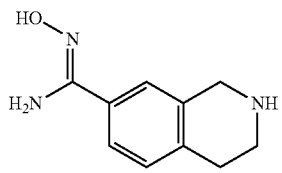 [SMILES: N/C(=N\O)c1ccc2c(c1)CNCC2]

The title compound was prepared following the procedure described for Intermediate 8 but starting from 1,2,3,4-tetrahydroisoquinoline-7-carbonitrile (Fluorochem; 1.01 g; 6.39 mmol), to give Intermediate 16 as a brown solid (1.18 g; 96%). $^1$H NMR: (DMSO-d$_6$, 400 MHz) δ 9.50 (1H, s), 7.42 (1H, d, J=8.06 Hz), 7.34 (1H, s), 7.07 (1H, d, J=8.01 Hz), 5.72 (2H, s), 3.86 (2H, s), 2.96 (2H, t, J=5.83 Hz), 2.70 (2H, t, J=5.80 Hz). LC/MS: 192 (M+H)$^+$. HPLC (Method D) Rt 9.30 min (Purity: 88.3%).

Intermediate 17 ethyl 1-(2-methylcyclohexyl)-5-phenyl-1H-pyrazole-4-carboxylate

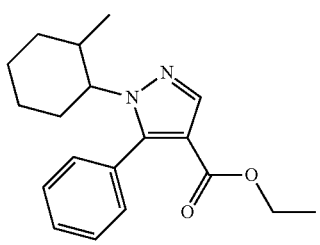 [SMILES: CCOC(=O)c1cnn(C2CCCCC2C)c1-c1ccccc1]

The title compound was prepared following the procedure described for Intermediate 14, but starting from ethyl benzoylacetate (0.14 mL; 0.80 mmol) and Intermediate 13 (184.1 mg; 0.80 mmol), to give Intermediate 17 as a clear oil (105 mg; 84%). $^1$H NMR (CDCl$_3$, 400 MHz) δ 8.03 & 7.97 (1H, m); 7.42 (3H, m); 7.25 (2H, m); 4.10* & 3.40‡ (3H, m); 2.25-2.08 (1H, m); 2.00-1.90 (1H, m); 1.90-1.59 (4H, m); 1.39-1.28 (2H, m); 1.20‡ & 0.90* (1H, m); 1.13 (3H, m); 0.75* & 0.56‡ (3H, m) (*=Major isomer, ‡=Minor isomer). LC/MS: 313 (M+H)$^+$. HPLC (Method A) Rt=4.46 min (Purity: 96.6%).

Intermediate 18 methyl 1-cyclohexyl-5-(methoxymethyl)-1H-pyrazole-4-carboxylate

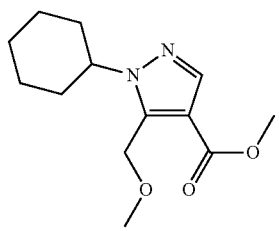 [SMILES: COCc1c(C(=O)OC)cnn1C1CCCCC1]

The title compound was prepared following the procedure described for Intermediate 14, but starting from methyl 4-methoxy-acetoacetate (Apollo; 3.1 mL; 24 mmol) and cyclohexylhydrazine hydrochloride (3.62 g; 24.0 mmol) to give Intermediate 18 as a red oil (5.22 g; 86%). $^1$H NMR (CDCl$_3$, 400 MHz) δ 7.89 (1 H, s), 4.85 (2 H, s), 4.27-4.18 (1 H, m), 3.82 (3 H, s), 3.35 (3 H, s), 2.04-1.86 (6 H, m), 1.73 (1 H, d, J=12.4 Hz), 1.50-1.20 (3H, m). LC/MS: 253 (M+H)$^+$. HPLC (Method A) Rt=3.64 min (Purity: 99.5%).

Intermediate 19 ethyl 1-isobutyl-5-(tetrahydro-2H-pyran-4-yl)-1H-pyrazole-4-carboxylate

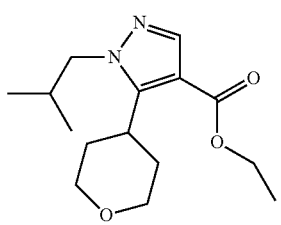 [SMILES: CCOC(=O)c1cnn(CC(C)C)c1C1CCOCC1]

The title compound was prepared following the procedure described for Intermediate 14, but starting from 3-oxo-3-(tetrahydro-pyran-4-yl)-propionic acid ethyl ester (Pharmacore; 0.63 g; 3.15 mmol) and 2-methylpropylhydrazine hydrochloride (0.39 g, 3.15 mmol) to give Intermediate 19 as a yellow oil. $^1$H NMR (CDCl$_3$, 400 MHz) δ 7.88 (1 H, s), 4.28 (2 H, q, J=8 Hz), 4.10 (2 H, dd, J=11.6, 4.4 Hz), 3.96 (2 H, d, J=7.6 Hz), 3.49 (2 H, t, J=11.9 Hz), 3.35 (1 H, tt, J=12.4, 3.8 Hz), 2.53 (2 H, qd, J=12.7, 4.5 Hz), 2.28-2.16 (1 H, m), 1.55-1.48 (2 H, m), 1.36 (3 H, t, J=8 Hz), 0.92 (6 H, dd, J=12.1, 6.7 Hz). LC/MS: 281 (M+H)⁺. HPLC (Method A) Rt=3.52 min (Purity: 98.4%).

Intermediate 20 ethyl 1-cyclohexyl-5-(tetrahydro-2H-pyran-4-yl)-1H-pyrazole-4-carboxylate

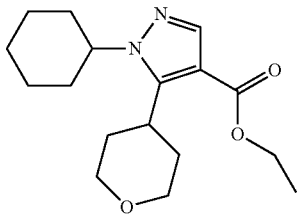 [SMILES: CCOC(=O)c1cnn(C2CCCCC2)c1C1CCOCC1]

The title compound was prepared following the procedure described for Intermediate 14, but starting from 3-oxo-3-(tetrahydro-pyran-4-yl)-propionic acid ethyl ester (Pharmacore; 1.1 g; 5.50 mmol) and cyclohexylhydrazine hydrochloride (0.83 g; 5.50 mmol). The product was obtained by precipitation from the reaction mixture by the addition of water. The resulting solid was dried to give Intermediate 20 as a white solid (1.20 g; 71%). ¹H NMR (CDCl₃, 400 MHz) δ 7.87 (1 H, s), 4.32-4.15 (3 H, m), 4.11 (2 H, dd, J=11.6, 4.4 Hz), 3.91-3.78 (1 H, m), 3.54 (2 H, t, J=11.8 Hz), 2.28 (2 H, qd, J=12.6, 4.5 Hz), 2.16-1.85 (6 H, m), 1.75 (1 H, d, J=12.61 Hz), 1.62-1.61 (2 H, m), 1.47-1.24 (6 H, m). LC/MS: 307 (M+H)⁺. HPLC (Method A) Rt=3.91 min (Purity: 96.2%).

Intermediate 21 methyl 1-isobutyl-5-(methoxymethyl)-1H-pyrazole-4-carboxylate

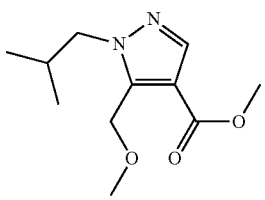 [SMILES: COCc1c(C(=O)OC)cnn1CC(C)C]

The title compound was prepared following the procedure described for Intermediate 7 but starting from methyl 4-methoxy-3-oxobutanoate (Apollo; 1.95 mL, 15 mmol) and isobutylhydrazine hydrochloride (1.9 g, 15 mmol) in step 2 to give Intermediate 21 as a brown oil. ¹H NMR: (CDCl₃, 400 MHz) δ 7.89 (1 H, s), 4.84 (2 H, s), 3.98 (2 H, d, J=7.5 Hz), 3.83 (3 H, s), 3.36 (3 H, s), 2.33 (1 H, septet, J=6.9 Hz), 0.92 (6 H, d, J=6.7 Hz). LC/MS: 227 (M+H)⁺. HPLC (Method A) Rt 3.29 min (Purity: 93.3%).

Intermediate 22 methyl 1-cyclohexyl-5-(2-methoxyethyl)-1H-pyrazole-4-carboxylate

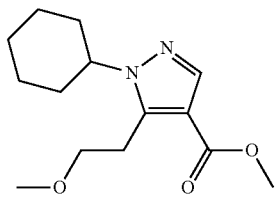 [SMILES: COCCc1c(C(=O)OC)cnn1C1CCCCC1]

The title compound was prepared following the procedure described for Intermediate 14, but starting from methyl 5-methoxy-3-oxopentanoate (5.0 mL; 34.3 mmol) and cyclohexylhydrazine hydrochloride (5.17 g; 34.3 mmol) to give Intermediate 22 as a yellow oil (6.7 g; 73%). ¹H NMR (CDCl₃, 400 MHz) δ 7.88 (1 H, s), 4.22-4.11 (1 H, m), 3.80 (3 H, s), 3.59 (2 H, t, J=6.4 Hz), 3.30 (3 H, s), 3.24 (2 H, t, J=6.4 Hz), 2.06-1.84 (6 H, m), 1.77-1.67 (1 H, m), 1.45-1.18 (3 H, m). LC/MS: 267 (M+H)⁺. HPLC (Method A) Rt 3.69 min (Purity: 98.8%).

Intermediate 23

1-cyclohexyl-5-(2-methoxyethyl)-1H-pyrazole-4-carboxylic acid

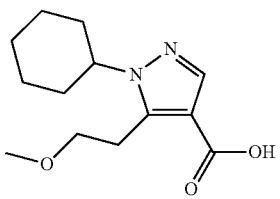 [SMILES: COCCc1c(C(=O)O)cnn1C1CCCCC1]

A mixture of Intermediate 22 (421 mg; 1.58 mmol) and lithium hydroxide monohydrate (79 mg; 1.89 mmol) in methanol (4.5 mL) and water (0.39 mL) was heated to 70 ° C. for 12 hours. The methanol was removed in vacuo and DCM (10 mL) added. The layers were separated and the aqueous layer acidified with 2M HCl$_{(aq)}$ and extracted with EtOAc (3×10 mL). The combined organic fractions were passed through a hydrophobic frit and the solvent removed in vacuo to give Intermediate 23 as a colourless oil. ¹H NMR (CDCl₃, 400 MHz) δ 7.97 (1 H, s), 4.24-4.14 (1 H, m), 3.61 (2 H, t, J=6.3 Hz), 3.30 (3 H, s), 3.26 (2 H, t, J=6.3 Hz), 2.05-1.83 (6 H, m), 1.78-1.67 (1 H, m), 1.47-1.20 (3 H, m). LC/MS: 253 (M+H)⁺. HPLC (Method A) Rt 3.00 min (Purity: 99.0%).

Intermediate 24

N'-hydroxy-4-(1H-imidazol-1-ylmethyl)benzenecarboximidamide

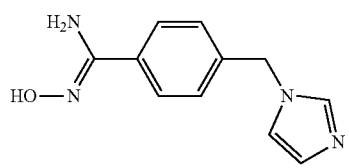 [SMILES: N/C(=N\O)c1ccc(Cn2ccnc2)cc1]

The title compound was prepared following the procedure described for Intermediate 3, but starting from 4-((1H-imidazol-1-yl)methyl)benzonitrile (Maybridge; 1 g; 5.5 mmol), to give Intermediate 24 as a white solid (1.12 g; 94%). $^1$H NMR: (DMSO-$d_6$, 400 MHz) δ 9.66 (1H, s), 7.79 (1H, s), 7.68 (2H, d, J=8.1 Hz), 7.27 (2H, d, J=8.1 Hz), 7.22 (1H, s), 6.94 (1H, s), 5.82 (2H, br s), 5.24 (2H, s). LC/MS: 217 (M+H)$^+$. HPLC (Method D) Rt 9.86 min (Purity: 94.0%).

Intermediate 25

N'-hydroxy-4-(1H-pyrazol-1-ylmethyl)benzenecarboximidamide

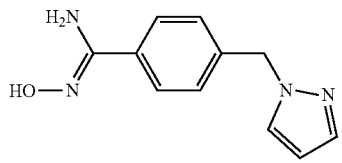 [SMILES: N/C(=N\O)c1ccc(Cn2cccn2)cc1]

To a solution of 4-((1H-pyrazol-1-yl)methyl)benzonitrile (Maybridge; 1 g; 5.5 mmol) in abs. EtOH (7 mL) was added hydroxylamine (1.8 mL; 27 mmol) (50% in water) and the mixture was heated to 78° C. for 18 hours. Brine (10 mL) was added and the EtOH removed in vacuo. The mixture was extracted with EtOAc (3×20 mL) and the combined organic fractions passed through a hydrophobic frit and the solvent removed in vacuo to give Intermediate 25 as an orange oil (1.14 g; 96%). $^1$H NMR: (DMSO-$d_6$, 400 MHz) δ 9.64 (1H, s), 7.86 (1H, d, J=2.3 Hz), 7.65 (2H, d, J=8.1 Hz), 7.50 (1H, d, J=1.8 Hz), 7.22 (2H, d, J=8.1 Hz), 6.31 (1H, t, J=2.1 Hz), 5.81 (2H, br s), 5.38 (2H, s). LC/MS: 217 (M+H)$^+$. HPLC (Method D) Rt 10.63 min (Purity: 92.0%).

Intermediate 26 ethyl 1-cyclohexyl-5-(tetrahydrofuran-2-yl)-1H-pyrazole-4-carboxylate

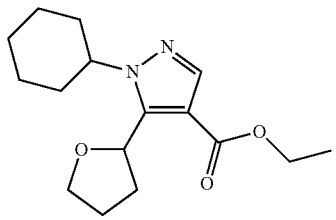 [SMILES: CCOC(=O)c1cnn(C2CCCCC2)c1C1CCCO1]

The title compound was prepared following the procedure described for Intermediate 7, but starting from ethyl 3-oxo-3-(tetrahydrofuran-2-yl)propanoate (Pharmacore; 186 mg; 1.0 mmol) and cyclohexylhydrazine hydrochloride (Fluorochem; 151 mg; 1.0 mmol), to give Intermediate 26 as a yellow oil. $^1$H NMR (CDCl$_3$, 400 MHz) δ 7.85 (1 H, s), 5.72 (1 H, dd, J=9.9, 6.7 Hz), 4.40 (1 H, tt, J=11.5, 3.9 Hz), 4.31-4.19 (2 H, m), 4.15-4.06 (1 H, m), 3.95-3.88 (1 H, m), 2.46-2.35 (1 H, m), 2.18-1.78 (9 H, m), 1.79-1.64 (1 H, m), 1.40-1.20 (6 H, m). LC/MS: 293 (M+H)$^+$. HPLC (Method A) Rt 4.12 min (Purity: 97.3%).

Intermediate 27 methyl 1-isobutyl-5-(methoxymethyl)-1H-pyrazole-4-carboxylate

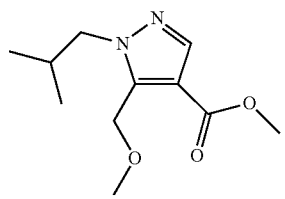 [SMILES: COCc1c(C(=O)OC)cnn1CC(C)C]

The title compound was prepared following the procedure described for Intermediate 7, but starting from methyl 4-methoxy-3-oxobutanoate (3.9 mL; 30 mmol) and isobutylhydrazine hydrochloride (151 mg; 1.0 mmol), to give Intermediate 27 as a brown oil. $^1$H NMR (CDCl$_3$, 400 MHz) δ 7.89 (1 H, s), 4.84 (2 H, s), 3.98 (2 H, d, J=7.5 Hz), 3.83 (3 H, s), 3.36 (3 H, s), 2.39-2.26 (1 H, m), 0.92 (6 H, d, J=6.7 Hz). LC/MS: 227 (M+H)$^+$. HPLC (Method A) Rt 3.29 min (Purity: 93.3%).

Intermediate 28 ethyl 1-(2-phenylethyl)-5-pyridin-4-yl-1H-pyrazole-4-carboxylate

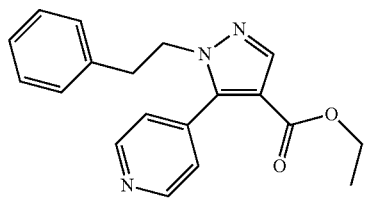 [SMILES: CCOC(=O)c1cnn(CCc2ccccc2)c1-c1ccncc1]

Step 1: (Z)-ethyl 3-(dimethylamino)-2-isonicotinoylacrylate

Pyridinium p-toluene sulfonate (7.8 mg; 0.031 mmol) and DMF.DMA (5.35 mL; 40.3 mmol) were added to a solution of ethyl isonicotinoylacetate (6.0 g; 31.0 mmol) in anhydrous toluene (40 mL) and the mixture was heated to 90° C. for 3 hours. The mixture was cooled, water (50 mL) was added and the product was extracted with DCM (3×50 mL). The combined organic fractions were passed through a hydrophobic frit and the solvent was removed in vacuo to give the title compound as a purple oil (7.68 g; 99.8%). The compound was used directly without any further purification.

Step 2: ethyl 1-(2-phenylethyl)-5-pyridin-4-yl-1H-pyrazole-4-carboxylate (Z)-ethyl 3-(dimethylamino)-2-isonicotinoylacrylate (1.86 g; 7.50 mmol), obtained from step 1, in ethanol (15 mL) was added to a mixture of phenethylhydrazine hydrochloride (2.58 g; 15.0 mmol) and sodium acetate (1.85 g; 22.50 mmol)

Intermediate 29 ethyl 1-(cyclopropyl methyl)-5-pyridin-4-yl-1H-pyrazole-4-carboxylate

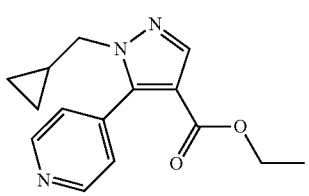 [SMILES: CCOC(=O)c1cnn(CC2CC2)c1-c1ccncc1]

The title compound was prepared following the procedure described for Intermediate 28, but starting from (cyclopropylmethyl)hydrazine hydrochloride (1.84 g; 15.0 mmol). Intermediate 29 was obtained as a yellow solid. $^1$H NMR: (CDCl$_3$, 400 MHz) δ 8.76 (2 H, d, J=4.5), 8.03 (1 H, s), 7.35 (2 H, d, 4.5 Hz), 4.18 (2 H, q), 3.85 (2 H, d, J=7.0 Hz), 1.19-1.07 (4 H, m), 0.54-0.48 (2 H, m), 0.18-0.13 (2 H, m). LC/MS: 272 (M+H)$^+$. HPLC (Method A) Rt 2.63 min (Purity: 58.5%).

Intermediate 30 ethyl 1-(2,2-dimethylpropyl)-5-pyridin-4-yl-1H-pyrazole-4-carboxylate

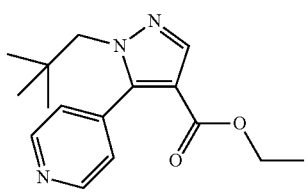 [SMILES: CCOC(=O)c1cnn(CC(C)(C)C)c1-c1ccncc1]

The title compound was prepared following the procedure described for Intermediate 28, but starting from neopentylhydrazine hydrochloride (2.08 g; 15.0 mmol). Intermediate 30 was obtained as a pale yellow solid (1.78 g; 82.6%). $^1$H NMR: (CDCl$_3$, 400 MHz) δ 8.75 (2 H, d, J=4.4 Hz), 8.05 (1 H, s), 7.29 (2 H, d, J=4.4 Hz), 4.16 (2 H, q, J=7.2 Hz), 3.86 (2 H, s), 1.17 (3 H, t, J=7.1 Hz), 0.81 (9 H, s). LC/MS: 288 (M+H)$^+$. HPLC (Method A) Rt 3.14 min (Purity: 91.5%).

Intermediate 31

1-cyclohexyl-5-(methoxymethyl)-1H-pyrazole-4-carboxylic acid

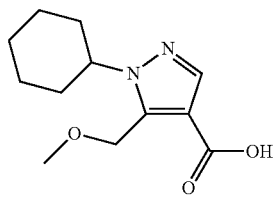 [SMILES: COCc1c(C(=O)O)cnn1C1CCCCC1]

Intermediate 18 (1.0 g; 4.0 mmol) was dissolved in methanol (10 mL) and water (1 mL) and lithium hydroxide monohydrate (336 mg; 8.0 mmol) was added. The mixture was heated to 80° C. for 18 hours. The solvent was removed in vacuo and the residue redissolved in DCM (20 mL) and extracted into water (3×10 mL). The aqueous phase was then acidified with 2M HCl and the product extracted into DCM (2×10 mL) and ethyl acetate (2×10 mL). The combined organic extracts were passed through a hydrophobic frit and concentrated in vacuo to give Intermediate 31 as a white solid (800 mg; 83.9%). $^1$H NMR: (DMSO-d$_6$, 400 MHz) δ 12.40 (1H, s), 7.84 (1 H, s), 4.84 (2 H, s), 4.30-4.23 (1 H, m), 3.25 (3 H, s), 1.88-1.77 (6 H, m), 1.70 (1 H, d, J=12.6 Hz), 1.50-1.38 (2 H, m), 1.30-1.15 (1 H, m). LC/MS: 239 (M+H)$^+$. HPLC (Method A) Rt 2.96 min (Purity: 99.5%).

Intermediate 32

N',3-dihydroxybenzenecarboximidamide

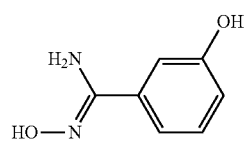

To a solution of 3-hydroxybenzonitrile (1.51 g; 12.68 mmol) in abs. EtOH (20 mL) was added hydroxylamine (4.0 mL; 60 mmol) (50% in water) and the mixture was heated to 78° C. for 18 hours. The mixture was poured into a crystallizing dish and the solvent allowed to evaporate. The residue was washed with copious amounts of EtOAc, dry MeOH and dry MeCN which was filtered through a hydrophobic frit and the solvent removed in vacuo to give Intermediate 32 as a white solid. $^1$H NMR: (DMSO-d$_6$, 400 MHz) δ 9.60 (1H, s), 9.49 (1H, s), 7.20-7.16 (1H, m), 7.19-7.10 (2H, m), 6.80-6.78 (1H, m), 5.74 (2H, s).

Intermediate 33

N'-hydroxy-4-(2-hydroxyethyl)benzenecarboximidamide

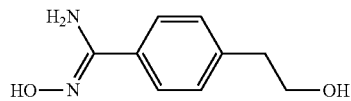

Hydroxylamine (5 mL) was added to a solution of 4-(2-hydroxyethyl)benzonitrile (2.43 g; 16.5 mmol) in ethanol (30 mL) and the mixture was heated to 80° C. in a sealed tube for 3 hours. The solvent was removed in vacuo and the residue triturated with water to yield Intermediate 33 (2.95 g; 99%) as a white solid which was used without further purification. ¹H NMR (DMSO-d₆, 400 MHz) δ 9.58 (1 H, s), 7.60 (2 H, d, J=7.9 Hz), 7.24 (2 H, d, J=7.9 Hz), 5.75 (2 H, s), 4.75-4.69 (1 H, m), 3.64 (2 H, d, J=6.6 Hz), 2.80-2.72 (2 H, m).

Intermediate 34

6-amino-N'-hydroxypyridine-3-carboximidamide

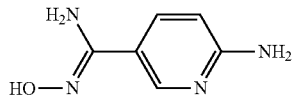

To a solution of 6-aminonicotinonitrile (Aldrich; 1.02 g, 8.57 mmol) in EtOH (10 mL) was added hydroxylamine (2.82 mL, 42.5 mmol) and the mixture stirred at 80° C. for 8 hours. The mixture was cooled to 0° C. and the precipitated solid was collected by filtration to give Intermediate 34 (1.15 g, 88%) as a brown solid. ¹H NMR: (DMSO-d₆, 400 MHz) δ 9.36 (1 H, s), 8.23 (1 H, d, J=2.4 Hz), 7.64 (1 H, dd, J=8.6, 2.4 Hz), 6.43 (1 H, d, J=8.6 Hz), 6.13 (2 H, s), 5.68 (2 H, s).

Intermediate 35 tert-butyl 3-[7-[amino(hydroxyimino)methyl]-3,4-dihydroisoquinolin-2(1H)-yl]propanoate

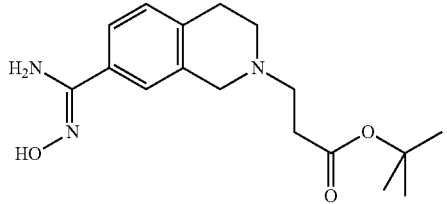 [SMILES: CC(C)(C)OC(=O)CCN1CCc2ccc(/C(N)=N/O)cc2C1]

Step 1: tert-butyl 3-(7-cyano-3,4-dihydroisoquinolin-2(1H)-yl)propanoate

7-Cyano-1,2,3,4-tetrahydroisoquinoline (7 g; 44.25 mmol; 1 eq.) and K₂CO₃ (7.34 g; 53.1 mmol; 1.2 eq) were suspended in CH₃CN (280 mL). tert-Butyl 3-bromopropionate (7.77 mL; 46.46 mmol; 1.05 eq.) was added. The reaction mixture was heated to 70° C. for 24 hours. As the reaction was not complete, tert-butyl 3-bromopropionate (3.70 mL; 22.12 mmol; 0.50 eq.) and K₂CO₃ (3.06 g; 22.12 mmol; 0.5 eq) were added and the mixture was stirred at 70° C. for additional 48 hours. Solvents were removed under vacuum and the solid residue was partitioned between NaHCO₃ sat (100 mL) and EtOAc (200 mL). The organic layer was then washed with brine and dried over magnesium to give the title compound as a yellow oil (11.9 g; 93.9%). It was used in the next step without further purification. ¹H NMR (DMSO-d₆, 400 MHz) δ 7.57-7.54 (m, 2H), 7.32-7.29 (m, 1H), 3.59 (s, 2H), 2.87-2.83 (t, J=5.94 Hz, 2H), 2.74-2.66 (m, 4H), 2.46-2.42 (t, J=7.01 Hz, 2H), 1.39 (s, 9H). HPLC/MS: 287.1 (M+H)⁺. HPLC (Method A) Rt 2.37 min (Purity: 96.4%).

Step 2: tert-butyl 3[7-[amino(hydroxyimino)methyl]-3,4-dihydroisoquinolin-2(1H)yl]propanoate tert-Butyl 3-(7-cyano-3,4-dihydroisoquinolin-2(1H)-yl)propanoate (11.85 g; 41.38 mmol; 1 eq.) was suspended in EtOH (237 mL). Hydroxylamine (6.1 mL; 206.90 mmol; 5 eq.) was added in one portion. The reaction mixture was stirred at RT for 48 h. The reaction mixture was concentrated under vacuum to give the title compound as a yellow oil. Diisopropyl ether (50 mL) was added. The resulting mixture was sonicated and concentrated under vacuum. This process was repeated 3 times, affording Intermediate 35 as a yellowish solid (13.2 g; quantitative). ¹H NMR: (DMSO-d₆, 400 MHz) δ 9.51 (br s, 1H), 7.43-7.34 (m, 2H), 7.09-7.06 (d, J=8.17 Hz, 1H), 5.71 (br s, 2H), 3.56 (s, 2H), 2.79-2.64 (m, 6H), 2.47-2.42 (t, J=6.93 Hz, 2H), 1.39 (s, 9H), traces of EtOH by NMR. HPLC/MS: 320.1.

Example 1

3-(2,5-difluorophenyl)-5-(5-(methoxymethyl)-1-phenyl-1H-pyrazol-4-yl)-1,2,4-oxadiazole

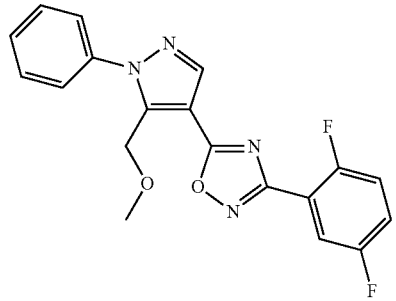

In a microwave vial, methyl 5-(methoxymethyl)-1-phenyl-1H-pyrazole-4-carboxylate (165 mg; 0.67 mmol) [prepared following the procedure described in Menozzi, G et al, *Farmaco*, 1990, 45, 167-186] was suspended in toluene (2 mL) and 2,5-difluoro-N'-hydroxybenzenecarboximidamide (Fluorochem, 144 mg; 0.74 mmol) was added followed by potassium carbonate (123 mg; 0.74 mmol). The Microwave vial was sealed and the mixture was heated to 180° C. in a microwave reactor for 25 min. MeCN (1 mL) was added and the mixture was heated to 180° C. in a microwave reactor for 15 min. DMF (0.5 mL) was added and the mixture was heated to 180° C. in a microwave reactor for 5 min. The reaction mixture was diluted with DCM and washed with water. The organic phase was passed through a hydrophobic frit and evaporated. The residue was purified by flash chromatography on a Biotage 25+S column, eluting with petrol containing increasing amounts of EtOAc. The product was triturated with isopropanol to give Example 1 as an off-white solid. ¹H NMR: (CDCl₃, 400 MHz) δ 8.34 (1H, s), 7.89-7.84 (1H, m), 7.73-7.69 (2H, m), 7.58-7.47 (3H, m), 7.27-7.17 (2H, m), 4.84 (2H, s), 3.53 (3H, s). LC/MS: 369 (M+H)⁺. HPLC (Method B) Rt 4.13 min (Purity: 98.7%).

Example 2

3-(2,5-difluorophenyl)-5-[1-(2-fluorophenyl)-5-phenyl-1H-pyrazol-4-yl]-1,2,4-oxadiazole

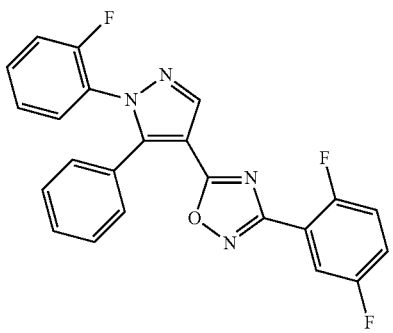 [SMILES: Fc1ccc(F)c(-c2noc(-c3cnn(-c4ccccc4F)c3-c3ccccc3)n2)c1]

To a solution of Intermediate 1 (100 mg; 0.33 mmol) in toluene (2.5 mL) was added DMF.DMA (57 µL) and PPTS (10 mg). The mixture was heated to 90° C. for 2 hours. DCM (10 mL) and water (10 mL) were added and the mixture passed through a hydrophobic frit. The solvent was removed in vacuo and the residue taken up into ethanol (2 mL). Acetic acid (0.03 mL) and (2-fluorophenyl)hydrazine hydrochloride (Fluorochem; 54 mg; 0.33 mmol) were added and the mixture heated to reflux for 3 hours. The solvent was removed in vacuo and the residue triturated with isopropanol and dried to give Example 2 as a white solid. $^1$H NMR: (CDCl$_3$, 400 MHz) δ 8.48 (1H, s), 7.77-7.71 (1H, m), 7.46-7.33 (7H, m), 7.24-7.12 (3H, m), 7.11-7.04 (1H, m). LC/MS: 419 (M+H)$^+$. HPLC (Method A) Rt 4.42 min (Purity: 98.6%).

Example 3

3-(2,5-difluorophenyl)-5-(1,5-diphenyl-1H-pyrazol-4-yl)-1,2,4-oxadiazole

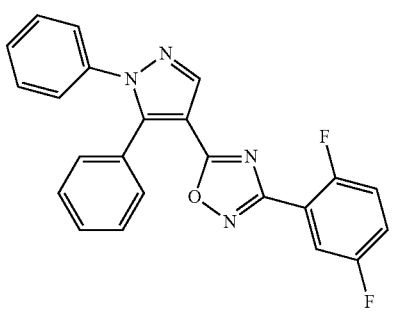 [SMILES: Fc1ccc(F)c(-c2noc(-c3cnn(-c4ccccc4)c3-c3ccccc3)n2)c1]

To a solution of Intermediate 1 (113 mg; 0.37 mmol) in toluene (2.5 mL) was added DMF.DMA (65 µL) and PPTS (10 mg). The mixture was heated to 90° C. for 2 hours. DCM (10 mL) and water (10 mL) were added and the mixture passed through a hydrophobic frit. The solvent was removed in vacuo and the residue taken up into ethanol (2 mL) and acetic acid (0.04 mL) and phenylhydrazine (0.04 mL; 0.37 mmol) added and the mixture heated to reflux for 6 hours. The solvent was removed in vacuo and the residue purified by flash chromatography on a Biotage 12+M column, eluting with petrol containing increasing amounts of EtOAc. The product was triturated with isopropanol and dried to give Example 3 as an off-white solid. $^1$H NMR: (CDCl$_3$, 400 MHz) δ 8.43 (1H, s), 7.76-7.70 (1H, m), 7.47-7.37 (5H, m), 7.35-7.25 (5H, m), 7.22-7.12 (2H, m). LC/MS: 401 (M+H)$^+$. HPLC (Method B) Rt 4.26 min (Purity: 97.5%).

Example 4

3-(2,5-difluorophenyl)-5-[1-(2-methoxyphenyl)-5-phenyl-1H-pyrazol-4-yl]-1,2,4-oxadiazole

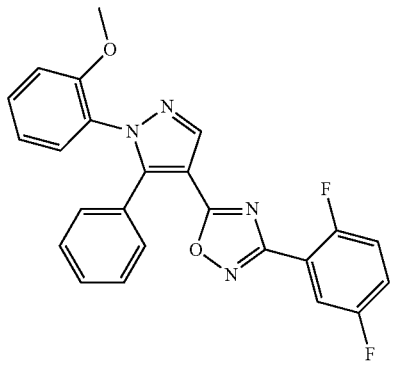 [SMILES: COc1ccccc1-n1ncc(-c2nc(-c3cc(F)ccc3F)no2)c1-c1ccccc1]

The title compound was prepared following the procedure described for Example 3 but starting from Intermediate 1 (0.37 mmol) and (2-methoxyphenyl)hydrazine hydrochloride (Fluorochem; 65 mg; 0.37 mmol), to give Example 4 as an off-white solid. $^1$H NMR: (CDCl$_3$, 400 MHz) δ 8.44 (1H, s), 7.77-7.71 (1H, m), 7.41-7.31 (7H, m), 7.22-7.14 (2H, m), 7.00 (1H, td, J=7.6, 1.2 Hz), 6.84 (1H, dd, J=8.4, 1.2 Hz), 3.53 (3H, s). LC/MS: 431 (M+H)$^+$. HPLC (Method B) Rt 4.10 min (Purity: 99.3%).

Example 5

3-(2,5-difluorophenyl)-5-(5-phenyl-1-o-tolyl-1H-pyrazol-4-yl)-1,2,4-oxadiazole

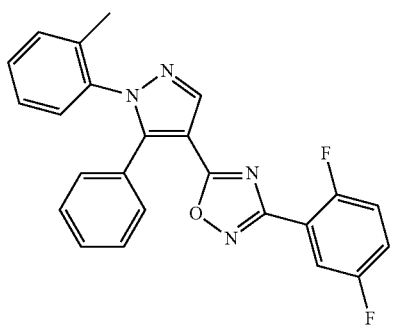 [SMILES: Cc1ccccc1-n1ncc(-c2nc(-c3cc(F)ccc3F)no2)c1-c1ccccc1]

The title compound was prepared following the procedure described for Example 3 but starting from Intermediate 1 (0.37 mmol) and o-tolylhydrazine hydrochloride (59 mg; 0.37 mmol), to give Example 5 as a yellow solid. $^1$H NMR: (CDCl$_3$, 400 MHz) δ 8.45 (1H, s), 7.77-7.71 (1H, m), 7.41-

7.15 (11 H, m), 2.05 (3H, s). LC/MS: 415 (M+H)+. HPLC (Method B) Rt 4.29 min (Purity: 96.0%).

Example 6

3-(2,5-difluorophenyl)-5-(1-(4-fluorophenyl)-5-phenyl-1H-pyrazol-4-yl)-1,2,4-oxadiazole

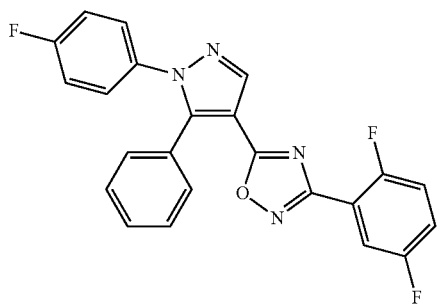 [SMILES: Fc1ccc(-n2ncc(-c3nc(-c4cc(F)ccc4F)no3)c2-c2ccccc2)cc1]

The title compound was prepared following the procedure described for Example 3 but starting from Intermediate 1 (0.37 mmol) and (4-fluorophenyl)hydrazine hydrochloride (60 mg; 0.37 mmol), to give Example 6 as a yellow solid. $^1$H NMR: (CDCl$_3$, 400 MHz) δ 8.42 (1H, s), 7.75-7.69 (1H, m), 7.49-7.34 (6H, m), 7.29-7.22 (1H, m), 7.21-7.14 (2H, m), 7.06-6.98 (2H, m). LC/MS: 419 (M+H)+. HPLC (Method B) Rt 4.26 min (Purity: 95.1%).

Example 7

3-(2,5-difluorophenyl)-5-(1-isobutyl-3-phenyl-1H-pyrazol-4-yl)-1,2,4-oxadiazole

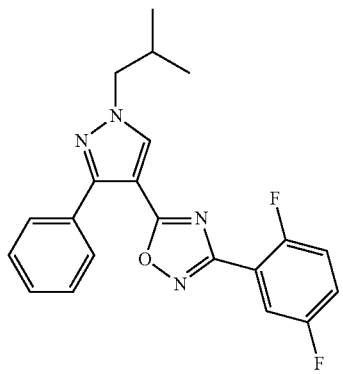 [SMILES: CC(C)Cn1cc(-c2nc(-c3cc(F)ccc3F)no2)c(-c2ccccc2)n1]

The title compound was prepared following the procedure described for Example 3 but starting from Intermediate 1 (0.37 mmol) and isobutylhydrazine hydrochloride (Fluorochem; 92 mg; 0.37 mmol), to give Example 7 as a yellow solid. $^1$H NMR: (CDCl$_3$, 400 MHz) δ 8.20 (1H, s), 7.91-7.86 (2H, m), 7.79-7.73 (1H, m), 7.50-7.40 (3H, m), 7.21-7.15 (2H, m), 4.04 (2H, d, J=7.3 Hz), 2.41-2.31 (1H, m), 1.01 (6H, d, J=6.7 Hz). LC/MS: 381 (M+H)+. HPLC (Method B) Rt 4.40 min (Purity: 97.9%).

Example 8

4-[4-[3-(2,5-difluorophenyl)-1,2,4-oxadiazol-5-yl]-1-(2-fluorophenyl)-1H-pyrazol-5-yl]pyridine

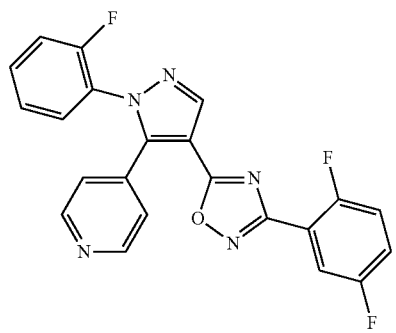 [SMILES: Fc1ccc(F)c(-c2noc(-c3cnn(-c4ccccc4F)c3-c3ccncc3)n2)c1]

The title compound was prepared following the procedure described for Example 3 but starting from Intermediate 2 (0.37 mmol) and (2-fluorophenyl)hydrazine hydrochloride (Fluorochem; 61 mg; 0.37 mmol), to give Example 8 as a brown gum. $^1$H NMR: (CDCl$_3$, 400 MHz) δ 8.68-8.64 (2H, m), 8.50 (1H, s), 7.74-7.68 (1H, m), 7.52-7.40 (2H, m), 7.34-7.30 (2H, m), 7.30-7.24 (1H, m), 7.22-7.15 (2H, m), 7.12-7.07 (1H, m). LC/MS: 420 (M+H)+. HPLC (Method B) Rt 3.69 min (Purity: 98.8%).

Example 9

4-(1-(2-fluorophenyl)-4-{3-[3-(methylsulfonyl)phenyl]-1,2,4-oxadiazol-5-yl}-1H-pyrazol-5-yl)pyridine

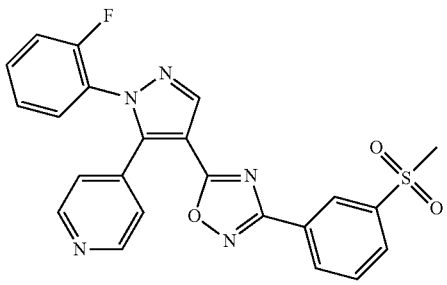 [SMILES: CS(=O)(=O)c1cccc(-c2noc(-c3cnn(-c4ccccc4F)c3-c3ccncc3)n2)c1]

To a solution of Intermediate 4 (70 mg; 0.2 mmol) in toluene (1.4 mL) was added DMF.DMA (40 μL) and PPTS (6 mg). The mixture was heated to 90° C. for 2 hours. DCM (10 mL) and water (10 mL) were added and the mixture passed through a hydrophobic frit. The solvent was removed in vacuo and redissolved in ethanol (1.2 mL) and acetic acid (0.02 mL) and (2-fluorophenyl)hydrazine hydrochloride (33 mg; 0.2 mmol) added and the mixture heated to reflux for 12 hours. The solvent was removed in vacuo and the residue purified by flash chromatography on a Biotage 12+M column, eluting with petrol containing increasing amounts of EtOAc to give Example 9 as an off-white solid. $^1$H NMR: (CDCl$_3$, 400 MHz) δ 8.69-8.66 (2H, m), 8.66 (1H, t, J=1.7 Hz), 8.51 (1H, s), 8.31 (1H, dt, J=7.8, 1.35 Hz), 8.09 (1H, dt, J=7.9, 1.4 Hz), 7.71 (1H, t, J=7.8 Hz, ArH), 7.53-7.41 (2H, m), 7.34-

7.31 (2H, m), 7.30-7.25 (1H, m), 7.13-7.06 (1H, m), 3.11 (3H, s). LC/MS: 462 (M+H)+. HPLC (Method A) Rt 3.20 min (Purity: 99.4%).

Example 10

3-(2,5-difluorophenyl)-5-(1-isopropyl-5-phenyl-1H-pyrazol-4-yl)-1,2,4-oxadiazole

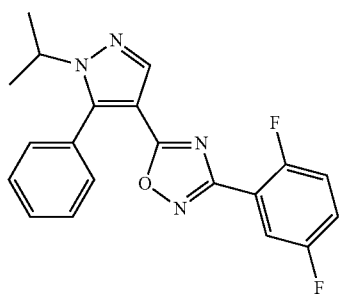 [SMILES: CC(C)n1ncc(-c2nc(-c3cc(F)ccc3F)no2)c1-c1ccccc1]

To a solution of Intermediate 1 (112 mg; 0.37 mmol) in toluene (2.8 mL) was added DMF.DMA (64 μL) and PPTS (11 mg). The mixture was heated to 90° C. for 2 hours. DCM (10 mL) and water (10 mL) were added and the mixture passed through a hydrophobic frit. The solvent was removed in vacuo and the residue taken up in ethanol (2 mL). This mixture was added to a solution of isopropylhydrazine hydrochloride (Matrix; 41 mg; 0.37 mmol) and sodium acetate (61 mg; 0.74 mmol) in ethanol (0.5 mL) and water (0.25 mL). The mixture was heated to reflux for 3 hours and then DCM (10 mL) and water (10 mL). The mixture was filtered through a hydrophobic frit and the solvent removed in vacuo. The residue was purified by flash chromatography on a Biotage 25+S column, eluting with petrol containing increasing amounts of DCM to give Example 10 as a golden gum. 1H NMR: (CDCl3, 400 MHz) δ 8.27 (1H, s), 7.71-7.65 (1H, m), 7.57-7.51 (3H, m), 7.46-7.41 (2H, m), 7.20-7.10 (2H, m), 4.43 (1H, septet, J=6.6 Hz), 1.49 (6H, d, J=6.6 Hz). LC/MS: 367 (M+H)+. HPLC (Method A) Rt 4.32 min (Purity: 95.4%).

Example 11

5-(1-cyclohexyl)-5-phenyl-1H-pyrazol-4-yl)-3-(2,5-difluorophenyl)-1,2,4-oxadiazole

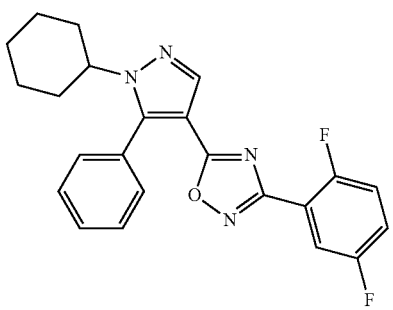 [SMILES: Fc1ccc(F)c(-c2noc(-c3cnn(C4CCCCC4)c3-c3ccccc3)n2)c1]

The title compound was prepared following the procedure described for Example 10 but starting from Intermediate 1 (0.37 mmol) and cyclohexylhydrazine hydrochloride (Fluorochem; 56 mg; 0.37 mmol), to give Example 11 as an off-white solid. 1H NMR: (CDCl3, 400 MHz) δ 8.25 (1H, s), 7.71-7.65 (1H, m), 7.57-7.51 (3H, m), 7.45-7.40 (2H, m), 7.19-7.10 (2H, m), 3.98 (1H, tt, J=11.7, 3.9 Hz), 2.12-1.99 (2H, m), 1.94-1.81 (4H, m), 1.70-1.63 (1H, m), 1.33-1.14 (3H, m). LC/MS: 407 (M+H)+. HPLC (Method B) Rt 4.84 min (Purity: 96.0%).

Example 12

3-(2,5-difluorophenyl)-5-(1-isobutyl-5-phenyl-1H-pyrazol-4-yl)-1,2,4-oxadiazole

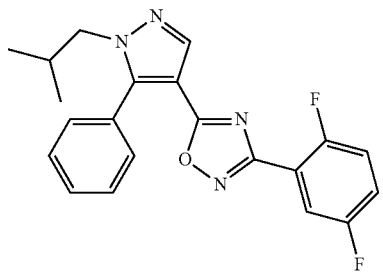 [SMILES: CC(C)Cn1ncc(-c2nc(-c3cc(F)ccc3F)no2)c1-c1ccccc1]

The title compound was prepared following the procedure described for Example 10 but starting from Intermediate 1 (0.37 mmol) and isobutylhydrazine hydrochloride (Fluorochem; 46 mg; 0.37 mmol), to give Example 12 as a white solid. 1H NMR: (CDCl3, 400 MHz) δ 8.26 (1H, s), 7.70-7.65 (1H, m), 7.55-7.50 (3H, m), 7.45-7.40 (2H, m), 7.19-7.11 (2H, m), 3.87 (2H, d, J=7.5 Hz), 2.28-2.18 (1H, m), 0.81 (6H, d, J=6.7 Hz). LC/MS: 381 (M+H)+. HPLC (Method A) Rt 4.45 min (Purity: 99.5%).

Example 13 ethyl {4-[3-(2,5-difluorophenyl)-1,2,4-oxadiazol-5-yl]-5-phenyl-1H-pyrazol-1-yl}acetate

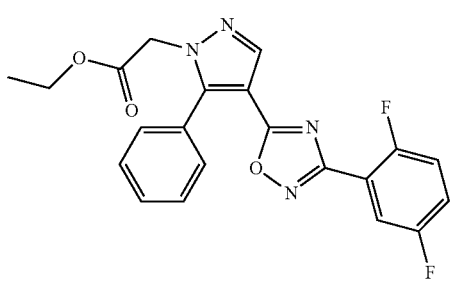 [SMILES: CCOC(=O)Cn1ncc(-c2nc(-c3cc(F)ccc3F)no2)c1-c1ccccc1]

The title compound was prepared following the procedure described for Example 10 but starting from Intermediate 1 (0.37 mmol) and ethyl 2-hydrazinylacetate hydrochloride (46 mg; 0.37 mmol). Purification by flash chromatography on a Biotage 25+S column, eluting with DCM containing increasing amounts of methanol to give Example 13 as a white solid. 1H NMR: (CDCl3, 400 MHz) δ 8.31 (1H, s), 7.72-7.66 (1H, m), 7.57-7.45 (5H, m), 7.21-7.11 (2H, m), 4.83 (2H, s), 4.22

(2H, q, J=7.1 Hz), 1.25 (3H, t, J=7.1 Hz). LC/MS: 411 (M+H)+. HPLC (Method A) Rt 4.00 min (Purity: 96.5%).

Example 14

3-(2,5-difluorophenyl)-5-(5-phenyl-1-propyl-1H-pyrazol-4-yl)-1,2,4-oxadiazole

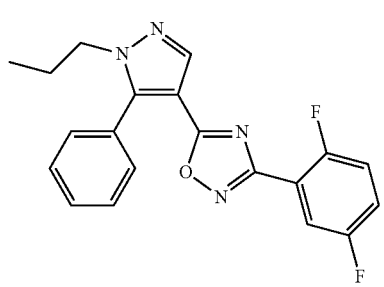 [SMILES: CCCn1ncc(-c2nc(-c3cc(F)ccc3F)no2)c1-c1ccccc1]

The title compound was prepared following the procedure described for Example 10 but starting from Intermediate 1 (0.37 mmol) and propylhydrazine oxalate (61 mg; 0.37 mmol), to give Example 14 as a white solid. ¹H NMR: (CDCl₃, 400 MHz) δ 8.26 (1H, s), 7.71-7.65 (1H, m), 7.57-7.51 (3H, m), 7.48-7.42 (2H, m), 7.20-7.10 (2H, m), 4.02 (2H, t, J=7.2 Hz), 1.85 (2H, app sextet, J=7.3 Hz), 0.84 (3H, t, J=7.4 Hz). LC/MS: 367 (M+H)+. HPLC (Method A) Rt 4.31 min (Purity: 97.6%).

Example 15

3-(2,5-difluorophenyl)-5-(5-methyl-1-phenyl-1H-pyrazol-4-yl)-1,2,4-oxadiazole

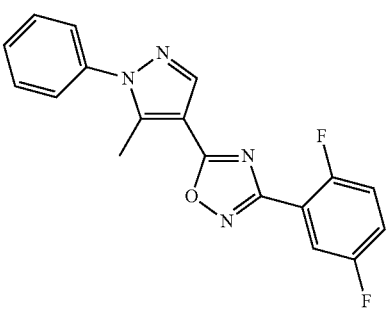 [SMILES: Cc1c(-c2nc(-c3cc(F)ccc3F)no2)cnn1-c1ccccc1]

In a microwave vial, methyl 5-methyl-1-phenyl-1H-pyrazole-4-carboxylate (Fluorochem; 145 mg; 0.67 mmol) was suspended in toluene (2 mL) and 2,5-difluoro-N'-hydroxybenzenecarboximidamide (JRD-Fluorochemical, 145 mg; 0.74 mmol) was added followed by potassium carbonate (123 mg; 0.74 mmol). The Microwave vial was sealed and the mixture was heated to 180° C. in a microwave reactor for 45 min. The reaction mixture was diluted with DCM (10 mL) and washed with water (10 mL). The organic phase was passed through a hydrophobic frit and evaporated. The residue was triturated with isopropanol to give Example 15 as an off-white solid. ¹H NMR: (CDCl₃, 400 MHz) δ 8.28 (1H, s), 7.91-7.85 (1H, m), 7.59-7.47 (5H, m), 7.27-7.16 (2H, m), 2.75 (3H, s). LC/MS: 339 (M+H)+. HPLC (Method A) Rt 4.17 min (Purity: 99.5%).

Example 16

5-(3-tert-butyl-1-methyl-1H-pyrazol-4-yl)-3-(2,5-difluorophenyl)-1,2,4-oxadiazole

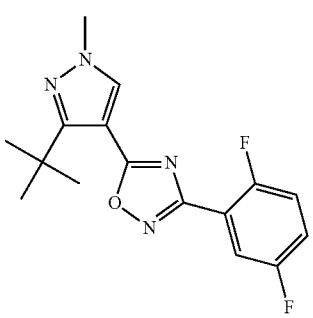 [SMILES: Cn1cc(-c2nc(-c3cc(F)ccc3F)no2)c(C(C)(C)C)n1]

To a solution of 3-tert-butyl-1-methyl-1H-pyrazole-4-carboxylic acid (Fulcrum; 55 mg; 0.3 mmol) in anhydrous MeCN (2 mL) was added 1-ethyl-3-(3-dimethylaminopropyl)carbodiimide hydrochloride (EDC) (80.5 mg; 0.42 mmol) followed by 2,5-difluoro-N'-hydroxybenzenecarboximidamide (JRD-Fluorochemical, 62 mg; 0.36 mmol) in a Microwave vial and the mixture stirred at RT for 18 h. Anhydrous pyridine (2 mL) was added and the reaction vessel was sealed and heated at 150° C. for 15 min in the microwave. This reaction was performed twice and the reaction mixtures were combined for workup. H₂O (10 mL) and DCM (10 mL) were added and the mixture was passed through a hydrophobic frit and the solvent removed in vacuo. The residue was purified by flash chromatography on a Biotage 12+M column, eluting with petrol containing increasing amounts of EtOAc to give Example 16 as a white solid. ¹H NMR: (CDCl₃, 400 MHz) δ 7.87-7.81 (1H, m), 7.27-7.20 (2H, m), 6.96 (1H, s), 4.32 (3H, s), 1.36 (9H, s). LC/MS: 319 (M+H)+. HPLC (Method A) Rt 4.49 min (Purity: 99.6%).

Example 17

3-(2,5-difluorophenyl)-5-(1-isobutyl-5-(methoxymethyl)-1H-pyrazol-4-yl)-1,2,4-oxadiazole

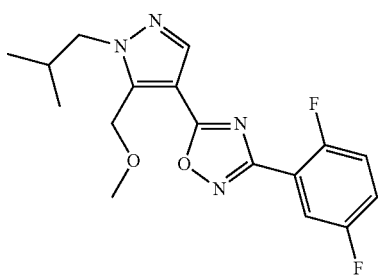 [SMILES: COCc1c(-c2nc(-c3cc(F)ccc3F)no2)cnn1CC(C)C]

The title compound was prepared following the procedure described for Example 10 but starting from Intermediate 5 (0.19 mmol) and isobutylhydrazine hydrochloride (Fluorochem; 24 mg; 0.19 mmol). Purification by flash chromatography on a Biotage 25+S column, eluting with petrol containing increasing amounts of DCM and then diethyl ether gave Example 17 as a golden gum. $^1$H NMR: (CDCl$_3$, 400 MHz) δ 8.15 (1H, s), 7.87-7.81 (1H, m), 7.26-7.16 (2H, m), 4.99 (2H, s), 4.07 (2H, d, J=7.5 Hz), 3.43 (3H, s), 2.42-2.33 (1H, m), 0.96 (6H, d, J=6.7 Hz). LC/MS: 349 (M+H)$^+$. HPLC (Method A) Rt 4.23 min (Purity: 92.9%).

Example 18

3-(2,5-difluorophenyl)-5-(5-ethyl-1-isobutyl-1H-pyrazol-4-yl)-1,2,4-oxadiazole

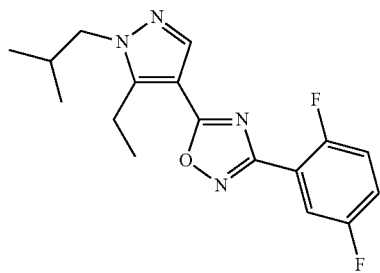 [SMILES: CCc1c(-c2nc(-c3cc(F)ccc3F)no2)cnn1CC(C)C]

The title compound was prepared following the procedure described for Example 10, but starting from Intermediate 6 (0.34 mmol) and isobutylhydrazine hydrochloride (Fluorochem; 42 mg; 0.34 mmol), to give Example 18 as an off-white solid. $^1$H NMR: (CDCl$_3$, 400 MHz) δ 8.11 (1H, s), 7.88-7.81 (1H, m), 7.27-7.15 (2H, m), 3.93 (2H, d, J=7.5 Hz), 3.14 (2H, q, J=7.5 Hz), 2.39-2.29 (1H, m), 1.32 (3H, t, J=7.5 Hz), 0.97 (6H, d, J=6.7 Hz). LC/MS: 333 (M+H)$^+$. HPLC (Method A) Rt 4.40 min (Purity: 98.5%).

Example 19

4-{4-[3-(2,5-difluorophenyl)-1,2,4-oxadiazol-5-yl]-1-isobutyl-1H-pyrazol-5-yl}pyridine

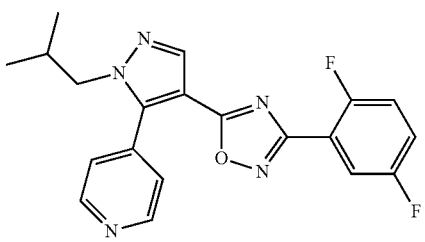 [SMILES: CC(C)Cn1ncc(-c2nc(-c3cc(F)ccc3F)no2)c1-c1ccncc1]

The title compound was prepared following the procedure described for Example 10, but starting from Intermediate 2 (0.37 mmol) and 2-methylpropylhydrazine hydrochloride (46.1 mg; 0.37 mmol), to give Example 19 as a golden gum. $^1$H NMR (CDCl$_3$, 400 MHz) δ 8.84 (2H, dd, J=4.6, 1.6 Hz), 8.28 (1 H, s), 7.68-7.60 (1 H, m), 7.40 (2 H, dd, J=4.5, 1.6 Hz), 7.21-7.10 (2 H, m), 3.88 (2 H, d, J=7.5 Hz), 2.30-2.17 (1 H, m), 0.82 (6 H, d, J=6.7 Hz). LC/MS: 382 (M+H)$^+$. HPLC (Method A) Rt=3.84 min (Purity: 99.1%).

Example 20 ethyl {4-[3-(2,5-difluorophenyl)-1,2,4-oxadiazol-5-yl]-5-pyridin-4-yl-1H-pyrazol-1-yl}acetate

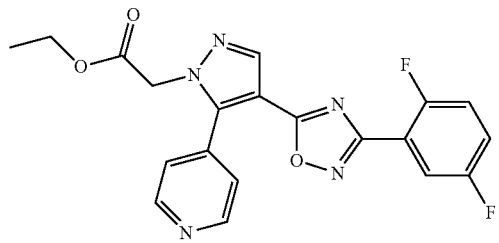 [SMILES: CCOC(=O)Cn1ncc(-c2nc(-c3cc(F)ccc3F)no2)c1-c1ccncc1]

The title compound was prepared following the procedure described for Example 10, but starting from Intermediate 2 (0.95 mmol) and ethyl hydrazinoacetate hydrochloride (146.9 mg; 0.95 mmol). The residue was purified by flash chromatography on a Biotage 25+M column, eluting with petrol containing increasing amounts of EtOAc. The residue was recrystallised from iso-propanol to give Example 20 as a white solid. $^1$H NMR (CDCl$_3$, 400 MHz) δ 8.84 (2 H, dd, J=4.6, 1.6 Hz), 8.33 (1 H, s), 7.67-7.62 (1 H, m), 7.46-7.43 (2 H, dd, J=4.5, 1.6 Hz), 7.19-7.14 (2 H, m), 4.84 (2 H, s), 4.23 (2 H, q, J=7.1 Hz), 1.27 (3 H, t, J=7.0 Hz). LC/MS: 412 (M+H)$^+$. HPLC (Method A) Rt=3.44 min (Purity: 97.7%).

Example 21

3-(2,5-difluorophenyl)-5-(1-phenyl-5-propyl-1H-pyrazol-4-yl)-1,2,4-oxadiazole

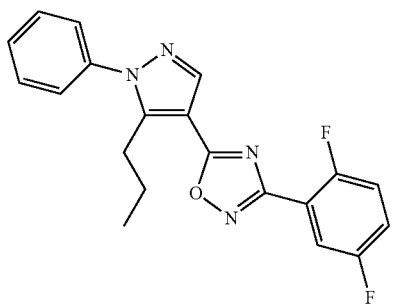

To a solution of 1-phenyl-5-propyl-1H-pyrazole-4-carboxylic acid (Acros; 69 mg; 0.3 mmol) in anhydrous MeCN (2 mL) was added 1-ethyl-3-(3-dimethylaminopropyl)carbodiimide hydrochloride (EDC) (80.5 mg; 0.42 mmol) followed by 2,5-difluoro-N'-hydroxybenzenecarboximidamide (JRD-Fluorochemical, 62 mg; 0.36 mmol) in a Microwave vial and the mixture stirred at RT for 18 h. Anhydrous pyridine (2 mL) was added and the reaction vessel was sealed and heated at 150° C. for 15 min in the microwave. H$_2$O (10 mL) and DCM (10 mL) were added and the mixture was passed through a hydrophobic frit and the solvent removed in vacuo. The residue was triturated with isopropanol to give Example 21 as an off-white solid. $^1$H NMR: (CDCl$_3$, 400 MHz) δ 8.28 (1H, s), 7.89-7.83 (1H, m), 7.58-7.44 (5H, m), 7.27-7.14 (2H, m), 3.13-3.04 (2H, m), 1.74-1.60 (2H, m), 0.93 (3H, t, J=7.4 Hz). LC/MS: 367 (M+H)⁺. HPLC (Method A) Rt 4.51 min (Purity: 98.5%).

Example 22

3-(3-(methylsulfonylphenyl)-5-(1-phenyl-5-propyl-1H-pyrazol-4-yl)-1,2,4-oxadiazole

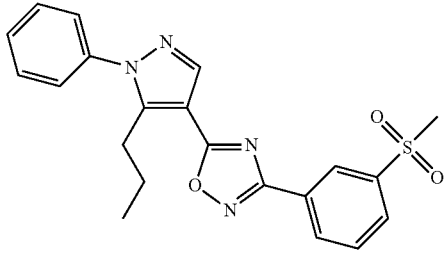 [SMILES: CCCc1c(-c2nc(-c3cccc(S(C)(=O)=O)c3)no2)cnn1-c1ccccc1]

The title compound was prepared following the procedure described for Example 21, with two identical reactions combined for workup but starting from 1-phenyl-5-propyl-1H-pyrazole-4-carboxylic acid (Acros; 69 mg; 0.3 mmol) and Intermediate 3 (77 mg; 0.36 mmol), to give Example 22 as an off-white solid. ¹H NMR: (CDCl₃, 400 MHz) δ 8.75 (1H, s), 8.45 (1H, d, J=7.8 Hz), 8.29 (1H, s), 8.11 (1H, d, J=7.9 Hz), 7.78-7.69 (1H, m), 7.59-7.45 (5H, m), 3.15-3.07 (2H, m), 3.14 (3H, s), 1.74-1.61 (2H, m), 0.94 (3H, t, J=7.4 Hz). LC/MS: 409 (M+H)⁺. HPLC (Method A) Rt 3.94 min (Purity: 99.1%).

Example 23

5-(1-cyclohexyl-5-(pyridin-4-yl)-1H-pyrazol-4-yl)-3-(2,5-difluorophenyl)-1,2,4-oxadiazole

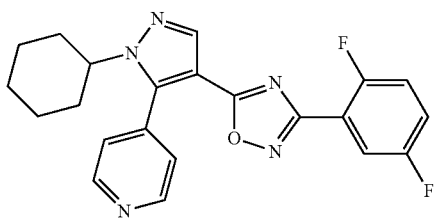 [SMILES: Fc1ccc(F)c(-c2noc(-c3cnn(C4CCCCC4)c3-c3ccncc3)n2)c1]

The title compound was prepared following the procedure described for Example 10, but starting from Intermediate 2 (0.32 mmol) and cyclohexylhydrazine hydrochloride (Fluorochem; 48.2 mg; 0.32 mmol). The residue was purified by flash chromatography on a Biotage 12+M column, eluting with petrol containing increasing amounts of EtOAc. The product was triturated with diethyl ether to give Example 23 as a white solid. ¹H NMR (CDCl₃, 400 MHz) δ 8.85 (2 H, d, J=4.9 Hz), 8.27 (1 H, s), 7.66-7.61 (1 H, m), 7.39 (2 H, d, J=5.0 Hz), 7.21-7.13 (2 H, m), 3.97-3.87 (1 H, m), 2.10-2.00 (2 H, m), 1.98-1.83 (4 H, m), 1.68 (1 H, s), 1.32-1.17 (3 H, m). LC/MS: 408 (M+H)⁺. HPLC (Method A) Rt=4.21 min (Purity: 97.9%).

Example 24

3-(2,5-difluorophenyl)-5-(5-(pyridin-4-yl)-1-(2,2,2-trifluoroethyl)-1H-pyrazol-4-yl)-1,2,4-oxadiazole

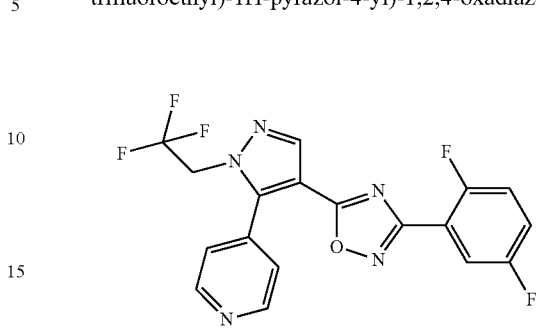

The title compound was prepared following the procedure described for Example 10, but starting from Intermediate 2 (0.32 mmol) and 2,2,2-trifluoroethyl hydrazine (52.1 mg; 70 wt % in water; 0.32 mmol). The residue was purified by flash chromatography on a Biotage 12+M column, eluting with petrol containing increasing amounts of EtOAc. The product was triturated with diethyl ether to give Example 24 as an off white solid. ¹H NMR (CDCl₃, 400 MHz) δ 8.88 (2 H, d, J=5.1 Hz), 8.38 (1 H, s), 7.66-7.60 (1 H, m), 7.42 (2 H, d, J=5.1 Hz), 7.18 (2 H, t, J=6.3 Hz), 4.67 (2 H, q, J=7.9 Hz). LC/MS: 408 (M+H)⁺. HPLC (Method A) Rt=3.62 min (Purity: 98.5%).

Example 25

4-{1-benzyl-4-[3-(2,5-difluorophenyl)-1,2,4-oxadiazol-5-yl]-1H-pyrazol-5-yl}pyridine

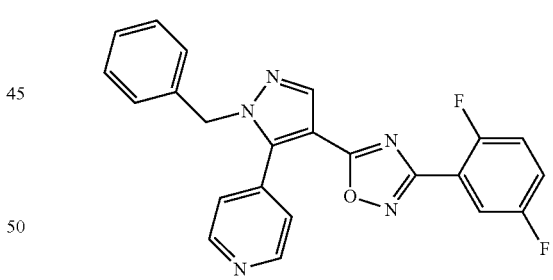

The title compound was prepared following the procedure described for Example 10, but starting from Intermediate 2 (0.32 mmol) and benzylhydrazine dihydrochloride (62.4 mg; 0.32 mmol). The residue was purified by flash chromatography on a Biotage 12+M column, eluting with petrol containing increasing amounts of EtOAc. The product was triturated with diethyl ether to give Example 25 as an off white solid. ¹H NMR (CDCl₃, 400 MHz) δ 8.79-8.74 (2 H, m), 8.33 (1 H, s), 7.66-7.61 (1 H, m), 7.35-7.27 (5 H, m), 7.21-7.11 (2 H, m), 7.06-7.02 (2 H, m), 5.30 (2 H, s). LC/MS: 416 (M+H)⁺. HPLC (Method A) Rt=3.84 min (Purity: 96.0%).

Example 26

4-(1-cyclohexyl-4-{3-[3-(methylsulfonyl)phenyl]-1,2,4-oxadiazol-5-yl}-1H-pyrazol-5-yl)pyridine

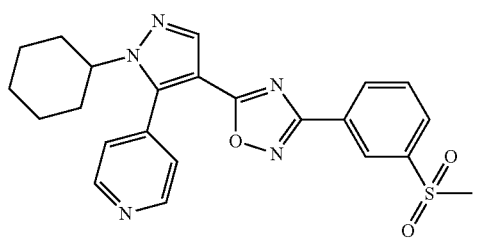 [SMILES: CS(=O)(=O)c1cccc(-c2noc(-c3cnn(C4CCCCC4)c3-c3ccncc3)n2)c1]

The title compound was prepared following the procedure described for Example 10, but starting from Intermediate 4 (0.21 mmol) and cyclohexylhydrazine hydrochloride (Fluorochem; 31.6 mg; 0.21 mmol). The residue was purified by flash chromatography on a Biotage 12+M column, eluting with petrol containing increasing amounts of EtOAc. The product was triturated with diethyl ether to give Example 26 as a white solid. $^1$H NMR (CDCl$_3$, 400 MHz) δ 8.87 (2 H, dd, J=4.4, 1.6 Hz), 8.60 (1 H, t, J=1.7 Hz), 8.28 (1H, s), 8.25 (1H, dt, J=7.9, 1.4 Hz), 8.06 (1 H, dt, J=7.9, 1.4 Hz), 7.67 (1 H, t, J=7.8 Hz), 7.40 (2 H, dd, J=4.4, 1.6 Hz), 3.97-3.88 (1 H, m), 3.09 (3 H, s), 2.13-2.01 (2 H, m), 1.92-1.85 (4 H, m), 1.72-1.67 (1 H, m), 1.32-1.18 (3 H, m). LC/MS: 450 (M+H)$^+$. HPLC (Method A) Rt=3.64 min (Purity: 98.4%).

Example 27

5-[1-cyclohexyl-5-(methoxymethyl)-1H-pyrazol-4-yl]-3-(2,5-difluorophenyl)-1,2,4-oxadiazole

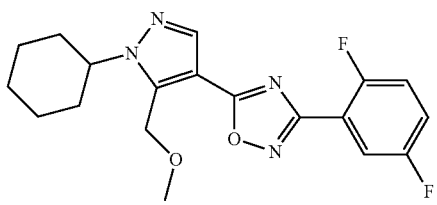 [SMILES: COCc1c(-c2nc(-c3cc(F)ccc3F)no2)cnn1C1CCCCC1]

The title compound was prepared following the procedure described for Example 10, but starting from Intermediate 5 (0.29 mmol) and cyclohexylhydrazine hydrochloride (Fluorochem; 43.7 mg; 0.29 mmol). The residue was purified by flash chromatography on a Biotage 12+M column, eluting with petrol containing increasing amounts of EtOAc. The product was triturated with diethyl ether to give Example 27 as a white solid. $^1$H NMR (CDCl$_3$, 400 MHz) δ 8.14 (1 H, s), 7.83 (1 H, ddd, J=8.6, 5.3, 2.9 Hz), 7.22-7.14 (2H, m), 5.01 (2 H, s), 4.36-4.25 (1 H, m), 3.42 (3 H, s), 2.08-1.92 (6 H, m), 1.76 (1 H, d, J=12.8 Hz), 1.52-1.24 (3 H, m). LC/MS: 375 (M+H)$^+$. HPLC (Method A) Rt=4.52 min (Purity: 99.5%).

Example 28

4-(1-cyclohexyl-4-{3-[3-(trifluoromethyl)phenyl]-1,2,4-oxadiazol-5-yl}-1H-pyrazol-5-yl)pyridine

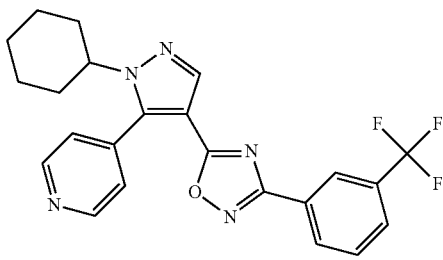 [SMILES: FC(F)(F)c1cccc(-c2noc(-c3cnn(C4CCCCC4)c3-c3ccncc3)n2)c1]

In a microwave vial, Intermediate 7 (200 mg; 0.67 mmol) was suspended in toluene (2 mL) and N'-hydroxy-3-(trifluoromethyl)benzenecarboximidamide (JRD-Fluorochemical, 151 mg; 0.74 mmol) was added followed by potassium carbonate (123 mg; 0.74 mmol). The Microwave vial was sealed and the mixture was heated to 180° C. in a microwave reactor for 2 hours. DCM (5 mL) and water (5 mL) were added and the mixture was passed through a hydrophobic frit and the solvent removed in vacuo. The residue was purified by flash chromatography on a Biotage 25+S column, eluting with petrol containing increasing amounts of EtOAc to give Example 28 as a white solid. $^1$H NMR: (CDCl$_3$, 400 MHz) δ 8.87-8.84 (2H, m), 8.28 (2H, s), 8.16 (1H, d, J=7.8 Hz), 7.73 (1H, d, J=7.9 Hz), 7.58 (1H, t, J=7.9 Hz), 7.41-7.38 (2H, m), 3.97-3.88 (1H, m), 2.14-1.99 (2H, m), 1.98-1.84 (4H, m), 1.76-1.64 (1H, m), 1.33-1.20 (3H, m). LC/MS: 440 (M+H)$^+$. HPLC (Method A) Rt 4.55 min (Purity: 97.5%).

Example 29

{4-[5(1-cyclohexyl-5-pyridin-4-yl-1H-pyrazol-4-yl)-1,2,4-oxadiazol-3-yl]phenyl}methanol

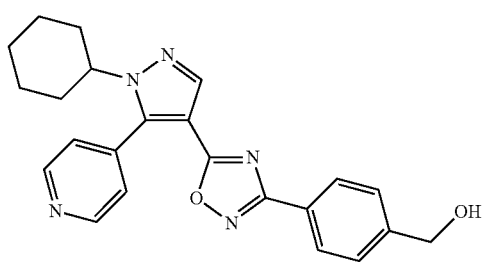 [SMILES: OCc1ccc(-c2noc(-c3cnn(C4CCCCC4)c3-c3ccncc3)n2)cc1]

In a microwave vial, Intermediate 7 (200 mg; 0.67 mmol) was suspended in toluene (2 mL) and MeCN (2 mL) and Intermediate 8 (123 mg; 0.74 mmol) was added followed by potassium carbonate (123 mg; 0.74 mmol). The Microwave vial was sealed and the mixture was heated to 180° C. in a microwave reactor for 2 hours. DCM (5 mL) and water (5 mL) were added and the mixture was passed through a hydrophobic frit and the solvent removed in vacuo. The residue was purified by flash chromatography on a Biotage 25+S column, eluting with petrol containing increasing amounts of EtOAc

Example 30

4-{1-cyclopentyl-4-[3-(2,5-difluorophenyl)-1,2,4-oxadiazol-5-yl]-1H-pyrazol-5-yl}Pyridine

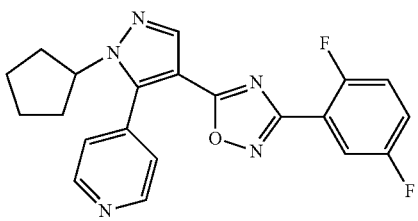 [SMILES: Fc1ccc(F)c(-c2noc(-c3cnn(C4CCCC4)c3-c3ccncc3)n2)c1]

The title compound was prepared following the procedure described for Example 10, but starting from Intermediate 2 (0.25 mmol) and cyclopentylhydrazine hydrochloride (Apollo; 34.0 mg; 0.25 mmol) to give Example 30 as a golden gum. $^1$H NMR (CDCl$_3$, 400 MHz) δ 8.84 (2 H, dd, J=4.5, 1.6 Hz), 8.27 (1 H, s), 7.67-7.62 (1 H, m), 7.41 (2 H, dd, J=4.5, 1.6 Hz), 7.20-7.12 (2 H, m), 4.49 (1 H, p, J=7.5 Hz), 2.22-2.11 (2 H, m), 2.07-1.94 (4 H, m), 1.70-1.60 (2 H, m). LC/MS: 394 (M+H)$^+$. HPLC (Method A) Rt=4.07 min (Purity: 99.5%).

Example 31

5-[1-cyclohexyl-5-(tetrahydro-2H-pyran-4-yl)-1H-pyrazol-4-yl]-3-(2,5-difluorophenyl)-1,2,4-oxadiazole

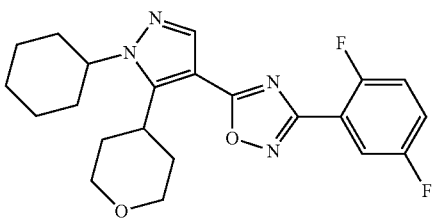 [SMILES: Fc1ccc(F)c(-c2noc(-c3cnn(C4CCCCC4)c3C3CCOCC3)n2)c1]

The title compound was prepared following the procedure described for Example 10, but starting from Intermediate 11 (0.22 mmol) and cyclohexylhydrazine hydrochloride (Fluorochem; 33.1 mg; 0.22 mmol) to give Example 31 as a white solid. $^1$H NMR (CDCl$_3$, 400 MHz) δ 8.11 (1 H, s), 7.87-7.80 (1 H, m), 7.26-7.13 (2 H, m), 4.29 (1 H, tt, J=11.5, 3.7 Hz), 4.17 (2 H, dd, J=11.6, 4.3 Hz), 3.92 (1 H, t, J=12.7 Hz), 3.60 (2 H, t, J=11.7 Hz), 2.39 (2 H, qd, J=12.6, 4.4 Hz), 2.13-2.00 (2 H, m), 1.96-1.90 (4 H, m), 1.78 (1 H, d, J=12.7 Hz), 1.70 (2 H, d, J=13.2 Hz), 1.52-1.22 (3 H, m). LC/MS: 415 (M+H)$^+$. HPLC (Method A) Rt=4.51 min (Purity: 97.2%).

Example 32

3-(2,5-difluorophenyl)-5-[1-isobutyl-5-(tetrahydro-2H-pyran-4-yl)-1H-pyrazol-4-yl]-1,2,4-oxadiazole

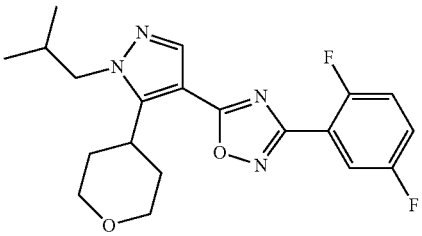 [SMILES: CC(C)Cn1ncc(-c2nc(-c3cc(F)ccc3F)no2)c1C1CCOCC1]

The title compound was prepared following the procedure described for Example 10, but starting from Intermediate 11 (0.22 mmol) and 2-methylpropylhydrazine hydrochloride (Fluorochem; 27.4 mg; 0.22 mmol) to give Example 32 as a white solid. $^1$H NMR (CDCl$_3$, 400 MHz) δ 8.13 (1 H, s), 7.85 (1 H, ddd, J=8.6, 5.3, 2.9 Hz), 7.27-7.13 (2 H, m), 4.16 (2 H, dd, J=11.6, 4.3 Hz), 4.05 (2 H, d, J=7.6 Hz), 3.59-3.43 (3 H, m), 2.71-2.56 (2 H, m), 2.35-2.23 (1 H, m), 1.64-1.59 (2 H, m), 0.98 (6 H, d, J=6.7 Hz). LC/MS: 389 (M+H)$^+$. HPLC (Method A) Rt=4.23 min (Purity: 99.1%).

Example 33

3-(2,5-difluorophenyl)-5-[5-phenyl-1-(tetrahydro-2H-pyran-4-yl)-1H-pyrazol-4-yl]-1,2,4-oxadiazole

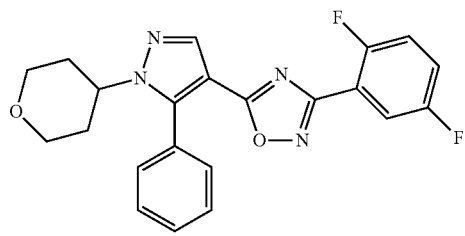 [SMILES: Fc1ccc(F)c(-c2noc(-c3cnn(C4CCOCC4)c3-c3ccccc3)n2)c1]

The title compound was prepared following the procedure described for Example 10, but starting from Intermediate 1 (0.25 mmol) and Intermediate 12 (69.0 mg; 0.30 mmol), to give Example 33 as a pale yellow solid. $^1$H NMR (CDCl$_3$, 400 MHz) δ 8.27 (1 H, s), 7.69-7.64 (1 H, m), 7.59-7.54 (3 H, m), 7.45-7.41 (2 H, m), 7.17-7.12 (2 H, m), 4.25-4.19 (1 H, m), 4.07 (2 H, dd, J=11.8, 4.46 Hz), 3.36 (2 H, t, J=12.0 Hz), 2.42 (2H, dd, J=12.4, 4.7 Hz), 1.80 (2 H, dd, J=13.1, 3.7 Hz). LC/MS: 409 (M+H)$^+$. HPLC (Method A) Rt=4.05 min (Purity: 99.5%).

--- to give Example 29 as a white solid. $^1$H NMR: (CDCl$_3$, 400 MHz) δ 8.88-8.81 (2H, m), 8.27 (1H, s), 7.98 (2H, d, J=8.1 Hz), 7.45 (2H, d, J=8.1 Hz), 7.42-7.38 (2H, m), 4.76 (2H, d, J=5.5 Hz), 3.96-3.88 (1H, m), 2.09-1.99 (2H, m), 1.95-1.83 (4H, m), 1.75 (1H, t, J=5.5 Hz), 1.75-1.64 (1H, m), 1.32-1.19 (3H, m). LC/MS: 402 (M+H)$^+$. HPLC (Method A) Rt 3.41 min (Purity: 95.7%).

Example 34

4-[4-[3-(2,5-difluorophenyl)-1,2,4-oxadiazol-5-yl]-1-(2-methylcyclohexyl)-1H-pyrazol-5-yl]pyridine

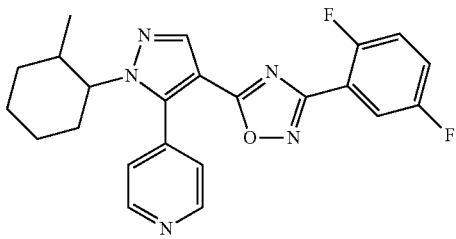 [SMILES: CC1CCCCC1n1ncc(-c2nc(-c3cc(F)ccc3F)no2)c1-c1ccncc1]

The title compound was prepared following the procedure described for Example 10, but starting from Intermediate 2 (0.25 mmol) and Intermediate 13 (34.0 mg; 0.25 mmol). A racemic mixture (43:55) of the title compound Example 34 was isolated as an off white solid. $^1$H NMR (CDCl$_3$, 400 MHz) δ 8.84-8.84 (2H, m), 8.24* & 8.30$^‡$ (1H, s), 7.65-7.60 (1H, m), 7.40-7.34 (2H, m), 7.20-7.10 (2H, m), 4.22-4.15* & 3.55-3.45$^‡$ (1H, m), 2.30-2.15 (1H, m), 2.15-1.99 (1H, m), 1.98-1.75 (3H, m), 1.75-1.62 (1H, m), 1.45-1.20 (3H, m), 1.02-1.35 (1H, m), 0.79* & 0.59$^‡$ (3H, d, J=7.2 Hz) (*=Major isomer, $^‡$=Minor isomer). LC/MS: 422 (M+H)$^+$. HPLC (Method A) Rt=4.45 min (Purity: 98.3%).

Example 35

N-(2-{4-[3-(2,5-difluorophenyl)-1,2,4-oxadiazol-5-yl]-5-phenyl-1H-pyrazol-1-yl}ethyl)cyclopropanamine

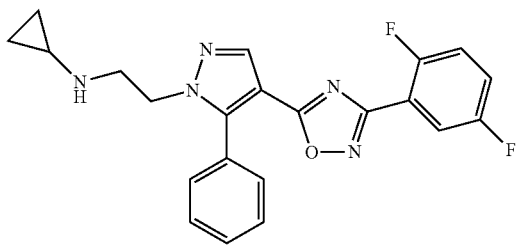 [SMILES: Fc1ccc(F)c(-c2noc(-c3cnn(CCNC4CC4)c3-c3ccccc3)n2)c1]

Step 1: 2-(4-(3-(2,5-difluorophenyl)-1,2,4-oxadiazol-5-yl)-5-phenyl-1H-pyrazol-1-yl)ethanol The title compound was prepared following the procedure described for Example 10 but starting from Intermediate 1 (3.80 mmol) and hydroxyethylhydrazine (69.0 mg; 0.30 mmol) to give the title compound as a white solid (1.19 g; 85%). $^1$H NMR (DMSO-d$_6$) δ 8.36 (1H, s), 7.68-7.62 (6H, m), 7.52-7.49 (2H, m), 5.00 (1H, s), 4.12-3.88 (2H, m), 3.84-3.79 (2H, m). LC/MS: 369 (M+H)$^+$. HPLC (Method A) Rt=3.46 min (Purity: 98.0%).

Step 2: 2-(4-(3-(2,5-difluorophenyl)-1,2,4-oxadiazol-5-yl)-5-phenyl-1H-pyrazol-1-yl)ethyl methanesulfonate Mesyl chloride (280 μL; 3.6 mmol) was added to a solution of 2-(4-(3-(2,5-difluorophenyl)-1,2,4-oxadiazol-5-yl)-5-phenyl-1H-pyrazol-1-yl)ethanol (663 mg; 1.8 mmol), obtained from step 1, and triethylamine (502 μL; 3.6 mmol) in dry DCM (5 mL) at 0° C. The tube was sealed and allowed to warm to room temperature overnight. The mixture was washed with saturated aqueous sodium hydrogen carbonate and the organic fraction passed through a hydrophobic frit and the solvent removed in vacuo to give the title compound as a pale yellow solid (785 mg; 97%). $^1$H NMR (CDCl$_3$, 400 MHz) δ 8.31 (1H, s), 7.69-7.64 (1H, m), 7.59-7.81 (3H, m), 7.50-7.45 (2H, m), 7.21-7.10 (2H, m), 4.64 (2H, t, J=5.2 Hz), 4.38 (2H, t, J=5.2 Hz), 2.90 (3H, s). LC/MS: 447 (M+H)$^+$. HPLC (Method A) Rt=3.69 min (Purity: 99.4%).

Step 3: N-(2-{4-[3-(2,5-difluorophenyl)-1,2,4-oxadiazol-5-yl]-5-phenyl-1H-pyrazol-1-yl}ethyl)cyclopropanamine Cyclopropylamine (166.2 μL; 2.40 mmol) and triethylamine (44.6 μL; 0.32 mmol) were added to 2-(4-(3-(2,5-difluorophenyl)-1,2,4-oxadiazol-5-yl)-5-phenyl-1H-pyrazol-1-yl)ethyl methanesulfonate, obtained from step 2, (71.4 mg; 0.16 mmol) in DCM (2 mL) and the mixture heated to 65° C. overnight. The solvent was removed in vacuo and the residue redissolved in DCM (10 mL) and washed with water (3×10 mL). The organic layer was passed through a hydrophobic frit and the solvent removed in vacuo. The residue was purified by flash chromatography on a Biotage 12+M column, eluting with petrol containing increasing amounts of EtOAc. The product was redissolved in methanol and stirred with polymer supported carbonate for 3 hours. The polymer beads were removed by filtration and the filtrate concentrated in vacuo to give Example 35 as a white solid. $^1$H NMR (DMSO-d$_6$) δ 8.37 (1H, s), 7.70-7.63 (6H, m), 7.56-7.53 (2H, m), 4.13 (2H, t, J=6.6 Hz), 2.98 (2H, t, J=6.5 Hz), 2.40-2.30 (1H, m), 1.95 (1H, tt, J=6.5, 3.6 Hz), 0.31-0.27 (2H, m), 0.11-0.08 (2H, m). LC/MS: 408 (M+H)$^+$. HPLC (Method C) Rt=12.03 min (Purity: 95.8%).

Example 36

7-[5-(1-isobutyl-5-pyridin-4-yl-1H-pyrazol-4-yl)-1,2,4-oxadiazol-3-yl]-1,2,3,4-tetrahydroisoquinoline

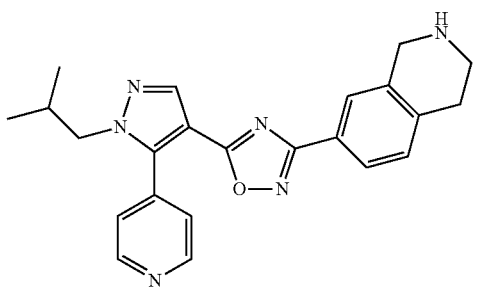 [SMILES: CC(C)Cn1ncc(-c2nc(-c3ccc4c(c3)CNCC4)no2)c1-c1ccncc1]

Sodium hydride (11.0 mg; 0.273 mmol) was added to Intermediate 16 (52.2 mg; 0.273 mmol) in THF (1 mL) and the mixture stirred for 10 minutes. The mixture was then added to a solution of Intermediate 14 (71.1 mg; 0.260 mmol) in THF (1 mL) and stirred at room temperature for 1 hour. The mixture was then heated at 90° C. overnight. An additional equivalent of sodium hydride was added (11.0 mg; 0.273 mmol) and the mixture heated at 90° C. for a further 4 hours. Water (10 mL) was added and the product extracted into DCM (3×10 mL). The combined organic fractions were passed through a hydrophobic frit and the solvent removed in vacuo. The residue was purified by flash chromatography using a Biotage 12+M column, eluting with DCM containing increasing amounts of methanol to give Example 36 as an off white solid. $^1$H NMR (CDCl$_3$, 400 MHz) δ 8.83 (2 H, dd, J=4.5, 1.6 Hz), 8.27 (1 H, s), 7.73 (1 H, d, J=8.0 Hz), 7.66 (1 H, s), 7.40 (2 H, dd, J=4.5, 1.6 Hz), 7.17 (1 H, d, J=8.0 Hz), 4.07 (2 H, s), 3.88 (2 H, d, J=7.5 Hz), 3.17 (2 H, t, J=5.9 Hz), 2.86 (2 H, t, J=5.9 Hz), 2.27-2.18 (1 H, m), 0.81 (6 H, d, J=6.7 Hz). LC/MS: 401 (M+H)$^+$. HPLC (Method B) Rt=3.42 min (Purity: 96.2%).

Example 37

4-(1-isobutyl-4-{3-[3-(trifluoromethyl)phenyl]-1,2,4-oxadiazol-5-yl}-1H-pyrazol-5-yl)pyridine

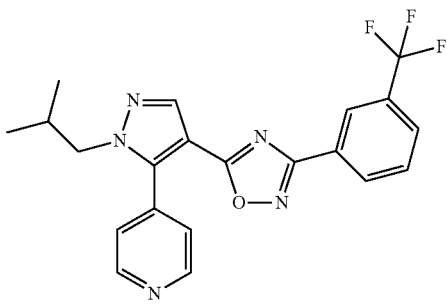 [SMILES: CC(C)Cn1ncc(-c2nc(-c3cccc(C(F)(F)F)c3)no2)c1-c1ccncc1]

The title compound was prepared following the procedure described for Example 36, but starting from N'-hydroxy-3-(trifluoromethyl)benzenecarboximidamide (JRD-Fluorochemical, 55.7 mg; 0.273 mmol) and Intermediate 14 (71.1 mg; 0.26 mmol), to give Example 37 as an off white solid. $^1$H NMR (CDCl$_3$, 400 MHz) δ 8.85 (2 H, dd, J=4.7, 1.8 Hz), 8.29 (2 H, d, J=3.9 Hz), 8.16 (1 H, d, J=7.8 Hz), 7.74 (1 H, d, J=7.9 Hz), 7.59 (1 H, t, J=7.9 Hz), 7.41 (2 H, dd, J=4.6, 1.9 Hz), 3.89 (2 H, d, J=7.4 Hz), 2.26-2.22 (1 H, m), 0.82 (6 H, d, J=6.6 Hz). LC/MS: 414 (M+H)$^+$. HPLC (Method A) Rt=4.24 min (Purity: 99.2%).

Example 38

5-[5-(1-cyclohexyl-5-pyridin-4-yl-1H-pyrazol-4-yl)-1,2,4-oxadiazol-3-yl]-1H-indazole

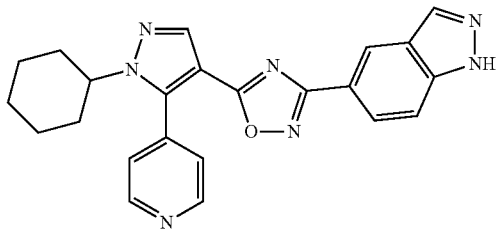 [SMILES: c1cc(-c2c(-c3nc(-c4ccc5[nH]ncc5c4)no3)cnn2C2CCCCC2)ccn1]

Sodium hydride (31.5 mg; 0.788 mmol) was added to a solution of Intermediate 7 (225 mg; 0.75 mmol) and Intermediate 15 (139 mg; 0.788 mmol) in THF (10 mL) and the mixture stirred for 10 minutes. The mixture was then heated to 130° C. in a microwave reactor for 16 hours. Water (10 mL) was added and the product extracted into DCM (3×10 mL). The combined organic fractions were passed through a hydrophobic frit and the solvent removed in vacuo. The residue was purified by flash chromatography using a Biotage 25+M column, eluting with petrol containing increasing amounts of EtOAc and then 5% methanol in DCM. The residue was triturated with diethyl ether to give Example 38 as an off white solid. $^1$H NMR (DMSO-d$_6$) δ 13.41 (1 H, s), 8.87 (2 H, d, J=6.0 Hz), 8.41 (2 H, d, J=11.98 Hz), 8.28 (1 H, s), 7.91 (1 H, dd, J=8.7, 1.5 Hz), 7.73-7.67 (3 H, m), 4.01-3.94 (1 H, m), 2.02-1.83 (4 H, m), 1.81 (2 H, d, J=11.1 Hz), 1.64 (1 H, s), 1.27-1.16 (3 H, m). LC/MS: 412 (M+H)$^+$. HPLC (Method B) Rt=3.28 min (Purity: 98.4%).

Example 39

7-[5-(1-cyclohexyl-5-pyridin-4-yl-1H-pyrazol-4-yl)-1,2,4-oxadiazol-3-yl]-1,2,3,4-tetrahydroisoquinoline

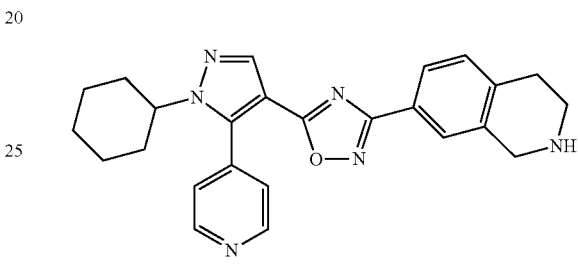

Step 1: 7-[5-(1-cyclohexyl-5-pyridin-4-yl-1H-pyrazol-4-yl)-1,2,4-oxadiazol-3-yl]-3,4-dihydroisoquinoline In a microwave vial, Intermediate 7 (200 mg; 0.67 mmol) was suspended in toluene (2 mL) and MeCN (2 mL) and Intermediate 16 (142 mg; 0.74 mmol) was added followed by potassium carbonate (123 mg; 0.74 mmol). The Microwave vial was sealed and the mixture was heated to 180° C. in a microwave reactor for 2 hours. The reaction mixture was diluted with DCM (5 mL) and washed with water (5 mL). The organic phase was passed through a hydrophobic frit and the solvent was removed in vacuo. The residue was purified by flash chromatography on a Biotage 25+S column, eluting with DCM containing increasing amounts of MeOH to give 7-[5-(1-cyclohexyl-5-pyridin-4-yl-1H-pyrazol-4-yl)-1,2,4-oxadiazol-3-yl]-3,4-dihydroisoquinoline as a white solid. $^1$H NMR: (CDCl$_3$, 400 MHz) δ 8.88-8.84 (2 H, m), 8.41-8.37 (1 H, m), 8.28 (1 H, s), 7.96 (1 H, dd, J=7.8, 1.7 Hz), 7.93-7.89 (1 H, m), 7.41-7.38 (2 H, m), 7.24 (1 H, s), 3.97-3.89 (1 H, m), 3.85-3.77 (2 H, m), 2.80 (2 H, t, J=7.8 Hz), 2.13-2.01 (2 H, m), 1.97-1.82 (4 H, m), 1.72-1.67 (1 H, m), 1.29-1.18 (3 H, m). LC/MS: 425 (M+H)$^+$. HPLC (Method A) Rt 2.23 min (Purity: 97.8%).

Step 2: 7-[5-(1-cyclohexyl-5-pyridin-4-yl-1H-pyrazol-4-yl)-1,2,4-oxadiazol-3-yl]-1,2,3,4-tetrahydroisoquinoline 7-[5-(1-Cyclohexyl-5-pyridin-4-yl-1H-pyrazol-4-yl)-1,2,4-oxadiazol-3-yl]-3,4-dihydroisoquinoline, obtained from step 1, (24.6 mg; 0.058 mmol) was suspended in ethanol (10 mL) and DCM (5 mL) and sodium borohydride (2.2 mg; 0.058 mmol) were added. The mixture was stirred at room temperature overnight. The solvent was removed in vacuo and the product redissolved in DCM (10 mL), washed with water (3×10 mL) and the combined organic fractions passed through a hydrophobic and the solvent removed in vacuo. The residue was purified by flash chromatography using a Biotage 12+M column, eluting with DCM containing increasing amounts of 7M methanolic ammonia, and then by preparative HPLC to give Example 39 as a white solid. $^1$H NMR (DMSO-d$_6$) δ 8.86 (2 H, d, J=5.1 Hz), 8.38 (1 H, s), 8.33 (1 H, s), 7.73 (1H, s), 7.71 (1 H, s) 7.64 (2 H, d, J=5.2 Hz), 7.36 (1 H, d, J=7.9 Hz), 4.16 (2 H, s), 4.05-3.90 (1 H, m), 3.21 (2 H, t, J=6.0 Hz), 2.94 (2 H, t, J=5.6 Hz), 1.95-4.90 (4 H, m), 1.83-1.75 (2 H, m), 1.65-1.59 (1H, m) 1.30-1.20 (3 H, m). LC/MS: 427 (M+H)$^+$. HPLC (Method A) Rt=2.24 min (Purity: 96.2%).

Example 40

5-[5-(1-isobutyl-5-pyridin-4-yl-1H-pyrazol-4-yl)-1,2,4-oxadiazol-3-yl]-1H-indazole

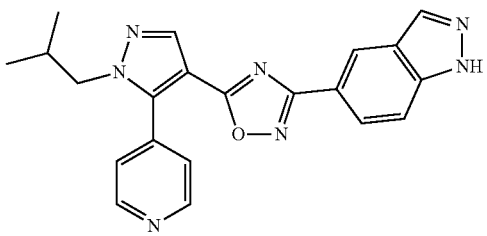 [SMILES: CC(C)Cn1ncc(-c2nc(-c3ccc4[nH]ncc4c3)no2)c1-c1ccncc1]

Sodium hydride (29.4 mg; 0.735 mmol) was added to a solution of Intermediate 14 (191.3 mg; 0.70 mmol) and Intermediate 15 (129.5 mg; 0.735 mmol) in THF (2 mL) and the mixture stirred for 10 minutes. The mixture was then heated at 130° C. in a microwave reactor for 3 hours. Water (5 mL) was added and the product extracted into DCM (3×5 mL). The combined organic fractions were passed through a hydrophobic frit and the solvent removed in vacuo. The residue was purified by flash chromatography on a Biotage 25+M column, eluting with petrol containing increasing amounts of EtOAc to give Example 40 as an off white solid. $^1$ H NMR (DMSO-d$_6$) δ 13.40 (1 H, s), 8.88 (2 H, d, J=12.0 Hz), 8.41 (1 H, s), 8.39 (1 H, s) 8.28 (1 H, s), 7.91 (1 H, dd, J=8.7, 1.5 Hz), 7.74-7.68 (3 H, m), 3.96 (2 H, d, J=7.3 Hz), 2.14-2.06 (1 H, m), 0.78 (6 H, d, J=6.7 Hz). LC/MS: 386 (M+H)$^+$. HPLC (Method A) Rt=3.14 min (Purity: 98.5%).

Example 41

1-{4-[5-(1-cyclohexyl-5-pyridin-4-yl-1H-pyrazol-4-yl)-1,2,4-oxadiazol-3-yl]phenyl}-N,N-dimethyl-methanamine

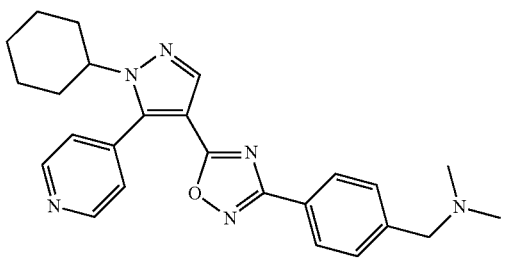 [SMILES: CN(C)Cc1ccc(-c2noc(-c3cnn(C4CCCCC4)c3-c3ccncc3)n2)cc1]

Step 1: {4-[5-(1-cyclohexyl-5-pyridin-4-yl-1H-pyrazol-4-yl)-1,2,4-oxadiazol-3-yl]phenyl}methanol A solution of Intermediate 7 (210 mg; 0.662 mmol) in toluene (3 mL) was added to a solution of Intermediate 8 (121 mg; 0.662 mmol) in DMF (2 mL) followed by addition of potassium carbonate (100 mg; 0.728 mmol). The reaction was heated at 180° C. for 1 hour. The solvent was removed in vacuo and the residue diluted with a mixture of IPA:water (1:1, 10 mL). The resulting precipitate was collected by filtration to yield the title compound as a yellow solid (145 mg; 73%), which was used directly without any purification. $^1$H NMR: (CDCl$_3$, 400 MHz) δ 8.88-8.81 (2H, m), 8.27 (1H, s), 7.98 (2H, d, J=8.1 Hz), 7.45 (2H, d, J=8.1 Hz), 7.42-7.38 (2H, m), 4.76 (2H, d, J=5.5 Hz), 3.96-3.88 (1H, m), 2.09-1.99 (2H, m), 1.95-1.83 (4H, m), 1.75 (1H, t, J=5.5 Hz), 1.75-1.64 (1H, m), 1.32-1.19 (3H, m). LC/MS: 402 (M+H)$^+$. HPLC (Method A) Rt 3.41 min (Purity: 95.7%).

Step 2: 4-(5-(1-cyclohexyl-5-(pyridin-4-yl)-1H-pyrazol-4-yl)-1,2,4-oxadiazol-3-yl)benzaldehyde The title compound was prepared following the procedure described for Example 64 (step 1), but starting from {4-[5-(1-cyclohexyl-5-pyridin-4-yl-1H-pyrazol-4-yl)-1,2,4-oxadiazol-3-yl]phenyl}methanol, obtained from step 1, (1.92 g; 4.78 mmol), to give the title compound as a white solid (1.90 g; 99%) which was used directly without any purification. $^1$H NMR (CDCl$_3$, 400 MHz): δ 10.07 (1 H, s), 8.87 (2 H, d, J=4.8 Hz), 8.28 (1 H, s), 8.15 (2 H, d, J=7.9 Hz), 7.96 (2 H, d, J=7.9 Hz), 7.40 (2 H, d, J=4.9 Hz), 3.98-3.89 (1 H, m), 2.09-2.05 (2 H, m), 1.90-1.88 (4 H, m), 1.70-1.69 (1 H, m), 1.28-1.26 (3 H, m).

Step 3: 1-{4-[5-(1-cyclohexyl-5-pyridin-4-yl-1H-pyrazol-4-yl)-1,2,4-oxadiazol-3-yl]phenyl}-N,N-dimethylmethanamine Sodium cyanoborohydride (8.3 mg; 0.135 mmol) was added to a solution of 4-(5-(1-cyclohexyl-5-(pyridin-4-yl)-1H-pyrazol-4-yl)-1,2,4-oxadiazol-3-yl)benzaldehyde, obtained from step 2, (50 mg; 0.124 mmol) and dimethylamine hydrochloride (19.8 mg; 0.248 mmol) in a mixture of methanol (3 mL), DCM (1 mL) and acetic acid (75 µl). The mixture was stirred at room temperature overnight and the solvent was then removed in vacuo. The residue was purified by preparative HPLC to give Example 41 as a white solid. $^1$H NMR (DMSO-d$_6$, 400 MHz) δ 8.86-8.83 (2H, m), 8.27 (1H, s), 7.94 (2 H, d, J=8.0 Hz), 7.42-7.37 (4H, m), 3.97-3.88 (1H, m), 3.49 (2H, s), 2.48-2.31 (1H, m), 2.27 (6H, s), 2.13-2.00 (2H, m), 1.95-1.84 (3H, m), 1.69 (1H, s), 1.32-1.17 (3H, m). LC/MS: 429 (M+H)$^+$. HPLC (Method B) Rt=4.40 min (Purity: 97.7%).

Example 42

1-{4-[5-(1-cyclohexyl-5-pyridin-4-yl-1H-pyrazol-4-yl)-1,2,4-oxadiazol-3-yl]benzyl}azetidine-3-carboxylic acid

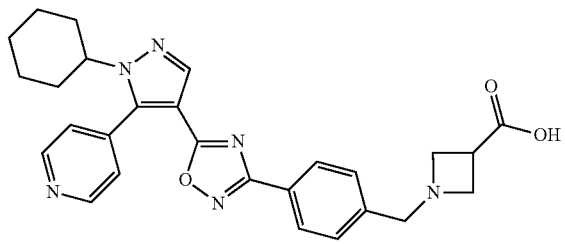 [SMILES: O=C(O)C1CN(Cc2ccc(-c3noc(-c4cnn(C5CCCCC5)c4-c4ccncc4)n3)cc2)C1]

Sodium cyanoborohydride (31.5 mg; 0.501 mmol) was added to a solution of 4-(5-(1-cyclohexyl-5-(pyridin-4-yl)-1H-pyrazol-4-yl)-1,2,4-oxadiazol-3-yl)benzaldehyde, obtained as described in Example 41 (step 2), (182 mg; 0.456 mmol) and 3-azetidine carboxylic acid (92.1 mg; 0.911 mmol) in methanol (3 mL) and acetic acid (75 µl) and the mixture was stirred at room temperature overnight. The solvent was removed in vacuo and the residue was recrystallised from DMSO and triturated with methanol to give Example 42 as a white solid. $^1$H NMR (DMSO-$d_6$, 400 MHz) δ 8.83 (2 H, dd, J=4.6, 1.5 Hz), 8.38 (1 H, s), 7.87 (2 H, d, J=8.1 Hz), 7.63 (2 H, dd, J=4.6, 1.6 Hz), 7.48 (2 H, d, J=8.0 Hz), 4.00-3.78 (3 H, m), 3.59 (2 H, t, J=8.0 Hz), 3.49-3.40 (2 H, m), 3.20 (1H, q), 1.95-1.88 (4 H, m), 1.87-1.72 (2 H, m), 1.64-1.58 (1 H, m), 1.3-1.18 (3 H, m). LC/MS: 485 (M+H)$^+$. HPLC (Method A) Rt=2.32 min (Purity: 96.3%).

Example 43

4-(1-isobutyl-4-{3-[3-(methylsulfonyl)phenyl]-1,2,4-oxadiazol-5-yl}-1H-pyrazol-5-yl)pyridine

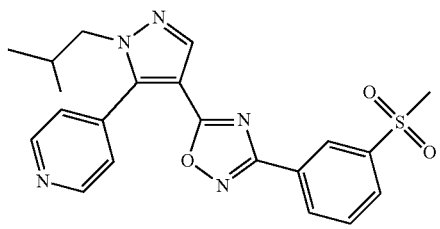 [SMILES: CC(C)Cn1ncc(-c2nc(-c3cccc(S(C)(=O)=O)c3)no2)c1-c1ccncc1]

The title compound was prepared following the procedure described for Example 36, but starting from Intermediate 3 (58.5 mg; 0.273 mmol) and Intermediate 14 (71.1 mg; 0.26 mmol) to give Example 43 as a white solid. $^1$H NMR (DMSO-$d_6$) δ 8.87-8.83 (2 H, m), 8.47-8.39 (2 H, m), 8.26 (1 H, d, J=7.8 Hz), 8.17 (1 H, d, J=7.9 Hz), 7.88 (1 H, t, J=7.8 Hz), 7.71-7.67 (2 H, m), 3.96 (2 H, d, J=7.3 Hz), 3.31 (3 H, s), 2.13-2.04 (1 H, m), 0.77 (6 H, d, J=6.6 Hz). LC/MS: 424 (M+H)$^+$. HPLC (Method B) Rt=3.67 min (Purity: 98.0%).

Example 44

4-{1-cyclobutyl-4-[3-(2,5-difluorophenyl)-1,2,4-oxadiazol-5-yl]-1H-pyrazol-5-yl}pyridine

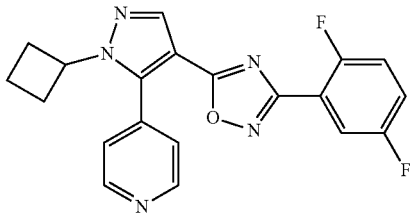 [SMILES: Fc1ccc(F)c(-c2noc(-c3cnn(C4CCC4)c3-c3ccncc3)n2)c1]

The title compound was prepared following the procedure described for Example 10, but starting from Intermediate 2 (0.25 mmol) and cyclobutylhydrazine hydrochloride (Pharm-Lab, 30.5 mg; 0.25 mmol) to give Example 44 as a brown solid. $^1$H NMR (CDCl$_3$, 400 MHz) δ 8.86 (2 H, d, J=4.9 Hz), 8.33 (1 H, s), 7.70-7.65 (1 H, m), 7.41 (2 H, d, J=5.0 Hz), 7.23-7.14 (2H, m), 4.70-4.59 (1 H, m), 2.91-2.79 (2 H, m), 2.40-2.31 (2 H, m), 1.97 (1 H, q, J=10.5 Hz), 1.89-1.71 (1 H, m). LC/MS: 380 (M+H)$^+$. HPLC (Method C) Rt=18.30 min (Purity: 99.1%).

Example 45

1-{4-[5-(1-cyclohexyl-5-pyridin-4-yl-1H-pyrazol-4-yl)-1,2,4-oxadiazol-3-yl]benzyl}pyrrolidin-3-ol

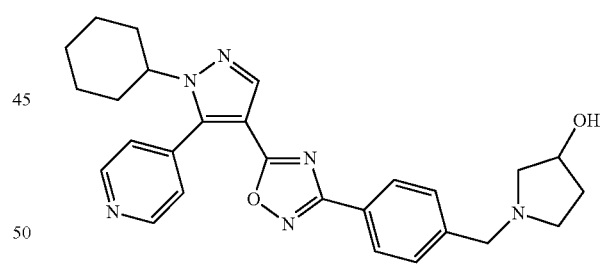

The title compound was prepared following the procedure described for Example 42 but using 3-pyrrolidinol (79.4 mg; 0.911 mmol). The residue was purified by preparative HPLC to give Example 45 as a white solid. $^1$H NMR (DMSO-$d_6$) δ 8.87 (2 H, dd, J=4.5, 1.6 Hz), 8.41 (1 H, s), 7.87 (2 H, d, J=8.1 Hz), 7.67 (2 H, dd, J=4.5, 1.6 Hz), 7.49 (2 H, d, J=8.0 Hz), 4.71 (1 H, d, J=4.5 Hz), 4.28-4.20 (1H, m), 4.04-3.95 (1H, m), 3.62 (2H, dd, J=7.7, 13.5), 2.71 (1 H, dd, J=9.6, 6.2 Hz), 2.63-2.55 (1 H, m), 2.48-2.40 (1H, m), 2.34 (1 H, dd, J=9.7, 3.8 Hz), 2.05-1.89 (5 H, m), 1.85-1.79 (2 H, m), 1.69-1.55 (2 H, m), 1.30-1.20 (3 H, m). LC/MS: 471 (M+H)$^+$. HPLC (Method A) Rt=2.24 min (Purity: 99.1%).

Example 46

3-(2,5-difluorophenyl)-5-{1-[(1S,2S)-2-methylcyclohexyl]-5-phenyl-1H-pyrazol-4-yl}-1,2,4-oxadiazole

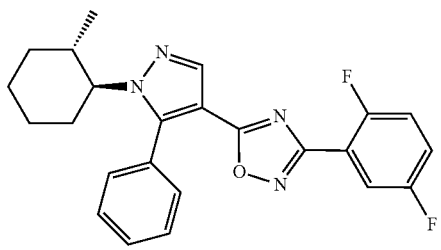 [SMILES: C[C@H]1CCCC[C@@H]1n1ncc(-c2nc(-c3cc(F)ccc3F)no2)c1-c1ccccc1]

Sodium hydride (10.4 mg; 0.260 mmol) was added to a solution of 2,5-difluoro-N'-hydroxybenzenecarboximidamide (JRD-Fluorochemical, 44.8 mg; 0.260 mmol) and Intermediate 17 (85.3 mg; 0.273 mmol) in THF (2 mL) and the mixture was stirred for 10 minutes. The mixture was heated in a microwave reactor at 130° C. for 6.25 hours. Water (10 mL) was added and the product was extracted into DCM (3×10 mL) and the combined organic fractions passed through a hydrophobic frit and the solvent removed in vacuo. The residue was purified by preparative HPLC to give Example 46 as a clear gum, together with 3-(2,5-difluorophenyl)-5-{1-[(1S,2R)-2-methylcyclohexyl]-5-phenyl-1H-pyrazol-4-yl}-1,2,4-oxadiazole (Example 47 below). $^1$H NMR (CDCl$_3$, 400 MHz) δ 8.29 (1 H, s), 7.71-7.65 (1 H, m), 7.55-7.50 (3 H, m), 7.42-7.37 (2 H, m), 7.19-7.10 (2 H, m), 3.59-3.52 (1 H, m), 2.24-2.13 (1 H, m), 2.11-1.75 (5 H, m), 1.43-1.16 (2 H, m), 1.00-0.89 (1 H, m), 0.60 (3 H, d, J=6.8 Hz). LC/MS: 421 (M+H)$^+$. HPLC (Method A) Rt=4.96 min (Purity: 93.2%).

Example 47

3-(2,5-difluorophenyl)-5-{1[(1S,2R)-2-methylcyclohexyl]-5-phenyl-1H-pyrazol-4-yl}-1,2,4-oxadiazole

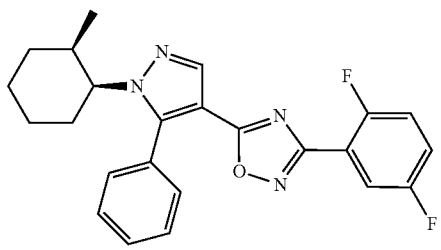 [SMILES: C[C@@H]1CCCC[C@@H]1n1ncc(-c2nc(-c3cc(F)ccc3F)no2)c1-c1ccccc1]

The title compound was isolated from the reaction described above for the synthesis of 3-(2,5-difluorophenyl)-5-{1-[(1S,2S)-2-methylcyclohexyl]-5-phenyl-1H-pyrazol-4-yl}-1,2,4-oxadiazole. Example 47 was isolated as a clear gum. $^1$H NMR (CDCl$_3$, 400 MHz) δ 8.22 (1 H, s), 7.70-7.64 (1 H, m), 7.56-7.50 (3 H, m), 7.44-7.38 (2 H, m), 7.19-7.09 (2 H, m), 4.27-4.22 (1 H, m), 2.31-2.20 (1 H, m), 2.07-1.98 (1 H, m), 1.96-1.85 (1 H, m), 1.82-1.50 (3 H, m), 1.43-1.33 (3 H, m), 0.80 (3 H, d, J=2 Hz). LC/MS: 421 (M+H)$^+$. HPLC (Method C) Rt=20.75 min (Purity: 83.2%).

Example 48

5-[1-cyclohexyl-5-(2-methylphenyl)-1H-pyrazol-4-yl]-3-(2,5-difluorophenyl)-1,2,4-oxadiazole

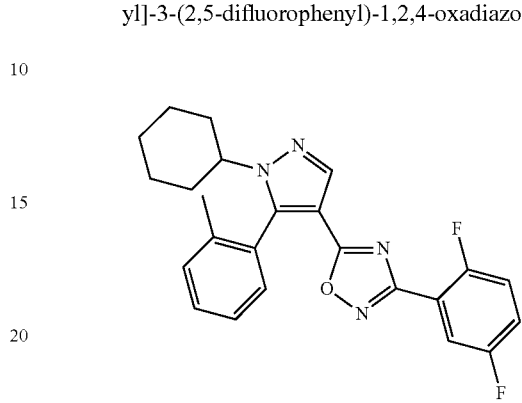

Step 1: 2-(3-(2,5-difluorophenyl)-1,2,4-oxadiazol-5-yl)-1-o-tolylethanone

A solution of ethyl 3-oxo-3-o-tolylpropanoate (0.44 mL; 2.5 mmol) and 2,5-difluoro-N'-hydroxybenzenecarboximidamide (JRD-Fluorochemical, 215 mg; 1.25 mmol) in toluene (1.5 mL) was heated to 120° C. 18 hours. The solvent was removed in vacuo and the residue purified by flash chromatography on a Biotage 25+M column, eluting with petrol containing increasing amounts of EtOAc. The residue was triturated with petrol to give the title compound as an off-white solid which was used directly without any further purification. $^1$H NMR (CDCl$_3$, 400 MHz) δ 11.62$^‡$ (1H, br s), 7.82-7.74 (1H, m), 7.55-7.12 (6H, m), 5.95$^‡$ (1H, s), 4.68* (2H, s), [2.58, 2.55 and 2.47] (3H, s) (compound isolated as a mixture of keto and enol forms and as a mixture of rotamers, *=keto form, $^‡$=enol form). LC/MS: 315 (M+H)$^+$. HPLC (Method D) Rt=4.28 min (Purity: 98.4%).

Step 2: 5-[1-cyclohexyl-5-(2-methylphenyl)-1H-pyrazol-4-yl]-3-(2,5-difluorophenyl)-1,2,4-oxadiazole To a solution of 2-(3-(2,5-difluorophenyl)-1,2,4-oxadiazol-5-yl)-1-o-tolylethanone (115 mg; 0.37 mmol), obtained from step 1, in toluene (2.5 mL) was added DMF.DMA (70 μL) and PPTS (10 mg). The mixture was heated to 90° C. for 7 hours. DCM (10 mL) and water (10 mL) were added and the mixture passed through a hydrophobic frit. The solvent was removed in vacuo and the residue redissolved in ethanol (2.3 mL) and water (0.23 mL). The solution was added to a mixture cyclohexylhydrazine hydrochloride (Fluorochem; 56 mg; 0.37 mmol), and sodium acetate (61 mg; 0.74 mmol). The mixture was heated to reflux for 7 hours and then DCM (10 mL) and water (10 mL). The mixture was filtered through a hydrophobic frit and the solvent removed in vacuo. The residue was purified by flash chromatography on a Biotage 25+S column, eluting with petrol containing increasing amounts of EtOAc to give Example 48 as a white solid. $^1$H NMR: (CDCl$_3$, 400 MHz) δ 8.28 (1H, s), 7.68-7.62 (1H, m), 7.50-7.30 (3H, m), 7.22-7.08 (3H, m), 3.80-3.70 (1H, m), 2.12 (3H, s), 2.13-1.82 (6H, m), 1.68-1.62 (1H, m), 1.31-1.15 (3H, m). LC/MS: 421 (M+H)⁺. HPLC (Method F) Rt 4.95 min (Purity: 99.7%).

Example 49

(4-{5-[1-cyclohexyl-5-(methoxymethyl)-1H-pyrazol-4-yl]-1,2,4-oxadiazol-3-yl}phenyl)methanol

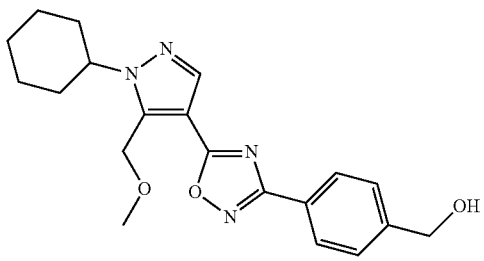 [SMILES: COCc1c(-c2nc(-c3ccc(CO)cc3)no2)cnn1C1CCCCC1]

Sodium hydride (294.0 mg; 7.35 mmol) was added to a suspension of Intermediate 18 (1.77 g; 7.00 mmol) and Intermediate 8 (1.22 g; 7.35 mmol) in THF (15 mL) and the mixture was stirred for 10 minutes. The mixture was then heated in a microwave reactor for 19 hours at 130° C. Water (10 mL) was added and the product was extracted into DCM (3×10 mL). The combined organic fractions were passed through a hydrophobic frit and the solvent removed in vacuo. The residue was purified by flash chromatography on a Biotage 40+M column, eluting with petrol containing increasing amounts of EtOAc to give Example 49 as a white solid. ¹H NMR (CDCl₃, 400 MHz) δ 8.16-8.11 (3 H, m), 7.50 (2 H, d, J=8.1 Hz), 5.03 (2 H, s), 4.79 (2 H, d, J=6.0 Hz), 4.35-4.28 (1 H, m), 3.42 (3 H, s), 2.09-1.90 (6 H, m), 1.82-1.73 (2 H, m), 1.52-1.25 (3 H, m). LC/MS: 369 (M+H)⁺. HPLC (Method A) Rt=3.87 min (Purity: 97.9%).

Example 50

5-[1-isobutyl-5-(tetrahydro-2H-pyran-4-yl)-1H-pyrazol-4-yl]-3-[3-(trifluoromethyl)phenyl]-1,2,4-oxadiazole

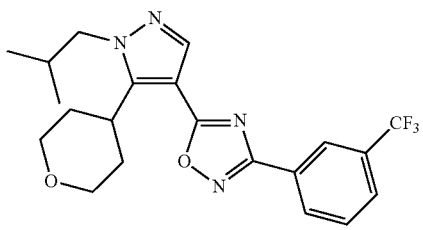 [SMILES: CC(C)Cn1ncc(-c2nc(-c3cccc(C(F)(F)F)c3)no2)c1C1CCOCC1]

Sodium hydride (11 mg; 0.273 mmol) was added to a suspension of Intermediate 19 (72.9 mg; 0.260 mmol) and N'-hydroxy-3-(trifluoromethyl)benzenecarboximidamide (JRD-Fluorochemical, 55.7 mg, 0.273 mmol) in THF (2 mL) and the mixture was stirred for 10 minutes. The mixture was then heated in a microwave reactor for 2 hours at 130° C. Water (10 mL) was added and the product extracted into DCM (3×10 mL). The combined organic fractions were passed through a hydrophobic frit and the solvent removed in vacuo. The residue was purified by flash chromatography on a Biotage 12+M column, eluting with DCM containing increasing amounts of methanol to give Example 50 as a white solid. ¹H NMR (CDCl₃, 400 MHz) δ 8.44 (1 H, s), 8.35 (1 H, d, J=7.8 Hz), 8.14 (1 H, s), 7.78 (1 H, d, J=7.9 Hz), 7.66 (1 H, t, J=7.8 Hz), 4.19-4.13 (2 H, m), 4.06 (2 H, d), 3.60-3.43 (3 H, m), 2.69 (2 H, qd, J=12.6, 4.5 Hz), 2.36-2.21 (1 H, m), 1.65-1.59 (2 H, m), 0.98 (6 H, d, J=6.7 Hz). LC/MS: 421 (M+H)⁺. HPLC (Method A) Rt=4.58 min (Purity: 97.4%).

Example 51

3-(1-cyclohexyl-5-phenyl-1H-pyrazol-4-yl)-5-phenyl-1,2,4-oxadiazole

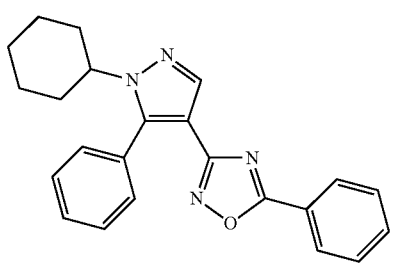 [SMILES: c1ccc(-c2nc(-c3cnn(C4CCCCC4)c3-c3ccccc3)no2)cc1]

In a microwave vial, Intermediate 9 (190 mg; 0.67 mmol) was suspended in toluene (2 mL) and methyl benzoate (0.09 mL; 0.74 mmol) was added followed by potassium carbonate (123 mg; 0.74 mmol). The Microwave vial was sealed and the mixture was heated to 180° C. in a microwave reactor for 2 hours and then DCM (10 mL) and water (10 mL) added. The mixture was filtered through a hydrophobic frit and the solvent removed in vacuo. The residue was triturated with isopropanol and dried to give Example 51 as a white solid. ¹H NMR: (CDCl₃, 400 MHz) δ 8.19 (1H, s), 8.08-8.03 (2H, m), 7.59-7.43 (8H, m), 4.01-3.91 (1H, m), 2.13-1.83 (6H, m), 1.71-1.58 (1H, m), 1.31-1.14 (3H, m). LC/MS: 371 (M+H)⁺. HPLC (Method B) Rt 4.98 min (Purity: 98.9%).

Example 52

3-(1-cyclohexyl-5-phenyl-1H-pyrazol-4-yl)-5-(2-fluorophenyl)-1,2,4-oxadiazole

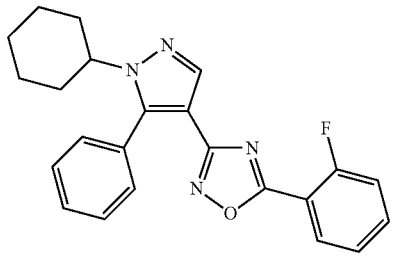 [SMILES: Fc1ccccc1-c1nc(-c2cnn(C3CCCCC3)c2-c2ccccc2)no1]

The title compound was prepared following the procedure described for Example 51 but starting from Intermediate 9 (190 mg; 0.67 mmol) and methyl 2-fluorobenzoate (Avocado; 0.94 mL; 0.74 mmol). The residue was purified by flash chromatography on a Biotage 12+M column, eluting with petrol containing increasing amounts of EtOAc. The residue was triturated with isopropanol to give Example 52 as a white solid. ¹H NMR: (CDCl₃, 400 MHz) δ 8.18 (1H, s), 8.07-8.01

(1H, m), 7.58-7.50 (4H, m), 7.46-7.41 (2H, m), 7.30-7.19 (2H, m), 4.01-3.93 (1H, m), 2.11-1.98 (2H, m), 1.96-1.80 (4H, m), 1.69-1.63 (1H, m), 1.31-1.18 (3H, m). LC/MS: 389 (M+H)$^+$. HPLC (Method A) Rt 4.61 min (Purity: 93.6%).

Example 53

3-[3-(1-cyclohexyl-5-phenyl-1H-pyrazol-4-yl)-1,2,4-oxadiazol-5-yl]pyridine

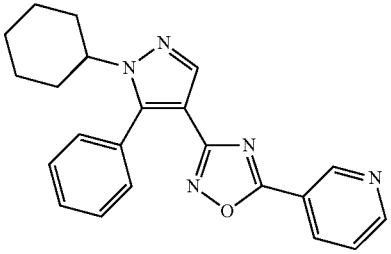 [SMILES: c1ccc(-c2c(-c3noc(-c4cccnc4)n3)cnn2C2CCCCC2)cc1]

The title compound was prepared following the procedure described for Example 51 but starting from Intermediate 9 (190 mg; 0.67 mmol) and methyl nicotinate (101 mg; 0.74 mmol) to give Example 53 as a white solid. $^1$H NMR: (CDCl$_3$, 400 MHz) δ 9.27 (1H, d, J=2.0 Hz), 8.78 (1H, dd, J=4.9, 1.7 Hz), 8.32 (1H, dt, J=8.0, 2.0 Hz), 8.18 (1H, s), 7.54-7.51 (3H, m), 7.46-7.40 (3H, m), 4.01-3.92 (1H, m), 2.12-1.98 (2H, m), 1.96-1.80 (4H, m), 1.71-1.60 (1H, m), 1.31-1.15 (3H, m). LC/MS: 372 (M+H)$^+$. HPLC (Method A) Rt 4.24 min (Purity: 99.5%).

Example 54

{4-[5-(1-isobutyl-5-pyridin-4-yl-1H-pyrazol-4-yl)-1,2,4-oxadiazol-3-yl]phenyl}methanol

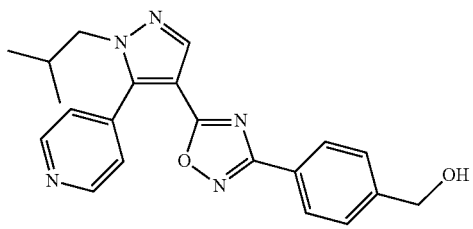 [SMILES: CC(C)Cn1ncc(-c2nc(-c3ccc(CO)cc3)no2)c1-c1ccncc1]

Sodium hydride (231.0 mg; 5.78 mmol) was added to a suspension of Intermediate 14 (1.50 g; 5.50 mmol) and Intermediate 8 (0.96 g; 5.78 mmol) in THF (15 mL) and the mixture was stirred for 10 minutes. The mixture was then heated in a microwave reactor for 3 hours at 130° C. Water (10 mL) was added and the product extracted into DCM (3×10 mL). The combined organic fractions were passed through a hydrophobic frit and the solvent removed in vacuo. The residue was purified by flash chromatography using a Biotage 40+M column, eluting with petrol containing increasing amounts of EtOAc to give Example 54 as a white solid. $^1$H NMR (CDCl$_3$, 400 MHz) δ 8.85-8.82 (2 H, d, J=4.4 Hz), 8.28 (1 H, s), 7.98 (2 H, d, J=8.1 Hz), 7.45 (2 H, d, J=8.1 Hz), 7.40 (2 H, d, 4.4 Hz), 4.76 (2 H, s), 3.88 (2 H, d, J=7.5 Hz), 2.24 (1 H, dt, J=13.8, 6.9 Hz), 1.78 (1 H, s), 0.82 (6 H, d, J=6.7 Hz). LC/MS: 376 (M+H)$^+$. HPLC (Method A) Rt=3.06 min (Purity: 96.3%).

Example 55

1-{4-[5-(1-cyclohexyl-5-pyridin-4-yl-1H-pyrazol-4-yl)-1,2,4-oxadiazol-3-yl]phenyl}-N-methylmethanamine

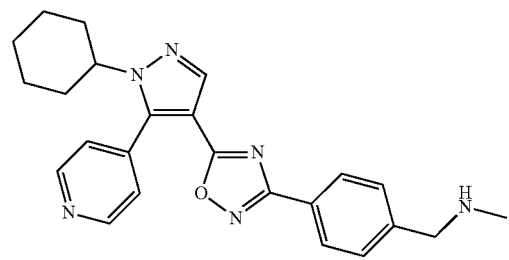 [SMILES: CNCc1ccc(-c2noc(-c3cnn(C4CCCCC4)c3-c3ccncc3)n2)cc1]

The title compound was prepared following the procedure described for Example 42 but using methylamine hydrochloride (61.5 mg; 0.911 mmol). The residue was purified by preparative HPLC to give Example 55 as a white solid. $^1$H NMR (DMSO-d$_6$) δ 8.83 (2 H, d, J=5.0 Hz), 8.37 (2 H, d, J=4.5 Hz), 7.93 (2 H, d, J=7.9 Hz), 7.64-7.60 (4 H, m), 4.08 (2 H, s), 3.99-3.88 (1 H, m), 2.54 (3H, s), 1.95-1.88 (4 H, m), 1.85-1.71 (2 H, m), 1.65-1.58 (1 H, m), 1.27-1.15 (3 H, m). LC/MS: 415 (M+H)$^+$. HPLC (Method C) Rt=13.16 min (Purity: 96.1%).

Example 56

2-({4-[5-(1-cyclohexyl-5-pyridin-4-yl-1H-pyrazol-4-yl)-1,2,4-oxadiazol-3-yl]benzyl}amino)ethanol

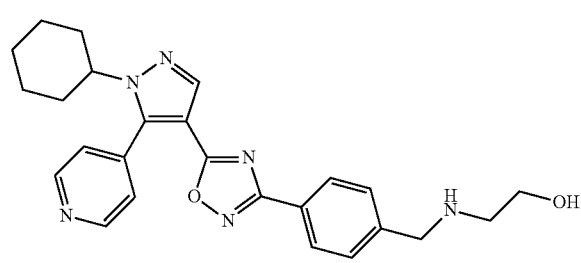 [SMILES: OCCNCc1ccc(-c2noc(-c3cnn(C4CCCCC4)c3-c3ccncc3)n2)cc1]

The title compound was prepared following the procedure described for Example 42 but using ethanolamine (55.7 mg; 0.911 mmol). The residue was purified by preparative HPLC to give Example 56 was obtained as a yellow solid. $^1$H NMR (DMSO-d$_6$) δ 8.79 (2 H, d, J=5.0 Hz), 8.38 (1 H, s), 8.30 (1 H, s), 7.86 (2 H, d, J=7.9 Hz), 7.60-7.51 (4 H, m), 3.92-3.89 (1 H, m), 3.61 (2 H, t, J=5.4 Hz), 2.83 (2 H, t, J=5.5 Hz), 2.54 (1 H, s), 1.90-1.85 (4 H, m), 1.85-1.69 (2H, m), 1.57-1.51 (1 H, m), 1.22-1.10 (3 H, m). LC/MS: 445 (M+H)$^+$. HPLC (Method C) Rt=12.91 min (Purity: 96.3%).

Example 57

3-(1-cyclohexyl-5-phenyl-1H-pyrazol-4-yl)-5-(2,5-difluorophenyl)-1,2,4-oxadiazole

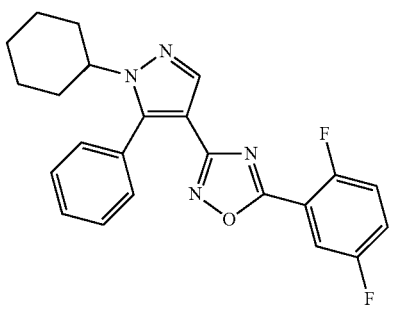 [SMILES: Fc1ccc(F)c(-c2nc(-c3cnn(C4CCCCC4)c3-c3ccccc3)no2)c1]

To a solution of 2,5-difluorobenzoic acid (Fluorochem; 48 mg; 0.3 mmol) in anhydrous MeCN (2 mL) was added 1-ethyl-3-(3-dimethylaminopropyl)carbodiimide hydrochloride (EDC) (80.5 mg; 0.42 mmol) followed by Intermediate 9 (102 mg; 0.36 mmol) in a Microwave vial and the mixture stirred at RT for 18 h. Anhydrous pyridine (2 mL) was added and the reaction vessel was sealed and heated at 150° C. for 45 min in the microwave. This reaction was performed twice, and the reaction mixtures were combined for workup. The solvents were removed in vacuo and H$_2$O (10 mL) and DCM (10 mL) were added. The mixture was passed through a hydrophobic frit and the solvent removed in vacuo. The residue was triturated with isopropanol and dried to give Example 57 as a white solid. $^1$H NMR: (CDCl$_3$, 400 MHz) δ 8.17 (1H, s), 7.75-7.69 (1H, m), 7.54-7.51 (3H, m), 7.45-7.41 (2H, m), 7.27-7.14 (2H, m), 4.02-3.92 (1H, m), 2.12-1.98 (2H, m), 1.96-1.79 (4H, m), 1.71-1.61 (1H, m), 1.32-1.14 (3H, m). LC/MS: 407 (M+H)$^+$. HPLC (Method F) Rt 4.63 min (Purity: 97.6%).

Example 58

3-(1-cyclohexyl-5-phenyl-1H-pyrazol-4-yl)-5-[3-(methylsulfonyl)phenyl]-1,2,4-oxadiazole

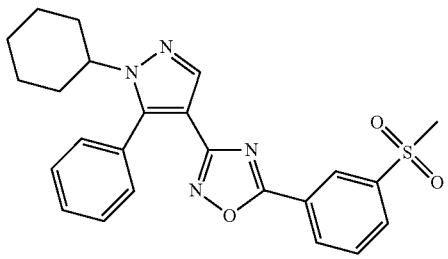 [SMILES: CS(=O)(=O)c1cccc(-c2nc(-c3cnn(C4CCCCC4)c3-c3ccccc3)no2)c1]

The title compound was prepared following the procedure described for Example 57, with two identical reactions combined for workup but starting from Intermediate 9 (102 mg; 0.36 mmol) and 3-(methylsulfonyl)benzoic acid (Apollo; 60 mg; 0.3 mmol) to give Example 58 as a white solid. $^1$H NMR: (CDCl$_3$, 400 MHz) δ 8.65 (1H, s), 8.31 (1H, d, J=7.9 Hz), 8.18 (1H, s), 8.13 (1H, d, J=7.9 Hz), 7.72 (1H, t, J=7.9 Hz), 7.59-7.49 (3H, m), 7.45-7.41 (2H, m), 4.02-3.92 (1H, m), 3.10 (3H, s), 2.14-1.96 (2H, m), 1.96-1.79 (4H, m), 1.72-1.57 (1H, m), 1.34-1.13 (3H, m). LC/MS: 449 (M+H)$^+$. HPLC (Method A) Rt 4.18 min (Purity: 99.5%).

Example 59

3-(1-cyclohexyl-5-phenyl-1H-pyrazol-4-yl)-5-[3-(trifluoromethyl)phenyl]-1,2,4-oxadiazole

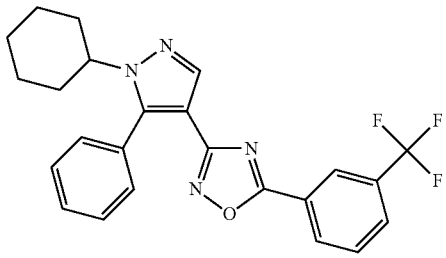 [SMILES: FC(F)(F)c1cccc(-c2nc(-c3cnn(C4CCCCC4)c3-c3ccccc3)no2)c1]

The title compound was prepared following the procedure described for Example 57, with two identical reactions combined for workup but starting from Intermediate 9 (102 mg; 0.36 mmol) and 3-(trifluoromethyl)benzoic acid (Fluorochem; 57 mg; 0.3 mmol) to give Example 59 as an off-white solid. $^1$H NMR: (CDCl$_3$, 400 MHz) δ 8.32 (1H, s), 8.23 (1H, d, J=7.9 Hz), 8.18 (1H, s), 7.81 (1H, d, J=7.9 Hz), 7.64 (1H, t, J=7.9 Hz), 7.55-7.52 (3H, m), 7.45-7.41 (2H, m), 4.01-3.92 (1H, m), 2.12-1.97 (2H, m), 1.96-1.79 (4H, m), 1.74-1.57 (1H, m), 1.30-1.17 (3H, m). LC/MS: 439 (M+H)$^+$. HPLC (Method G) Rt 4.94 min (Purity: 97.8%).

Example 60

3-(2,5-difluorophenyl)-5-[1-(2-fluorophenyl)-5-methyl-1H-pyrazol-4-yl]-1,2,4-oxadiazole

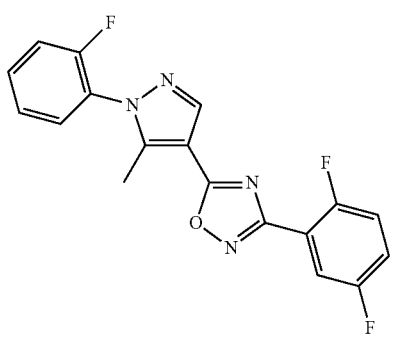 [SMILES: Cc1c(-c2nc(-c3cc(F)ccc3F)no2)cnn1-c1ccccc1F]

The title compound was prepared following the procedure described for Example 51 but starting from Intermediate 10 (157 mg; 0.67 mmol) and 2,5-difluoro-N'-hydroxybenzenecarboximidamide (JRD-Fluorochem, 127 mg; 0.74 mmol) to give Example 60 as an off-white solid. $^1$H NMR: (CDCl$_3$, 400 MHz) δ 8.32 (1H, s), 7.89-7.84 (1H, m), 7.57-7.49 (2H, m), 7.39-7.27 (2H, m), 7.27-7.14 (2H, m), 2.65 (3H, s). LC/MS: 357 (M+H)$^+$. HPLC (Method A) Rt 4.13 min (Purity: 99.6%).

Example 61

N-{4-[5-(1-cyclohexyl-5-pyridin-4-yl-1H-pyrazol-4-yl)-1,2,4-oxadiazol-3-yl]benzyl}-N-methylglycine

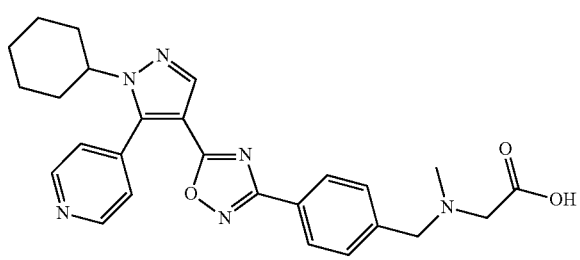 [SMILES: CN(CC(=O)O)Cc1ccc(-c2noc(-c3cnn(C4CCCCC4)c3-c3ccncc3)n2)cc1]

The title compound was prepared following the procedure described for Example 42 but using 2-methylamineoacetic acid (81.2 mg; 0.911 mmol). The residue was purified by preparative HPLC to give Example 61 as a white solid. $^1$H NMR (DMSO-d$_6$) δ 8.85 (2 H, dd, J=4.5, 1.6 Hz), 8.39 (1 H, s), 7.90 (2 H, d, J=8.0 Hz), 7.65 (2 H, dd, J=4.5, 1.6 Hz), 7.55 (2 H, d, J=8.0 Hz), 4.00-3.95 (1H, m), 3.87 (2 H, s), 3.26 (2H, s), 2.38 (3 H, s), 1.99-1.88 (4H, m), 1.85-1.78 (2H, m), 1.69-1.60 (1H, m), 1.30-1.15 (3 H, m). LC/MS: 473 (M+H)$^+$. HPLC (Method A) Rt=2.50 min (Purity: 99.2%).

Example 62

1-{4-[5-(1-cyclohexyl-5-pyridin-4-yl-1H-pyrazol-4-yl)-1,2,4-oxadiazol-3-yl]benzyl}azetidin-3-ol

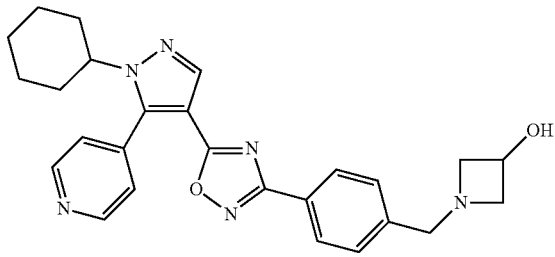 [SMILES: OC1CN(Cc2ccc(-c3noc(-c4cnn(C5CCCCC5)c4-c4ccncc4)n3)cc2)C1]

The title compound was prepared following the procedure described for Example 42 but using 3-azetidinol hydrochloride (66.6 mg; 0.911 mmol). The residue was purified by preparative HPLC to give Example 62 as a white solid. $^1$H NMR (DMSO-d$_6$) δ 8.87 (2 H, d, J=5.0 Hz), 8.41 (1 H, s), 7.86 (2 H, d, J=7.9 Hz), 7.67 (2 H, d, J=5.0 Hz), 7.44 (2 H, d, J=7.9 Hz), 5.33 (1 H, d, J=6.4 Hz), 4.24-4.18 (1H, q, J=5.6 Hz), 4.02-3.96 (1H, m), 3.63 (2 H, s), 3.52 (2 H, t, J=6.7 Hz), 2.80 (2 H, t, J=6.5 Hz), 1.98-1.89 (4 H, m), 1.85-1.78 (2 H, m), 1.68-1.60 (1H, m), 1.31-1.22 (3 H, m). LC/MS: 457 (M+H)$^+$. HPLC (Method B) Rt=2.21 min (Purity: 99.2%).

Example 63

(4-{5-[1-isobutyl-54tetrahydro-2H-pyran-4-yl)-1H-pyrazol-4-yl]-1,2,4-oxadiazol-3-yl}phenyl)methanol

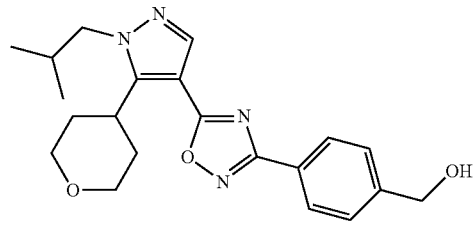 [SMILES: CC(C)Cn1ncc(-c2nc(-c3ccc(CO)cc3)no2)c1C1CCOCC1]

Sodium hydride (65.1 mg; 1.63 mmol) was added to a suspension of Intermediate 19 (434.6 mg; 1.55 mmol) and Intermediate 8 (270.5 mg; 1.628 mmol) in THF (10 mL) and the mixture was stirred for 10 minutes. The mixture was then heated in a microwave reactor for 900 minutes at 130° C. Water (10 mL) was added and the product extracted into DCM (3×10 mL). The combined organic fractions were passed through a hydrophobic frit and the solvent removed in vacuo. The residue was purified by flash chromatography using a Biotage 25+M column, eluting with DCM containing increasing amounts of methanol to give Example 63 as a white solid. $^1$H NMR (CDCl$_3$, 400 MHz) δ 8.13 (2 H, d, J=8.0 Hz), 8.10 (1 H, s), 7.50 (2 H, d, J=8.0 Hz), 4.77 (2 H, d, J=3.8 Hz), 4.15 (2 H, dd, J=11.6, 4.3 Hz), 4.04 (2 H, d, J=7.6 Hz), 3.58-3.52, (2H, m), 3.49-3.40 (1 H, m), 2.77-2.64 (3 H, m), 2.34-2.20 (1 H, m), 1.61-1.58 (2H, m), 0.97 (6 H, d, J=6.7 Hz). LC/MS: 383 (M+H)$^+$. HPLC (Method G) Rt=3.47 min (Purity: 99.9%).

Example 64

1-(4-{5-[1-cyclohexyl-5-(methoxymethyl)-1H-pyrazol-4-yl]-1,2,4-oxadiazol-3-yl}benzyl)piperidine-4-carboxylic acid

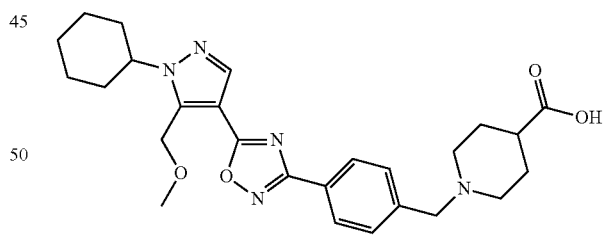

Step 1: 4-(5-(1-cyclohexyl-5-(methoxymethyl)-1H-pyrazol-4-yl)-1,2,4-oxadiazol-3-yl)benzaldehyde Example 49 (1.25 g; 3.40 mmol) was dissolved in dioxane (50 mL) and manganese dioxide (12.5 g; 42.3 mmol) was added. The mixture was heated at 70° C. overnight and then the solvent was removed in vacuo. The residue was triturated with a mixture of petrol/diethyl ether to give the title compound as a white solid (1.22 g; 97%). $^1$H NMR (CDCl$_3$, 400 MHz) δ 10.11 (1 H, s), 8.33 (2 H, d, J=8.0 Hz), 8.15 (1 H, s), 8.02 (2 H, d, J=8.1 Hz), 5.03 (2 H, s), 4.32 (1 H, td, J=10.3, 4.9 Hz), 3.44 (3 H, s), 2.07-1.93 (6 H, m), 1.76 (1 H, d, J=12.6

Hz), 1.52-1.25 (3 H, m). LC/MS: 367 (M+H)+. HPLC (Method A) Rt=4.36 min (Purity: 97.7%).

Step 2: 1-(4-{5-[1-cyclohexyl-5-(methoxymethyl)-1H-pyrazol-4-yl]-1,2,4-oxadiazol-3-yl}benzyl)piperidine-4-carboxylic acid Sodium cyanoborohydride (32.5 mg; 0.517 mmol) was added to a solution of 4-(5-(1-cyclohexyl-5-(methoxymethyl)-1H-pyrazol-4-yl)-1,2,4-oxadiazol-3-yl)benzaldehyde, obtained from step 1, (172 mg; 0.47 mmol) and isonipecotic acid (121.4 mg; 0.94 mmol) in a mixture of methanol (3 mL) and acetic acid (80.7 µl; 0.141 mmol) and the mixture was stirred at room temperature overnight. The solvent was removed in vacuo and the residue purified by preparative HPLC to give Example 64 as a white solid. $^1$H NMR (DMSO-$d_6$) δ 8.23 (1 H, s), 8.04 (2 H, d, J=8.1 Hz), 7.54 (2 H, d, J=8.0 Hz), 5.02 (2 H, s), 4.44-4.34 (1 H, m), 3.56 (2 H, s), 3.34 (3 H, s), 2.78 (2 H, d, J=11.0 Hz), 2.26-2.17 (1 H, m), 2.06 (2 H, t, J=11.2 Hz), 1.96-1.76 (8 H, m), 1.71 (1 H, d, J=12.8 Hz), 1.66-1.52 (2 H, m), 1.53-1.37 (2 H, m), 1.25 (1 H, t, J=13.0 Hz). LC/MS: 480 (M+H)+. HPLC (Method G) Rt=2.39 min (Purity: 96.7%).

Example 65

N-{4-[5-(1-cyclohexyl-5-pyridin-4-yl-1H-pyrazol-4-yl)-1,2,4-oxadiazol-3-yl]benzyl}-beta-alanine

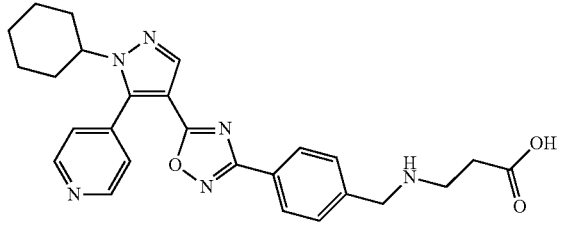 [SMILES: O=C(O)CCNCc1ccc(-c2noc(-c3cnn(C4CCCCC4)c3-c3ccncc3)n2)cc1]

The title compound was prepared following the procedure described for Example 42 but using β-alanine (81.2 mg; 0.911 mmol) to give Example 65 as a white solid. $^1$H NMR (DMSO-$d_6$) δ 8.85 (2 H, d, J=5.2 Hz), 8.39 (1 H, s), 7.90 (2 H, d, J=8.0 Hz), 7.65 (2 H, d, J=5.2 Hz), 7.56 (2 H, d, J=8.0 Hz), 4.04-3.90 (3 H, m), 2.83 (2 H, t, J=6.6 Hz), 2.34 (2 H, t, J=6.59 Hz), 1.99-1.88 (4 H, m), 1.88-1.78 (2 H, m), 1.65-1.58 (1 H, m), 1.30-1.20 (3 H, m). LC/MS: 473 (M+H)+. HPLC (Method A) Rt=2.27 min (Purity: 98.5%).

Example 66

4-(4-{3-[4-(azetidin-1-ylmethyl)phenyl]-1,2,4-oxadiazol-5-yl}-1-cyclohexyl-1H-pyrazol-5-yl)pyridine

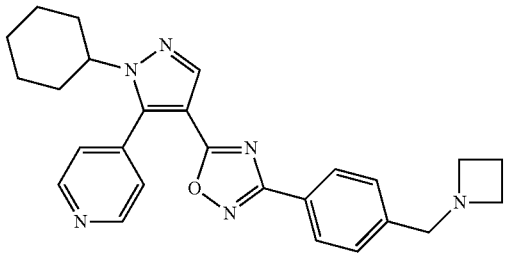 [SMILES: c1cc(-c2c(-c3nc(-c4ccc(CN5CCC5)cc4)no3)cnn2C2CCCCC2)ccn1]

The title compound was prepared following the procedure described for Example 42 but using azetidine hydrochloride (93.8 mg; 0.911 mmol). The residue was purified preparative HPLC to give Example 66 as an off white solid. $^1$H NMR (DMSO-$d_6$) δ 8.86 (2 H, d, J=4.9 Hz), 8.40 (1 H, s), 7.86 (2 H, d, J=7.8 Hz), 7.67 (2 H, d, J=5.0 Hz), 7.45 (2 H, d, J=7.9 Hz), 4.02-3.90 (1 H, m), 3.60 (2 H, s), 3.16 (4 H, t, J=6.9 Hz), 2.05-1.89 (6 H, m), 1.84-1.78 (2 H, m), 1.66-1.60 (1 H, m), 1.30-1.19 (3 H, m). LC/MS: 473 (M+H)+. HPLC (Method C) Rt=13.66 min (Purity: 96.5%).

Example 67

N-(4-{5-[1-cyclohexyl-5-(methoxymethyl)-1H-pyrazol-4-yl]-1,2,4-oxadiazol-3-yl}benzyl)-beta-alanine

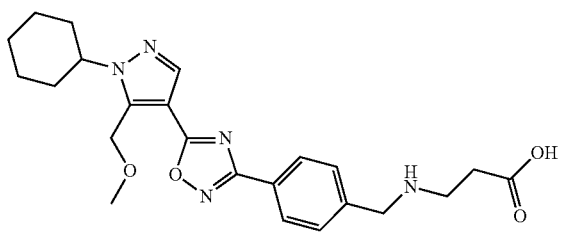 [SMILES: COCc1c(-c2nc(-c3ccc(CNCCC(=O)O)cc3)no2)cnn1C1CCCCC1]

The title compound was prepared following the procedure described for Example 64, but using β-Alanine (83.7 mg; 0.94 mmol) to give Example 67 as a white solid. $^1$H NMR (DMSO-$d_6$) δ 8.25 (1 H, s), 8.07 (2 H, d, J=8.0 Hz), 7.59 (2 H, d, J=8.0 Hz), 5.05 (2 H, s), 4.45-4.38 (1 H, m), 3.88 (2 H, s), 3.38 (3 H, s), 2.80 (2 H, t, J=6.7 Hz), 2.39 (2 H, t, J=6.7 Hz), 1.95-1.84 (6 H, m), 1.78-1.69 (1 H, m), 1.55-1.40 (2 H, m), 1.35-1.26 (1 H, m). LC/MS: 440 (M+H)+. HPLC (Method C) Rt=17.22 min (Purity: 98.1%).

Example 68

1-(4-{5-[1-cyclohexyl-5-(methoxymethyl)-1H-pyrazol-4-yl]-1,2,4-oxadiazol-3-yl}benzyl)azetidine-3-carboxylic acid

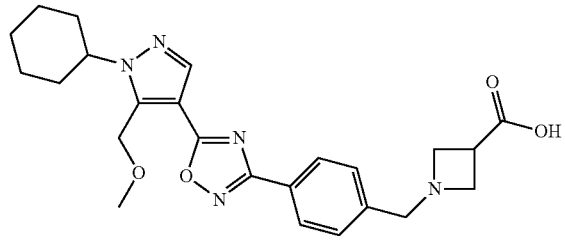 [SMILES: COCc1c(-c2nc(-c3ccc(CN4CC(C(=O)O)C4)cc3)no2)cnn1C1CCCCC1]

The title compound was prepared following the procedure described for Example 64, but using 3-azetidine carboxylic acid (95.0 mg; 0.94 mmol) to give Example 68 as a white solid. $^1$H NMR (DMSO-$d_6$) δ 8.23 (1 H, s), 8.04 (2 H, d, J=8.1 Hz), 7.52 (2 H, d, J=8.1 Hz), 5.01 (2 H, s), 4.42-4.32 (1 H, m), 3.67 (2 H, s), 3.52 (2 H, t, J=7.7 Hz), 3.38-3.31 (5 H, m), 3.28-3.19 (1 H, m), 1.93-1.79 (6 H, m), 1.75-1.68 (1 H, m), 1.50-1.39 (2 H, m), 1.30-1.20 (1 H, m). LC/MS: 452 (M+H)⁺. HPLC (Method G) Rt=2.47 min (Purity: 99.5%).

Example 69

(4-{5-[1-isobutyl-5-(methoxymethyl)-1H-pyrazol-4-yl]-1,2,4-oxadiazol-3-yl}phenyl)methanol

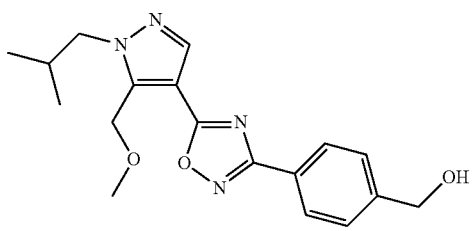 [SMILES: COCc1c(-c2nc(-c3ccc(CO)cc3)no2)cnn1CC(C)C]

Sodium hydride (0.23 g; 5.88 mmol) was added to a suspension of Intermediate 21 (1.27 g; 5.60 mmol) and Intermediate 8 (0.98 g; 5.88 mmol) in THF (15 mL) and the mixture was stirred for 10 minutes. The mixture was then heated in a microwave reactor for 60 minutes at 130° C. Water (10 mL) was added and the product extracted into DCM (3×10 mL). The combined organic fractions were passed through a hydrophobic frit and the solvent removed in vacuo. The residue was purified by flash chromatography on a Biotage 25+M column, eluting with petrol containing increasing amounts of EtOAc to give Example 69 as a white solid. ¹H NMR (CDCl₃, 400 MHz) δ 8.16-8.11 (3 H, m), 7.51 (2 H, d, J=8.4 Hz), 5.02 (2 H, s), 4.79 (2 H, s), 4.07 (2 H, d, J=7.5 Hz), 3.43 (3 H, s), 2.43-2.32 (1 H, m), 1.82 (1 H, t, J=5.8 Hz), 0.96 (6 H, d, J=6.7 Hz). LC/MS: 343 (M+H)⁺. HPLC (Method C) Rt=15.47 min (Purity: 94.5%).

Example 70

(4-{5-[1-cyclohexyl-5-(tetrahydro-2H-pyran-4-yl)-1H-pyrazol-4-yl]-1,2,4-oxadiazol-3-yl}phenyl)methanol

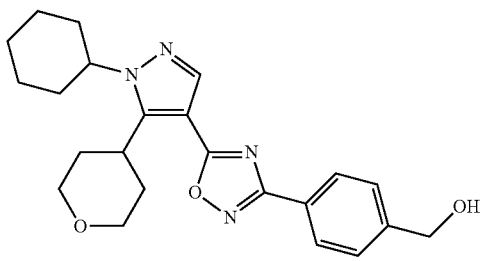 [SMILES: OCc1ccc(-c2noc(-c3cnn(C4CCCCC4)c3C3CCOCC3)n2)cc1]

The title compound was prepared following the procedure described for Example 69, but starting from Intermediate 20 (796.7 mg; 2.60 mmol) and Intermediate 8 (453.7 mg; 2.73 mmol) to give Example 70 as a white solid (750 mg; 70%). ¹H NMR (CDCl₃, 400 MHz) δ 8.13 (2 H, d, J=8.0 Hz), 8.10 (1 H, s), 7.52 (2 H, d, J=8.0 Hz), 4.79 (2 H, s), 4.32-4.24 (1 H, m), 4.17 (2 H, dd, J=11.6, 4.3 Hz), 3.96-3.85 (1 H, m), 3.61 (2 H, t, J=11.7 Hz), 2.44 (2 H, dd, J=12.8, 4.4 Hz), 2.13-2.00 (2 H, m), 1.99-1.90 (4 H, m), 1.82-1.68 (4 H, m), 1.55-1.23 (3 H, m). LC/MS: 409 (M+H)⁺. HPLC (Method A) Rt=3.85 min (Purity: 95.4%).

Example 71

1-{4-[5-(1-cyclohexyl-5-pyridin-4-yl-1H-pyrazol-4-yl)-1,2,4-oxadiazol-3-yl]benzyl}piperidine-4-carboxylic acid

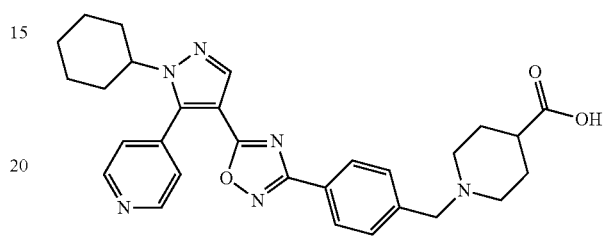

The title compound was prepared following the procedure described for Example 42 but using iso-nipecotic acid (117.7 mg; 0.911 mmol). The product was purified by preparative HPLC to give Example 71 as a white solid. ¹H NMR (DMSO-d₆) δ 8.85-8.82 (2 H, dd, J=4.4, 1.7 Hz), 8.38 (1 H, s), 7.86 (2 H, d, J=8.1 Hz), 7.64 (2 H, dd, J=4.4, 1.7 Hz), 7.48 (2 H, d, J=8.0 Hz), 3.99-3.90 (1 H, m), 3.55 (2 H, s), 2.80-2.70 (2 H, m), 2.25-2.16 (1 H, m), 2.09-1.98 (2 H, m), 1.98-1.88 (4 H, m), 1.82-1.79 (4 H, m), 1.63-1.50 (3 H, m), 1.30-1.15 (3 H, m). LC/MS: 513 (M+H)⁺. HPLC (Method B) Rt=2.44 min (Purity: 99.1%).

Example 72

N-(4-{5-[1-cyclohexyl-5-(methoxymethyl)-1H-pyrazol-4-yl]-1,2,4-oxadiazol-3-yl}benzyl)-N-methylglycine

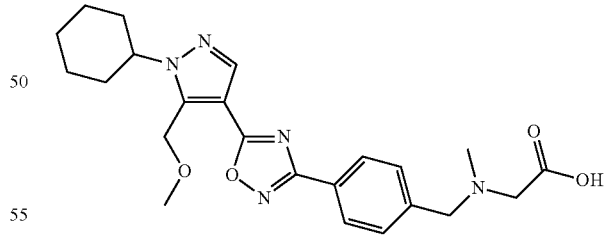

The title compound was prepared following the procedure described for Example 64, but using 2-methylaminoacetic acid (83.7 mg; 0.94 mmol) to give Example 72 as a white solid. ¹H NMR (DMSO-d₆) δ 8.22 (1 H, s), 8.11 (2 H, d, J=8.1 Hz), 7.68 (2 H, d, J=8.1 Hz), 5.00 (2 H, s), 4.42-4.32 (1 H, m), 4.14 (2 H, s), 3.36-3.34 (5 H, m), 2.59 (3 H, s), 1.92-1.79 (6 H, m), 1.70 (1 H, d, J=12.7 Hz), 1.50-1.34 (2 H, m), 1.29-1.14 (1 H, m). LC/MS: 440 (M+H)⁺. HPLC (Method B) Rt=2.59 min (Purity: 98.9%).

Example 73

1-(4-{5-[1-cyclohexyl-5-(methoxymethyl)-1H-pyrazol-4-yl]-1,2,4-oxadiazol-3-yl}benzyl)azetidin-3-ol

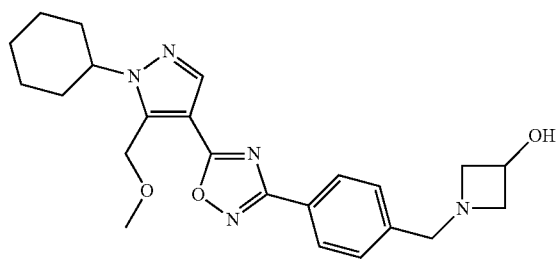 [SMILES: COCc1c(-c2nc(-c3ccc(CN4CC(O)C4)cc3)no2)cnn1C1CCCCC1]

The title compound was prepared following the procedure described for Example 64, but using 3-hydroxyazetidine hydrochloride (103.0 mg; 0.94 mmol) to give Example 73 as a clear oil. $^1$H NMR (CDCl$_3$, 400 MHz) δ 8.13 (1 H, s), 8.09 (2 H, d, J=8.1 Hz), 7.41 (2 H, d, J=8.0 Hz), 5.03 (2 H, s), 4.49 (1 H, t, J=5.9 Hz), 4.32-4.28 (1 H, m), 3.71-3.65 (4 H, m), 3.42 (3H, s), 2.99-2.94 (2 H, m), 2.05-1.90 (6 H, m), 1.80-1.70 (1 H, m), 1.53-1.28 (3 H, m). LC/MS: 424 (M+H)$^+$. HPLC (Method A) Rt=2.33 min (Purity: 99.0%).

Example 74

1-(4-{5-[1-cyclohexyl-5-(methoxymethyl)-1H-pyrazol-4-yl]-1,2,4-oxadiazol-3-yl}benzyl)pyrrolidin-3-ol

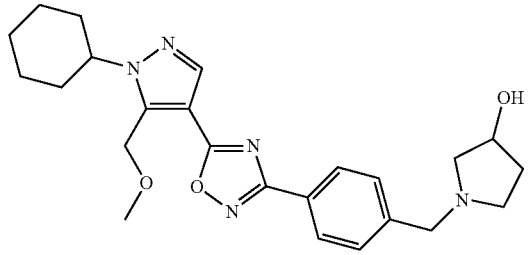 [SMILES: COCc1c(-c2nc(-c3ccc(CN4CCC(O)C4)cc3)no2)cnn1C1CCCCC1]

The title compound was prepared following the procedure described for Example 64, but using 3-pyrrolidinol (76.1 μL; 0.94 mmol) to give Example 74 as a clear oil. $^1$H NMR (CDCl$_3$, 400 MHz) δ 8.14 (1 H, s), 8.09 (2 H, d, J=8.0 Hz), 7.47 (2 H, d, J=8.0 Hz), 5.03 (2 H, s), 4.37-4.27 (2 H, m), 3.71 (2 H, s), 3.42 (3 H, s), 2.90 (1 H, td, J=8.6, 5.1 Hz), 2.70 (1 H, d, J=10.2 Hz), 2.57 (1 H, dd, J=10.1, 5.1 Hz), 2.37-2.30 (1 H, m), 2.29-2.18 (1 H, m), 2.05-1.90 (6 H, m), 1.83-1.73 (2 H, m), 1.50-1.23 (3 H, m). LC/MS: 438 (M+H)$^+$. HPLC (Method A) Rt=2.35 min (Purity: 99.6%).

Example 75

1-(4-{5-[1-cyclohexyl-5-(methoxymethyl)-1H-pyrazol-4-yl]-1,2,4-oxadiazol-3-yl}phenyl)-N,N-dimethylmethanamine

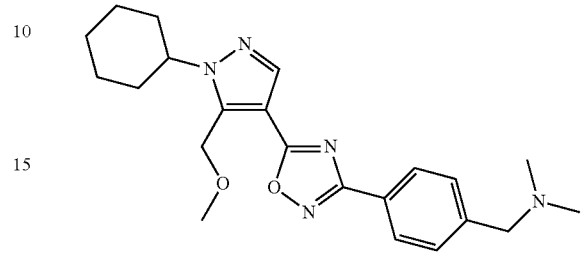

The title compound was prepared following the procedure described for Example 64, but using dimethylamine hydrochloride (76.7 mg; 0.94 mmol) to give Example 75 as a white solid. $^1$H NMR (CDCl$_3$, 400 MHz) δ 8.15-8.07 (3 H, m), 7.46 (2 H, d, J=8.0 Hz), 5.03 (2 H, s), 4.35-4.27 (1 H, m), 3.51 (2 H, s), 3.42 (3 H, s), 2.28 (6 H, s), 2.07-1.89 (6 H, m), 1.76 (1 H, d, J=12.9 Hz), 1.47-1.27 (3 H, m). LC/MS: 396 (M+H)$^+$. HPLC (Method B) Rt=4.17 min (Purity: 98.4%).

Example 76

1-(4-{5-[1-isobutyl-5-(methoxymethyl)-1H-pyrazol-4-yl]-1,2,4-oxadiazol-3-yl}benzyl)azetidine-3-carboxylic acid

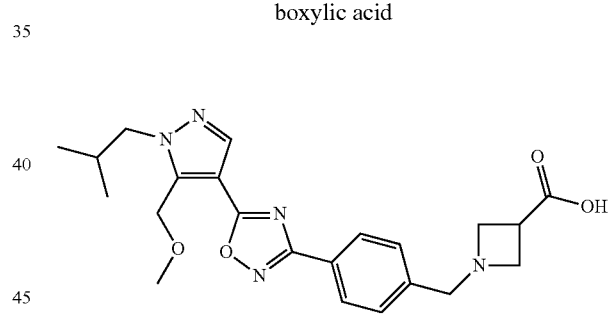

Step 1: 4-{5-[1-isobutyl-5-(methoxymethyl)-1H-pyrazol-4-yl]-1,2,4-oxadiazol-3-yl}benzaldehyde The title compound was prepared following the procedure described for Example 64 (step 1), but starting from Example 69 (907.4 mg; 2.65 mmol) to give the title compound as a white solid (880.0 mg; 97%). $^1$H NMR (CDCl$_3$, 400 MHz) δ 10.10 (1 H, s), 8.33 (2 H, d, J=8.1 Hz), 8.14 (1 H, s), 8.05 (2 H, d, J=8.1 Hz), 5.02 (2 H, s), 4.08 (2 H, d, J=7.5 Hz), 3.47 (3 H, s), 2.44-2.33 (1 H, m), 0.97 (6 H, d, J=6.7 Hz). LC/MS: 341 (M+H)$^+$. HPLC (Method D) Rt=19.39 min (Purity: 92.4%).

Step 2: 1-(4-{5-[1-isobutyl-5-(methoxymethyl)-1H-pyrazol-4-yl]-1,2,4-oxadiazol-3-yl}benzyl)azetidine-3-carboxylic acid The title compound was prepared following the procedure described for Example 64 (step 2), but starting from 4-{5-[1- isobutyl-5-(methoxymethyl)-1H-pyrazol-4-yl]-1,2,4-oxadiazol-3-yl}benzaldehyde, obtained from step 1, (170.2 mg; 0.50 mmol) and using 3-azetidine carboxylic acid (101.1 mg; 1.0 mmol) to give Example 76 as a white solid. $^1$H NMR (CDCl$_3$, 400 MHz) δ 8.14-8.11 (3 H, m), 7.56 (2 H, d, J=8.0 Hz), 4.99 (2 H, s), 4.17 (2 H, s), 4.13-4.09 (2 H, m), 4.05 (2 H, d, J=7.6 Hz), 3.97 (2 H, t, J=9.3 Hz), 3.43-3.38 (4 H, m), 2.41-2.32 (1 H, m), 0.95 (6 H, d, J=6.7 Hz). LC/MS: 426 (M+H)$^+$. HPLC (Method A) Rt=2.32 min (Purity: 99.3%).

Example 77

N-{4-[5-(1-isobutyl-5-pyridin-4-yl-1H-pyrazol-4-yl)-1,2,4-oxadiazol-3-yl]benzyl}-N-methylglycine

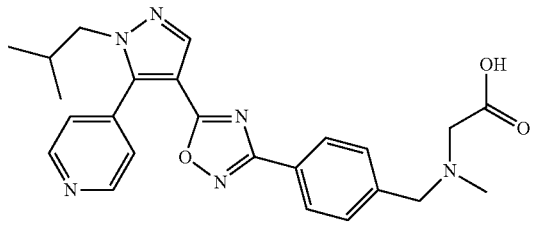 [SMILES: CC(C)Cn1ncc(-c2nc(-c3ccc(CN(C)CC(=O)O)cc3)no2)c1-c1ccncc1]

Step 1: 4-(5-(1-isobutyl-5-(pyridin-4-yl)-1H-pyrazol-4-yl)-1,2,4-oxadiazol-3-yl)benzaldehyde The title compound was prepared following the procedure described for Example 64 (step 1), but starting from Example 54 (1.07 g; 2.85 mmol), to give the title compound as an off white solid (1.03 g; 96%). $^1$H NMR (CDCl$_3$, 400 MHz) δ 10.07 (1 H, s), 8.86 (2 H, dd, J=4.5, 1.6 Hz), 8.29 (1 H, s), 8.16 (2 H, d, J=8.1 Hz), 7.96 (2 H, d, J=8.1 Hz), 7.41 (2 H, dd, J=4.4, 1.7 Hz), 3.89 (2 H, d, J=7.5 Hz), 2.29-2.20 (1 H, m), 0.83 (6 H, d, J=6.7 Hz). LC/MS: 374 (M+H)$^+$. HPLC (Method A) Rt=3.63 min (Purity: 95.3%).

Step 2: N-{4-[5-(1-isobutyl-5-pyridin-4-yl-1H-pyrazol-4-yl)-1,2,4-oxadiazol-3-yl]benzyl}-N-methylglycine The title compound was prepared following the procedure described for Example 64 (step 2), but starting from 4-(5-(1-isobutyl-5-(pyridin-4-yl)-1H-pyrazol-4-yl)-1,2,4-oxadiazol-3-yl)benzaldehyde, obtained from step 1, (56.0 mg; 0.15 mmol) and using 2-methylaminoacetic acid (26.7 mg; 0.30 mmol), to give Example 77 as a white solid (40.0 mg; 89%). $^1$H NMR (CDCl$_3$, 400 MHz) δ 8.83 (2 H, d, J=5.1 Hz), 8.26 (1 H, s), 7.98 (2 H, d, J=8.2 Hz), 7.50 (2 H, d, J=8.4 Hz), 7.41 (2 H, d, J=5.3 Hz), 4.08 (2 H, s), 3.88 (2 H, d, J=7.3 Hz), 3.42 (2 H, s), 2.64 (3 H, s), 2.23 (1 H, dt, J=13.7, 6.9 Hz), 0.82 (6 H, d, J=6.6 Hz). LC/MS: 447 (M+H)$^+$. HPLC (Method B) Rt=2.24 min (Purity: 98.9%).

Example 78

N-(4-(5-(1-cyclohexyl-5-(pyridin-4-yl)-1H-pyrazol-4-yl)-1,2,4-oxadiazol-3-yl)benzyl)-2-methoxyethanamine

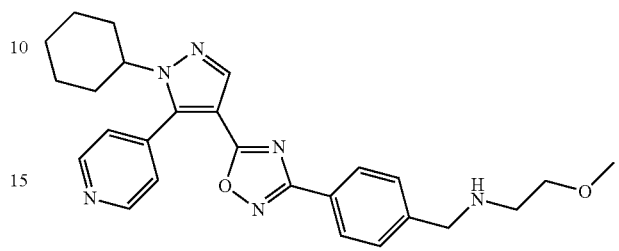

Sodium cyanoborohydride (31.5 mg; 0.501 mmol) was added to a solution of 4-(5-(1-cyclohexyl-5-(pyridin-4-yl)-1H-pyrazol-4-yl)-1,2,4-oxadiazol-3-yl)benzaldehyde (182 mg; 0.456 mmol), obtained as described in step 2 of Example 41, and methoxyethylamine (68.4 mg; 0.911 mmol) in methanol (3 mL) and acetic acid (75 μL) and the mixture was stirred at room temperature overnight. The solvent was removed in vacuo and the residue was purified by reverse phase preparative HPLC to give Example 78 as a pale yellow solid. $^1$H NMR (CDCl$_3$, 400 MHz) δ 8.85-8.82 (2 H, m), 8.26 (1 H, s), 7.93 (2 H, d, J=7.9 Hz), 7.42-7.38 (4H, m), 3.97-3.87 (1 H, m), 3.86 (2 H, s), 3.54-3.49 (2 H, m), 3.35 (3 H, d, J=1.1 Hz), 2.82-2.77 (2 H, m), 2.13-1.99 (2 H, m), 1.95-1.82 (3 H, m), 1.79-1.60 (3 H, m), 1.33-1.17 (2 H, m). LC/MS: 459 (M+H)$^+$. HPLC (Method B) Rt=3.39 min (Purity: 96.0%).

Example 79

1-(4-(5-(1-isobutyl-5-(pyridin-4-yl)-1H-pyrazol-4-yl)-1,2,4-oxadiazol-3-yl)benzyl)azetidine-3-carboxylic acid

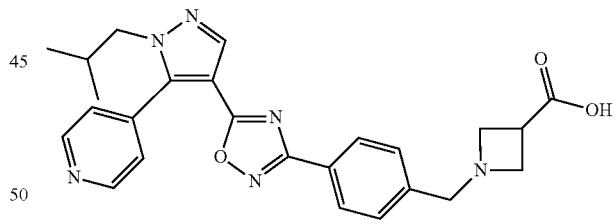

Step 1: (4-(5-(1-isobutyl-5-(pyridin-4-yl)-1H-pyrazol-4-yl)-1,2,4-oxadiazol-3-yl)phenyl)methanol Sodium hydride (0.23 g; 5.78 mmol) was added to a suspension of Intermediate 14 (1.5 g; 5.50 mmol) and Intermediate 8 (0.96 g; 5.78 mmol) in THF (15 mL) and the mixture was stirred for 10 minutes. The mixture was then heated in a microwave reactor 180 minutes at 130° C. Water (20 mL) was added and the product extracted into DCM (3×20 mL). The combined organic fractions were passed through a hydrophobic frit and the solvent removed in vacuo. The residue was purified by flash chromatography on a 40+M Biotage column, eluting with petrol containing increasing amounts of ethyl acetate to give the title compound as a white solid. $^1$H NMR:

(CDCl₃, 400 MHz) δ 8.85-8.82 (2 H, d, J=4.4 Hz), 8.28 (1 H, s), 7.98 (2 H, d, J=8.1 Hz), 7.45 (2 H, d, J=8.1 Hz), 7.40 (2 H, d, 4.4 Hz), 4.76 (2 H, s), 3.88 (2 H, d, J=7.5 Hz), 2.24 (1 H, dt, J=13.8, 6.9 Hz), 1.78 (1 H, s), 0.82 (6 H, d, J=6.7 Hz). LC/MS: 376 (M+H)⁺. HPLC (Method A) Rt 3.06 min (Purity: 96.3%).

Step 2: 4-(5-(1-isobutyl-5-(pyridin-4-yl)-1H-pyrazol-4-yl)-1,2,4-oxadiazol-3-yl)benzaldehyde The title compound was prepared following the procedure described for Example 88 (step 2), but starting from (4-(5-(1-isobutyl-5-(pyridin-4-yl)-1H-pyrazol-4-yl)-1,2,4-oxadiazol-3-yl)phenyl)methanol (1.07 g; 2.85 mmol), obtained from step 1. The title compound was obtained as an off white solid (1.03 g; 96.8%). ¹H NMR: (CDCl₃, 400 MHz) δ 10.07 (1 H, s), 8.86 (2 H, dd, J=4.5, 1.6 Hz), 8.29 (1 H, s), 8.16 (2 H, d, J=8.1 Hz), 7.96 (2 H, d, J=8.1 Hz), 7.41 (2 H, dd, J=4.4, 1.7 Hz), 3.89 (2 H, d, J=7.5 Hz), 2.29-2.20 (1 H, m), 0.83 (6 H, d, J=6.7 Hz) LC/MS: 374 (M+H)⁺. HPLC (Method A) Rt 3.63 min (Purity: 96.8%).

Step 3: 1-(4-(5-(1-isobutyl-5-(pyridin-4-yl)-1H-pyrazol-4-yl)-1,2,4-oxadiazol-3-yl)benzyl)azetidine-3-carboxylic acid Sodium cyanoborohydride (31 mg; 0.495 mmol) was added to a solution of 4-(5-(1-isobutyl-5-(pyridin-4-yl)-1H-pyrazol-4-yl)-1,2,4-oxadiazol-3-yl)benzaldehyde (168 mg; 0.45 mmol), obtained from step 2, and 3-azetidine carboxylic acid (91.0 mg; 0.90 mmol) in methanol (3 mL) and acetic acid (77 μL; 1.35 mmol) and the mixture was stirred at room temperature overnight. The solvent was removed in vacuo and the purified by reverse-phase preparative HPLC. The residue was dissolved in chloroform & washed with NaHCO₃ to give Example 79 as a white solid. ¹H NMR: (CDCl₃, 400 MHz) δ 8.74 (2 H, d, J=5.3 Hz), 8.15 (1 H, s), 7.72 (2 H, d, J=7.9 Hz), 7.32 (2 H, d, J=5.3 Hz), 7.14 (2 H, d, J=7.9 Hz), 5.80-4.80 (1 H, br s), 3.81 (2 H, d, J=7.4 Hz), 3.40-3.35 (4 H, m), 3.14 (2 H, s), 2.88 (1 H, s), 2.24-2.10 (1 H, m), 0.77 (6 H, d, J=6.7 Hz). LC/MS: 459 (M+H)⁺. HPLC (Method D) Rt 12.88 min (Purity: 94.1%).

Example 80

1-(4-(5-(1-isobutyl-5-(pyridin-4-yl)-1H-pyrazol-4-yl)-1,2,4-oxadiazol-3-yl)benzyl)pyrrolidin-3-ol, formate

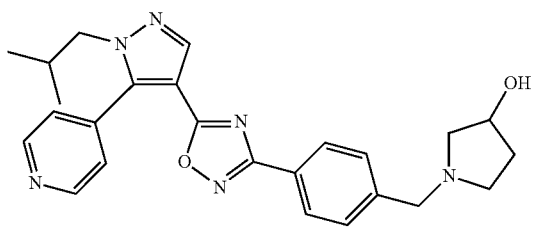 [SMILES: CC(C)Cn1ncc(-c2nc(-c3ccc(CN4CCC(O)C4)cc3)no2)c1-c1ccncc1]

Sodium cyanoborohydride (31 mg; 0.495 mmol) was added to a solution of 4-(5-(1-isobutyl-5-(pyridin-4-yl)-1H-pyrazol-4-yl)-1,2,4-oxadiazol-3-yl)benzaldehyde (168 mg; 0.45 mmol), obtained as described in Example 79 (steps 1-2), and 3-pyrrolidinol (72.9 μL; 0.90 mmol) in methanol (3 mL) and acetic acid (77 μL; 1.35 mmol) and the mixture was stirred at room temperature overnight. The solvent was removed in vacuo and the residue purified by reverse-phase preparative HPLC to give Example 80 as a white solid. ¹H NMR: (CDCl₃, 400 MHz) δ 8.84 (2 H, d, J=5.1 Hz), 8.43 (1 H, s), 8.27 (1 H, s), 8.00 (2 H, d, J=7.9 Hz), 7.55 (2 H, d, J=7.9 Hz), 7.43 (2 H, d, J=5.1 Hz), 4.52 (1 H, s), 4.19 (1 H, d, J=12.9 Hz), 4.06 (1 H, d, J=12.9 Hz), 3.88 (2 H, d, J=7.4 Hz), 3.52-3.42 (1 H, m), 3.26 (1 H, d, J=11.8 Hz), 3.05-3.00 (1 H, m), 3.00-2.90 (1 H, m), 2.35-2.16 (2 H, m), 2.12-2.04 (1 H, m), 0.82 (6 H, d, J=6.7 Hz). LC/MS: 445 (M+H)⁺. HPLC (Method D) Rt 16.96 min (Purity: 98.1%).

Example 81

1-(4-(5-(1-isobutyl-5-(pyridin-4-yl)-1H-pyrazol-4-yl)-1,2,4-oxadiazol-3-yl)phenyl)-N,N-dimethyl-methanamine, formate

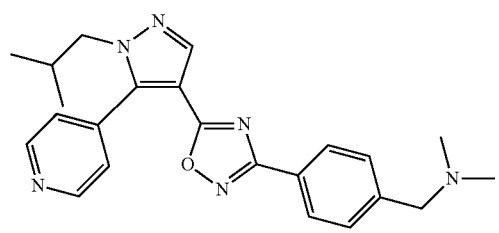 [SMILES: CC(C)Cn1ncc(-c2nc(-c3ccc(CN(C)C)cc3)no2)c1-c1ccncc1]

Sodium cyanoborohydride (10.4 mg; 0.165 mmol) was added to a solution of 4-(5-(1-isobutyl-5-(pyridin-4-yl)-1H-pyrazol-4-yl)-1,2,4-oxadiazol-3-yl)benzaldehyde (56 mg; 0.15 mmol), obtained as described in Example 79 (steps 1-2) and dimethylamine hydrochloride (24.5 mg; 0.30 mmol) in methanol (3 mL) and acetic acid (26 μL; 0.45 mmol) and the mixture was stirred at room temperature overnight. The solvent was removed in vacuo and the residue redissolved in DMSO and submitted for reverse phase preparative HPLC. Example 81 was obtained as a white solid. ¹H NMR: (CDCl₃, 400 MHz) δ 8.85 (2 H, d, J=5.3 Hz), 8.44 (1 H, s), 8.28 (1 H, s), 8.00 (2 H, d, J=8.0 Hz), 7.49 (2 H, d, J=8.0 Hz), 7.43 (2 H, d, J=5.3 Hz), 3.89-3.87 (4 H, m), 2.51 (6 H, s), 2.31-2.17 (1 H, m), 0.82 (6 H, d, J=6.7 Hz). LC/MS: 403 (M+H)⁺. HPLC (Method A) Rt 2.12 min (Purity: 97.3%).

Example 82

1-(4-(5-(1-isobutyl-5-(pyridin-4-yl)-1H-pyrazol-4-yl)-1,2,4-oxadiazol-3-yl)benzyl)azetidin-3-ol, formate

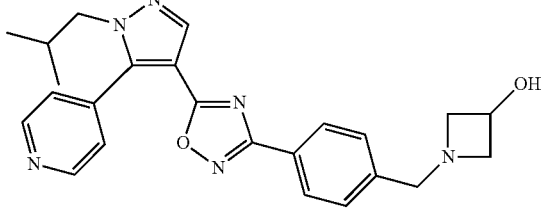

Sodium cyanoborohydride (10.4 mg; 0.165 mmol) was added to a solution of 4-(5-(1-isobutyl-5-(pyridin-4-yl)-1H-pyrazol-4-yl)-1,2,4-oxadiazol-3-yl)benzaldehyde (56 mg; 0.15 mmol), obtained as described in Example 79 (steps 1-2)

and 3-hydroxyazetidine hydrochloride (32.9 mg; 0.30 mmol) in methanol (3 mL) and acetic acid (26 μL; 0.45 mmol) and stirred at room temperature overnight. The solvent was removed in vacuo and the residue redissolved in DMSO and submitted for reverse phase preparative HPLC. Example 82 was obtained as a golden gum (63.6 mg; 98.5%). $^1$H NMR: (CDCl$_3$, 400 MHz) δ 8.84 (2 H, d, J=6.0 Hz), 8.44 (1 H, s), 8.27 (1 H, s), 8.01 (2 H, d, J=7.9 Hz), 7.47 (2 H, d, J=7.9 Hz), 7.41 (2 H, d, J=6.0 Hz), 4.55-4.50 (1 H, m), 4.05 (2 H, s), 3.99-3.93 (2 H, m), 3.81 (2 H, d, J=7.2 Hz), 3.81-3.79 (2 H, m), 2.23 (1 H, dq, J=13.8, 6.9 Hz), 0.82 (6 H, d, J=6.7 Hz). LC/MS: 431 (M+H)$^+$. HPLC (Method D) Rt 16.29 min (Purity: 97.9%).

Example 83

5-(1-cyclohexyl-3-methyl-1H-pyrazol-4-yl)-3-(2,5-difluorophenyl)-1,2,4-oxadiazole

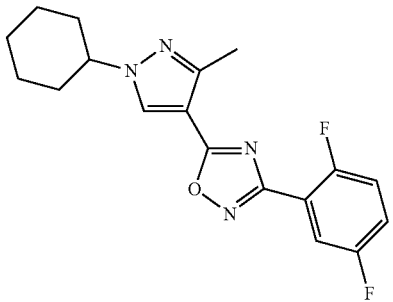 [SMILES: Cc1nn(C2CCCCC2)cc1-c1nc(-c2cc(F)ccc2F)no1]

Step 1: methyl 1-cyclohexyl-3-methyl-1H-pyrazole-4-carboxylate and methyl 1-cyclohexyl-5-methyl-1H-pyrazole-4-carboxylate To a solution of methyl 3-oxobutanoate (1.6 mL; 15 mmol) in toluene (100 mL) was added DMF.DMA (2.65 mL; 20 mmol) and PPTS (375 mg). The mixture was heated to 90° C. for 2 hours. The solvent was removed in vacuo and DCM (25 mL) and water (25 mL) were added and the mixture passed through a hydrophobic frit. The solvent was removed in vacuo and the residue redissolved in EtOH (90 mL). Acetic acid (1.5 mL) and cyclohexylhydrazine hydrochloride (2.26 g; 15 mmol) were added and the mixture heated to reflux for 7 hours. The solvent was removed in vacuo and the residue purified by flash chromatography on a Biotage 40+M column, eluting with petrol containing increasing amounts of EtOAc to give an approximately 1:9 mixture of methyl 1-cyclohexyl-3-methyl-1H-pyrazole-4-carboxylate [minor product] and methyl 1-cyclohexyl-5-methyl-1H-pyrazole-4-carboxylate [major product] (1.7 g; 51%). Minor product: LC/MS: 223 (M+H)$^+$. HPLC: (15 cm_Formic_Slow_Sunfire_HPLC) Rt=15.11 min. Major product: LC/MS: 223 (M+H)$^+$. HPLC: (Method C) Rt=15.45 min.

Step 2: 5-(1-cyclohexyl-3-methyl-1H-pyrazol-4-yl)-3-(2,5-difluorophenyl)-1,2,4-oxadiazole In a microwave vial, a mixture of methyl 1-cyclohexyl-3-methyl-1H-pyrazole-4-carboxylate and methyl 1-cyclohexyl-5-methyl-1H-pyrazole-4-carboxylate (149 mg), obtained from step 1, was suspended in toluene (2 mL) and 2,5-difluoro-N'-hydroxybenzenecarboximidamide (Fluoro-chem, 144 mg; 0.74 mmol) was added followed by potassium carbonate (123 mg; 0.74 mmol). The Microwave vial was sealed and the mixture was heated to 180° C. in a microwave reactor for 1 hour. DCM (10 mL) and water (5 mL) were added and the mixture passed through a hydrophobic frit. The solvent was removed in vacuo and the residue purified by flash chromatography on a Biotage 25+S column, eluting with petrol containing increasing amounts of DCM to give Example 83 as a white solid, together with 5-(1-cyclohexyl-5-methyl-1H-pyrazol-4-yl)-3-(2,5-difluorophenyl)-1,2,4-oxadiazole (Example 86 below). $^1$H NMR (CDCl$_3$, 400 MHz) δ 8.11 (1 H, s), 7.88-7.82 (1 H, m), 7.25-7.14 (2 H, m), 4.12 (1 H, tt, J=11.8, 3.8 Hz), 2.63 (3 H, s), 2.29-2.17 (2 H, m), 1.99-1.88 (2 H, m), 1.80-1.66 (3 H, m), 1.54-1.38 (2 H, m), 1.34-1.22 (1 H, m). LC/MS: 345 (M+H)$^+$. HPLC (Method B) Rt=4.16 min (Purity: 90.1%).

Example 84

3-(4-(5-(1-isobutyl-5-(methoxymethyl)-1H-pyrazol-4-yl)-1,2,4-oxadiazol-3-yl)benzylamino)propanoic acid

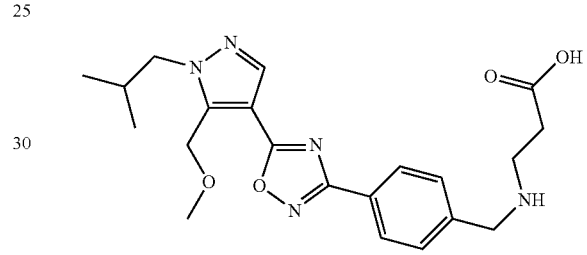

Step 1: (4-(5-(1-isobutyl-5-(methoxymethyl)-1H-pyrazol-4-yl)-1,2,4-oxadiazol-3-yl)phenyl)methanol Sodium hydride (0.23 g; 5.88 mmol) was added to a suspension of Intermediate 27 (1.27 g; 5.60 mmol) and Intermediate 8 (0.98 g, 5.88 mmol) in THF (15 mL) and the mixture was stirred for 10 minutes. The mixture was then heated in a microwave reactor 1 hour at 130° C. Water (20 mL) was added and the product extracted into DCM (3×20 mL). The combined organic fractions were passed through a hydrophobic frit and the solvent removed in vacuo. The residue was purified by flash chromatography on a 25+M Biotage column, eluting with petrol containing increasing amounts of ethyl acetate to give the title compound as a white solid. $^1$H NMR: (CDCl$_3$, 400 MHz) δ 8.16-8.11 (3 H, m), 7.51 (2 H, d, J=8.4 Hz), 5.02 (2 H, s), 4.79 (2 H, s), 4.07 (2 H, d, J=7.52 Hz), 3.43 (3 H, s), 2.43-2.32 (1 H, m), 1.82 (1 H, t, J=5.8 Hz), 0.96 (6 H, d, J=6.7 Hz). LC/MS: 343 (M+H)$^+$. HPLC (Method C) Rt 15.47 min (Purity: 94.5%).

Step 2: 4-(5-(1-isobutyl-5-(methoxymethyl)-1H-pyrazol-4-yl)-1,2,4-oxadiazol-3-yl)benzaldehyde The title compound was prepared following the procedure described for Example 88 (step 2), but starting from (4-(5-(1-isobutyl-5-(methoxymethyl)-1H-pyrazol-4-yl)-1,2,4-oxadiazol-3-yl)phenyl)methanol (0.91 g; 2.65 mmol), obtained from step 1. The title compound was obtained as a white solid (880 mg; 97.6%). $^1$H NMR: (CDCl$_3$, 400 MHz) δ 10.10 (1 H, s), 8.33 (2 H, d, J=8.1 Hz), 8.14 (1 H, s), 8.05 (2 H, d, J=8.1 Hz), 5.02 (2 H, s), 4.08 (2 H, d, J=7.5 Hz), 3.47 (3 H, s), 2.44-2.33 (1 H, m), 0.97 (6 H, d, J=6.7 Hz). LC/MS: 341 (M+H)+. HPLC (Method D) Rt 19.39 min (Purity: 92.4%).

Step 3: 3-(4-(5-(1-isobutyl-5-(methoxymethyl)-1H-pyrazol-4-yl)-1,2,4-oxadiazol-3-yl)benzylamino) propanoic acid Sodium cyanoborohydride (34.6 mg; 0.55 mmol) was added to a solution of 4-(5-(1-isobutyl-5-(methoxymethyl)-1H-pyrazol-4-yl)-1,2,4-oxadiazol-3-yl)benzaldehyde (170 mg; 0.50 mmol), obtained from step 2, and β-alanine (89.1 mg; 1.0 mmol) in methanol (3 mL) and acetic acid (86 μL; 1.50 mmol) and the mixture was stirred at room temperature overnight. The solvent was removed in vacuo and the product recrystallised from a mixture of DMSO and water to give Example 84 as a white solid. $^1$H NMR: (CD$_3$OD, 400 MHz) δ 8.26 (2 H, d, J=8.1 Hz), 8.21 (1 H, s), 7.73 (2 H, d, J=8.1 Hz), 5.08 (2 H, s), 4.34 (2 H, s), 4.15 (2 H, d, J=7.5 Hz), 3.52 (3 H, s), 3.18 (2 H, t, J=6.4 Hz), 2.56 (2 H, t, J=6.4 Hz), 2.43-2.36 (1 H, m), 1.01 (6 H, d, J=6.7 Hz). LC/MS: 414 (M+H)+. HPLC (Method B) Rt 2.33 min (Purity: 94.2%).

Example 85

1-(4-(5-(1-isobutyl-5-(pyridin-4-yl)-1H-pyrazol-4-yl)-1,2,4-oxadiazol-3-yl)phenyl)-N-methylmethanamine

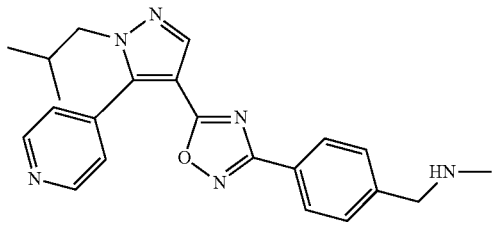 [SMILES: CNCc1ccc(-c2noc(-c3cnn(CC(C)C)c3-c3ccncc3)n2)cc1]

Sodium cyanoborohydride (31 mg; 0.495 mmol) was added to a solution of 4-(5-(1-isobutyl-5-(pyridin-4-yl)-1H-pyrazol-4-yl)-1,2,4-oxadiazol-3-yl)benzaldehyde (168 mg; 0.45 mmol), obtained as described in Example 79 (steps 1-2) and methylamine hydrochloride (60.8 mg; 0.90 mmol) in methanol (3 mL) and acetic acid (77 μL; 1.35 mmol) and the mixture was stirred at room temperature overnight. The solvent was removed in vacuo and the purified by reverse-phase preparative HPLC. The residue was purified by flash chromatography on a 12+M Biotage column, eluting with DCM containing increasing amounts of 3% NH$_3$/MeOH in DCM to give Example 85 as a white solid. $^1$H NMR: (CDCl$_3$, 400 MHz) δ 8.84 (2 H, d, J=5.0 Hz), 8.28 (1 H, s), 7.95 (2 H, d, J=7.9 Hz), 7.43-7.38 (4 H, m), 3.88 (2 H, d, J=7.5 Hz), 3.80 (2 H, s), 2.46 (3 H, s), 2.31-2.17 (1 H, m), 0.82 (6 H, d, J=6.7 Hz). LC/MS: 389 (M+H)+. HPLC (Method B) Rt 2.87 min (Purity: 99.1%).

Example 86

5-(1-cyclohexyl-5-methyl-1H-pyrazol-4-yl)-3-(2,5-difluorophenyl)-1,2,4-oxadiazole

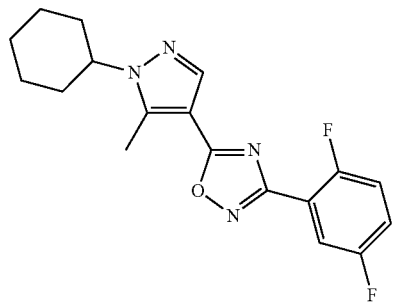 [SMILES: Cc1c(-c2nc(-c3cc(F)ccc3F)no2)cnn1C1CCCCC1]

The title compound was isolated from the reaction described above for the synthesis of 5-(1-cyclohexyl-3-methyl-1H-pyrazol-4-yl)-3-(2,5-difluorophenyl)-1,2,4-oxadiazole (Example 83). Example 86 was isolated as white solid. $^1$H NMR (CDCl$_3$, 400 MHz) δ 8.10 (1 H, s), 7.88-7.82 (1 H, m), 7.26-7.14 (2 H, m), 4.13-4.04 (1 H, m), 2.73 (3 H, s), 2.11-1.91 (6 H, m), 1.83-1.71 (1 H, m), 1.50-1.23 (3 H, m). LC/MS: 345 (M+H)+. HPLC (Method A) Rt=4.51 min (Purity: 98.9%).

Example 87

5-(1-cyclohexyl-5-(tetrahydro-2H-pyran-4-yl)-1H-pyrazol-4-yl)-3-(3-(trifluoromethyl)phenyl)-1,2,4-oxadiazole

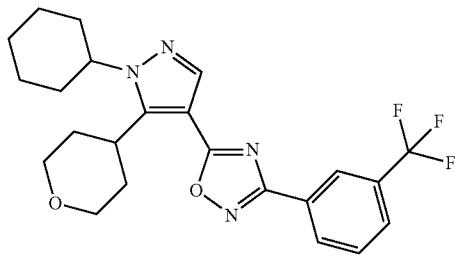 [SMILES: FC(F)(F)c1cccc(-c2noc(-c3cnn(C4CCCCC4)c3C3CCOCC3)n2)c1]

Sodium hydride (14 mg; 0.347 mmol) was added to a suspension of Intermediate 20 (100 mg; 0.33 mmol) and N'-hydroxy-3-(trifluoromethyl)benzenecarboximidamide (Bionet, 71 mg; 0.347 mmol) in THF (2 mL) and the mixture was stirred for 10 minutes. The mixture was then heated to 130° C. in a microwave reactor for 1 hour. Water (5 mL) was added and the product was extracted into DCM (3×10 mL). The combined organic fractions were passed through a hydrophobic, dried in vacuo and the residue purified by reverse-phase preparative HPLC to give Example 87 as a brown solid. $^1$H NMR: (CDCl$_3$, 400 MHz) δ 8.43 (1 H, s), 8.34 (1 H, d, J=7.8 Hz), 8.12 (1 H, s), 7.78 (1 H, d, J=7.9 Hz), 7.65 (1 H, t, J=7.8 Hz), 4.29 (1 H, tt, J=11.5, 3.8 Hz), 4.18 (2 H, dd, J=11.6, 4.3 Hz), 3.98-3.87 (1 H, m), 3.65-3.55 (2 H, m), 2.42 (2 H, qd, J=12.6, 4.5 Hz), 2.18-1.89 (6 H, m), 1.79 (1 H, d, J=12.8 Hz), 1.71 (2 H, d, J=13.2 Hz), 1.51-1.36 (2 H, m), 1.36-1.28 (1 H, m). LC/MS: 447 (M+H)+. HPLC (Method B) Rt 4.47 min (Purity: 99.4%).

Example 88

1-(4-(5-(1-cyclohexyl-5-(tetrahydro-2H-pyran-4-yl)-1H-pyrazol-4-yl)-1,2,4-oxadiazol-3-yl)phenyl)-N-methylmethanamine

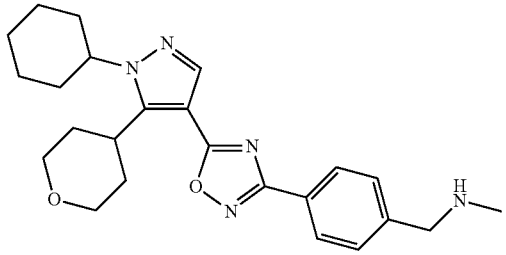 [SMILES: CNCc1ccc(-c2noc(-c3cnn(C4CCCCC4)c3C3CCOCC3)n2)cc1]

Step 1: (4-(5-(1-cyclohexyl-5-(tetrahydro-2H-pyran-4-yl)-1H-pyrazol-4-yl)-1,2,4-oxadiazol-3-yl)phenyl)methanol Sodium hydride (0.11 g; 2.73 mmol) was added to a suspension of Intermediate 20 (0.80 g; 2.60 mmol) and Intermediate 8 (0.45 g; 2.73 mmol) in THF (15 mL) and stirred for 10 minutes. The mixture was then heated in the microwave for 60 minutes at 130° C. Water (20 mL) was added and the product extracted into DCM (3×20 mL). The combined organic fractions were passed through a hydrophobic frit and the solvent removed in vacuo. The residue was purified on a 25+M Biotage column, eluting with petrol containing increasing amounts of ethyl acetate. The title compound was obtained as a white solid (750 mg; 70.6%). $^1$H NMR: (CDCl$_3$, 400 MHz) δ 8.13 (2 H, d, J=8.0 Hz), 8.10 (1 H, s), 7.52 (2 H, d, J=8.0 Hz), 4.79 (2 H, s), 4.32-4.24 (1 H, m), 4.17 (2 H, dd, J=11.6, 4.3 Hz), 3.96-3.85 (1 H, m), 3.61 (2 H, t, J=11.7 Hz), 2.44 (1 H, dd, J=12.8, 4.44 Hz), 2.13-2.00 (2 H, m), 1.99-1.90 (4 H, m), 1.82-1.68 (4 H, m), 1.55-1.23 (3 H, m). LC/MS: 409 (M+H)+. HPLC (Method A) Rt 3.85 min (Purity: 95.4%).

Step 2: 4-(5-(1-cyclohexyl-5-(tetrahydro-2H-pyran-4-yl)-1H-pyrazol-4-yl)-1,2,4-oxadiazol-3-yl)benzaldehyde (4-(5-(1-cyclohexyl-5-(tetrahydro-2H-pyran-4-yl)-1H-pyrazol-4-yl)-1,2,4-oxadiazol-3-yl)phenyl)methanol (0.71 g; 1.75 mmol), obtained from step 1, was dissolved in dioxane (25 mL) and manganese dioxide (7.15 g; 47.0 mmol) was added. The mixture was heated at 70° C. for 18 hours. The mixture was filtered through a small pad of celite which was washed with dioxane and DCM. The solvent was removed in vacuo and the residue triturated with a mixture of petrol/diethyl ether to give the title compound as an off white solid (500 mg; 70.3%). $^1$H NMR: (CDCl$_3$, 400 MHz) δ 10.11 (1 H, s), 8.33 (2 H, d, J=8.1 Hz), 8.12 (1 H, s), 8.03 (2 H, d, J=8.2 Hz), 4.29 (1 H, s), 4.19 (2 H, dd, J=11.5, 4.3 Hz), 3.92-3.83 (1 H, s), 3.62 (2 H, dd, J=12.4, 10.7 Hz), 2.47 (2 H, dd, J=12.8, 4.52 Hz), 2.10-2.04 (2 H, m), 2.00-1.90 (4 H, m), 1.82-1.75 (1 H, m), 1.70 (2 H, d, J=13.17 Hz), 1.52-1.25 (3 H, m). LC/MS: 407 (M+H)+. HPLC (Method A) Rt 4.35 min (Purity: 96.9%).

Step 3: 1-(4-(5-(1-cyclohexyl-5-(tetrahydro-2H-pyran-4-yl)-1H-pyrazol-4-yl)-1,2,4-oxadiazol-3-yl)phenyl)-N-methylmethanamine Sodium cyanoborohydride (28 mg; 0.440 mmol) was added to a solution of 4-(5-(1-cyclohexyl-5-(tetrahydro-2H-pyran-4-yl)-1H-pyrazol-4-yl)-1,2,4-oxadiazol-3-yl)benzaldehyde (163 mg; 0.40 mmol), obtained from step 2, and methylamine hydrochloride (54.0 mg; 0.80 mmol) in methanol (3 mL) and acetic acid (69 μL; 1.20 mmol) and the mixture was stirred at room temperature overnight. The solvent was removed in vacuo and the residue purified by reverse-phase preparative HPLC. The residue was dissolved in chloroform & washed with NaHCO$_3$ to give Example 88 as a brown gum. $^1$H NMR: (CDCl$_3$, 400 MHz) δ 8.11 (3 H, d, J=7.5 Hz), 7.47 (2 H, d, J=8.0 Hz), 4.32-4.23 (2 H, m), 4.20-4.09 (2 H, m), 3.92 (1 H, t, J=12.7 Hz), 3.84 (2 H, s), 3.61 (2 H, t, J=11.7 Hz), 2.52-2.34 (5 H, m), 2.12-2.00 (2 H, m), 2.00-1.96 (4 H, m), 1.78 (1 H, d, J=12.8 Hz), 1.71-1.60 (2 H, m), 1.51-1.39 (2H, m), 1.39-1.25 (1H, m). LC/MS: 422 (M+H)+. HPLC (Method A) Rt 2.36 min (Purity: 94.6%).

Example 89

3-(4-(5-(1-isobutyl-5-(pyridin-4-yl)-1H-pyrazol-4-yl)-1,2,4-oxadiazol-3-yl)benzylamino)propanoic acid

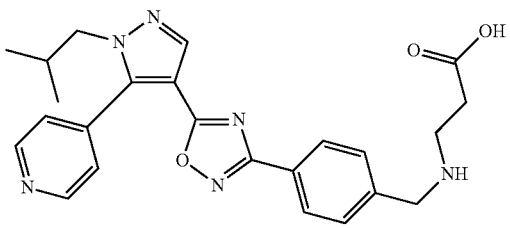 [SMILES: CC(C)Cn1ncc(-c2nc(-c3ccc(CNCCC(=O)O)cc3)no2)c1-c1ccncc1]

Sodium cyanoborohydride (31 mg; 0.495 mmol) was added to a solution of 4-(5-(1-isobutyl-5-(pyridin-4-yl)-1H-pyrazol-4-yl)-1,2,4-oxadiazol-3-yl)benzaldehyde (168 mg; 0.45 mmol), obtained as described in Example 79 (step 1-2), and β-alanine (80.2 mg; 0.90 mmol) in methanol (3 mL) and acetic acid (77 μL; 1.35 mmol) and the mixture was stirred at room temperature overnight. The solvent was removed in vacuo and the residue purified by reverse-phase preparative HPLC to give Example 89 as a white solid. $^1$H NMR: (DMSO-d$_6$, 400 MHz) δ 8.86-8.82 (2 H, d, J=4.6 Hz), 8.40 (1 H, s), 7.92 (2 H, d, J=8.0 Hz), 7.66 (2 H, d, J=4.6 Hz), 7.58 (2 H, d, J=8.1 Hz), 4.02 (2 H, s), 3.93 (2 H, d, J=7.0 Hz), 2.88 (2 H, t, J=6.6 Hz), 2.34 (2 H, t, J=6.6 Hz), 2.11-2.02 (1 H, m), 0.75 (6 H, d, J=6.7 Hz). LC/MS: 447 (M+H)+. HPLC (Method D) Rt 13.39 min (Purity: 94.0%).

Example 90

5-(1-neopentyl-5-(pyridin-4-yl)-1H-pyrazol-4-yl)-3-(3-(trifluoromethyl)phenyl)-1,2,4-oxadiazole

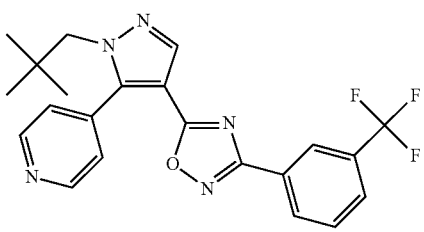 [SMILES: CC(C)(C)Cn1ncc(-c2nc(-c3cccc(C(F)(F)F)c3)no2)c1-c1ccncc1]

In a microwave vial, Intermediate 30 (103 mg; 0.36 mmol) was suspended in toluene (1 mL) and N'-hydroxy-3-(trifluoromethyl)benzenecarboximidamide (Bionet, 82 mg; 0.40 mmol) was added followed by potassium carbonate (66 mg; 0.40 mmol). The Microwave vial was sealed and the mixture was heated to 180° C. in a microwave reactor for 15 min. MeCN (0.5 mL) and DMF (0.5 mL) were added and the mixture was heated to 180° C. in a microwave reactor for 4 hours. DCM (10 mL) and water (5 mL) were added and the mixture passed through a hydrophobic frit. The solvent was removed in vacuo and the residue purified by flash chromatography on a Biotage 12+M column, eluting with petrol containing increasing amounts of EtOAc to give Example 90 as an off-white solid. $^1$H NMR (CDCl$_3$, 400 MHz) δ 8.86-8.81 (2 H, m), 8.32-8.26 (2 H, m), 8.16 (1 H, d, J=7.9 Hz), 7.74 (1 H, d, J=7.9 Hz), 7.59 (1 H, t, J=7.9 Hz), 7.42-7.40 (2 H, m), 3.97 (2 H, s), 0.86 (9 H, s). LC/MS: 428 (M+H)$^+$. HPLC (Method B) Rt=4.10 min (Purity: 92.0%).

Example 91

3-(4-((1H-1,2,4-triazol-1-yl)methyl)phenyl)-5-(1-cyclohexyl-5-(pyridin-4-yl)-1H-pyrazol-4-yl)-1,2,4-oxadiazole

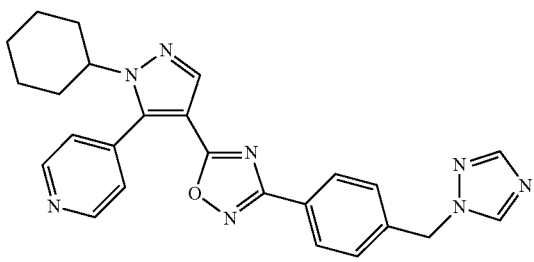 [SMILES: c1cc(-c2c(-c3nc(-c4ccc(Cn5cncn5)cc4)no3)cnn2C2CCCCC2)ccn1]

In a microwave vial, Intermediate 7 (201 mg; 0.67 mmol) was suspended in toluene (2 mL) and 4-((1H-1,2,4-triazol-1-yl)methyl)-N'-hydroxy benzenecarboximidamide (Aurora, 161 mg; 0.74 mmol) was added followed by potassium carbonate (123 mg; 0.74 mmol). The Microwave vial was sealed and the mixture was heated to 180° C. in a microwave reactor for 15 min. MeCN (1 mL) was added and the mixture was heated to 180° C. in a microwave reactor for 1.5 hours. DCM (10 mL) and water (5 mL) were added and the mixture passed through a hydrophobic frit. The solvent was removed in vacuo and the residue purified by flash chromatography on a Biotage 12+M column, eluting with petrol containing increasing amounts of EtOAc to give Example 91 as a white solid. $^1$H NMR (CDCl$_3$, 400 MHz) δ 8.86-8.81 (2 H, m), 8.26 (1 H, s), 8.10 (1 H, s), 8.02-7.95 (3 H, m), 7.43-7.35 (2 H, m), 7.33 (2 H, d, J=8.0 Hz), 5.39 (2 H, s), 3.98-3.85 (1 H, m), 2.10-1.99 (2 H, m), 1.97-1.82 (4 H, m), 1.81-1.57 (1 H, m), 1.32-1.17 (3 H, m). LC/MS: 453 (M+H)$^+$. HPLC (Method B) Rt=3.15 min (Purity: 97.1%).

Example 92

3-(4-bromophenyl)-5-(1-cyclohexyl-5-(pyridin-4-yl)-1H-pyrazol-4-yl)-1,2,4-oxadiazole

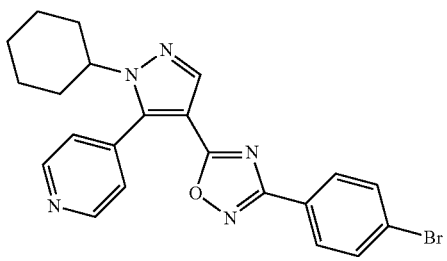 [SMILES: Brc1ccc(-c2noc(-c3cnn(C4CCCCC4)c3-c3ccncc3)n2)cc1]

The title compound was prepared following the procedure described for Example 15, but starting from Intermediate 7 (401 mg; 1.34 mmol) and 4-bromo-N'-hydroxy benzenecarboximidamide (Apollo, 318 mg; 1.48 mmol), to give Example 92 as a white solid. $^1$H NMR (CDCl$_3$, 400 MHz) δ 8.86-8.83 (2 H, m), 8.26 (1 H, s), 7.86-7.82 (2 H, m), 7.60-7.56 (2 H, m), 7.40-7.38 (2 H, m), 3.97-3.87 (1 H, m), 2.14-2.01 (2 H, m), 1.98-1.81 (4 H, m), 1.82-1.55 (1 H, m), 1.34-1.17 (3 H, m). LC/MS: 450 (M+H)$^+$. HPLC (Method B) Rt=4.22 min (Purity: 98.7%).

Example 93

3-(2,5-difluorophenyl)-5-(1-neopentyl-5-(pyridin-4-yl)-1H-pyrazol-4-yl)-1,2,4-oxadiazole

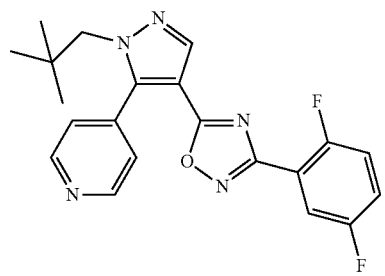 [SMILES: CC(C)(C)Cn1ncc(-c2nc(-c3cc(F)ccc3F)no2)c1-c1ccncc1]

Sodium Hydride (13 mg; 0.315 mmol) was added to a suspension of Intermediate 30 (86 mg; 0.30 mmol) and 2,5-difluoro-N'-hydroxybenzenecarboximidamide (JRD-Fluorochemical, 54.2 mg; 0.315 mmol) in THF (2 mL) and the mixture was stirred for 10 minutes. The mixture was then heated to 130° C. in a microwave reactor for four hours. Water (10 mL) was added and the product extracted into DCM (3×10 mL). The combined organic fractions were passed through a hydrophobic frit and the solvent removed in vacuo. The residue was purified by flash chromatography on a 12+M Biotage column, eluting with petrol containing increasing

Example 94

(4-(5-(1-(cyclopropylmethyl)-5-(pyridin-4-yl)-1H-pyrazol-4-yl)-1,2,4-oxadiazol-3-yl)phenyl)methanol

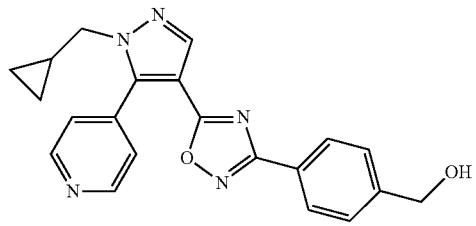 [SMILES: OCc1ccc(-c2noc(-c3cnn(CC4CC4)c3-c3ccncc3)n2)cc1]

Sodium hydride (24 mg; 0.60 mmol) was added to a suspension of Intermediate 29 (270 mg; 1.0 mmol) and Intermediate 8 (100 mg; 1.60 mmol) in THF (10 mL) and the mixture was stirred for 10 minutes. The mixture was then heated to 130° C. in a microwave reactor for 4 hours before an additional 0.1 equivalents of sodium hydride and Intermediate 8 were added and the mixture heated to 130° C. in a microwave reactor for 4 hours. A further 0.1 equivalents of sodium hydride and Intermediate 8 were added and the mixture heated to 130° C. in a microwave reactor for 4 hours. Water (20 mL) was added and the mixture washed with a mixture of ether (20 mL) and DCM (20 mL). The solid formed was removed by filtration and dried to give Example 94 as a white solid. $^1$H NMR: (Acetone-$d_6$, 400 MHz) δ 8.83 (2 H, d, J=5.1 Hz), 8.25 (1 H, s), 7.93 (2 H, d, J=7.8 Hz), 7.64 (2 H, d, J=5.1 Hz), 7.50 (2 H, d, J=7.8 Hz), 4.71 (2 H, s), 4.35 (1 H, s), 4.06 (2 H, d, J=7.0 Hz), 1.25-1.09 (1 H, m), 0.51-0.47 (2 H, m), 0.28-0.20 (2 H, m). LC/MS: 374 (M+H)$^+$. HPLC (Method A) Rt 2.88 min (Purity: 99.5%).

Example 95

5-(1-cyclohexyl-5-(pyridin-4-yl)-1H-pyrazol-4-yl)-3-(imidazo[1,2-a]pyridin-6-yl)-1,2,4-oxadiazole

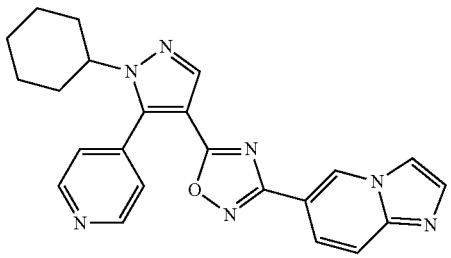 [SMILES: c1cc(-c2c(-c3nc(-c4ccc5nccn5c4)no3)cnn2C2CCCCC2)ccn1]

The title compound was prepared following the procedure described for Example 15, but starting from Intermediate 7 (201 mg; 0.67 mmol) and N'-hydroxyimidazo[1,2-a]pyridine-6-carboximidamide (Key Organics; 130 mg, 0.74 mmol), to give Example 95 as a white solid. $^1$H NMR (CDCl$_3$, 400 MHz) δ 8.88-8.85 (2 H, m), 8.80 (1 H, s), 8.27 (1 H, s), 7.76-7.65 (4 H, m), 7.42-7.37 (2 H, m), 3.95-3.88 (1 H, m), 2.10-2.01 (2 H, m), 1.98-1.82 (4 H, m), 1.74-1.65 (1 H, m), 1.31-1.20 (3 H, m). LC/MS: 412 (M+H)$^+$. HPLC (Method B) Rt=3.18 min (Purity: 96.8%).

Example 96

1-(4-(5-(1-isobutyl-5-(tetrahydro-2H-pyran-4-yl)-1H-pyrazol-4-yl)-1,2,4-oxadiazol-3-yl)benzyl)azetidine-3-carboxylic acid

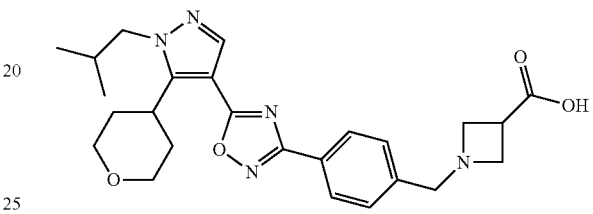

Step 1: (Z)-ethyl 3-(dimethylamino)-2-(tetrahydro-2H-pyran-4-carbonyl)acrylate

Pyridinium p-toluene sulfonate (20.1 mg; 0.080 mmol) and DMF.DMA (1.38 mL; 10.40 mmol) were added to a solution of 3-oxo-3-(tetrahydro-pyran-4-yl)-propionic acid ethyl ester (1.6 g; 8.0 mmol) in anhydrous toluene (20 mL) and heated in a sealed tube at 90° C. for 2.5 hours.

Water (50 mL) was added and the product extracted several times into DCM (3×30 mL). The combined organic fractions were passed through a hydrophobic frit and the solvent removed in vacuo. The residue was used directly without any further purification.

Step 2: ethyl 1-isobutyl-5-(tetrahydro-2H-pyran-4-yl)-1H-pyrazole-4-carboxylate (Z)-ethyl 3-(dimethylamino)-2-(tetrahydro-2H-pyran-4-carbonyl)acrylate (804 mg; 3.15 mmol), obtained from step 1, in ethanol (8 mL) was added to a mixture of 2-methylpropylhydrazine hydrochloride (0.39 g; 3.15 mmol) and sodium acetate (0.51 g; 6.30 mmol) in ethanol (2 mL) and water (1 mL). Reagents were heated at 90° C. for 2 hours. Water (20 mL) was added and the product extracted into DCM (3×20 mL). The combined organic fractions were passed through a hydrophobic frit and the solvent removed in vacuo. The residue was purified on a 25+M Biotage column, eluting with DCM containing increasing amounts of methanol. The title compound was obtained as a yellow oil. $^1$H NMR: (CDCl$_3$, 400 MHz) δ 7.88 (1 H, s), 4.28 (2 H, q, J=8.0 Hz), 4.10 (2 H, dd, J=11.6, 4.4 Hz), 3.96 (2 H, d, J=7.6 Hz), 3.49 (2 H, t, J=11.9 Hz), 3.35 (1 H, tt, J=12.4, 3.8 Hz), 2.53 (2 H, qd, J=12.7, 4.5 Hz), 2.28-2.16 (1 H, m), 1.55-1.48 (2 H, m), 1.36 (3 H, t, J=8.0 Hz), 0.92 (6 H, dd, J=12.1, 6.0 Hz). LC/MS: 281 (M+H)$^+$. HPLC (Method A) Rt 3.52 min (Purity: 98.4%).

Step 3: 4-(5-(1-isobutyl-5-(tetrahydro-2H-pyran-4-yl)-1H-pyrazol-4-yl)-1,2,4-oxadiazol-3-yl)phenyl)methanol Sodium hydride (65.1 mg, 1.63 mmol) was added to a suspension of ethyl 1-isobutyl-5-(tetrahydro-2H-pyran-4-yl)-1H-pyrazole-4-carboxylate (434.6 mg; 1.55 mmol), obtained from step 2, and Intermediate 8 (270.5 mg; 1.628 mmol) in THF (10 mL) and stirred for 10 minutes. The mixture was then heated in the microwave for 900 minutes at 130° C. Water (20 mL) was added and the product extracted into DCM (3×20 mL). The combined organic fractions were passed through a hydrophobic frit and the solvent removed in vacuo. The residue purified on a 25+M Biotage column, eluting with DCM containing increasing amounts of methanol. The title compound was obtained as a white solid. $^1$H NMR: (CDCl$_3$, 400 MHz) δ 8.13 (2 H, d, J=8.0 Hz), 8.10 (1 H, s), 7.50 (2 H, d, J=8.0 Hz), 4.77 (2 H, d, J=3.8 Hz), 4.15 (2 H, dd, J=11.6, 4.3 Hz), 4.04 (2 H, d, J=7.6 Hz), 3.58-3.52, (2H, m), 3.49-3.40 (1 H, m), 2.77-2.64 (3 H, m), 2.34-2.20 (1 H, m), 1.61-1.58 (2H, m), 0.97 (6 H, d, J=6.7 Hz). LC/MS: 383 (M+H)$^+$. HPLC (Method G) Rt 3.47 min (Purity: 99.9%).

Step 4: 4-(5-(1-isobutyl-5-(tetrahydro-2H-pyran-4-yl)-1H-pyrazol-4-yl)-1,2,4-oxadiazol-3-yl)benzaldehyde The title compound was prepared following the procedure described for Example 88 (step 2), but starting from 4-(5-(1-isobutyl-5-(tetrahydro-2H-pyran-4-yl)-1H-pyrazol-4-yl)-1,2,4-oxadiazol-3-yl)phenyl)methanol (0.19 g; 0.5 mmol), obtained from step 3. The title compound was obtained as a grey solid (183 mg; 96.2%). $^1$H NMR: (CDCl$_3$, 400 MHz) δ 10.11 (1 H, s), 8.34 (2 H, d, J=8.1 Hz), 8.14 (1 H, s), 8.03 (2 H, d, J=8.1 Hz), 4.18 (2 H, dd, J=11.6, 4.3 Hz), 4.06 (2 H, d, J=7.6 Hz), 3.57 (2 H, t, J=11.8 Hz), 3.50-3.40 (1 H, m), 2.73 (2 H, qd, J=12.6, 4.5 Hz), 2.33-2.25 (1 H, m), 1.62-1.56 (2 H, m), 0.98 (6 H, d, J=6.7 Hz). LC/MS: 381 (M+H)$^+$. HPLC (Method C) Rt 17.23 min (Purity: 96.1%).

Step 5: 1-(4-(5-(1-isobutyl-5-(tetrahydro-2H-pyran-4-yl)-1H-pyrazol-4-yl)-1,2,4-oxadiazol-3-yl)benzyl)azetidine-3-carboxylic acid Sodium cyanoborohydride (33 mg; 0.528 mmol) was added to a solution of 4-(5-(1-isobutyl-5-(tetrahydro-2H-pyran-4-yl)-1H-pyrazol-4-yl)-1,2,4-oxadiazol-3-yl)benzaldehyde (182 mg; 0.48 mmol), obtained from step 4, and 3-azetidine carboxylic acid (97 mg; 0.96 mmol) in methanol (3 mL) and acetic acid (86.5 μL; 0.144 mmol) and the mixture was stirred at room temperature overnight. The solvent was removed in vacuo and the residue purified by reverse-phase preparative HPLC. The residue was dissolved in methanol and loaded onto an SCX-2 column. The product was eluted using 3-20% NH$_3$/methanol in DCM to give Example 96 as a golden gum. $^1$H NMR: (CDCl$_3$, 400 MHz) δ 8.13 (2 H, d, J=8.0 Hz), 8.09 (1 H, s), 7.55 (2 H, d, J=8.0 Hz), 4.18-4.09 (4 H, m), 4.05-3.95 (6 H, m), 3.59-3.50 (2 H, m), 3.48-3.37 (2 H, m), 2.75-2.59 (2 H, m), 2.34-2.10 (1 H, m), 1.59-1.52 (2 H, m), 0.95 (6 H, dd, J=12.6, 6.7 Hz). LC/MS: 466 (M+H)$^+$. HPLC (Method B) Rt 2.31 min (Purity: 95.8%).

Example 97

1-(4-(5-(1-cyclohexyl-5-(tetrahydro-2H-pyran-4-yl)-1H-pyrazol-4-yl)-1,2,4-oxadiazol-3-yl)benzyl)azetidine-3-carboxylic acid

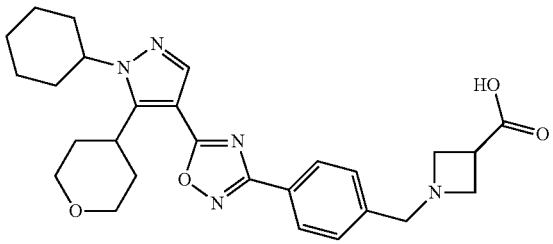 [SMILES: O=C(O)C1CN(Cc2ccc(-c3noc(-c4cnn(C5CCCCC5)c4C4CCOCC4)n3)cc2)C1]

Sodium cyanoborohydride (28 mg; 0.440 mmol) was added to a solution of 4-(5-(1-cyclohexyl-5-(tetrahydro-2H-pyran-4-yl)-1H-pyrazol-4-yl)-1,2,4-oxadiazol-3-yl)benzaldehyde (163 mg; 0.40 mmol), obtained as described in Example 88, steps 1 and 2, and 3-azetidine carboxylic acid (80.9 mg, 0.80 mmol) in methanol (3 mL) and acetic acid (69 μL; 1.20 mmol) and the mixture was stirred at room temperature overnight. The solvent was removed in vacuo and the residue purified by reverse-phase preparative HPLC. The residue was dissolved in methanol and loaded onto an SCX-2 column. The product was eluted with 0-20% NH$_3$/methanol in DCM. The residue was recrystallised from acetone to give Example 97 as a white solid. $^1$H NMR: (DMSO-d$_6$, 400 MHz) δ 8.15 (1 H, s), 8.05 (2 H, d, J=7.9 Hz), 7.55 (2 H, d, J=7.9 Hz), 4.51-4.45 (1 H, m), 4.01 (2 H, d, J=11.2 Hz), 3.90-3.82 (2 H, m), 3.70-3.60 (3 H, m), 3.58-3.48 (4 H, m), 3.25-3.19 (1 H, m), 2.50-2.38 (2 H, m), 1.90-1.79 (6 H, m), 1.70 (1 H, d, J=12.8 Hz), 1.59 (2 H, d, J=12.9 Hz), 1.55-1.45 (2 H, m), 1.30-1.18 (1 H, m). LC/MS: 492 (M+H)$^+$. HPLC (Method A) Rt 2.50 min (Purity: 97.6%).

Example 98

(E)-3-(4-(5-(1-cyclohexyl-5-(methoxymethyl)-1H-pyrazol-4-yl)-1,2,4-oxadiazol-3-yl)phenyl)acrylic acid

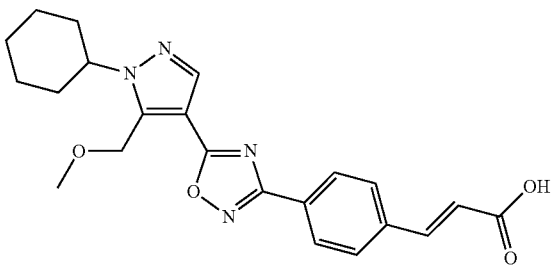 [SMILES: COCc1c(-c2nc(-c3ccc(/C=C/C(=O)O)cc3)no2)cnn1C1CCCCC1]

Step 1: (E)-methyl 3-(4-(5-(1-cyclohexyl-5-(methoxymethyl)-1H-pyrazol-4-yl)-1,2,4-oxadiazol-3-yl)phenyl)acrylate Methyl (triphenylphosphoranylidene) (250 mg; 0.721 mmol) was added to a solution of 4-(5-(1-cyclohexyl-5-(methoxymethyl)-1H-pyrazol-4-yl)-1,2,4-oxadiazol-3-yl)

benzaldehyde (250 mg; 0.68 mmol), obtained as described in Example 121 (step 1), in DCM (10 mL) and the mixture was stirred at room temperature overnight. Additional DCM was added (20 mL) and the mixture was washed with water (3×20 mL). The organic layer was passed through a hydrophobic frit and the solvent removed in vacuo. The residue was purified by flash chromatography on a 25+M Biotage column, eluting with petrol containing increasing amounts of ethyl acetate to give the title compound as a white solid (251 mg; 87.4%). $^1$H NMR: (CDCl$_3$, 400 MHz) δ 8.18-8.11 (3 H, m), 7.73 (1 H, d, J=15.8 Hz), 7.65 (2 H, d, J=8.2 Hz), 6.53 (1 H, d, J=15.8 Hz), 5.03 (2 H, s), 4.36-4.27 (1 H, m), 3.83 (3 H, s), 3.43 (3 H, s), 2.07-1.93 (6 H, m), 1.80-1.70 (1 H, m), 1.52-1.25 (3 H, m). LC/MS: 423 (M+H)$^+$. HPLC (Method G) Rt 20.89 min (Purity: 96.9%).

Step 2: (E)-3-(4-(5-(1-cyclohexyl-5-(methoxymethyl)-1H-pyrazol-4-yl)-1,2,4-oxadiazol-3-yl)phenyl)acrylic acid (E)-methyl 3-(4-(5-(1-cyclohexyl-5-(methoxymethyl)-1H-pyrazol-4-yl)-1,2,4-oxadiazol-3-yl)phenyl)acrylate (240 mg; 0.57 mmol), obtained from step 1, was dissolved in methanol (10 mL) and water (1 mL) and lithium hydroxide monohydrate (48 mg; 1.14 mmol) added. The mixture was heated to 80° C. overnight. The solvent was removed in vacuo and water (20 mL) added to the residue. The mixture was acidified to pH 3 with dilute HCl and the product extracted into DCM (5×20 mL). The combined organic fractions were passed through a hydrophobic frit and the solvent removed in vacuo. The residue was purified by flash chromatography on a 25+M Biotage column, eluting with DCM containing increasing amounts of methanol to give Example 98 as a white solid. $^1$H NMR: CDCl$_3$, 400 MHz) δ 8.18 (2 H, d, J=8.2 Hz), 8.15 (1 H, s), 7.81 (1 H, d, J=15.9 Hz), 7.68 (2 H, d, J=8.2 Hz), 6.55 (1 H, d, J=15.9 Hz), 5.04 (2 H, s), 4.36-4.28 (1 H, m), 3.44 (3 H, s), 2.05-1.90 (6 H, m), 1.76 (1 H, d, J=12.6 Hz), 1.52-1.20 (3 H, m). LC/MS: 407 (M+H)$^+$. HPLC (Method H) Rt 4.51 min (Purity: 99.6%).

Example 99

3-(2,5-difluorophenyl)-5-(1-phenethyl-5-(pyridin-4-yl)-1H-pyrazol-4-yl)-1,2,4-oxadiazole

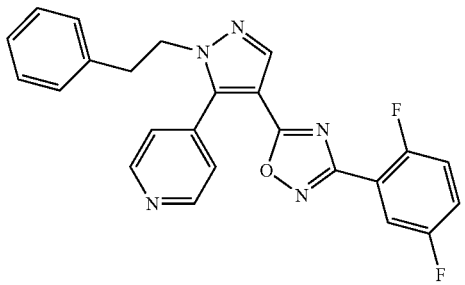 [SMILES: Fc1ccc(F)c(-c2noc(-c3cnn(CCc4ccccc4)c3-c3ccncc3)n2)c1]

Sodium hydride (12 mg; 0.30 mmol) was added to a suspension of Intermediate 28 (96 mg; 0.30 mmol) and 2,5-difluoro-N'-hydroxybenzenecarboximidamide (JRD-Fluorochemical, 52 mg; 0.30 mmol) in THF (2 mL) and the mixture was stirred for 10 minutes. The mixture was then heated to 130° C. in a microwave reactor for 30 hours. Water (10 mL) was added and the product extracted into DCM (3×10 mL). The combined organic fractions were passed through a hydrophobic frit and the solvent removed in vacuo and the residue purified by reverse-phase preparative HPLC to give Example 99 as an off white solid. $^1$H NMR: (CDCl$_3$, 400 MHz) δ 8.63 (2 H, d, J=4.4 Hz), 8.34 (1 H, s), 7.63-7.58 (1 H, m), 7.26-7.12 (5 H, m), 6.85-6.83 (2 H, m), 6.79-6.77 (2 H, m), 4.25 (2 H, t, J=6.5 Hz), 3.17 (2 H, t, J=6.5 Hz). LC/MS: 430 (M+H)$^+$. HPLC (Method B) Rt 3.64 min (Purity: 92.2%).

Example 100

(4-(5-(1-neopentyl-5-(pyridin-4-yl)-1H-pyrazol-4-yl)-1,2,4-oxadiazol-3-yl)phenyl)methanol

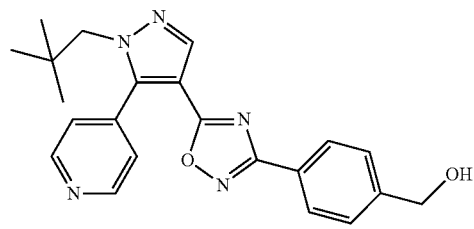 [SMILES: CC(C)(C)Cn1ncc(-c2nc(-c3ccc(CO)cc3)no2)c1-c1ccncc1]

Sodium hydride (214 mg; 0.536 mmol) was added to a suspension of Intermediate 30 (1466 mg; 5.10 mmol) and Intermediate 8 (890 mg; 5.36 mmol) in THF (20 mL) and the mixture was stirred for 10 minutes. The mixture was then heated to 130° C. in a microwave reactor for 3 hours. Water (30 mL) was added and the product extracted into DCM (3×30 mL). The combined organic fractions were passed through a hydrophobic frit and the solvent removed in vacuo. The residue was purified by flash chromatography on a 40+M Biotage column, eluting with DCM containing increasing amounts of methanol. The residue was triturated with diethyl ether to give Example 100 as a white solid. $^1$H NMR: (CDCl$_3$, 400 MHz) δ 8.84 (2 H, dd, J=4.5, 1.6 Hz), 8.28 (1 H, s), 7.99 (2 H, d, J=8.1 Hz), 7.47 (2 H, d, J=8.1 Hz), 7.42 (2 H, dd, J=4.5, 1.6 Hz), 4.77 (2 H, d, J=6.0 Hz), 3.97 (2 H, s), 1.80 (1 H, t, J=6.0 Hz), 0.85 (9 H, s). LC/MS: 390 (M+H)$^+$. HPLC (Method A) Rt 3.27 min (Purity: 95.8%).

Example 101

1-(4-(5-(1-(cyclopropylmethyl)-5-(pyridin-4-yl)-1H-pyrazol-4-yl)-1,2,4-oxadiazol-3-yl)benzyl)azetidine 3-carboxylic acid, formate

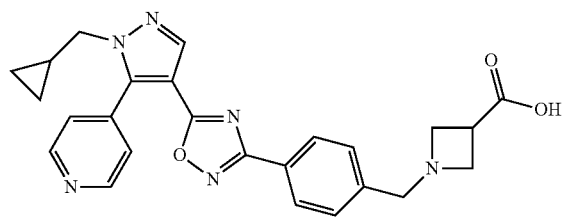 [SMILES: O=C(O)C1CN(Cc2ccc(-c3noc(-c4cnn(CC5CC5)c4-c4ccncc4)n3)cc2)C1]

Step 1: (4-(5-(1-(cyclopropylmethyl)-5-(pyridin-4-yl)-1H-pyrazol-4-yl)-1,2,4-oxadiazol-3-yl)phenyl)methanol Sodium hydride (24 mg; 0.60 mmol) was added to a suspension of Intermediate 29 (270 mg; 1.0 mmol) and Intermediate 8 (100 mg; 1.60 mmol) in THF (10 mL) and stirred for 10 minutes. The mixture was then heated in the microwave for 240 minutes at 130° C. An additional 0.2 equivalents of sodium hydride and amidoxime were added and the mixture heated at 130° C. for 4 hours. Water (20 mL) was added resulting in the formation of a suspended solid which was filtered off, washed with a mixture of diethyl ether and DCM and dried in vacuo to give the title compound as a white solid. $^1$H NMR: (Acetone-$d_6$, 400 MHz) δ 8.83 (2 H, d, J=5.1 Hz), 8.25 (1 H, s), 7.93 (2 H, d, J=7.8 Hz), 7.64 (2 H, d, J=5.1 Hz), 7.50 (2 H, d, J=7.8 Hz), 4.71 (2 H, s), 4.35 (1 H, s), 4.06 (2 H, d, J=7.0 Hz), 1.25-1.09 (1 H, m), 0.51-0.47 (2 H, m), 0.28-0.20 (2 H, m). LC/MS: 374 (M+H)$^+$. HPLC (Method A) Rt 2.88 min (Purity: 99.5%).

Step 2: 4-(5-(1-(cyclopropylmethyl)-5-(pyridin-4-yl)-1H-pyrazol-4-yl)-1,2,4-oxadiazol-3-yl)benzaldehyde The title compound was prepared following the procedure described for Example 88 (step 2), but starting from (4-(5-(1-(cyclopropylmethyl)-5-(pyridin-4-yl)-1H-pyrazol-4-yl)-1,2,4-oxadiazol-3-yl)phenyl)methanol (74.7 mg; 0.20 mmol), obtained from step 1. The title compound was obtained as a white solid (73 mg; 98.3%). $^1$H NMR: (CDCl$_3$, 400 MHz) δ 10.08 (1 H, s), 8.85 (2 H, d, J=4.6 Hz), 8.28 (1 H, d, J=4.2 Hz), 8.16 (2 H, d, J=7.7 Hz), 7.96 (2 H, d, J=7.6 Hz), 7.46 (2 H, d, J=4.6 Hz), 3.97 (2 H, d, J=6.8 Hz), 1.25-1.15 (1 H, m), 0.57-0.51 (2 H, m), 0.24-0.19 (2 H, m). LC/MS: 372 (M+H)$^+$. HPLC (Method A) Rt 3.41 min (Purity: 96.9%).

Step 3: 1-(4-(5-(1-(cyclopropylmethyl)-5-(pyridin-4-yl)-1H-pyrazol-4-yl)-1,2,4-oxadiazol-3-yl)benzyl)azetidine-3-carboxylic acid, formate Sodium cyanoborohydride (13.8 mg; 0.220 mmol) was added to a solution of 4-(5-(1-(cyclopropylmethyl)-5-(pyridin-4-yl)-1H-pyrazol-4-yl)-1,2,4-oxadiazol-3-yl)benzaldehyde (74.3 mg; 0.20 mmol), obtained from step 2, and 3-azetidine carboxylic acid (40.4 mg; 0.40 mmol) in methanol (3 mL) and acetic acid (36 μL; 0.60 mmol) and the mixture was stirred at room temperature overnight. The solvent was removed in vacuo and the residue purified by reverse-phase preparative HPLC to give Example 101 as a white solid. $^1$H NMR: (CD$_3$OD, 400 MHz) δ 8.81 (2 H, d, J=4.0 Hz), 8.35 (1 H, s), 8.22 (1 H, s), 8.08 (2 H, d, J=7.8 Hz), 7.62 (2 H, d, J=5.2 Hz), 7.37 (2 H, d, J=7.8 Hz), 4.43 (2 H, s), 4.22 (4 H, d, J=8.2 Hz), 4.08 (2 H, d, J=7.0 Hz), 3.53-3.44 (1 H, m), 1.26-1.17 (1H, m), 0.60-0.54 (2 H, m), 0.29-0.25 (2 H, m). LC/MS: 457 (M+H)$^+$. HPLC (Method D) Rt 12.73 min (Purity: 98.6%).

Example 102

3-(4-(5-(1-cyclohexyl-5-(tetrahydro-2H-pyran-4-yl)-1H-pyrazol-4-yl)-1,2,4-oxadiazol-3-yl)benzylamino)propanoic acid

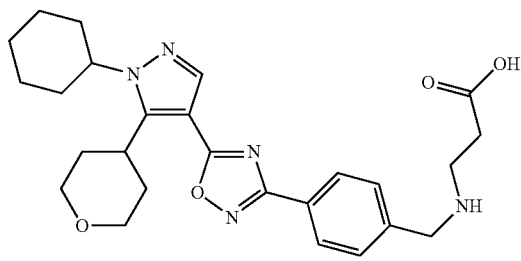 [SMILES: O=C(O)CCNCc1ccc(-c2noc(-c3cnn(C4CCCCC4)c3C3CCOCC3)n2)cc1]

Sodium cyanoborohydride (28 mg; 0.440 mmol) was added to a solution of 4-(5-(1-cyclohexyl-5-(tetrahydro-2H-pyran-4-yl)-1H-pyrazol-4-yl)-1,2,4-oxadiazol-3-yl)benzaldehyde (163 mg; 0.40 mmol), obtained as described in Example 88, steps 1 and 2, and R-alanine (71.3 mg; 0.80 mmol) in methanol (3 mL) and acetic acid (69 μL; 1.20 mmol) and the mixture was stirred at room temperature overnight. The solvent was removed in vacuo and the residue purified by reverse-phase preparative HPLC. The residue was dissolved in methanol and loaded onto an SCX-2 column. The product was eluted with 0-20% NH$_3$/methanol in DCM. The residue was then recrystallised from acetone to give Example 102 a white solid. $^1$H NMR: (Acetone-$d_6$, 400 MHz) δ 7.99 (2 H, d, J=8.0 Hz), 7.94 (1 H, s), 7.46 (2 H, d, J=8.0 Hz), 4.46-4.37 (1 H, m), 3.92 (2 H, dd, J=11.5, 4.3 Hz), 3.84 (2 H, s), 3.75 (1 H, t, J=12.3 Hz), 3.43 (2 H, t, J=11.7 Hz), 2.82 (2 H, t, 6.0 Hz), 2.51-2.32 (4 H, m), 1.85-1.70 (6 H, m), 1.61 (1 H, d, J=12.9 Hz), 1.53 (2 H, d, J=12.9 Hz), 1.47-1.32 (2 H, m), 1.23-1.10 (1 H, m). LC/MS: 480 (M+H)$^+$. HPLC (Method D) Rt 15.428 min (Purity: 99.4%).

Example 103

5-(1-cyclohexyl-5-(2-methoxyethyl)-1H-pyrazol-4-yl)-3-(2,5-difluorophenyl)-1,2,4-oxadiazole

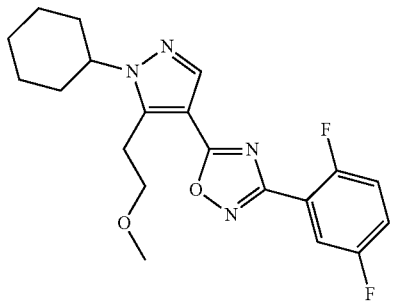 [SMILES: COCCc1c(-c2nc(-c3cc(F)ccc3F)no2)cnn1C1CCCCC1]

Sodium hydride (8 mg; 0.2 mmol) was added to a solution of Intermediate 22 (53 mg; 0.2 mmol) and 2,5-difluoro-N'-hydroxybenzenecarboximidamide (JRD-Fluorochemical, 38 g; 0.22 mmol) in THF (2 mL) and the mixture stirred for 10 minutes. The mixture was then heated to 140° C. in a microwave reactor for 2 hours. An additional portion of 2,5-difluoro-N'-hydroxybenzenecarboximidamide (19 mg; 0.11 mmol) was added and the mixture heated to 140° C. in a microwave reactor for 2 hours. DCM (10 mL) and water (5 mL) were added and the mixture passed through a hydrophobic frit and the solvent removed in vacuo. The residue was purified by flash chromatography on a Biotage 12+M column, eluting with petrol containing increasing amounts of EtOAc. The residue was triturated with isopropanol to give Example 103 as a white solid. $^1$H NMR (CDCl$_3$, 400 MHz) δ 8.13 (1 H, s), 7.85-7.79 (1 H, m), 7.25-7.16 (2 H, m), 4.33-4.20 (1 H, m), 3.69 (2 H, t, J=6.3 Hz), 3.41 (2 H, t, J=6.3 Hz), 3.33 (3 H, s), 2.08-1.89 (6 H, m), 1.79-1.68 (1 H, m), 1.50-1.27 (3 H, m). LC/MS: 389 (M+H)$^+$. HPLC (Method B) Rt=4.23 min (Purity: 95.4%).

Example 104

N-methyl-1-(4-(5-(1-neopentyl-5-(pyridin-4-yl)-1H-pyrazol-4-yl)-1,2,4-oxadiazol-3-yl)phenyl)methanamine

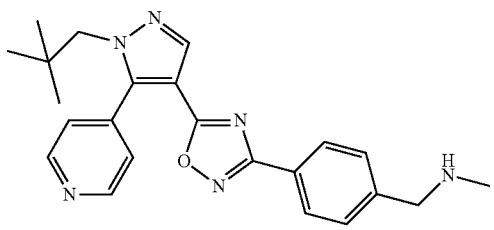 [SMILES: CNCc1ccc(-c2noc(-c3cnn(CC(C)(C)C)c3-c3ccncc3)n2)cc1]

Step 1: (4-(5-(1-neopentyl-5-(pyridin-4-yl)-1H-pyrazol-4-yl)-1,2,4-oxadiazol-3-yl)phenyl)methanol Sodium hydride (214 mg; 0.536 mmol) was added to a suspension of Intermediate 30 (1.47 g; 5.10 mmol) and Intermediate 8 (890 mg; 5.36 mmol) in THF (20 mL) and the mixture was stirred for 10 minutes. The mixture was then heated in a microwave reactor 3 hours at 130° C. Water (20 mL) was added and the product extracted into DCM (3×20 mL). The combined organic fractions were passed through a hydrophobic frit and the solvent removed in vacuo. The residue was purified by flash chromatography on a 40+M Biotage column, eluting with DCM containing increasing amounts of methanol. The residue was triturated with diethyl ether and dried to give the target compound as a white solid. $^1$H NMR: (CDCl$_3$, 400 MHz) δ 8.84 (2 H, dd, J=4.5, 1.6 Hz), 8.28 (1 H, s), 7.99 (2 H, d, J=8.1 Hz), 7.47 (2H, d, J=8.1 Hz), 7.42 (2 H, dd, J=4.5, 1.6 Hz), 4.77 (2 H, d, J=6.0 Hz), 3.97 (2 H, s), 1.80 (1 H, t, J=6.0 Hz), 0.85 (9 H, s). LC/MS: 390 (M+H)$^+$. HPLC (Method A) Rt 3.27 min (Purity: 95.8%).

Step 2: 4-(5-(1-neopentyl-5-(pyridin-4-yl)-1H-pyrazol-4-yl)-1,2,4-oxadiazol-3-yl)benzaldehyde The title compound was prepared following the procedure described for Example 88 (step 2), but starting from (4-(5-(1-neopentyl-5-(pyridin-4-yl)-1H-pyrazol-4-yl)-1,2,4-oxadiazol-3-yl)phenyl)methanol (390 mg; 1.0 mmol), obtained from step 1. The title compound was obtained as a white solid (367 mg; 94.7%). $^1$H NMR: (CDCl$_3$, 400 MHz) δ 10.07 (1 H, s), 8.85 (2 H, dd, J=4.5, 1.6 Hz), 8.28 (1 H, d, J=12.0 Hz), 8.16 (2 H, d, J=8.1 Hz), 7.96 (2 H, d, J=8.2 Hz), 7.43 (2 H, dd, J=4.5, 1.6 Hz), 3.97 (2 H, s), 0.86 (9 H, s). LC/MS: 388 (M+H)$^+$. HPLC (Method A) Rt 3.85 min (Purity: 94.0%).

Step 3: N-methyl-1-(4-(5-(1-neopentyl-5-(pyridin-4-yl)-1H-pyrazol-4-yl)-1,2,4-oxadiazol-3-yl)phenyl)methanamine Sodium cyanoborohydride (32 mg; 0.51 mmol) was added to a solution of 4-(5-(1-neopentyl-5-(pyridin-4-yl)-1H-pyrazol-4-yl)-1,2,4-oxadiazol-3-yl)benzaldehyde (178 mg; 0.46 mmol), obtained from step 2, and methylamine hydrochloride (62.1 mg; 0.92 mmol) in methanol (3 mL) and acetic acid (79 μL; 1.38 mmol) and the mixture was stirred at room temperature overnight. The solvent was removed in vacuo and water (3 mL) was added and the product extracted into DCM (3×2 mL). The combined organic fractions were passed through a hydrophobic frit and the solvent removed in vacuo. The residue purified by flash chromatography on a 12+M Biotage column, eluting with DCM containing increasing amounts of 7M methanolic ammonia in DCM to give Example 104 as a white solid. $^1$H NMR: (CDCl$_3$, 400 MHz) δ 8.83 (2 H, dd, J=2.8, 1.6 Hz), 8.27 (1H, s), 7.94 (2 H, d, J=8.1 Hz), 7.44-7.37 (4 H, m), 3.97 (2 H, s), 3.79 (2 H, s), 2.45 (3 H, s), 0.85 (9 H, s). LC/MS: 403 (M+H)$^+$. HPLC (Method D) Rt 16.67 min (Purity: 94.5%).

Example 105

1-(4-(5-(1-neopentyl-5-(pyridin-4-yl)-1H-pyrazol-4-yl)-1,2,4-oxadiazol-3-yl)benzyl)azetidine-3-carboxylic acid

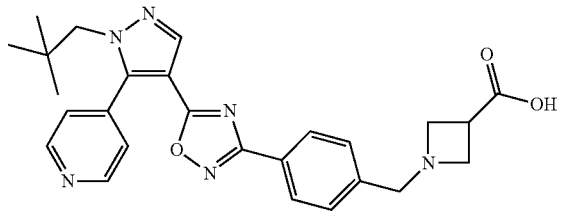 [SMILES: CC(C)(C)Cn1ncc(-c2nc(-c3ccc(CN4CC(C(=O)O)C4)cc3)no2)c1-c1ccncc1]

Sodium cyanoborohydride (32 mg; 0.51 mmol) was added to a solution of 4-(5-(1-neopentyl-5-(pyridin-4-yl)-1H-pyrazol-4-yl)-1,2,4-oxadiazol-3-yl)benzaldehyde (178 mg; 0.46 mmol), obtained according to Example 104 (step 1-2), and 3-azetidine carboxylic acid (93.0 mg; 0.92 mmol) in methanol (3 mL) and acetic acid (79 μL; 1.38 mmol) and the mixture was stirred at room temperature overnight. The solvent was removed in vacuo and the residue purified by reverse-phase preparative HPLC to give Example 105 as a white solid. $^1$H NMR: (DMSO-d$_6$, 400 MHz) δ 8.81 (2 H, dd, J=4.6, 1.6 Hz), 8.38 (1 H, s), 7.87 (2 H, d, J=8.0 Hz), 7.66 (2 H, dd, J=4.5, 1.7 Hz), 7.47 (2 H, d, J=8.0 Hz), 4.00 (2 H, s), 3.62 (2 H, s), 3.55 (2 H, t, J=8.0 Hz), 3.39 (2 H, t, J=8.0 Hz), 3.25-3.15 (1 H, m), 0.77 (9 H, s). LC/MS: 473 (M+H)$^+$. HPLC (Method B) Rt 2.31 min (Purity: 98.1%).

Example 106

N-methyl-1-(4-(5-(1-phenethyl-5-(pyridin-4-yl)-1H-pyrazol-4-yl)-1,2,4-oxadiazol-3-yl)phenyl)methanamine

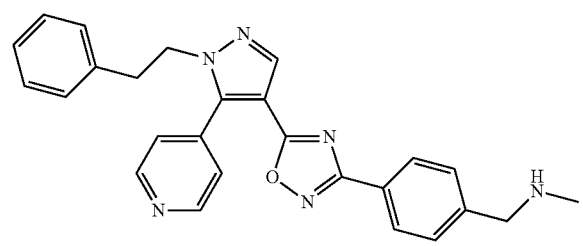 [SMILES: CNCc1ccc(-c2noc(-c3cnn(CCc4ccccc4)c3-c3ccncc3)n2)cc1]

Step 1: (4-(5-(1-phenethyl-5-(pyridin-4-yl)-1H-pyrazol-4-yl)-1,2,4-oxadiazol-3-yl)phenyl)methanol The title compound was prepared following the procedure described for Example 104 (step 1), but starting from Intermediate 28 (707 mg; 2.20 mmol) and Intermediate 8 (219.4 mg; 1.32 mmol). The target compound was obtained as an off white solid. $^1$H NMR: (DMSO-d$_6$, 400 MHz) δ 8.71 (2 H, dd, J=4.5, 1.6 Hz), 8.45 (1 H, s), 7.88 (2 H, d, J=8.1 Hz), 7.50 (2 H, d, J=8.0 Hz), 7.25-7.23 (3 H, m), 7.19 (2 H, dd, J=4.5, 1.6 Hz), 6.95-6.91 (2 H, m), 5.36 (1 H, t, J=5.7 Hz), 4.59 (2 H, d, J=5.7 Hz), 4.31 (2 H, t, J=6.7 Hz), 3.10 (2 H, t, J=6.7 Hz). LC/MS: 424 (M+H)⁺. HPLC (Method B) Rt 2.97 min (Purity: 97.6%).

Step 2: 4-(5-(1-phenethyl-5-(pyridin-4-yl)-1H-pyrazol-4-yl)-1,2,4-oxadiazol-3-yl)benzaldehyde The title compound was prepared following the procedure described for Example 88 (step 2), but starting from (4-(5-(1-phenethyl-5-(pyridin-4-yl)-1H-pyrazol-4-yl)-1,2,4-oxadiazol-3-yl)phenyl)methanol (152.5 mg; 0.36 mmol), obtained from step 1. Title compound was obtained as a pale orange solid (150 mg; 98.9%). ¹H NMR: (CDCl₃, 400 MHz) δ 10.05 (1 H, s), 8.65 (2 H, d, J=5.3 Hz), 8.35 (1 H, s), 8.12 (2 H, d, J=8.1 Hz), 7.94 (2 H, d, J=8.1 Hz), 7.26-7.19 (3 H, m), 6.86-6.77 (4 H, m), 4.26 (2 H, t, J=6.5 Hz), 3.18 (2 H, t, J=6.5 Hz). LC/MS: 422 (M+H)⁺. HPLC (Method A) Rt 3.66 min (Purity: 93.9%).

Step 3: N-methyl-1-(4-(5-(1-phenethyl-5-(pyridin-4-yl)-1H-pyrazol-4-yl)-1,2,4-oxadiazol-3-yl)phenyl)methanamine Sodium cyanoborohydride (12 mg; 0.19 mmol) was added to a solution of 4-(5-(1-phenethyl-5-(pyridin-4-yl)-1H-pyrazol-4-yl)-1,2,4-oxadiazol-3-yl)benzaldehyde (74 mg, 0.17 mmol), obtained from step 2, and 3-azetidine carboxylic acid (35.4 mg; 0.35 mmol) in methanol (3 mL) and acetic acid (30 µL; 0.53 mmol) and the mixture was stirred at room temperature overnight. The solvent was removed in vacuo and water (3 mL) added. The product was extracted into DCM (3×2 mL) and the combined organic fractions were passed through a hydrophobic frit. The solvent was removed in vacuo and the residue purified by flash chromatography on a 12+M Biotage column, eluting with DCM containing increasing amounts of methanol to give Example 106 as a white solid. ¹H NMR: (CDCl₃, 400 MHz) δ 8.62 (2 H, dd, J=4.7, 1.6 Hz), 8.33 (1 H, s), 7.92 (2 H, d, J=8.0 Hz), 7.40 (2 H, d, J=8.0 Hz), 7.25-7.14 (3 H, m), 6.83 (2 H, dd, J=6.0, 1.6 Hz), 6.78 (2 H, dd, J=2.8, 1.6 Hz), 4.25 (2 H, t, J=6.5 Hz), 3.84 (2 H, s), 3.17 (2 H, t, J=6.5 Hz), 2.48 (3 H, s). LC/MS: 437 (M+H)⁺. HPLC (Method B) Rt 2.94 min (Purity: 97.4%).

Example 107

3-(4-((1H-1,2,4-triazol-1-yl)methyl)phenyl)-5-(1-cyclohexyl-5-(methoxymethyl)-1H-pyrazol-4-yl)-1,2,4-oxadiazole

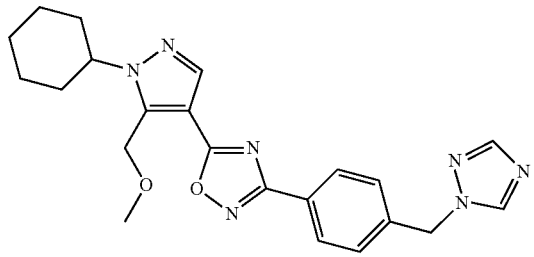 [SMILES: COCc1c(-c2nc(-c3ccc(Cn4cncn4)cc3)no2)cnn1C1CCCCC1]

Sodium Hydride (20 mg; 0.525 mmol) was added to a suspension of Intermediate 18 (126 mg; 0.50 mmol) and 4-((1H-1,2,4-triazol-1-yl)methyl)-N'-hydroxy benzenecarboximidamide (Aurora, 114 mg; 0.525 mmol) in THF (2 mL) and the mixture was stirred for 10 minutes. The mixture was heated to 140° C. in a microwave reactor for 4 hours. Water (3 mL) was added and the product extracted into DCM (3×2 mL). The combined organic fractions were passed through a hydrophobic frit and the solvent removed in vacuo. The residue was purified by flash chromatography on a 12+M Biotage column, eluting with DCM containing increasing amounts of methanol in DCM to give Example 107 as a clear gum. ¹H NMR: (CDCl₃, 400 MHz) δ 8.20-8.06 (4 H, m), 8.01 (1 H, s), 7.39 (2 H, d, J=8.4 Hz), 5.43 (2 H, s), 5.02 (2 H, s), 4.36-4.25 (1 H, m), 3.42 (3 H, s), 2.06-1.90 (6 H, m), 1.76 (1 H, d, J=12.7 Hz), 1.52-1.39 (2 H, m), 1.39-1.23 (1 H, m). LC/MS: 420 (M+H)⁺. HPLC (Method A) Rt 3.78 min (Purity: 97.6%).

Example 108

5-(1-cyclohexyl-5-(2-methoxyethyl)-1H-pyrazol-4-yl)-3-(3-(trifluoromethyl)phenyl)-1,2,4-oxadiazole

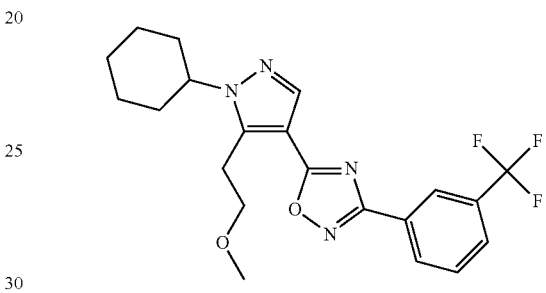

The title compound was prepared following the procedure described for Example 16, with two identical reactions combined for workup, but starting from Intermediate 23 (76 mg; 0.3 mmol) and N'-hydroxy-3-(trifluoromethyl)benzenecarboximidamide (Bionet, 73 mg, 0.36 mmol). The residue was purified by flash chromatography on a Biotage 12+M column, eluting with DCM containing increasing amounts of methanol to give Example 108 as a clear gum. ¹H NMR (CDCl₃, 400 MHz) δ 8.40 (1 H, s), 8.32 (1 H, d, J=7.9 Hz), 8.14 (1 H, s), 7.77 (1 H, d, J=7.9 Hz), 7.63 (1 H, t, J=7.8 Hz), 4.31-4.22 (1 H, m), 3.71 (2 H, t, J=6.3 Hz), 3.43 (2 H, t, J=6.3 Hz), 3.35 (3 H, s), 2.09-1.89 (6 H, m), 1.81-1.70 (1 H, m), 1.50-1.24 (3 H, m). LC/MS: 421 (M+H)⁺. HPLC (Method C) Rt=20.72 min (Purity: 99.1%).

Example 109

2-(4-(5-(1-cyclohexyl-5-(methoxymethyl)-1H-pyrazol-4-yl)-1,2,4-oxadiazol-3-yl)phenyl)ethanol

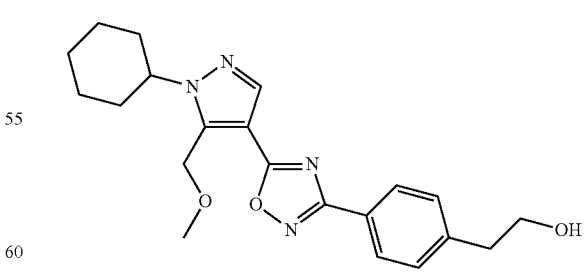

To a solution of Intermediate 18 (0.27 g; 1.1 mmol) in toluene (3 mL) and DMF (2 mL) was added Intermediate 33 (0.21 g; 1.21 mmol) and potassium carbonate (0.16 g; 1.21 mmol) and the mixture stirred for 10 minutes. The mixture was then heated to 180° C. in a microwave reactor for 2 hours. Water (5 mL) was added and the product extracted into DCM (3×5 mL). The combined organic fractions were passed through a hydrophobic frit and the solvent removed in vacuo. The residue was purified by flash chromatography on an Isolute Flash Si II 20 g column, eluting with petrol containing increasing amounts of EtOAc to give Example 109 as a colourless oil. $^1$H NMR: (CDCl$_3$, 400 MHz) δ 8.13 (1 H, s), 8.09 (2 H, d, J=7.9 Hz), 7.37 (2 H, d, J=7.9 Hz), 5.03 (2 H, s), 4.36-4.26 (1 H, m), 3.96-3.88 (3 H, m), 3.42 (3 H, s), 2.99-2.91 (2 H, m), 2.07-1.89 (6 H, m), 1.81-1.70 (1 H, m), 1.52-1.24 (3 H, m). LC/MS: 383 (M+H)$^+$. HPLC (Method A) Rt=3.93 min (Purity: 99.3%).

Example 110

1-(4-(5-(1-phenethyl-5-(pyridin-4-yl)-1H-pyrazol-4-yl)-1,2,4-oxadiazol-3-yl)benzyl)azetidine-3-carboxylic acid, formate

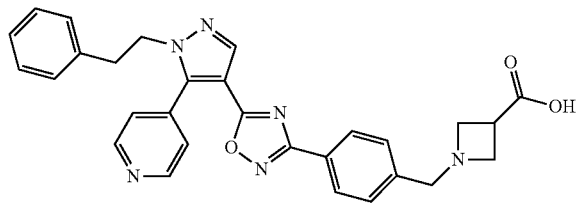 [SMILES: O=C(O)C1CN(Cc2ccc(-c3noc(-c4cnn(CCc5ccccc5)c4-c4ccncc4)n3)cc2)C1]

Sodium cyanoborohydride (12 mg; 0.19 mmol) was added to a solution of 4-(5-(1-phenethyl-5-(pyridin-4-yl)-1H-pyrazol-4-yl)-1,2,4-oxadiazol-3-yl)benzaldehyde (74 mg, 0.17 mmol), obtained as described in Example 106 (step 1-2), and 3-azetidine carboxylic acid (35.4 mg; 0.35 mmol) in methanol (3 mL) and acetic acid (30 μL; 0.53 mmol) and the mixture was stirred at room temperature overnight. The solvent was removed in vacuo and the residue purified by reverse-phase preparative HPLC to give Example 110 as a white solid. $^1$H NMR: (DMSO-d$_6$, 400 MHz) δ 8.62 (2 H, d, J=4.6 Hz), 8.35 (1 H, s), 8.20 (1 H, s), 7.89 (2 H, d, J=8.0 Hz), 7.53 (2 H, d, J=8.0 Hz), 7.20-7.13 (3 H, m), 7.05 (2 H, d, J=5.1 Hz), 6.84 (2 H, d, J=7.0 Hz), 4.29 (2 H, t, J=6.7 Hz), 4.18 (2 H, s), 3.99-3.84 (4 H, m), 3.35-3.25 (1 H, m), 3.06 (2 H, t, J=6.7 Hz). LC/MS: 507 (M+H)$^+$. HPLC (Method B) Rt 2.29 min (Purity: 97.9%).

Example 111

3-(4-((1H-1,2,4-triazol-1-yl)methyl)phenyl)-5-(1-cyclohexyl-5-(2-methoxyethyl)-1H-pyrazol-4-yl)-1,2,4-oxadiazole

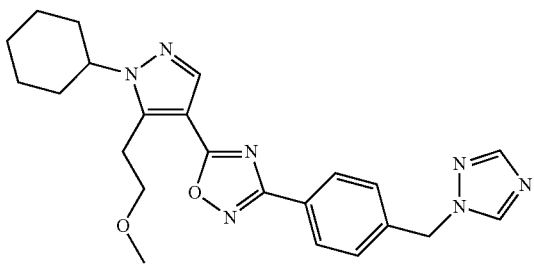 [SMILES: COCCc1c(-c2nc(-c3ccc(Cn4cncn4)cc3)no2)cnn1C1CCCCC1]

The title compound was prepared following the procedure described for Example 16, with two identical reactions combined for workup, but starting from Intermediate 23 (51 mg; 0.2 mmol) and 4-((1H-1,2,4-triazol-1-yl)methyl)-N'-hydroxy benzenecarboximidamide (Aurora, 52 mg, 0.24 mmol), to give Example 111 as a clear gum. $^1$H NMR (CDCl$_3$, 400 MHz) δ 8.14 (2 H, d, J=8.1 Hz), 8.12 (2 H, s), 8.00 (1 H, s), 7.38 (2 H, d, J=8.1 Hz), 5.43 (2 H, s), 4.31-4.21 (1 H, m), 3.69 (2 H, t, J=6.3 Hz), 3.41 (2 H, t, J=6.3 Hz), 3.33 (3 H, s), 2.06-1.90 (6 H, m), 1.80-1.69 (1 H, m), 1.50-1.24 (3 H, m). LC/MS: 434 (M+H)$^+$. HPLC (Method A) Rt=3.84 min (Purity: 99.8%).

Example 112

3-(2,5-difluorophenyl)-5-(5-ethoxy-1-o-tolyl-1H-pyrazol-4-yl)-1,2,4-oxadiazole

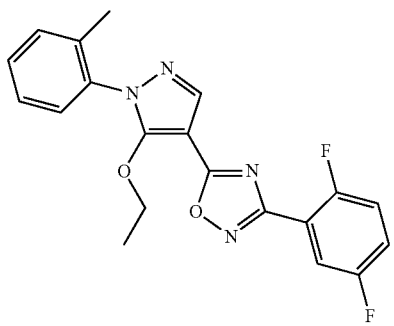 [SMILES: CCOc1c(-c2nc(-c3cc(F)ccc3F)no2)cnn1-c1ccccc1C]

Step 1: ethyl 2-(3-(2,5-difluorophenyl)-1,2,4-oxadiazol-5-yl)acetate

Ethyl 3-chloro-3-oxopropanoate (1.7 mL; 13.2 mmol) was added to 2,5-difluoro-N'-hydroxybenzenecarboximidamide (JRD-Fluorochemical, 1.13 g; 0.6 mmol) in pyridine (30 mL). The mixture was heated to reflux for 4 hours and the solvent removed in vacuo. The residue was taken up into DCM (20 mL) and washed with water (10 mL). The organic phase was passed through a hydrophobic frit and the solvent removed in vacuo. The residue was purified on a Biotage 25+M column, eluting with petrol containing increasing amounts of EtOAc to give ethyl 2-(3-(2,5-difluorophenyl)-1,2,4-oxadiazol-5-yl)acetate (1.24 g, 70%).

Step 2: 4-(3-(2,5-difluorophenyl)-1,2,4-oxadiazol-5-yl)-1-o-tolyl-1H-pyrazol-5-ol To a solution of ethyl 2-(3-(2,5-difluorophenyl)-1,2,4-oxadiazol-5-yl)acetate (1.24 g; 4.6 mmol), obtained from step 1, in toluene (25 mL) was added DMF.DMA (0.79 mL; 5.98 mmol) and PPTS (100 mg). The mixture was heated to 90° C. for 2 hours. The solvent was removed in vacuo and DCM (50 mL) and water (25 mL) were added and the mixture passed through a hydrophobic frit. The solvent was removed in vacuo and the residue redissolved in water (10 mL) and MeCN (10 mL). The mixture was stirred at RT for 18 hours and then DCM (25 mL) and water (10 mL) added. The mixture was passed through a hydrophobic frit and the solvent removed in vacuo. The residue was redissolved in a mixture of methanol (16 mL), water (16 mL) and triethylamine (5.3 mL) and the mixture heated to 100° C. for 4 hours. The solvent was removed in vacuo and the residue partitioned between DCM (10 mL) and water (5 mL). The mixture was passed through hydrophobic frit and the solvent removed in vacuo. The residue was purified on a Biotage 25+S column, eluting with petrol containing increasing amounts of EtOAc and then recrystallised from acetone/diethyl ether to give 4-(3-(2,5- difluorophenyl)-1,2,4-oxadiazol-5-yl)-1-o-tolyl-1H-pyrazol-5-ol as an off-white solid. $^1$H NMR: (DMSO-$d_6$, 400 MHz) δ 7.93-7.83 (1 H, m), 7.72 (1 H, s), 7.51-7.44 (2 H, m), 7.29-7.21 (4 H, m), 2.25 (3 H, s). LC/MS: 355 (M+H)$^+$. HPLC (Method D) Rt=13.20 min (Purity: 98.0%).

Step 3: 3-(2,5-difluorophenyl)-5-(5-ethoxy-1-o-tolyl-1H-pyrazol-4-yl)-1,2,4-oxadiazole A mixture of 4-(3-(2,5-difluorophenyl)-1,2,4-oxadiazol-5-yl)-1-o-tolyl-1H-pyrazol-5-ol (50 mg; 0.14 mmol), obtained from step 2, and potassium carbonate (26 mg; 0.19 mmol) in MeCN (1 mL) was heated to reflux for 1 hour. The mixture was allowed to cool and ethyl iodide (0.01 mL; 0.14 mmol) was added. The mixture was stirred at RT for 18 hours and then further ethyl iodide (0.02 mL; 0.28 mmol) was added and the mixture heated to 40° C. for 8 hours. DCM (10 mL) and water (5 mL) were added and the mixture passed through a hydrophobic frit. The solvent was removed in vacuo and the residue purified on a Biotage 12+M column, eluting with petrol containing increasing amounts of EtOAc to give Example 112 as an off-white solid. $^1$H NMR (CDCl$_3$, 400 MHz) δ 8.20 (1 H, s), 7.87-7.81 (1 H, m), 7.45-7.30 (4 H, m), 7.25-7.15 (2 H, m), 4.42 (2 H, q, J=7.1 Hz), 2.21 (3 H, s), 1.27 (3 H, t, J=7.1 Hz). LC/MS: 383 (M+H)$^+$. HPLC (Method B) Rt=3.98 min (Purity: 99.4%).

Example 113

5-(1-(cyclopropylmethyl)-5-(pyridin-4-yl)-1H-pyrazol-4-yl)-3-(3-(trifluoromethyl)phenyl)-1,2,4-oxadiazole

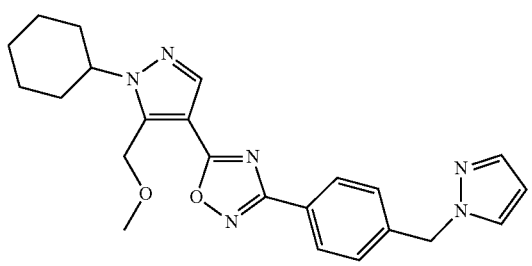 [SMILES: COCc1c(-c2nc(-c3ccc(Cn4cccn4)cc3)no2)cnn1C1CCCCC1]

Sodium hydride (18.0 mg; 0.45 mmol) was added to a suspension of Intermediate 29 (204 mg; 0.75 mmol) and N'-hydroxy-3-(trifluoromethyl)benzenecarboximidamide (Bionet, 92 mg; 0.45 mmol) in THF (2 mL) and the mixture was stirred for 10 minutes. The mixture was then heated in a microwave reactor 8.5 hours at 130° C. Water (5 mL) was added and the product extracted into DCM (3×5 mL). The combined organic fractions were passed through a hydrophobic frit and the solvent removed in vacuo. The residue was purified by reverse-phase preparative HPLC. The residue was recrystallised from iso-propanol to give Example 113 as a white solid. $^1$H NMR: (CDCl$_3$, 400 MHz) δ 8.86 (2 H, d, J=5.1 Hz), 8.29 (2 H, s), 8.14 (1 H, d, J=7.8 Hz), 7.73 (1 H, d, J=7.9 Hz), 7.58 (1 H, t, J=7.8 Hz), 7.42 (2 H, d, J=5.1 Hz), 3.99 (2 H, d, J=7.0 Hz), 1.35-1.14 (1 H, m), 0.59-0.52 (2 H, m), 0.27-0.20 (2 H, m). LC/MS: 412 (M+H)$^+$. HPLC (Method E) Rt 21.52 min (Purity: 97.4%).

Example 114

3-(4-((1H-pyrazol-1-yl)methyl)phenyl)-5-(1-cyclohexyl-5-(methoxymethyl)-1H-pyrazol-4-yl)-1,2,4-oxadiazole

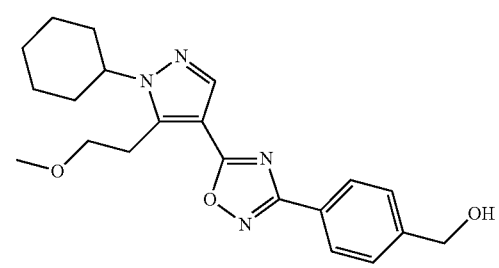 [SMILES: COCCc1c(-c2nc(-c3ccc(CO)cc3)no2)cnn1C1CCCCC1]

Sodium Hydride (20 mg; 0.525 mmol) was added to a suspension of Intermediate 18 (126 mg; 0.50 mmol) and Intermediate 25 (114 mg; 0.525 mmol) in THF (2 mL) and the mixture was stirred for 10 minutes. The mixture was heated to 140° C. in a microwave reactor for 2 hours. Water (3 mL) was added and the product was extracted into DCM (3×2 mL). The combined organic fractions were passed through a hydrophobic frit and the solvent was removed in vacuo. The residue was purified by flash chromatography on a 12+M Biotage column, eluting with petrol containing increasing amounts of 1:1 DCM:diethyl ether to give Example 114 as a white solid. $^1$H NMR: (CDCl$_3$, 400 MHz) δ 8.14-8.08 (3 H, m), 7.58 (1 H, d, J=1.9 Hz), 7.43 (1 H, d, J=2.3 Hz), 7.31 (2 H, d, J=8.4 Hz), 6.32 (1 H, t, J=2.1 Hz), 5.40 (2 H, s), 5.02 (2 H, s), 4.36-4.25 (1 H, m), 3.41 (3 H, s), 2.07-1.90 (6 H, m), 1.80-1.70 (1 H, m), 1.51-1.19 (3 H, m). LC/MS: 419 (M+H)$^+$. HPLC (Method A) Rt 4.18 min (Purity: 99.6%).

Example 115

(4-(5-(1-cyclohexyl-5-(2-methoxyethyl)-1H-pyrazol-4-yl)-1,2,4-oxadiazol-3-yl)phenyl)methanol 1-ethyl-3-(3-dimethylaminopropyl)carbodiimide hydrochloride (214.7 mg; 1.12 mmol) was added to a solution of Intermediate 23 (202 mg; 0.80 mmol) in MeCN (1.5 mL), followed by Intermediate 8 (133 mg, 0.80 mmol). The mixture was stirred at room temperature for 18 hours and then pyridine (1.5 mL) added. The mixture was heated to 150° C. in a microwave reactor for 75 minutes. The solvent was removed in vacuo and water (10 mL) added. The product was extracted into DCM (3×10 mL) and the combined organic fractions passed through a hydrophobic frit and the solvent removed in vacuo. The residue was purified by flash chromatography on a 12+M Biotage column, eluting with petrol containing increasing amounts of ethyl acetate to give Example 115 as a white solid. $^1$H NMR: (CDCl$_3$, 400 MHz) δ 8.11-8.09 (3 H, m), 7.48 (2 H, d, J=8.0 Hz), 4.77 (2 H, s), 4.30-4.21 (1 H, m), 3.70 (2 H, t, J=6.3 Hz), 3.42 (2 H, t, J=6.3 Hz), 3.33 (3 H, s), 2.06-1.90 (6 H, m), 1.75 (1 H, d, J=12.7 Hz), 1.50-1.25 (3 H, m). LC/MS: 383 (M+H)$^+$. HPLC (Method A) Rt 3.91 min (Purity: 98.8%).

Example 116

5-(1-cyclohexyl-5-(methoxymethyl)-1H-pyrazol-4-yl)-3-(1,2,3,4-tetrahydroisoquinolin-6-yl)-1,2,4-oxadiazole

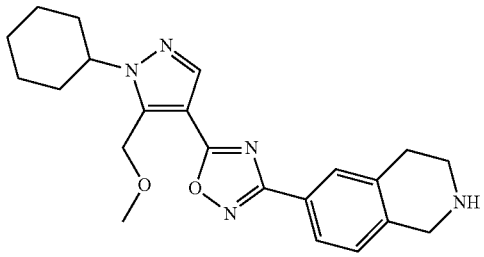 [SMILES: COCc1c(-c2nc(-c3ccc4c(c3)CCNC4)no2)cnn1C1CCCCC1]

Step 1:
N-(3-bromophenethyl)-2,2,2-trifluoroacetamide

To a solution of 3-bromophenethylamine (2.46 g; 12.3 mmol) in DCM (15 mL) was added diisopropylamine (3.18 g; 24.6 mmol) and trifluoroacetic anhydride (2.84 g; 13.5 mmol) and the mixture was stirred for 16 hours. The solvent was removed in vacuo and the residue was triturated with DCM (1 mL) and petrol (10 mL) to give the title compound (2.57 g; 70%) as a pale yellow solid. $^1$H NMR (CDCl$_3$, 400 MHz) δ 7.40 (1 H, d, J=8.0 Hz), 7.36 (1 H, s), 7.21 (1 H, t, J=7.8 Hz), 7.12 (1 H, d, J=7.7 Hz), 6.37 (1 H, br s), 3.65-3.57 (2 H, m), 2.87 (2 H, t, J=7.1 Hz).

Step 2: 1-(6-bromo-3,4-dihydroisoquinolin-2(1H)-yl)-2,2,2-trifluoroethanone

To a solution of N-(3-bromophenethyl)-2,2,2-trifluoroacetamide, obtained from step 1, (1.51 g; 0.51 mmol) in acetic acid (10 mL) at 0° was added sulfuric acid (5 mL) followed by paraformaldehyde (0.25 g) portionwise over 30 minutes. The mixture was then stirred at RT for 16 hours, diluted with water (200 mL) and the product extracted with EtOAc (3×20 mL). The combined organic fractions were washed with saturated sodium bicarbonate solution (200 mL), dried (MgSO$_4$) and the solvent removed in vacuo. The residue was purified by flash chromatography on an Isolute Flash Si II 50 g column, eluting with petrol containing increasing amounts of EtOAc to give a yellow oil (1.12 g; 71%) as a 3:1 mixture of 1-(6-bromo-3,4-dihydroisoquinolin-2(1H)-yl)-2,2,2-trifluoroethanone and 1-(5-bromo-3,4-dihydroisoquinolin-2(1H)-yl)-2,2,2-trifluoroethanone respectively. Data for the major component of the mixture: $^1$H NMR (CDCl$_3$, 400 MHz) δ 7.36-7.32 (1 H, m), 7.12 (1 H, s), 6.98-7.07 (1 H, m), 4.73 (2 H, s), 3.89-3.81 (2 H, m), 2.98-2.91 (2 H, m).

Step 3: 2-(2,2,2-trifluoroacetoyl)-1,2,3,4-tetrahydroisoquinoline-6-carbonitrile 1-(6-bromo-3,4-dihydroisoquinolin-2(1H)-yl)-2,2,2-trifluoroethanone, obtained from step 2 as a 3:1 mixture with 1-(5-bromo-3,4-dihydroisoquinolin-2(1H)-yl)-2,2,2-trifluoroethanone as the minor component, (0.79 g; 2.54 mmol), S-Phos (93.8 mg; 0.229 mmol), Pd$_2$(dba)$_3$ (93.0 mg; 0.102 mmol) and zinc cyanide (337.0 mg; 2.87 mmol) were suspended in degassed water:DMF (1:99, 11.5 mL) in a microwave vial and further degassed for 10 minutes in a sonicator. The vial was then sealed and heated to 150° C. in a microwave reactor for 45 minutes. The solid material was removed by filtration, the solvent was removed in vacuo and the residue purified by flash chromatography on an Isolute Flash Si II 50 g column, eluting with petrol containing increasing amounts of EtOAc to give a yellow oil as a 3:1 mixture of 2-(2,2,2-trifluoroacetoyl)-1,2,3,4-tetrahydroisoquinoline-6-carbonitrile and 2-(2,2,2-trifluoroacetoyl)-1,2,3,4-tetrahydroisoquinoline-5-carbonitrile respectively. Data for the major component of the mixture: $^1$H NMR (CDCl$_3$, 400 MHz) δ 7.59-7.23 (3 H, m), 4.84 (2 H, s), 3.93-3.86 (2 H, m), 3.02-2.99 (2 H, m). LC/MS: 255 (M+H)$^+$. HPLC (Method I) Rt=3.54 min (Purity: 90.7%).

Step 4: N'-hydroxy-1,2,3,4-tetrahydroisoquinoline-6-carboximidamide

To a solution of 2-(2,2,2-trifluoroacetoyl)-1,2,3,4-tetrahydroisoquinoline-6-carbonitrile, obtained from step 3 as a 3:1 mixture with 2-(2,2,2-trifluoroacetoyl)-1,2,3,4-tetrahydroisoquinoline-5-carbonitrile as the minor component, (0.31 g; 1.23 mmol) in EtOH (30 mL) was added 50% hydroxylamine in water (1.0 mL) and the mixture heated to 80° C. for 1 hour. The solvent was removed in vacuo and the residue redissolved in THF (10 mL). The mixture was dried (MgSO$_4$) and the solvent removed in vacuo to give a pale yellow oil (0.25 g; 100%) as a 3:1 mixture of N'-hydroxy-1,2,3,4-tetrahydroisoquinoline-6-carboximidamide and N'-hydroxy-1,2,3,4-tetrahydroisoquinoline-5-carboximidamide respectively. Data for the major component of the mixture: $^1$H NMR: (DMSO-d$_6$, 400 MHz) δ 9.61-9.56 (1 H, m), 7.59-7.52 (2 H, m), 7.19 (1 H, m), 5.80 (2 H, br s), 4.18 (2 H, s), 3.30-3.28 (2 H, m), 2.96-2.87 (2 H, m). LC/MS: 192 (M+H)$^+$. HPLC (Method I) Rt=1.51 min (Purity: 58.7%).

Step 5: 5-(1-cyclohexyl-5-(methoxymethyl)-1H-pyrazol-4-yl)-3-(1,2,3,4-tetrahydroisoquinolin-6-yl)-1,2,4-oxadiazole To a solution of Intermediate 18 (0.13 g; 0.52 mmol) and N'-hydroxy-1,2,3,4-tetrahydroisoquinoline-6-carboximidamide, obtained from step 4 as a 3:1 mixture with N'-hydroxy-1,2,3,4-tetrahydroisoquinoline-5-carboximidamide as the minor component, (0.11 g; 0.57 mmol) in THF (4 mL) was added sodium hydride as a 60% dispersion in mineral oil (23 mg; 0.57 mmol) and the mixture stirred for 15 minutes. The mixture was then heated in a microwave reactor for 2 hours. Water (5 mL) was added and the product extracted into DCM (3×5 mL). The combined organic fractions were passed through a hydrophobic frit and the solvent removed in vacuo. The residue was purified by flash chromatography on an Isolute Flash Si II 20 g column, eluting with DCM containing increasing amounts of MeOH to give Example 116 as a colourless oil. $^1$H NMR: (CDCl$_3$, 400 MHz) δ 8.13 (1 H, s), 7.90-7.88 (2 H, m), 7.16-7.14 (1 H, m), 5.02 (2 H, s), 4.33-4.28 (1 H, m), 4.12 (2 H, s), 3.43 (3 H, s), 3.24-3.21 (2 H, m), 2.95-2.92 (2 H, m), 2.06-1.92 (5 H, m), 1.77-1.74 (1 H, m), 1.59-1.25 (4 H, m). LC/MS: 394 (M+H)$^+$. HPLC (Method A) Rt=2.34 min (Purity: 96.3%).

Example 117

(4-(5-(1-cyclohexyl-5-(tetrahydrofuran-2-yl)-1H-pyrazol-4-yl)-1,2,4-oxadiazol-3-yl)phenyl)methanol

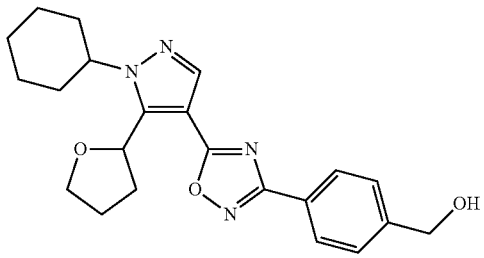 [SMILES: OCc1ccc(-c2noc(-c3cnn(C4CCCCC4)c3C3CCCO3)n2)cc1]

Sodium hydride (24.8 mg; 0.62 mmol) was added to a suspension of Intermediate 26 (181.3 mg; 0.62 mmol) and Intermediate 8 (108 mg; 0.651 mmol) in THF (2 mL) and the mixture was stirred for 10 minutes. The reaction was then heated to 140° C. in the microwave for 10 hours. Water (3 mL) was added and the product extracted into DCM (3×2 mL). The combined organic fractions were passed through a hydrophobic frit and the solvent removed in vacuo. The residue was purified by flash chromatography on a 12+M Biotage column, eluting with petrol containing increasing amounts of ethyl acetate to give Example 117 as a white solid. $^1$H NMR: (CDCl$_3$, 400 MHz) δ 8.11 (3 H, d, J=7.6 Hz), 7.49 (2 H, d, J=8.0 Hz), 5.81 (1 H, dd, J=9.7, 6.8 Hz), 4.78 (2 H, d, J=5.5 Hz), 4.49-4.40 (1 H, m), 4.24-4.15 (1 H, m), 4.01 (1 H, td, J=8.1, 6.0 Hz), 2.57-2.47 (1 H, m), 2.28-2.18 (2 H, m), 1.10-1.91 (7 H, m), 1.85-1.80 (1 H, m), 1.79-1.70 (1 H, m), 1.45-1.22 (3 H, m). LC/MS: 395 (M+H)$^+$. HPLC (Method B) Rt 3.64 min (Purity: 95.3%).

Example 118

3-(7-(5-(1-cyclohexyl-5-(methoxymethyl)-1H-pyrazol-4-yl)-1,2,4-oxadiazol-3-yl)-3,4-dihydroisoquinolin-2(1H)-yl)propanoic acid

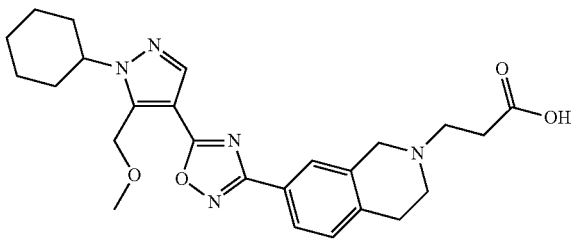 [SMILES: COCc1c(-c2nc(-c3ccc4c(c3)CN(CCC(=O)O)CC4)no2)cnn1C1CCCCC1]

Step 1: tert-butyl 3-(7-(5-(1-cyclohexyl-5-(methoxymethyl)-1H-pyrazol-4-yl)-1,2,4-oxadiazol-3-yl)-3,4-dihydroisoquinolin-2(1H)-yl)propanoate To a solution of Intermediate 31 (0.14 g; 0.58 mmol) and Intermediate 35 (0.20 g; 0.64 mmol) in MeCN (2 mL) was added 1-ethyl-3-(3-dimethylaminopropyl)carbodiimide hydrochloride (0.15 g; 0.82 mmol) and the mixture was stirred for 16 hours. Pyridine (1 mL) was added and the mixture was heated to 150° C. in a microwave reactor for 2 hours. Water (5 mL) was added and the product extracted into DCM (3×5 mL). The combined organic fractions were passed through a hydrophobic frit and the solvent removed in vacuo. The residue was purified by flash chromatography on an Isolute Flash Si II 20 g column, eluting with petrol containing increasing amounts of EtOAc to give tert-butyl 3-(7-(5-(1-cyclohexyl-5-(methoxymethyl)-1H-pyrazol-4-yl)-1,2,4-oxadiazol-3-yl)-3,4-dihydroisoquinolin-2(1H)-yl)propanoate as a colourless oil. $^1$H NMR: (CDCl$_3$, 400 MHz) δ 8.14-8.10 (1 H, m), 7.88 (1 H, d, J=8.0 Hz), 7.80 (1 H, s), 5.05-4.99 (2 H, m), 4.35-4.27 (1 H, m), 3.74 (2 H, s), 3.44-3.38 (3 H, m), 2.98-2.91 (2 H, m), 2.90-2.83 (2 H, m), 2.79 (2 H, t, J=6.0 Hz), 2.58-2.50 (2 H, m), 2.06-1.90 (7 H, m), 1.75 (1 H, d, J=12.3 Hz), 1.54-1.33 (9 H, m), 1.40-1.21 (2 H, m). LC/MS: 522 (M+H)$^+$. HPLC (Method A) Rt=2.74 min (Purity: 99.3%).

Step 2: 3-(7-(5-(1-cyclohexyl-5-(methoxymethyl)-1H-pyrazol-4-yl)-1,2,4-oxadiazol-3-yl)-3,4-dihydroisoquinolin-2(1H)-yl)propanoic acid To a solution of tert-butyl 3-(7-(5-(1-cyclohexyl-5-(methoxymethyl)-1H-pyrazol-4-yl)-1,2,4-oxadiazol-3-yl)-3,4-dihydroisoquinolin-2(1H)-yl)propanoate (57 mg; 0.10 mmol), obtained from step 1, in 1,4-dioxane (1 mL) was added hydrochloric acid (1 mL) and the mixture heated to 50° C. for 16 hours. The solvent was removed in vacuo to give the title compound Example 118 as an off-white solid. $^1$H NMR: (CDCl$_3$, 400 MHz) δ 8.21 (1 H, s), 7.99 (1 H, d, J=8.1 Hz), 7.93 (1 H, s), 7.49 (1 H, d, J=8.1 Hz), 5.00 (2 H, s), 4.70 (1 H, s), 4.48-4.30 (3 H, m), 3.80-3.60 (2 H, m), 3.58-3.40 (2 H, m), 3.34 (3 H, s), 3.27-3.14 (2 H, m), 2.94-2.86 (2 H, m), 1.91-1.76 (6 H, m), 1.72-1.63 (1 H, m), 1.50-1.35 (2 H, m), 1.29-1.19 (1 H, m). LC/MS: 466 (M+H)$^+$. HPLC (Method E) Rt=15.44 min (Purity: 93.6%).

Example 119

3-(4-((1H-imidazol-1-yl)methyl)phenyl)-5-(1-cyclohexyl-5-(methoxymethyl)-1H-pyrazol-4-yl)-1,2,4-oxadiazole

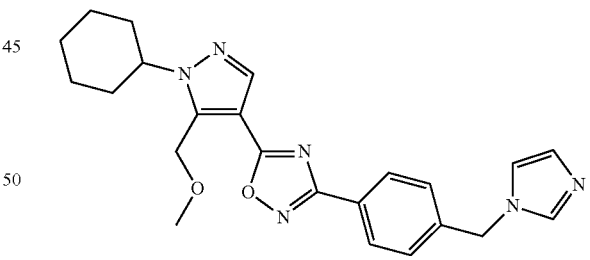

Sodium Hydride (20 mg; 0.525 mmol) was added to a suspension of Intermediate 18 (126 mg; 0.50 mmol) and Intermediate 24 (114 mg; 0.525 mmol) in THF (2 mL) and the mixture was stirred for 10 minutes. The mixture was heated to 140° C. in a microwave reactor for 20 hours. Water (3 mL) was added and the product extracted into DCM (3×2 mL). The combined organic fractions were passed through a hydrophobic frit and the solvent removed in vacuo. The residue was purified by flash chromatography on a 12+M Biotage column, eluting with petrol containing increasing amounts of 5% methanol in ethyl acetate to give Example 119 as a white solid. $^1$H NMR: (CDCl$_3$, 400 MHz) δ 8.15-8.10 (3 H, m), 7.59 (1 H, s), 7.26 (2 H, d, J=6.8 Hz), 7.12 (1 H, s), 6.93 (1 H, s), 5.20 (2 H, s), 5.11 (2 H, s), 4.36-4.26 (1 H, m), 3.42 (3 H, s), 2.05-1.89 (6 H, m), 1.75 (1 H, d, J=12.5 Hz), 1.50-1.40 (2 H, m), 1.40-1.25 (1 H, m). LC/MS: 419 (M+H)+. HPLC (Method A) Rt 2.46 min (Purity: 98.7%).

Example 120

1-(4-(5-(1-cyclohexyl-5-(2-methoxyethyl)-1H-pyrazol-4-yl)-1,2,4-oxadiazol-3-yl)benzyl)azetidine-3-carboxylic acid

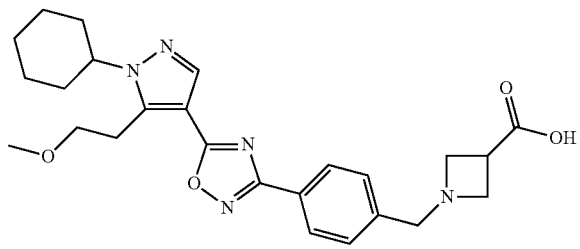 [SMILES: COCCc1c(-c2nc(-c3ccc(CN4CC(C(=O)O)C4)cc3)no2)cnn1C1CCCCC1]

Step 1: 4-(5-(1-cyclohexyl-5-(2-methoxyethyl)-1H-pyrazol-4-yl)-1,2,4-oxadiazol-3-yl)benzaldehyde The title compound was prepared following the procedure described for Example 88 (step 2), but starting from Example 115 (141.5 mg; 0.37 mmol). Title compound was obtained as a white solid (125 mg; 88.8%). $^1$H NMR: (CDCl$_3$, 400 MHz) δ 10.09 (1 H, s), 8.30 (2 H, d, J=6.8 Hz), 8.14 (1 H, s), 8.05 (2 H, d, J=6.8 Hz), 4.33-4.25 (1 H, m), 3.74-3.69 (2 H, m), 3.44 (2 H, t, J=6.4 Hz), 3.35 (3 H, s), 2.06-1.86 (6 H, m), 1.80-1.70 (1 H, m), 1.50-1.25 (3 H, m). LC/MS: 381 (M+H)+. HPLC (Method A) Rt 4.39 min (Purity: 72.4%).

Step 2: 1-(4-(5-(1-cyclohexyl-5-(2-methoxyethyl)-1H-pyrazol-4-yl)-1,2,4-oxadiazol-3-yl)benzyl)azetidine-3-carboxylic acid Sodium cyanoborohydride (23 mg; 0.363 mmol) was added to a solution of 4-(5-(1-cyclohexyl-5-(2-methoxyethyl)-1H-pyrazol-4-yl)-1,2,4-oxadiazol-3-yl)benzaldehyde (125.5 mg; 0.33 mmol), obtained from step 1, and 3-azetidine carboxylic acid (66.7 mg, 0.66 mmol) in methanol (3 mL) and acetic acid (60 μL; 0.99 mmol) and the mixture was stirred at room temperature overnight. The solvent was removed in vacuo and the residue was purified by reverse-phase preparative HPLC to give Example 120 as an off white solid. $^1$H NMR: (Acetone-d$_6$, 400 MHz) δ 8.08-80.6 (3 H, m), 7.52 (2 H, d, J=8.0 Hz), 4.51-4.41 (1 H, m), 3.77-3.69 (4 H, m), 3.57-3.48 (4 H, m), 3.42-3.28 (3 H, m), 3.30 (3 H, s), 2.03-1.88 (6 H, m), 1.75 (1 H, d, J=13.0 Hz), 1.59-1.45 (2 H, m), 1.38-1.25 (1 H, m). LC/MS: 466 (M+H)+. HPLC (Method B) Rt 2.53 min (Purity: 99.3%).

Example 121

N-(4-(5-(1-cyclohexyl-5-(methoxymethyl)-1H-pyrazol-4-yl)-1,2,4-oxadiazol-3-yl)benzyl)propan-2-amine

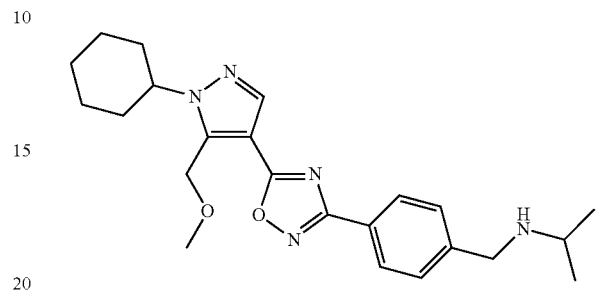

Step 1: 4-(5-(1-cyclohexyl-5-(methoxymethyl)-1H-pyrazol-4-yl)-1,2,4-oxadiazol-3-yl)benzaldehyde The title compound was prepared following the procedure described for Example 88 (step 2), but starting from (4-(5-(1-cyclohexyl-5-(methoxymethyl)-1H-pyrazol-4-yl)-1,2,4-oxadiazol-3-yl)phenyl)methanol (320 mg; 0.87 mmol), obtained as described in Example 133 (step 1). It was obtained as an off white solid (285 mg; 89.4%). $^1$H NMR: (CDCl$_3$, 400 MHz) δ 10.11 (1 H, s), 8.33 (2 H, d, J=8.0 Hz), 8.15 (1 H, s), 8.02 (2 H, d, J=8.1 Hz), 5.03 (2 H, s), 4.32 (1 H, td, J=10.3, 4.9 Hz), 3.44 (3 H, s), 2.07-1.93 (6 H, m), 1.76 (1 H, d, J=12.6 Hz), 1.52-1.25 (3 H, m). LC/MS: 367 (M+H)+. HPLC (Method B) Rt 3.97 min (Purity: 89.4%).

Step 2: N-(4-(5-(1-cyclohexyl-5-(methoxymethyl)-1H-pyrazol-4-yl)-1,2,4-oxadiazol-3-yl)benzyl)propan-2-amine Sodium cyanoborohydride (18.0 mg; 0.286 mmol) was added to a solution of 4-(5-(1-cyclohexyl-5-(methoxymethyl)-1H-pyrazol-4-yl)-1,2,4-oxadiazol-3-yl)benzaldehyde (95.3 mg; 0.26 mmol) and isopropylamine (44.3 μL; 0.52 mmol) in methanol (3 mL) and acetic acid (47 μL; 0.78 mmol) and the mixture was stirred at room temperature overnight. The solvent was removed in vacuo and water (3 mL) was added and the product extracted into DCM (3×2 mL). The combined organic fractions were passed through a hydrophobic frit and the solvent removed in vacuo. The residue was purified by flash chromatography on a 12+M Biotage column, eluting with DCM containing increasing amounts of 5% methanol in DCM to give Example 121 as an off white solid. $^1$H NMR: (CDCl$_3$, 400 MHz) δ 8.15-8.06 (3 H, m), 7.48 (2 H, d, J=7.8 Hz), 5.03 (2 H, s), 4.36-4.26 (1 H, m), 3.89 (2 H, s), 3.47 (3 H, m), 3.00-2.88 (1 H, m), 2.04-1.90 (6 H, m), 1.75 (1 H, d, J=12.3 Hz), 1.50-1.40 (2 H, m), 1.40-1.25 (1 H, m), 1.18 (6 H, d, J=6.4 Hz). LC/MS: 410 (M+H)+. HPLC (Method A) Rt 2.46 min (Purity: 99.0%).

Example 122

3-(4-(5-(1-cyclohexyl-5-(methoxymethyl)-1H-pyrazol-4-yl)-1,2,4-oxadiazol-3-yl)benzylamino)propane-1,2-diol

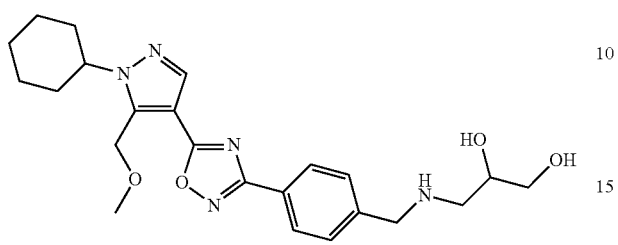

Sodium cyanoborohydride (18.0 mg; 0.286 mmol) was added to a solution of 4-(5-(1-cyclohexyl-5-(methoxymethyl)-1H-pyrazol-4-yl)-1,2,4-oxadiazol-3-yl)benzaldehyde (95.3 mg; 0.26 mmol), obtained as described in Example 121 (step 1), and isopropylamine (44.3 μL; 0.52 mmol) in methanol (3 mL) and acetic acid (47 μL; 0.78 mmol) and the mixture was stirred at room temperature overnight. The solvent was removed in vacuo and water (3 mL) added. The product was extracted into ethyl acetate (3×2 mL) and the combined organic fractions were passed through a hydrophobic frit and the solvent removed in vacuo. The residue was purified by flash chromatography on a 12+M Biotage column, eluting with petrol containing increasing amounts of 5% methanol in ethyl acetate. The residue was redissolved in ethyl acetate (5 mL) and washed with water (3×5 mL) to give Example 122 as a clear gum. $^1$H NMR: (CDCl$_3$, 400 MHz) δ 8.13-8.11 (3 H, m), 7.49 (2 H, t, J=8.0 Hz), 5.02 (2 H, s), 4.30 (1 H, td, J=10.2, 4.9 Hz), 4.01-3.95 (2 H, m), 3.90-3.84 (1 H, m), 3.76 (1 H, dd, J=11.5, 3.5 Hz), 3.62 (1 H, dd, J=11.5, 4.5 Hz), 3.42 (3 H, s), 2.95 (2 H, dd, J=12.3, 3.8 Hz), 2.08-1.93 (6 H, m), 1.76 (1 H, d, J=12.7 Hz), 1.52-1.40 (2 H, m), 138-1.25 (1H, m). LC/MS: 442 (M+H)$^+$. HPLC (Method C) Rt 12.10 min (Purity: 95.8%).

Example 123

4-(5-(1-cyclohexyl-5-(methoxymethyl)-1H-pyrazol-4-yl)-1,2,4-oxadiazol-3-yl)phenol

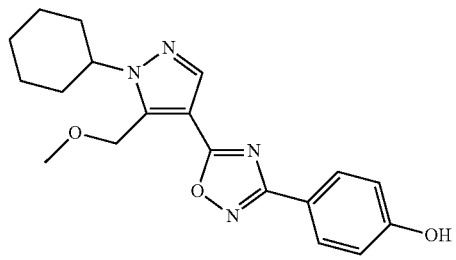 [SMILES: COCc1c(-c2nc(-c3ccc(O)cc3)no2)cnn1C1CCCCC1]

1-ethyl-3-(3-dimethylaminopropyl)carbodiimide hydrochloride (107 mg; 056 mmol) was added to a solution of Intermediate 31 (95 mg; 0.40 mmol) in MeCN (1.5 mL), followed by N',4-dihydroxy benzenecarboximidamide (Fluorochem, 61 mg; 0.40 mmol). The mixture was stirred at room temperature for 18 hours. Pyridine (1.5 mL) was added and the mixture was heated to 150° C. in a microwave reactor for 1 hour. The solvent was removed in vacuo, water (5 mL) added and the product extracted into DCM (3×5 mL). The combined organic fractions were passed through a hydrophobic frit and the solvent removed in vacuo. The residue was purified by flash chromatography on a 12+M Biotage column, eluting with petrol containing increasing amounts of ethyl acetate to give Example 123 as a purple gum. $^1$H NMR: (CDCl$_3$, 400 MHz) δ 8.15 (1 H, s), 8.03 (2 H, d, J=8.5 Hz), 6.94 (2 H, d, J=8.5 Hz), 6.33 (1 H, s), 5.03 (2 H, s), 4.37-4.26 (1 H, m), 3.43 (3 H, s), 2.10-1.88 (6 H, m), 1.80-1.70 (1 H, m), 1.51-1.40 (2 H, m), 1.39-1.25 (1 H, m). LC/MS: 355 (M+H)$^+$. HPLC (Method A) Rt 3.90 min (Purity: 97.9%).

Example 124

5-(5-(1-cyclohexyl-5-(methoxymethyl)-1H-pyrazol-4-yl)-1,2,4-oxadiazol-3-yl)pyridin-2-amine

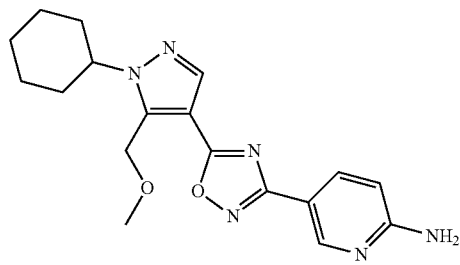 [SMILES: COCc1c(-c2nc(-c3ccc(N)nc3)no2)cnn1C1CCCCC1]

The title compound was prepared following the procedure described for Example 118 (step 1), but starting from Intermediate 34 (64 mg; 0.46 mmol) to give Example 124 as a white solid. $^1$H NMR: (CDCl$_3$, 400 MHz) δ 8.84 (1 H, d, J=2.3 Hz), 8.15-8.11 (2 H, m), 6.58 (1 H, d, J=8.6 Hz), 5.01 (2 H, s), 4.80 (2 H, s), 4.36-4.26 (1 H, m), 3.42 (3 H, s), 2.04-1.89 (5 H, m), 1.75 (1 H, d, J=12.9 Hz), 1.52-1.25 (4 H, m). LC/MS: 355 (M+H)$^+$. HPLC (10 cm_ESCl_formic) Rt=2.95 min (Purity: 97.5%).

Example 125

1-(4-(5-(1-cyclohexyl-5-(tetrahydrofuran-2-yl)-1H-pyrazol-4-yl)-1,2,4-oxadiazol-3-yl)benzyl)piperidine-4-carboxylic acid

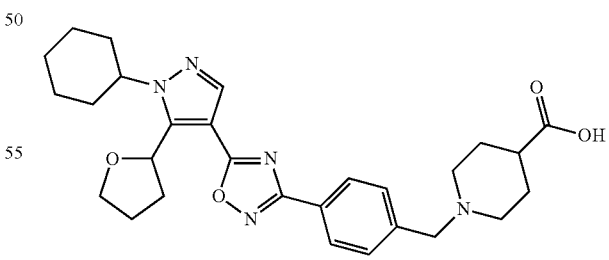

Step 1: (4-(5-(1-cyclohexyl-5-(tetrahydrofuran-2-yl)-1H-pyrazol-4-yl)-1,2,4-oxadiazol-3-yl)phenyl)methanol Sodium hydride (24.8 mg; 0.62 mmol) was added to a suspension of Intermediate 26 (181.3 mg; 0.62 mmol) and Intermediate 8 (108 mg; 0.651 mmol) in THF (2 mL) and the mixture was stirred for 10 minutes. The reaction was then heated to 140° C. in a microwave reactor for 10 hours. Water (3 mL) was added and the product extracted into DCM (3×2 mL). The combined organic fractions were passed through a hydrophobic frit and the solvent removed in vacuo. The residue was purified by flash chromatography on a 12+M Biotage column, eluting with petrol containing increasing amounts of ethyl acetate. The target compound was obtained as a white solid. $^1$H NMR: (CDCl$_3$, 400 MHz) δ 8.11 (3 H, d, J=7.6 Hz), 7.49 (2 H, d, J=8.0 Hz), 5.81 (1 H, dd, J=9.7, 6.8 Hz), 4.78 (2 H, d, J=5.5 Hz), 4.49-4.40 (1 H, m), 4.24-4.15 (1 H, m), 4.01 (1 H, td, J=8.1, 6.0 Hz), 2.57-2.47 (1 H, m), 2.28-2.18 (2H, m), 1.10-1.91 (7 H, m), 1.85-1.80 (1H, m), 1.79-1.70 (1 H, m), 1.45-1.22 (3 H, m). LC/MS: 395 (M+H)$^+$. HPLC (Method B) Rt 3.64 min (Purity: 95.3%).

Step 2: 4-(5-(1-cyclohexyl-5-(tetrahydrofuran-2-yl)-1H-pyrazol-4-yl)-1,2,4-oxadiazol-3-yl)benzaldehyde The title compound was prepared following the procedure described for Example 88 (step 2), but starting from (4-(5-(1-cyclohexyl-5-(tetrahydrofuran-2-yl)-1H-pyrazol-4-yl)-1,2,4-oxadiazol-3-yl)phenyl)methanol (130.2 mg; 0.33 mmol), obtained from step 1. The title compound was obtained as a pale yellow oil (100 mg; 77.2%). $^1$H NMR: (CDCl$_3$, 400 MHz) δ 10.11 (1 H, s), 8.30 (2 H, d, J=8.1 Hz), 8.12 (1 H, s), 8.03 (2 H, d, J=8.1 Hz), 5.81 (1 H, dd, J=9.7, 6.8 Hz), 4.49-4.40 (1 H, m), 4.21 (1 H, q, J=7.6 Hz), 4.02 (1 H, td, J=8.0, 6.1 Hz), 2.57-2.48 (1 H, m), 2.28-2.18 (2 H, m), 2.15-1.90 (7 H, m), 1.75 (1 H, d, J=11.1 Hz), 1.45-1.23 (3 H, m). LC/MS: 393 (M+H)$^+$. HPLC (Method E) Rt 23.85 min (Purity: 91.7%).

Step 3: 1-(4-(5-(1-cyclohexyl-5-(tetrahydrofuran-2-yl)-1H-pyrazol-4-yl)-1,2,4-oxadiazol-3-yl)benzyl)piperidine-4-carboxylic acid Sodium cyanoborohydride (17.3 mg; 0.275 mmol) was added to a solution of 4-(5-(1-cyclohexyl-5-(tetrahydrofuran-2-yl)-1H-pyrazol-4-yl)-1,2,4-oxadiazol-3-yl)benzaldehyde (99 mg; 0.25 mmol), obtained from step 2, and isonipecotic acid (64.6 mg; 0.50 mmol) in methanol (3 mL) and acetic acid (45 µL; 0.75 mmol) and the mixture was stirred at room temperature overnight. The solvent was removed in vacuo and the crude material purified by reverse phase preparative HPLC to give Example 125 as a white solid. $^1$H NMR: (DMSO-d$_6$, 400 MHz) δ 8.20 (1 H, s), 8.04 (2 H, d, J=8.0 Hz), 7.54 (2 H, d, J=8.0 Hz), 5.72 (1 H, dd, J=9.5, 6.9 Hz), 4.47 (1 H, d, J=8.2 Hz), 4.16 (1 H, q, J=7.5 Hz), 3.97 (1 H, q, J=7.5 Hz), 3.57 (2 H, s), 2.79 (2 H, d, J=10.9 Hz), 2.55-2.50 (1 H, m), 2.26-2.13 (3 H, m), 2.11-1.78 (11 H, m), 1.72 (1 H, d, J=12.5 Hz), 1.65-1.52 (2 H, m), 1.50-1.35 (2 H, m), 1.35 (1 H, m). LC/MS: 506 (M+H)$^+$. HPLC (Method B) Rt 2.77 min (Purity: 99.2%).

Example 126

3-(5-(1-cyclohexyl-5-(methoxymethyl)-1H-pyrazol-4-yl)-1,2,4-oxadiazol-3-yl)phenol

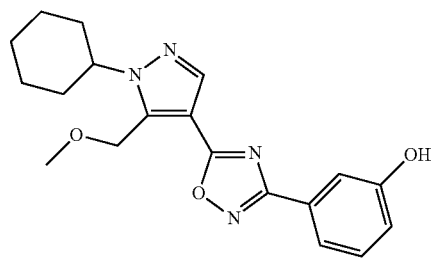 [SMILES: COCc1c(-c2nc(-c3cccc(O)c3)no2)cnn1C1CCCCC1]

1-ethyl-3-(3-dimethylaminopropyl)carbodiimide hydrochloride (107 mg; 056 mmol) was added to a solution of Intermediate 31 (95 mg; 0.40 mmol) in MeCN (1.5 mL), followed by Intermediate 32 (61 mg; 0.40 mmol). The mixture was stirred at room temperature for 18 hours. Pyridine (1.5 mL) was added and the mixture was heated to 150° C. in a microwave reactor for 1.5 hours. The solvent was removed in vacuo, water (5 mL) added and the product extracted into DCM (3×5 mL). the combined organic fractions were passed through a hydrophobic frit and the solvent removed in vacuo. The residue was purified by flash chromatography on a 12+M Biotage column, eluting with petrol containing increasing amounts of ethyl acetate to give Example 126 as a white solid. $^1$H NMR: (CDCl$_3$, 400 MHz) δ 8.14 (1 H, s), 7.73 (1 H, dt, J=7.7, 1.2 Hz), 7.61 (1 H, dd, J=2.6, 1.5 Hz), 7.38 (1 H, t, J=7.9 Hz), 7.00 (1 H, ddd, J=8.1, 2.7, 1.0 Hz), 5.10 (1 H, s), 5.03 (2 H, s), 4.35-4.28 (1 H, m), 3.42 (3 H, s), 2.05-1.90 (6 H, m), 1.76 (1 H, d, J=12.6 Hz), 1.51-1.25 (3 H, m). LC/MS: 355 (M+H)$^+$. HPLC (Method A) Rt 3.92 min (Purity: 99.8%).

Example 127

2-(4-(5-(1-cyclohexyl-5-(methoxymethyl)-1H-pyrazol-4-yl)-1,2,4-oxadiazol-3-yl)phenyl)-N,N-dimethylethanamine

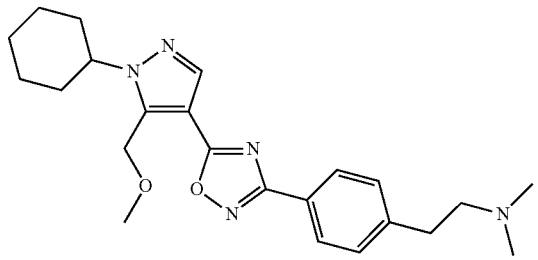 [SMILES: COCc1c(-c2nc(-c3ccc(CCN(C)C)cc3)no2)cnn1C1CCCCC1]

Step 1: 4-(5-(1-cyclohexyl-5-(methoxymethyl)-1H-pyrazol-4-yl)-1,2,4-oxadiazol-3-yl)phenethyl methanesulfonate To a solution of Example 109 (0.45 g; 1.18 mmol) in DCM (10 mL) was added, at 0° C., diisopropylethylamine (0.30 g; 2.36 mmol) and mesyl chloride (0.14 g; 1.29 mmol) and the mixture stirred for 10 minutes. The mixture was then stirred at RT for 2 hours and diluted with DCM (20 mL). Saturated sodium bicarbonate solution (20 mL) was added and the product was extracted into DCM (3×5 mL). The combined organic fractions were passed through a hydrophobic frit and the solvent removed in vacuo. The residue was purified by flash chromatography on an Isolute Flash Si II 20 g column, eluting with petrol containing increasing amounts of EtOAc to give 4-(5-(1-cyclohexyl-5-(methoxymethyl)-1H-pyrazol-4-yl)-1,2,4-oxadiazol-3-yl)phenethyl methanesulfonate (0.42 g; 79%) as a colourless oil. $^1$H NMR: (CDCl$_3$, 400 MHz) δ 8.15-8.06 (3 H, m), 7.41-7.33 (2 H, m), 5.03 (2 H, s), 4.51-4.41 (2 H, m), 4.35-4.26 (1 H, m), 3.43 (3 H, s), 3.16-3.09 (2 H, m), 2.92-2.85 (3 H, m), 2.05-1.90 (6 H, m), 1.76 (1 H, d, J=12.7 Hz), 1.50-1.25 (3 H, m).

Step 2: 2-(4-(5-(1-cyclohexyl-5-(methoxymethyl)-1H-pyrazol-4-yl)-1,2,4-oxadiazol-3-yl)phenyl)-N,N-dimethylethanamine To a solution of 4-(5-(1-cyclohexyl-5-(methoxymethyl)-1H-pyrazol-4-yl)-1,2,4-oxadiazol-3-yl)phenethyl methanesulfonate, obtained from step 1, (0.14 g; 0.31 mmol) in 1,4-dioxane (2 mL) was added potassium carbonate (94 mg; 0.68 mmol) and dimethylamine hydrochloride (50 mg; 0.62 mmol) and the mixture heated to 60° C. for 16 hours. DCM (10 mL) and water (10 mL) were added to the mixture and the aqueous layer was extracted with DCM (3×20 mL). The combined organic fractions were dried (MgSO$_4$), filtered and the solvent removed in vacuo. The crude residue was purified by reverse phase preparative HPLC to give Example 127 as a white solid. $^1$H NMR: (CDCl$_3$, 400 MHz) δ 8.28-8.20 (1 H, m), 8.02 (2 H, d, J=7.9 Hz), 7.48 (2 H, d, J=7.9 Hz), 5.04 (2 H, s), 4.41 (1 H, t, J=10.1 Hz), 3.38 (3 H, s), 2.85 (2 H, t, J=7.6 Hz), 2.58 (2 H, t, J=7.6 Hz), 2.25 (6 H, s), 1.97-1.83 (6 H, m), 1.77-1.66 (1 H, m), 1.55-1.39 (2 H, m), 1.34-1.20 (1 H, m). LC/MS: 410 (M+H)$^+$. HPLC (Method C) Rt=12.68 min (Purity: 97.2%).

Example 128

N-(4-(5-(1-cyclohexyl-5-(methoxymethyl)-1H-pyrazol-4-yl)-1,2,4-oxadiazol-3-yl)phenethyl)propan-2-amine formate

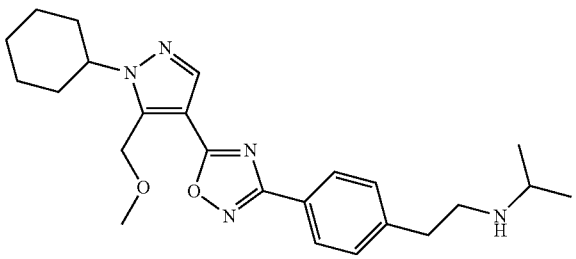 [SMILES: COCc1c(-c2nc(-c3ccc(CCNC(C)C)cc3)no2)cnn1C1CCCCC1]

The title compound was prepared following the procedure described for Example 127 (step 2), but starting from isopropylamine (36 mg; 0.62 mmol) to give Example 128 as a white solid. $^1$H NMR: (DMSO-d$_6$, 400 MHz) δ 8.38 (1 H, s), 8.25 (1 H, s), 8.04 (2 H, d, J=8.0 Hz), 7.50 (2 H, d, J=8.0 Hz), 5.05 (2 H, s), 4.47-4.37 (1 H, m), 3.38 (3 H, s), 3.03-2.89 (5 H, m), 1.96-1.83 (6 H, m), 1.73 (1 H, d, J=12.7 Hz), 1.54-1.40 (2 H, m), 1.28 (1 H, t, J=12.4 Hz), 1.11 (6 H, d, J=6.3 Hz). LC/MS: 424 (M+H)$^+$. HPLC (Method A) Rt=2.53 min (Purity: 99.0%).

Example 129

Methyl 1-(4-(5-(1-cyclohexyl-5-(methoxymethyl)-1H-pyrazol-4-yl)-1,2,4-oxadiazol-3-yl)phenethyl)piperidine-4-carboxylate

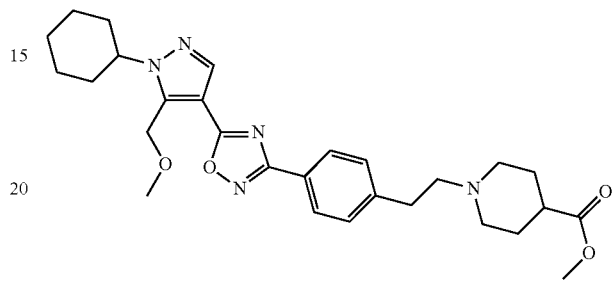

The title compound was prepared following the procedure described for Example 127 (step 2), but starting from methyl piperidine-4-carboxylate hydrochloride (0.11 g; 0.62 mmol) to give Example 129 as a white solid. $^1$H NMR: (DMSO-d$_6$, 400 MHz) δ 8.24 (1 H, s), 8.01 (2 H, d, J=8.0 Hz), 7.47 (2 H, d, J=8.0 Hz), 5.04 (2 H, s), 4.46-4.37 (1 H, m), 3.64 (3 H, s), 3.38 (3 H, s), 2.93-2.80 (4 H, m), 2.65-2.51 (3 H, m), 2.42-2.28 (1 H, m), 2.17-1.98 (2 H, m), 1.99-1.81 (7 H, m), 1.78-1.67 (1 H, m), 1.67-1.39 (4 H, m), 1.34-1.19 (1H, m). LC/MS: 507 (M+H)$^+$. HPLC (Method C) Rt=13.10 min (Purity: 89.7%).

Example 130

1-(4-(5-(1-cyclohexyl-5-(methoxymethyl)-1H-pyrazol-4-yl)-1,2,4-oxadiazol-3-yl)phenethyl)piperidine-4-carboxylic acid

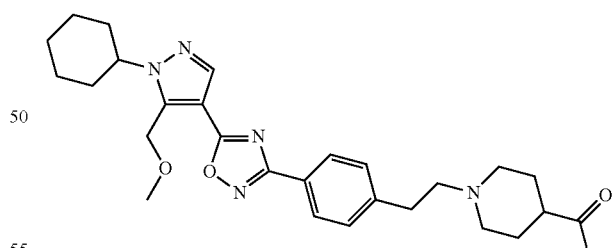

To a solution of Example 129 (40 mg; 0.078 mmol) in MeOH (1 mL) was added lithium hydroxide (6 mg; 0.15 mmol) and water (0.3 mL) and the mixture heated to 50° C. for 16 hours. The solvent was removed in vacuo, the residue dissolved in water (1 mL) and the mixture acidified to pH 5 with HCl. The precipitated solid was collected by filtration to give Example 130 as a white solid. $^1$H NMR: (DMSO-d$_6$, 400 MHz) δ 8.08 (1 H, s), 8.00-7.98 (2 H, m), 7.47-7.45 (2 H, m), 4.98 (2 H, s), 4.41-4.39 (1 H, m), 3.39 (3 H, s), 3.29-2.47 (9 H, m), 2.08-1.80 (8 H, m), 1.79-1.70 (1 H, m), 1.52-1.39 (4 H, m), 1.37-1.25 (1 H, m). LC/MS: 494 (M+H)⁺. HPLC (Method A) Rt=2.48 min (Purity: 93.6%).

Example 131

5-(1-cyclohexyl-5-(methoxymethyl)-1H-pyrazol-4-yl)-3-(4-(pyrrolidin-3-yloxy)phenyl)-1,2,4-oxadiazole

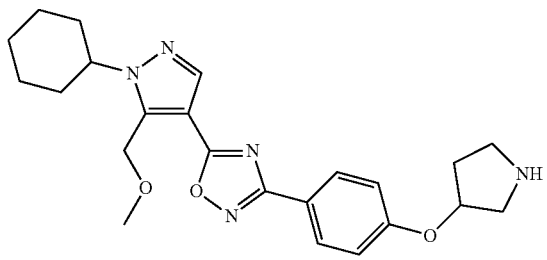 [SMILES: COCc1c(-c2nc(-c3ccc(OC4CCNC4)cc3)no2)cnn1C1CCCCC1]

Step 1: tert-butyl 3-(methylsulfonyloxy)pyrrolidine-1-carboxylate

To a solution of tert-butyl 3-hydroxypyrrolidine-1-carboxylate (Aldrich; 7.42 g, 39.6 mmol), in DCM (20 mL) was added, at 0° C., triethylamine (8.44 mL; 48.5 mmol) and then mesylchloride (3.13 mL; 40 mmol). The mixture was stirred for 18 hours at RT and then water was added and the product was extracted with DCM (3×20 mL). The combined organic fractions were dried (MgSO₄), filtered and the solvent removed in vacuo to give tert-butyl 3-(methylsulfonyloxy)pyrrolidine-1-carboxylate (8.26 g; 77%) as a brown oil. ¹H NMR: (CDCl3, 400 MHz) δ 5.27-5.20 (1 H, m), 3.70-3.49 (4 H, m), 3.04 (3 H, s), 2.90-2.05 (2 H, m), 1.46 (9 H, s).

Step 2: tert-butyl 3-(4-(5-(1-cyclohexyl-5-(methoxymethyl)-1H-pyrazol-4-yl)-1,2,4-oxadiazol-3-yl)phenoxy)pyrrolidine-1-carboxylate To a solution of tert-butyl 3-(methylsulfonyloxy)pyrrolidine-1-carboxylate, obtained from step 1, (0.15 g; 0.56 mmol), in DMF (2 mL) was added Example 123 (0.10 g; 0.28 mmol) and potassium carbonate (42 mg; 0.31 mmol) and the mixture stirred at 60° C. for 16 hours. The mixture was diluted with water (10 mL), the product extracted with EtOAc (3×10 mL) and the combined organic fractions dried (MgSO₄), filtered and the solvent was removed in vacuo. The residue was purified by flash chromatography on an Isolute Flash Si II 20 g column, eluting with petrol containing increasing amounts of EtOAc to give tert-butyl 3-(4-(5-(1-cyclohexyl-5-(methoxymethyl)-1H-pyrazol-4-yl)-1,2,4-oxadiazol-3-yl)phenoxy)pyrrolidine-1-carboxylate as a colourless oil. ¹H NMR: (CDCl3, 400 MHz) δ 8.13 (1 H, s), 8.08 (2 H, d, J=8.2 Hz), 6.97 (2 H, d, J=8.6 Hz), 5.03 (2 H, s), 4.97 (1 H, s), 4.35-4.27 (1 H, m), 3.72-3.47 (4 H, m), 3.42 (3 H, s), 2.30-2.07 (2 H, m), 2.08-1.89 (5 H, m), 1.80-1.70 (1 H, m), 1.47 (9 H, s), 1.44-1.25 (4 H, m). LC/MS: 524 (M+H)⁺. HPLC (Method C) Rt=23.0 min (Purity: 98.2%).

Step 3: 5-(1-cyclohexyl-5-(methoxymethyl)-1H-pyrazol-4-yl)-3-(4-(pyrrolidin-3-yloxy)phenyl)-1,2,4-oxadiazole To a solution of tert-butyl 3-(4-(5-(1-cyclohexyl-5-(methoxymethyl)-1H-pyrazol-4-yl)-1,2,4-oxadiazol-3-yl)phenoxy)pyrrolidine-1-carboxylate, obtained from step 2, (92 mg; 0.17 mmol) in DCM (3 mL) was added TFA (1 mL) and the mixture stirred for 16 hours. The mixture was poured into a saturated NaHCO₃ solution (50 mL) and the product was extracted with DCM (3×20 mL). The combined organic fractions were dried (MgSO₄), filtered and the solvent removed in vacuo to give Example 131 as a yellow oil. ¹H NMR: (CDCl₃, 400 MHz) δ 8.12 (1 H, s), 8.06 (2 H, d, J=8.4 Hz), 6.96 (2 H, d, J=8.4 Hz), 5.02 (2 H, s), 4.95 (1 H, s), 4.33-4.26 (1 H, m), 3.41 (3 H, s), 3.41-3.00 (4 H, m), 2.21-1.91 (8 H, m), 1.85-1.65 (1 H, m), 1.49-1.21 (4 H, m). LC/MS: 424 (M+H)⁺. HPLC (Method A) Rt=2.43 min (Purity: 98.7%).

Example 132

1-(4-(5-(1-cyclohexyl-5-(tetrahydro-2H-pyran-4-yl)-1H-pyrazol-4-yl)-1,2,4-oxadiazol-3-yl)benzyl)piperidine-4-carboxylic acid

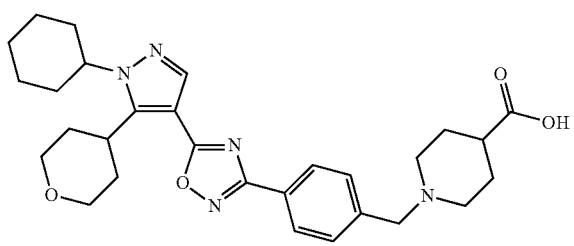 [SMILES: O=C(O)C1CCN(Cc2ccc(-c3noc(-c4cnn(C5CCCCC5)c4C4CCOCC4)n3)cc2)CC1]

Sodium cyanoborohydride (23 mg; 0.363 mmol) was added to a solution of 4-(5-(1-cyclohexyl-5-(2-methoxyethyl)-1H-pyrazol-4-yl)-1,2,4-oxadiazol-3-yl)benzaldehyde (125.5 mg; 0.33 mmol), obtained as described in Example 120 (step 1), and 3-azetidine carboxylic acid (66.7 mg; 0.66 mmol) in methanol (3 mL) and acetic acid (60 μL; 0.99 mmol) and the mixture was stirred at room temperature overnight. The solvent was removed in vacuo and the residue purified by reverse-phase preparative HPLC to give Example 132 as a white solid. ¹H NMR: (DMSO-d₆, 400 MHz) δ 8.18 (1 H, s), 8.05 (2 H, d, J=8.0 Hz), 7.55 (2 H, d, J=8.0 Hz), 4.55-4.48 (1 H, m), 4.04 (2 H, dd, J=11.3, 4.1 Hz), 3.74 (1 H, t, J=12.6 Hz), 3.57 (4 H, t, J=11.7 Hz), 2.80 (2 H, d, J=11.0 Hz), 2.51-2.89 (2 H, m), 2.27-2.18 (1 H, m), 2.06 (2 H, t, J=11.2 Hz), 1.91-1.80 (8 H, m), 1.75 (1 H, d, J=11.5 Hz), 1.66-1.50 (6 H, m), 1.31-1.20 (1 H, m). LC/MS: 520 (M+H)⁺. HPLC (Method A) Rt 2.42 min (Purity: 98.1%).

Example 133

4-(4-(5-(1-cyclohexyl-5-(methoxymethyl)-1H-pyrazol-4-yl)-1,2,4-oxadiazol-3-yl)benzyloxy)butanoic acid

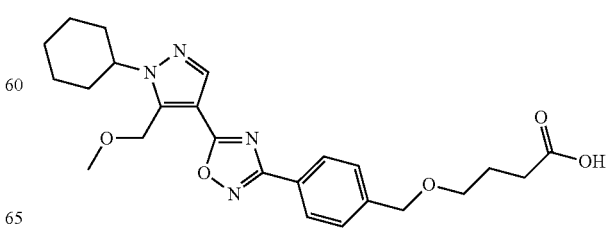

Step 1: (4-(5-(1-cyclohexyl-5-(methoxymethyl)-1H-pyrazol-4-yl)-1,2,4-oxadiazol-3-yl)phenyl)methanol The title compound was prepared following the procedure described for Example 125 (step 1), but starting from Intermediate 18 (757 mg; 3.0 mmol) and Intermediate 8 (523.5 mg; 3.15 mmol). The title compound was obtained as a red oil. ¹H NMR: (CDCl₃, 400 MHz) δ 8.16-8.11 (3 H, m), 7.50 (2 H, d, J=8.1 Hz), 5.03 (2 H, s), 4.79 (2 H, d, J=6.0 Hz), 4.35-4.28 (1 H, m), 3.42 (3 H, s), 2.09-1.90 (6 H, m), 1.82-1.73 (2 H, m), 1.52-1.25 (3 H, m). LC/MS: 369 (M+H)⁺. HPLC (Method B) Rt 3.47 min (Purity: 88.0%).

Step 2: tert-butyl 4-(4-(5-(1-cyclohexyl-5-(methoxymethyl)-1H-pyrazol-4-yl)-1,2,4-oxadiazol-3-yl)benzyloxy)butanoate To a solution of (4-(5-(1-cyclohexyl-5-(methoxymethyl)-1H-pyrazol-4-yl)-1,2,4-oxadiazol-3-yl)phenyl)methanol (85 mg; 0.23 mmol), obtained from step 1, and tetrabutylammonium hydrogen sulfate (8 mg; 0.023 mmol) in toluene (0.6 mL) was added a solution of sodium hydroxide (368 mg; 9.2 mmol) in water (0.6 mL) followed by tert-butyl 4-bromobutanoate (58 mg; 0.26 mmol). The mixture was heated to 70° C. for 18 hours. An additional portion of tert-butyl 4-bromobutanoate (116 mg; 0.52 mmol) was added and the mixture was heated to 70° C. for 5 hours. A third portion of tert-butyl 4-bromobutanoate (116 mg; 0.52 mmol) was added and the mixture was heated to 70° C. for 18 hours. DCM (5 mL) was added and the mixture passed through a hydrophobic frit and the solvent removed in vacuo. The residue was purified on a Biotage 25+M column, eluting with petrol containing increasing amounts of EtOAc to give tert-butyl 4-(4-(5-(1-cyclohexyl-5-(methoxymethyl)-1H-pyrazol-4-yl)-1,2,4-oxadiazol-3-yl)benzyloxy)butanoate as a colourless oil. ¹H NMR (CDCl₃, 400 MHz) δ 8.14 (1 H, s), 8.12 (2 H, d, J=8.0 Hz), 7.46 (2 H, d, J=8.0 Hz), 5.03 (2 H, s), 4.57 (2 H, s), 4.36-4.30 (1 H, m), 3.53 (2 H, t, J=6.3 Hz), 3.43 (3 H, s), 2.36 (2 H, t, J=7.4 Hz), 2.03-1.89 (8 H, m), 1.78-1.73 (1 H, m), 1.44 (9 H, s), 1.46-1.26 (3 H, m). LC/MS: 511 (M+H)⁺. HPLC (Method H) Rt=4.96 min (Purity: 97.7%).

Step 3: 4-(4-(5-(1-cyclohexyl-5-(methoxymethyl)-1H-pyrazol-4-yl)-1,2,4-oxadiazol-3-yl)benzyloxy)butanoic acid A solution of tert-butyl 4-(4-(5-(1-cyclohexyl-5-(methoxymethyl)-1H-pyrazol-4-yl)-1,2,4-oxadiazol-3-yl)benzyloxy)butanoate (41 mg; 0.08 mmol), obtained from step 1, in 4M HCl in dioxane (1 mL) was heated to 70° C. for 2 hours. The solvent was removed in vacuo to give Example 133 as a colourless oil. ¹H NMR (CDCl₃, 400 MHz) δ 8.14 (1 H, s), 8.12 (2 H, d, J=8.0 Hz), 7.46 (2 H, d, J=8.0 Hz), 5.03 (2 H, s), 4.58 (2 H, s), 4.36-4.28 (1 H, m), 3.58 (2 H, t, J=6.0 Hz), 3.43 (3 H, s), 2.52 (2 H, t, J=7.2 Hz), 2.07-1.91 (8 H, m), 1.79-1.70 (1 H, m), 1.50-1.27 (3 H, m). LC/MS: 455 (M+H)⁺. HPLC (Method H) Rt=4.47 min (Purity: 96.9%).

Example 134

4-(4-(5-(1-cyclohexyl-5-(methoxymethyl)-1H-pyrazol-4-yl)-1,2,4-oxadiazol-3-yl)Phenoxy)butanoic acid

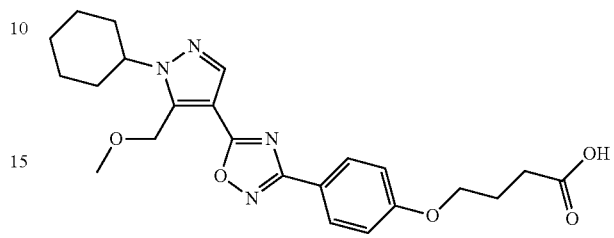

Step 1: tert-butyl 4-(4-(5-(1-cyclohexyl-5-(methoxymethyl)-1H-pyrazol-4-yl)-1,2,4-oxadiazol-3-yl)phenoxy)butanoate To a solution of Example 123 (124 mg; 0.35 mmol) and tetrabutylammonium hydrogen sulfate (12 mg; 0.035 mmol) in toluene (0.9 mL) was added a solution of sodium hydroxide (560 mg; 14.0 mmol) in water (0.9 mL) followed by tert-butyl 4-bromobutanoate (89 mg; 0.40 mmol). The mixture was heated to 70° C. for 18 hours. MeCN (1 mL) and an additional portion of tert-butyl 4-bromobutanoate (178 mg; 0.80 mmol) was added and the mixture was heated to 70° C. for 5 hours. A third portion of tert-butyl 4-bromobutanoate (178 mg; 0.80 mmol) was added and the mixture was heated to 70° C. for 18 hours. DCM (10 mL) was added and the mixture passed through a hydrophobic frit and the solvent removed in vacuo. The residue was purified on a Biotage 12+M column, eluting with petrol containing increasing amounts of EtOAc to give tert-butyl 4-(4-(5-(1-cyclohexyl-5-(methoxymethyl)-1H-pyrazol-4-yl)-1,2,4-oxadiazol-3-yl)phenoxy)butanoate as a white solid (139 mg, 80%). ¹H NMR (CDCl₃, 400 MHz) δ 8.12 (1 H, s), 8.06 (2 H, d, J=8.7 Hz), 6.99 (2 H, d, J=8.7 Hz), 5.03 (2 H, s), 4.36-4.23 (1 H, m), 4.07 (2 H, t, J=6.2 Hz), 3.42 (3 H, s), 2.45 (2 H, t, J=7.3 Hz), 2.15-2.04 (2 H, m), 2.11-1.90 (6 H, m), 1.81-1.68 (1 H, m), 1.46 (9 H, s), 1.47-1.26 (3 H, m). LC/MS: 497 (M+H)⁺. HPLC (Method J) Rt=25.85 min (Purity: 97.6%).

Step 2: 4-(4-(5-(1-cyclohexyl-5-(methoxymethyl)-1H-pyrazol-4-yl)-1,2,4-oxadiazol-3-yl)phenoxy)butanoic acid A solution of tert-butyl 4-(4-(5-(1-cyclohexyl-5-(methoxymethyl)-1H-pyrazol-4-yl)-1,2,4-oxadiazol-3-yl)phenoxy)butanoate (130 mg; 0.26 mmol), obtained from step 1, in 4M HCl in dioxane (4 mL) was heated to 70° C. for 8 hours. The solvent was removed in vacuo and the residue triturated with petrol to give Example 134 as a white solid. ¹H NMR (CDCl₃, 400 MHz) δ 8.13 (1 H, s), 8.07 (2 H, d, J=8.7 Hz), 6.99 (2 H, d, J=8.7 Hz), 5.03 (2 H, s), 4.33-4.28 (1 H, m), 4.11 (2 H, t, J=6.0 Hz), 3.42 (3 H, s), 2.63 (2 H, t, J=7.2 Hz), 2.21-2.12 (2 H, m), 2.07-1.89 (6 H, m), 1.79-1.70 (1 H, m), 1.49-1.26 (3 H, m). LC/MS: 439 (M+H)⁺. HPLC (Method H) Rt=4.45 min (Purity: 97.2%).

Example 135

{3-[5-(1-Cyclohexyl-5-methoxymethyl-1H-pyrazol-4-yl)-[1,2,4]oxadiazol-3-yl]-benzyloxy}-acetic acid

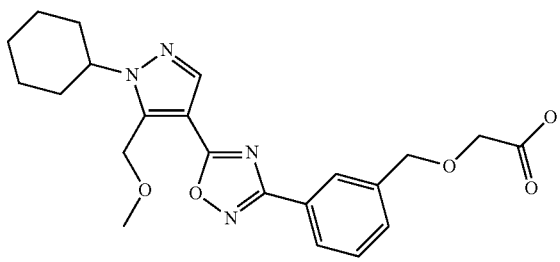 [SMILES: COCc1c(-c2nc(-c3cccc(COCC(=O)O)c3)no2)cnn1C1CCCCC1]

The title compound was prepared following the procedure described for Example 133, replacing tert-butyl 4-bromobutanoate with tert-butyl 2-bromoacetate. It was isolated as a colorless oil. LC/MS: 427 (M+H)⁺. 425 (M−H)⁻. HPLC (Method H) Rt=4.52 min (Purity: 98.1%).

Example 136

4-{2-Cyclohexyl-4-[3-(4-imidazol-1-ylmethyl-phenyl)-[1,2,4]oxadiazol-5-yl]-2H-pyrazol-3-yl}-pyridine

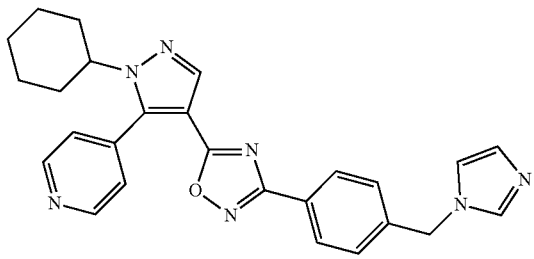 [SMILES: c1cc(-c2c(-c3nc(-c4ccc(Cn5ccnc5)cc4)no3)cnn2C2CCCCC2)ccn1]

The title compound was prepared following the procedure described for Example 119, replacing Intermediate 18 with Intermediate 7. It was isolated as an off-white solid. LC/MS: 452 (M+H)⁺. HPLC (Method A) Rt=3.37 min (Purity: 99.4%).

Example 137

4-{2-Cyclohexyl-4-[3-(4-pyrazol-1-ylmethyl-phenyl)-[1,2,4]oxadiazol-5-yl]-2H-pyrazol-3-yl}-pyridine

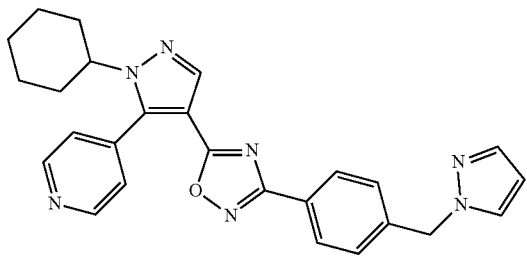 [SMILES: c1cnn(Cc2ccc(-c3noc(-c4cnn(C5CCCCC5)c4-c4ccncc4)n3)cc2)c1]

The title compound was prepared following the procedure described for Example 114, replacing Intermediate 18 with Intermediate 7. It was isolated as an off-white solid. LC/MS: 452 (M+H)⁺. HPLC (Method A) Rt=3.66 min (Purity: 98.2%).

Example 156

In Vitro Assays

Receptor binding assay: Membranes were prepared from CHO cells expressing S1P1 or S1P3 for use in ligand and 355-GTPγS binding studies. Cells were suspended in 50 mM TRIS, pH 7.4, 2 mM EDTA, 250 mM Sucrose (buffer A) and 1× Complete protease inhibitor cocktail (Roche), and disrupted at 4° C. by N2 decompression using a cell disruption bomb (Parr Instrument). Following centrifugation at 1000 RPM for 10 min at 4° C., the supernatant was suspended in buffer A and centrifuged again at 19000 RPM for 60 min at 4° C. The pellet was then suspended in 10 mM HEPES, pH 7.4, 1 mM EDTA, 250 mM Sucrose (Buffer B), and 1× Complete EDTA-free protease inhibitor cocktail and homogenized using a potter. Membranes were flash frozen in liquid N2 and stored at −80° C. [33P]sphingosine 1-phosphate (3000 Ci/mmol; American Radiolabeled Chemicals, Inc.) was added to test compounds in DMSO. Membranes and WGA SPA beads (GE Healthcare) were added to give a final volume of 100 µl in 96-well plates with assay concentrations of 25 pM or 10 pM [33P]sphingosine 1-phosphate (respectively for S1P1 or S1P3), 50 mM HEPES, pH 7.5, 5 mM MgCl2, 100 mM NaCl, 0.4% fatty acid-free BSA, 1-5 µg/well of proteins and 100 µg/well of WGA SPA beads. Binding was performed for 60 min at RT on a shaker and bound radioactivity was measured on a PerkinElmer 1450 MicroBeta counter. Specific binding was calculated by subtracting remaining radioactivity in the presence of 1000-fold excess of unlabeled S1P. Binding data were analyzed using the GraphPad Prism program.

Measurements of 35S-GTPγS Binding: Membranes (1 to 10 µg protein) prepared as described above, were incubated in 96-well Scintiplates (PerkinElmer) with test compounds diluted in DMSO, in 180 µl of 20 mM HEPES, pH 7.4, 10 mM MgCl2, 2 µg/well Saponin, 0.2% fatty acid free BSA (Assay buffer), 140 mM NaCl and 1.7 µM GDP. The assay was initiated with the addition of 20 µl of 1.5 nM [35S]-GTPγS (1100 Ci/mmol; GE Healthcare) in assay buffer. After 60 min incubation at 30° C. on a shaker, plates were centrifuged for 10 min at 2000 RPM. Supernatant was discarded and membrane bound radioactivity was measured on a PerkinElmer 1450 MicroBeta counter. Triplicate samples were averaged and expressed as % response relative to S1P activation in absence of compound (n=2).

The compounds of formula I have utility as immunoregulatory agents as demonstrated by their activity as potent and selective agonists of the S1P1 receptor over the S1P3 receptor as measured in the assays described above. In particular, the compounds of formula I exhibit a selectivity for the S1P1 receptor over the S1P3 receptor as measured by the ratio of EC50 for the S1P1 receptor to the EC50 for the S1P3 receptor as evaluated in the 355-GTPγS binding assay described above.

The following results have been obtained:

| Example Nb | Formula | S1P1 Binding Ki (μM) | S1P1 GTPγS EC50 (μM) | S1P3 GTPγs EC50 (μM) |
|---|---|---|---|---|
| 1 | | 0.272 | 0.304 | >20 |
| 2 | | — | 0.024 | — |
| 3 | | 0.008 | 0.077 | — |
| 4 | | — | 0.284 | — |

-continued

| Example Nb | Formula | S1P1 Binding Ki (μM) | S1P1 GTPγS EC50 (μM) | S1P3 GTPγs EC50 (μM) |
|---|---|---|---|---|
| 5 | | 0.013 | 0.255 | — |
| 6 | | 0.013 | 0.235 | — |
| 7 | | — | 0.288 | — |
| 8 | | 0.003 | 0.003 | — |

-continued

| Example Nb | Formula | S1P1 Binding Ki (μM) | S1P1 GTPγS EC50 (μM) | S1P3 GTPγs EC50 (μM) |
|---|---|---|---|---|
| 9 | | 0.005 | 0.028 | >20 |
| 10 | | — | 0.172 | — |
| 11 | | 0.009 | 0.006 | 0.142 |
| 12 | | 0.007 | 0.036 | — |
| 13 | | 0.023 | 0.096 | — |

-continued

| Example Nb | Formula | S1P1 Binding Ki (μM) | S1P1 GTPγS EC50 (μM) | S1P3 GTPγs EC50 (μM) |
|---|---|---|---|---|
| 14 | | — | 0.201 | — |
| 15 | | — | 0.192 | — |
| 16 | | — | 0.901 | — |
| 17 | | — | 0.648 | — |
| 18 | | — | 0.776 | — |

-continued

| Example Nb | Formula | S1P1 Binding Ki (μM) | S1P1 GTPγS EC50 (μM) | S1P3 GTPγs EC50 (μM) |
|---|---|---|---|---|
| 19 | | 0.009 | 0.018 | — |
| 20 | | — | 0.172 | — |
| 21 | | — | 0.081 | — |
| 22 | | — | 0.37 | — |
| 23 | | 0.005 | 0.004 | — |
| 24 | | — | 0.292 | — |

-continued

| Example Nb | Formula | S1P1 Binding Ki (μM) | S1P1 GTPγS EC50 (μM) | S1P3 GTPγs EC50 (μM) |
|---|---|---|---|---|
| 25 | | — | 0.148 | — |
| 26 | | — | 0.029 | — |
| 27 | | — | 0.027 | — |
| 28 | | — | 0.016 | 2.66 |
| 29 | | — | 0.024 | — |
| 30 | | — | 0.02 | — |

-continued

| Example Nb | Formula | S1P1 Binding Ki (μM) | S1P1 GTPγS EC50 (μM) | S1P3 GTPγs EC50 (μM) |
|---|---|---|---|---|
| 31 | | — | 0.012 | >20 |
| 32 | | — | 0.18 | — |
| 33 | | — | 0.216 | — |
| 34 | | — | 0.006 | 1.61 |
| 35 | | — | 0.931 | — |
| 36 | | — | 0.114 | — |

-continued

| Example Nb | Formula | S1P1 Binding Ki (μM) | S1P1 GTPγS EC50 (μM) | S1P3 GTPγs EC50 (μM) |
|---|---|---|---|---|
| 37 | | — | 0.009 | >20 |
| 38 | | 0.068 | 0.003 | 0.474 |
| 39 | | — | 0.016 | — |
| 40 | | — | 0.011 | 0.523 |
| 41 | | — | 0.009 | 0.486 |
| 42 | | — | 0.001 | 1.022 |

-continued
| Example Nb | Formula | S1P1 Binding Ki (μM) | S1P1 GTPγS EC50 (μM) | S1P3 GTPγs EC50 (μM) |
|---|---|---|---|---|
| 43 | 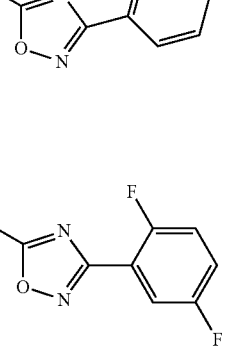 | — | 0.292 | — |
| 44 | 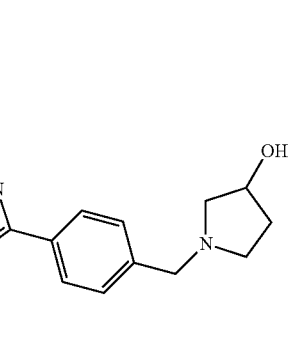 | — | 0.402 | — |
| 45 | 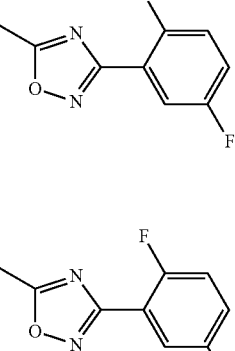 | — | 0.01 | — |
| 46 | 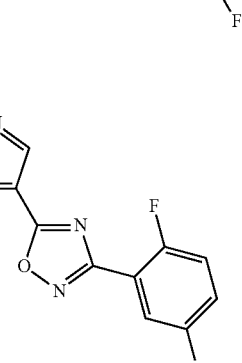 | — | 0.026 | — |
| 47 |  | — | 0.008 | 0.571 |
| 48 | | — | 0.047 | — |

-continued

| Example Nb | Formula | S1P1 Binding Ki (μM) | S1P1 GTPγS EC50 (μM) | S1P3 GTPγs EC50 (μM) |
|---|---|---|---|---|
| 49 | | — | 0.229 | — |
| 50 | | — | 0.211 | — |
| 51 | | — | 0.31 | — |
| 52 | | — | 0.313 | — |
| 53 | | — | 0.164 | — |
| 54 | | — | 0.189 | — |

-continued
| Example Nb | Formula | S1P1 Binding Ki (μM) | S1P1 GTPγS EC50 (μM) | S1P3 GTPγs EC50 (μM) |
|---|---|---|---|---|
| 55 | 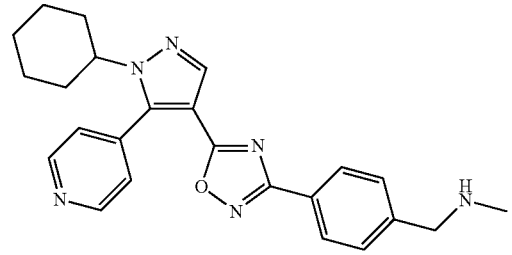 [SMILES: CNCc1ccc(-c2noc(-c3cnn(C4CCCCC4)c3-c3ccncc3)n2)cc1] | — | 0.024 | — |
| 56 | 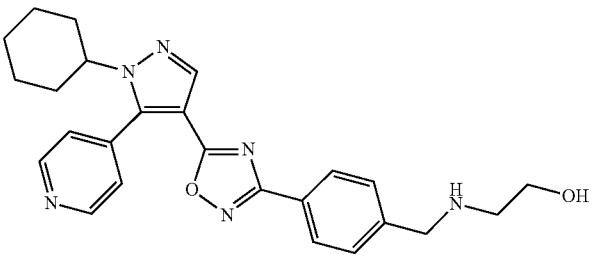 [SMILES: OCCNCc1ccc(-c2noc(-c3cnn(C4CCCCC4)c3-c3ccncc3)n2)cc1] | — | 0.011 | — |
| 57 | 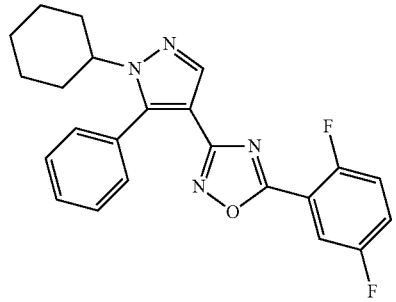 [SMILES: Fc1ccc(F)c(-c2nc(-c3cnn(C4CCCCC4)c3-c3ccccc3)no2)c1] | — | 0.049 | — |
| 58 | 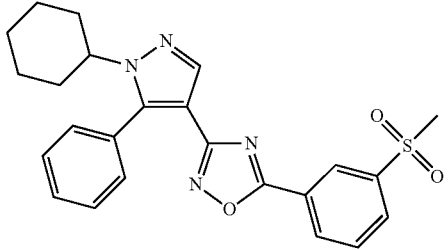 [SMILES: CS(=O)(=O)c1cccc(-c2nc(-c3cnn(C4CCCCC4)c3-c3ccccc3)no2)c1] | — | 0.157 | — |
| 59 | 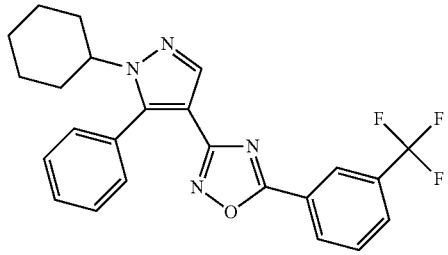 [SMILES: FC(F)(F)c1cccc(-c2nc(-c3cnn(C4CCCCC4)c3-c3ccccc3)no2)c1] | — | 0.335 | — |

-continued

| Example Nb | Formula | S1P1 Binding Ki (μM) | S1P1 GTPγS EC50 (μM) | S1P3 GTPγs EC50 (μM) |
|---|---|---|---|---|
| 60 | | — | 0.32 | — |
| 61 | | — | 0.022 | — |
| 62 | | — | 0.003 | — |
| 63 | | — | 0.428 | — |
| 64 | | — | 0.099 | — |

-continued
| Example Nb | Formula | S1P1 Binding Ki (μM) | S1P1 GTPγS EC50 (μM) | S1P3 GTPγs EC50 (μM) |
|---|---|---|---|---|
| 65 | 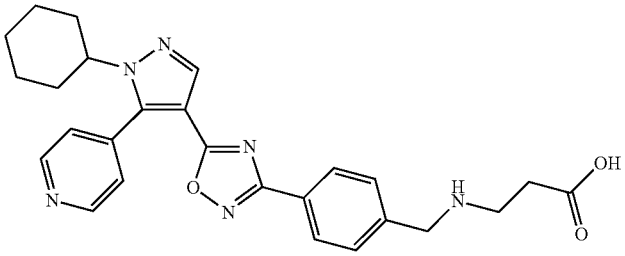 [SMILES: O=C(O)CCNCc1ccc(-c2noc(-c3cnn(C4CCCCC4)c3-c3ccncc3)n2)cc1] | — | 0.001 | — |
| 66 | 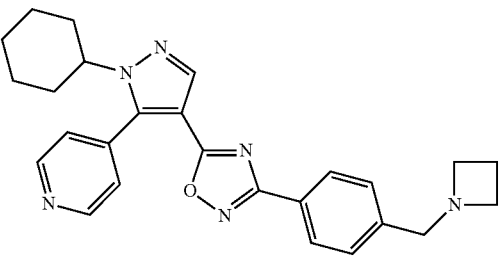 [SMILES: c1cc(-c2c(-c3nc(-c4ccc(CN5CCC5)cc4)no3)cnn2C2CCCCC2)ccn1] | — | 0.013 | — |
| 67 | 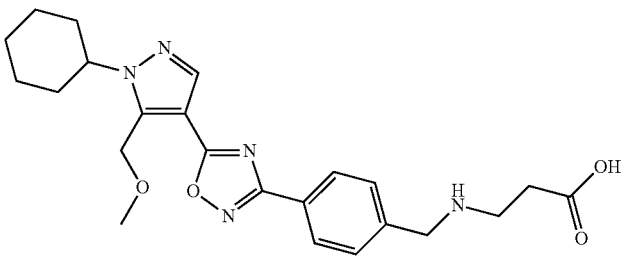 [SMILES: COCc1c(-c2nc(-c3ccc(CNCCC(=O)O)cc3)no2)cnn1C1CCCCC1] | — | 0.0014 | — |
| 68 | 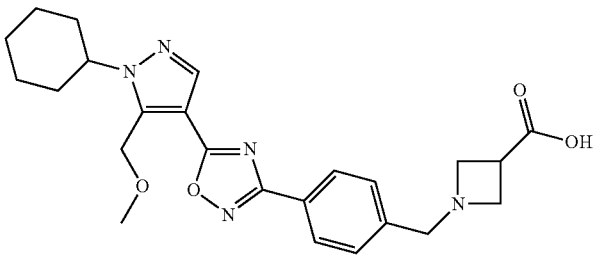 [SMILES: COCc1c(-c2nc(-c3ccc(CN4CC(C(=O)O)C4)cc3)no2)cnn1C1CCCCC1] | — | 0.0003 | — |
| 69 | 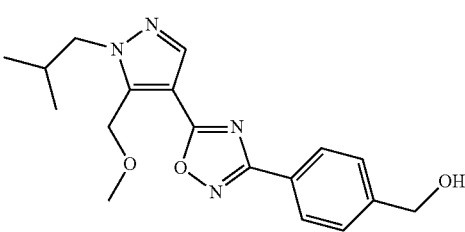 [SMILES: COCc1c(-c2nc(-c3ccc(CO)cc3)no2)cnn1CC(C)C] | — | 0.437 | — |

| Example Nb | Formula | S1P1 Binding Ki (µM) | S1P1 GTPγS EC50 (µM) | S1P3 GTPγs EC50 (µM) |
|---|---|---|---|---|
| 70 | | — | 0.082 | — |
| 71 | | — | 0.006 | — |
| 72 | | — | 0.119 | — |
| 73 | | — | 0.03 | — |
| 74 | | — | 0.086 | — |

-continued

| Example Nb | Formula | S1P1 Binding Ki (μM) | S1P1 GTPγS EC50 (μM) | S1P3 GTPγs EC50 (μM) |
|---|---|---|---|---|
| 75 | | — | 0.063 | — |
| 76 | | — | 0.023 | — |
| 77 | | — | 0.837 | — |
| 78 | | — | 0.067 | — |
| 79 | | 0.0023 | 0.0095 | 1.47 |
| 80 | | — | 0.252 | — |

| Example Nb | Formula | S1P1 Binding Ki (μM) | S1P1 GTPγS EC50 (μM) | S1P3 GTPγS EC50 (μM) |
|---|---|---|---|---|
| 81 | | — | 0.195 | — |
| 82 | | — | 0.156 | — |
| 83 | | — | 0.313 | — |
| 84 | | — | 0.288 | — |
| 85 | | — | 0.179 | — |
| 86 | | — | 0.306 | — |

-continued

| Example Nb | Formula | S1P1 Binding Ki (μM) | S1P1 GTPγS EC50 (μM) | S1P3 GTPγs EC50 (μM) |
|---|---|---|---|---|
| 87 | | — | 0.361 | — |
| 88 | | — | 0.047 | — |
| 89 | | — | 0.012 | 1.64 |
| 90 | | — | 0.035 | — |
| 91 | | — | 0.0085 | 0.147 |
| 92 | | — | 0.158 | — |

| Example Nb | Formula | S1P1 Binding Ki (μM) | S1P1 GTPγS EC50 (μM) | S1P3 GTPγs EC50 (μM) |
|---|---|---|---|---|
| 93 | | — | 0.301 | — |
| 94 | | — | 0.387 | — |
| 95 | | — | 0.096 | — |
| 96 | | 0.0065 | 0.031 | 2.25 |
| 97 | | 0.0007 | 0.0014 | 0.138 |

-continued
| Example Nb | Formula | S1P1 Binding Ki (μM) | S1P1 GTPγS EC50 (μM) | S1P3 GTPγs EC50 (μM) |
|---|---|---|---|---|
| 98 | 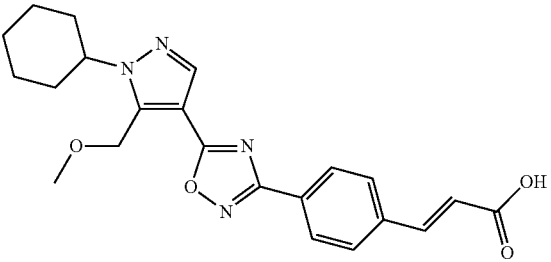 [SMILES: COCc1c(-c2nc(-c3ccc(/C=C/C(=O)O)cc3)no2)cnn1C1CCCCC1] | 0.409 | — | — |
| 99 | 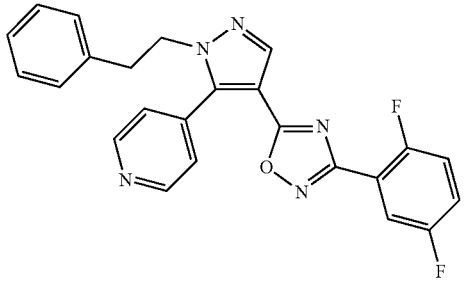 [SMILES: Fc1ccc(F)c(-c2noc(-c3cnn(CCc4ccccc4)c3-c3ccncc3)n2)c1] | — | 0.496 | — |
| 100 | 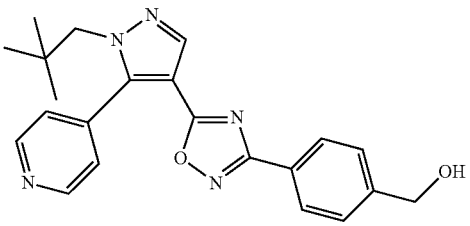 [SMILES: CC(C)(C)Cn1ncc(-c2nc(-c3ccc(CO)cc3)no2)c1-c1ccncc1] | — | 0.377 | — |
| 101 | 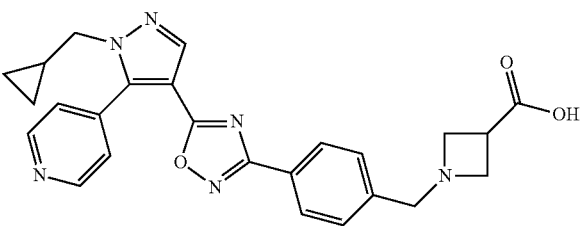 [SMILES: O=C(O)C1CN(Cc2ccc(-c3noc(-c4cnn(CC5CC5)c4-c4ccncc4)n3)cc2)C1] | 0.0018 | 0.012 | 1.62 |
| 102 | 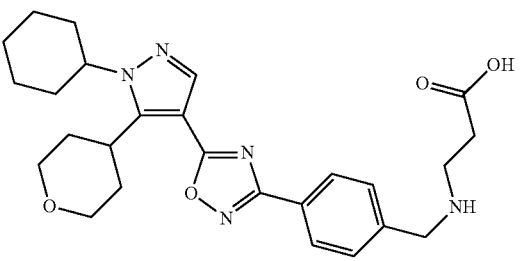 [SMILES: O=C(O)CCNCc1ccc(-c2noc(-c3cnn(C4CCCCC4)c3C3CCOCC3)n2)cc1] | 0.0008 | 0.0021 | 0.214 |

-continued

| Example Nb | Formula | S1P1 Binding Ki (μM) | S1P1 GTPγS EC50 (μM) | S1P3 GTPγS EC50 (μM) |
| --- | --- | --- | --- | --- |
| 103 | | — | 0.035 | — |
| 104 | | — | 0.314 | — |
| 105 | | 0.034 | 0.042 | — |
| 106 | | — | 0.458 | — |
| 107 | | — | 0.045 | — |
| 108 | | — | 0.102 | — |

-continued
| Example Nb | Formula | S1P1 Binding Ki (μM) | S1P1 GTPγS EC50 (μM) | S1P3 GTPγs EC50 (μM) |
|---|---|---|---|---|
| 109 | 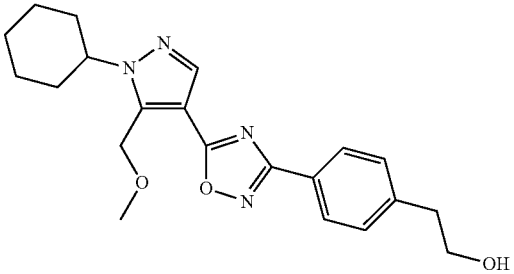 [SMILES: COCc1c(-c2nc(-c3ccc(CCO)cc3)no2)cnn1C1CCCCC1] | — | 0.312 | — |
| 110 | 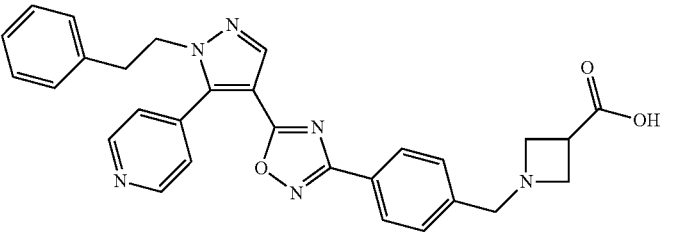 [SMILES: O=C(O)C1CN(Cc2ccc(-c3noc(-c4cnn(CCc5ccccc5)c4-c4ccncc4)n3)cc2)C1] | — | 0.040 | — |
| 111 | 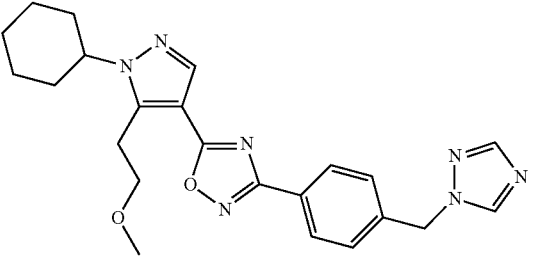 [SMILES: COCCc1c(-c2nc(-c3ccc(Cn4cncn4)cc3)no2)cnn1C1CCCCC1] | — | 0.029 | — |
| 112 | 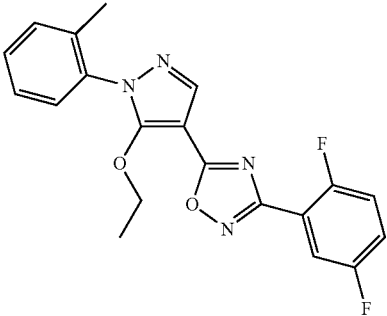 [SMILES: CCOc1c(-c2nc(-c3cc(F)ccc3F)no2)cnn1-c1ccccc1C] | — | 0.094 | — |
| 113 | 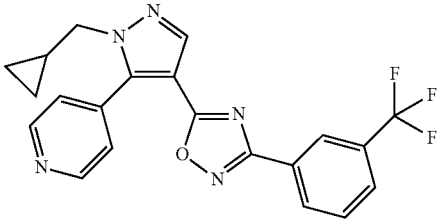 [SMILES: FC(F)(F)c1cccc(-c2noc(-c3cnn(CC4CC4)c3-c3ccncc3)n2)c1] | — | 0.024 | — |

| Example Nb | Formula | S1P1 Binding Ki (μM) | S1P1 GTPγS EC50 (μM) | S1P3 GTPγs EC50 (μM) |
|---|---|---|---|---|
| 114 | | — | 0.094 | — |
| 115 | | — | 0.134 | — |
| 116 | | — | 0.086 | — |
| 117 | | 0.002 | 0.011 | 0.622 |
| 118 | | — | 0.398 | — |

-continued

| Example Nb | Formula | S1P1 Binding Ki (μM) | S1P1 GTPγS EC50 (μM) | S1P3 GTPγs EC50 (μM) |
|---|---|---|---|---|
| 119 | | — | 0.066 | — |
| 120 | | 0.0001 | 0.0005 | 0.489 |
| 121 | | — | 0.04 | — |
| 122 | | — | 0.157 | — |
| 123 | | — | 0.082 | — |

| Example Nb | Formula | S1P1 Binding Ki (μM) | S1P1 GTPγS EC50 (μM) | S1P3 GTPγs EC50 (μM) |
|---|---|---|---|---|
| 124 | | — | 0.382 | — |
| 125 | | 0.0006 | 0.0019 | 0.427 |
| 126 | | — | 0.168 | — |
| 127 | | — | 0.172 | — |
| 128 | | — | 0.158 | — |

| Example Nb | Formula | S1P1 Binding Ki (μM) | S1P1 GTPγS EC50 (μM) | S1P3 GTPγs EC50 (μM) |
|---|---|---|---|---|
| 129 | | — | 0.438 | — |
| 130 | | — | 0.036 | — |
| 131 | | — | 0.181 | — |
| 132 | | — | 0.0180 | — |
| 133 | | 0.122 | — | — |

-continued

| Example Nb | Formula | S1P1 Binding Ki (μM) | S1P1 GTPγS EC50 (μM) | S1P3 GTPγs EC50 (μM) |
|---|---|---|---|---|
| 134 | | 0.128 | — | — |
| 135 | | 0.04145 | | |
| 136 | | 0.002065 | | 0.0583 |
| 137 | | 0.00516 | | |
| 138 | | 0.025 | — | — |

| Example Nb | Formula | S1P1 Binding Ki (μM) | S1P1 GTPγS EC50 (μM) | S1P3 GTPγs EC50 (μM) |
|---|---|---|---|---|
| 139 | | 0.393 | — | — |
| 140 | | 0.253 | — | — |
| 141 | | 0.180 | — | — |
| 142 | | 0.191 | — | — |
| 143 | | 0.0415 | — | — |

-continued

| Example Nb | Formula | S1P1 Binding Ki (μM) | S1P1 GTPγS EC50 (μM) | S1P3 GTPγs EC50 (μM) |
|---|---|---|---|---|
| 144 | | 0.031 | — | — |
| 145 | | 0.116 | — | — |
| 146 | | 0.0099 | — | — |
| 147 | | 0.257 | — | — |
| 148 | | 0.0021 | — | — |

| Example Nb | Formula | S1P1 Binding Ki (μM) | S1P1 GTPγS EC50 (μM) | S1P3 GTPγs EC50 (μM) |
|---|---|---|---|---|
| 149 | | 0.0052 | — | — |
| 150 | | 0.0034 | — | — |
| 151 | | 0.0046 | — | — |
| 152 | | 0.0033 | — | — |
| 153 | | 0.028 | — | — |

-continued

| Example Nb | Formula | S1P1 Binding Ki (μM) | S1P1 GTPγS EC50 (μM) | S1P3 GTPγS EC50 (μM) |
|---|---|---|---|---|
| 154 | 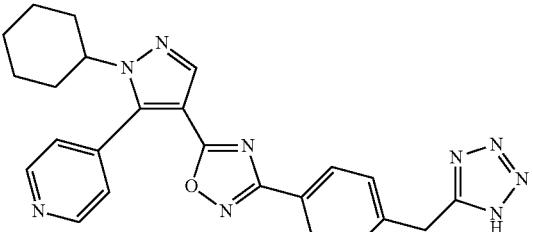 | 0.076 | — | — |
| 155 | 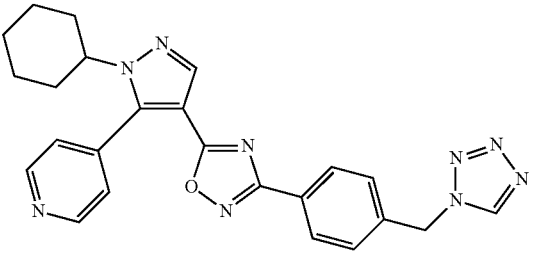 [SMILES: c1cc(-c2c(-c3nc(-c4ccc(Cn5cnnn5)cc4)no3)cnn2C2CCCCC2)ccn1] | 0.006 | — | — |

Example 157

In Vivo Models Evaluating the In Vivo Efficacy of S1P Agonists

Model of S1P Agonists-Induced Lymphopenia in Mice

Female C57BL/6 mice (Elevage Janvier) (8 week old) receive S1P agonists by oral route. Blood is sampled in heparinized (100 IU/kg, ip) mice by intracardiac or retroorbital puncture under isoflurane anesthesia 2 to 120 hrs after drug treatment. The white blood cells (lymphocytes and neutrophils) are counted using a Beckman/Coulter counter. The quality of blood sampling is assessed by counting erythocytes and platelets. Compounds of Formula (I) are tested according to the above assay and have an $ED_{50}$ of less than 100 mg/kg, more preferable below 50 mg/kg at 24 hours.

Model of MOG-Induced Experimental Autoimmune Encephalomyelytis (EAE) in Mice

EAE was induced in 9 weeks old female mice (C57BL/6, Elevage Janvier) by an immunization against MOG. The mice received Pertussis toxin (Alexis, 300 ng/mouse in 200 μl of PBS) by ip route and 100 μl of an emulsion containing MOG35-55 peptide (NeoMPS, 200 μg/mouse), *Mycobacterium Tuberculosis* (0.25 mg/mouse) in Complete Freund's Adjuvant (DIFCO) by subcutaneous injection into the back. Two days later an additional injection of Pertussis toxin (Alexis, 300 ng/mouse in 200 μl of PBS) was done by ip route. After EAE induction, mice were weighed daily and the neurological impairment was quantified using a 15-points clinical scale assessing the paralysis (tail, hind limbs and fore limbs), the incontinency and the death.

Clinical Score:

-1- Tail
  Score=0 A normal mouse holds its tail erect when moving.
  Score=1 If the extremity of the tail is flaccid with a tendency to fall.
  Score=2 If the tail is completely flaccid and drags on the table.

-2- Hind limbs
  Score=0 A normal mouse has an energetic walk and doesn't drag his paws.
  Score=1 Either one of the following tests is positive:
    -a- Flip test: while holding the tail between thumb and index finger, flip the animal on his back and observe the time it takes to right itself. A healthy mouse will turn itself immediately. A delay suggests hind-limb weakness.
    -b- Place the mouse on the wire cage top and observe as it crosses from one side to the other. If one or both limbs frequently slip between the bars we consider that there is a partial paralysis.
  Score=2 Both previous tests are positive.
  Score=3 One or both hind limbs show signs of paralysis but some movements are preserved; for example: the animal can grasp and hold on to the underside of the wire cage top for a short moment before letting go
  Score=4 When both hind legs are paralyzed and the mouse drags them when moving.

-3- Fore limbs:
  Score=0 A normal mouse uses his front paws actively for grasping and walking and holds his head erect.
  Score=1 Walking is possible but difficult due to a weakness in one or both of the paws, for example, the front paws are considered weak when the mouse has difficulty grasping the underside of the wire top cage. Another sign of weakness is head drooping.
  Score=2 When one forelimb is paralyzed (impossibility to grasp and the mouse turns around the paralyzed limb). At this time the head has also lost much of its muscle tone.
  Score=3 Mouse cannot move, and food and water are unattainable.

-4- Bladder:
  Score=0 A normal mouse has full control of his bladder.
  Score=1 A mouse is considered incontinent when his lower body is soaked with urine.

-5- Death:
Score=15
The final score for each animal is determined by the addition of all the above-mentioned categories. The maximum score for live animals is 10.

At day 12 (first signs of paralysis) the mice were stratified in experimental groups (n=10) according to the clinical score and the body weight loss. The semi-curative treatment started at day 14.

Example 158

Preparation of a Pharmaceutical Formulation

Formulation 1—Tablets

A compound of formula (I) is admixed as a dry powder with a dry gelatin binder in an approximate 1:2 weight ratio. A minor amount of magnesium stearate is added as a lubricant. The mixture is formed into 240-270 mg tablets (80-90 mg of active compound according to the invention per tablet) in a tablet press.

Formulation 2—Capsules

A compound of formula (I) is admixed as a dry powder with a starch diluent in an approximate 1:1 weight ratio. The mixture is filled into 250 mg capsules (125 mg of active compound according to the invention per capsule).

Formulation 3—Liquid

A compound of formula (I) (1250 mg), sucrose (1.75 g) and xanthan gum (4 mg) are blended, passed through a No. 10 mesh U.S. sieve, and then mixed with a previously prepared solution of microcrystalline cellulose and sodium carboxymethyl cellulose (11:89, 50 mg) in water. Sodium benzoate (10 mg), flavor, and color are diluted with water and added with stirring. Sufficient water is then added to produce a total volume of 5 mL.

Formulation 4—Tablets

A compound of formula (I) is admixed as a dry powder with a dry gelatin binder in an approximate 1:2 weight ratio. A minor amount of magnesium stearate is added as a lubricant. The mixture is formed into 450-900 mg tablets (150-300 mg of active compound according to the invention) in a tablet press.

Formulation 5—Injection

A compound of formula (I) is dissolved in a buffered sterile saline injectable aqueous medium to a concentration of approximately 5 mg/mL.

The invention claimed is:
1. A compound of formula (I):

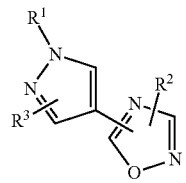

wherein
$R^1$ is

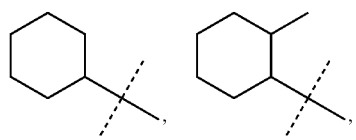

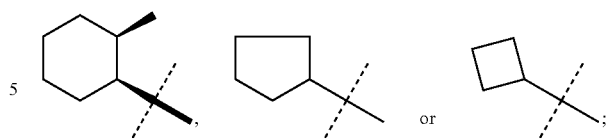

$R^2$ is selected from the following groups:

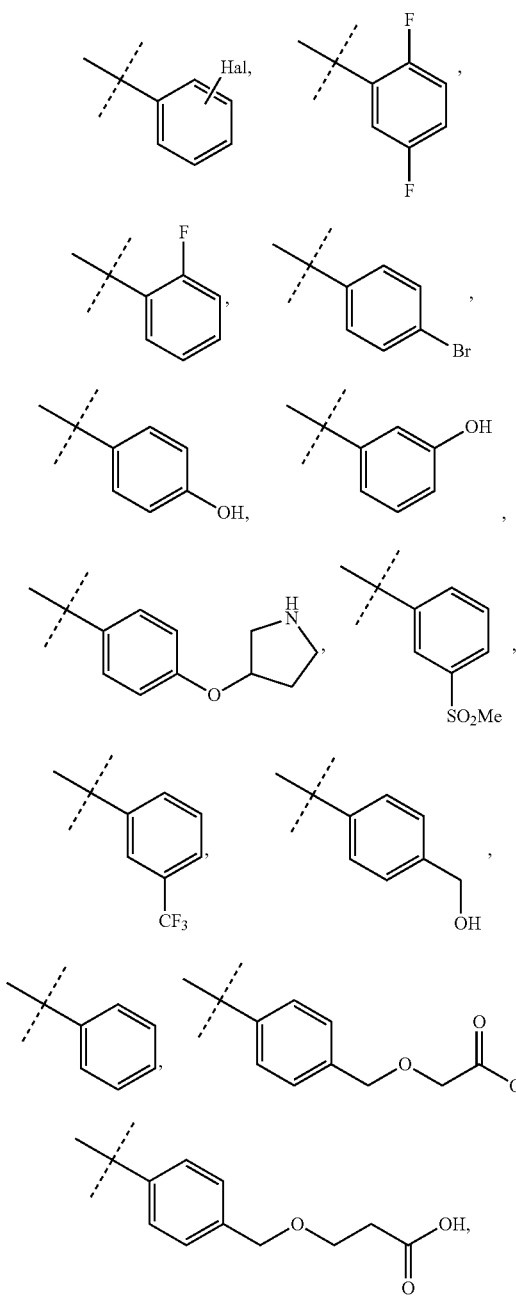

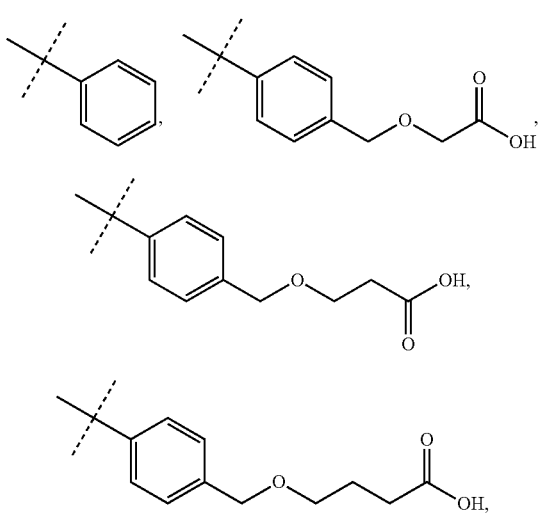

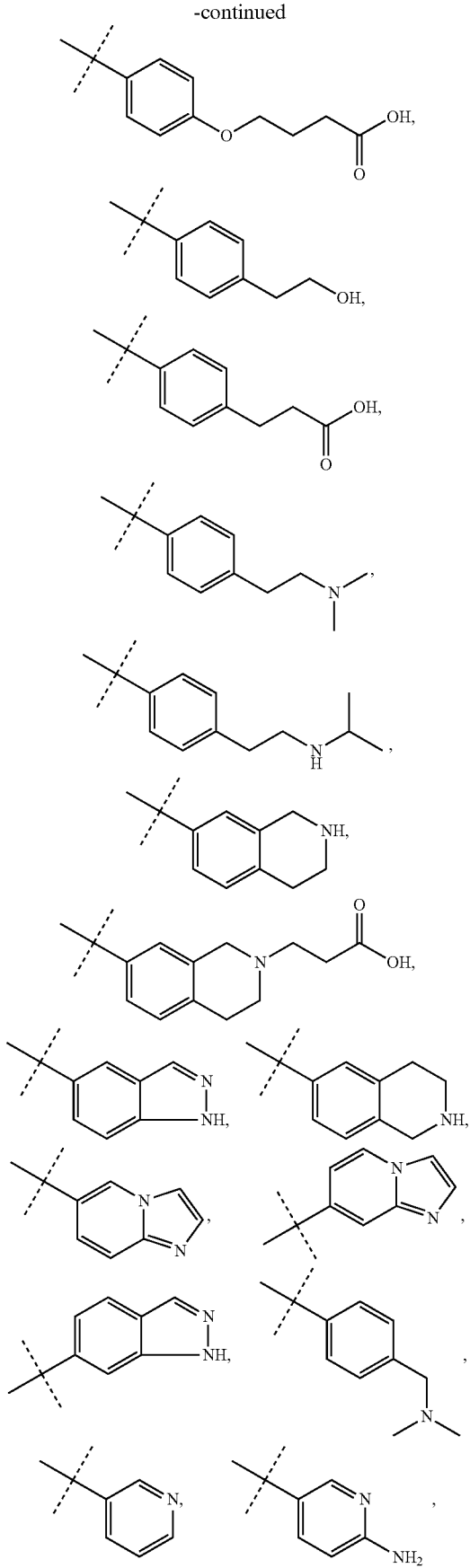
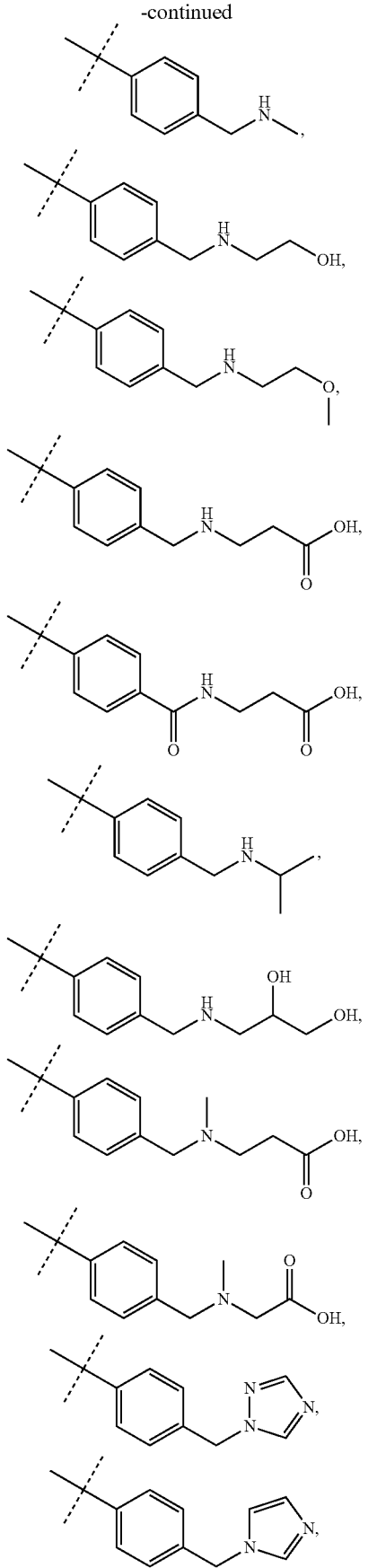

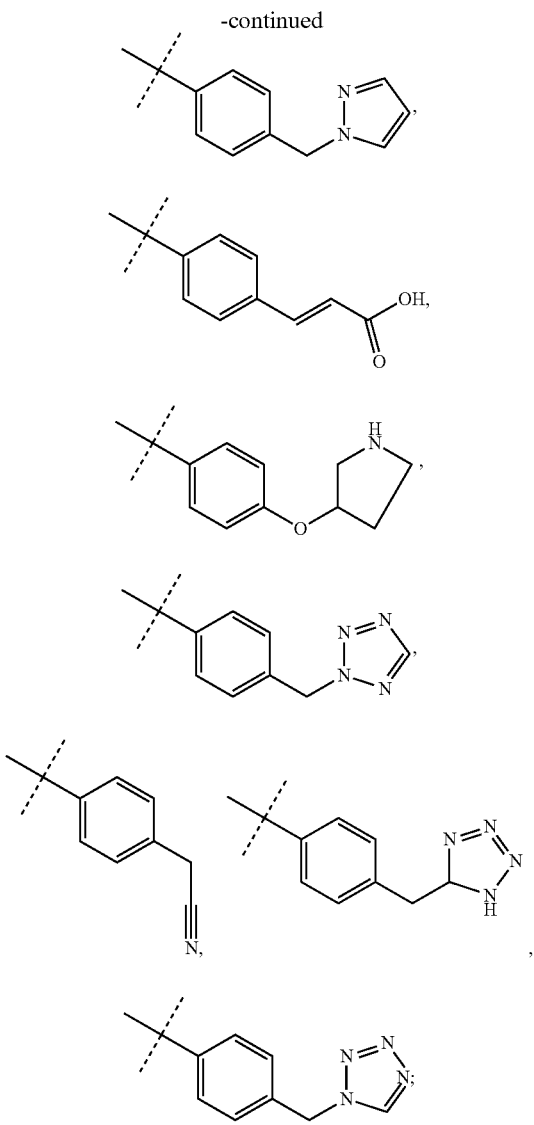

R³ is Ar², Het¹, Cyc, A, CH₃, or S—(C₁-C₆-alkyl);

A is a branched or linear alkyl having 2 to 12 C-atoms, wherein one or more H-atoms may be replaced by Hal, OR⁴, CN, CO₂R⁴, or CF₃; cycloalkyl having 3 to 7 ring carbon atoms; Ar², or N(R⁴)₂ and wherein one or more non-adjacent CH₂-groups may be replaced by O, NR⁴, —CO—, NR⁴CO₂—, —CO₂—, —NR⁴CONR⁴—, —CH=CH—, —C≡C—, or A is cycloalkyl or cycloalkylalkylene having 3-7 ring C atoms, or A is Het²;

Z is a branched or linear alkyl having 2 to 12 C-atoms, wherein one or more H-atoms are replaced by Hal, OR⁴, CN, CO₂R⁴, CF₃, cycloalkyl having 3 to 7 ring carbon atoms, Ar², N(R⁴)₂and/or wherein one or more CH₂-groups are replaced by O, NR⁴, S, —CO—, NR⁴CO₂—, —NR⁴CONR⁴—, —CH=CH—, —C≡C—, or Z is cycloalkyl or cycloalkylalkylene having 3-7 ring C atoms;

Hal is F, Cl, Br or I;

Ar² is a monocyclic or bicyclic, unsaturated or aromatic carbocyclic ring having 6 to 14 carbon atoms which may be unsubstituted, monosubstituted, disubstituted or trisubstituted by substituents selected from Z, F, Br, I, —OR⁴, —(CH₂)OR⁴, —(CH₂)N(R⁴)₂, Perfluoro-alkoxy, —SO₂R⁴, —CN, —NO₂, —N(R⁴)₂, —CO (NR⁴)₂, (NR⁴)COR⁴, —CO₂R⁴, —COR⁴, —SO₂N (R⁴)₂, —SO₂alkyl, NR⁴SO₂(C₁-C₆)alkyl, —(CH₂)ₙ Het¹, —OHet¹, or CF₃;

Het¹ is a monocyclic saturated, unsaturated or aromatic heterocyclic ring or a bicyclic, saturated, or unsaturated heterocyclic ring having 1 to 4 N, O and/or S atoms which may be unsubstituted, monosubstituted, disubstituted or trisubstituted by substituents selected from A, Hal, —OR⁴, —(CH₂)OR⁴, Perfluoro-alkyl, Perfluoro-alkoxy, —SO₂(R⁴)₂, CN, NO₂, —N(R⁴)₂, —CO(NR⁴)₂, (NR⁴)COR⁴, —CO₂R⁴, —COR⁴, —SO₂N(R⁴)₂, —SO₂alkyl, NR⁴SO₂alkyl, NR⁴SO₂alkyl, or C₁-C₆ alkyl;

Cyc is a saturated or unsaturated carbocyclic ring containing 3 to 7 carbon atoms which may be substituted by Hal, A, (C₁-C₆)alkyl, [C(R⁴)₂]ₙ-cycloalkyl, OR⁴, CF₃, OCF₃, N(R⁴)₂, NR⁴CON(R⁴)₂, NO₂, CN, —[C(R⁴)₂]ₙ—COOR⁴, —[C(R⁴)₂]ₙ—CON(R⁴)₂, NR⁴COA, NR⁴SO₂A, COR⁴, SO₂N(R⁴)₂, SOA, and/or SO₂A;

R⁴ is H, A, Cyc or (C₁-C₆)alkyl;

n is 0, 1, 2, 3 or 4;

and pharmaceutically acceptable solvates, tautomers, salts and stereo-isomers thereof.

2. The compound according to claim 1, wherein the compound is of Formula (IA) or (IA')

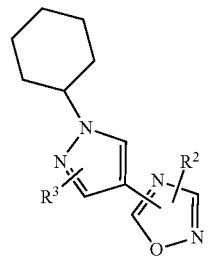
(IA)

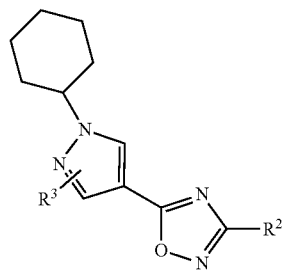
(IA')

wherein R² and R³ are as defined in claim 1;

and pharmaceutically acceptable solvates, tautomers, salts and stereoisomers thereof.

3. The compound according to claim 1, wherein said compound is selected from:

| Example Nb | Formula |
|---|---|
| 11 | 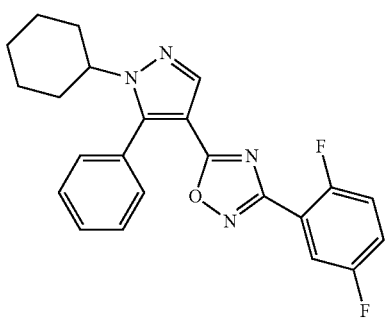 [SMILES: Fc1ccc(F)c(-c2noc(-c3cnn(C4CCCCC4)c3-c3ccccc3)n2)c1] |
| 23 | 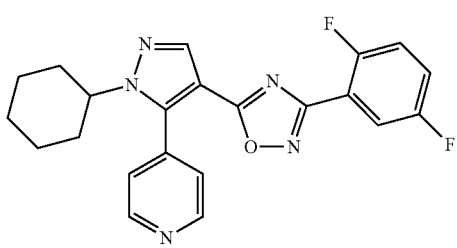 [SMILES: Fc1ccc(F)c(-c2noc(-c3cnn(C4CCCCC4)c3-c3ccncc3)n2)c1] |
| 26 | 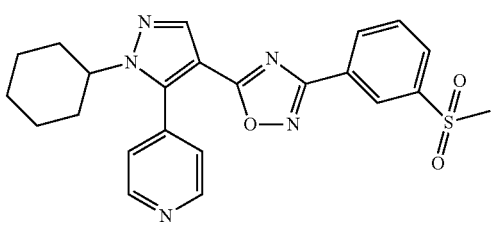 [SMILES: CS(=O)(=O)c1cccc(-c2noc(-c3cnn(C4CCCCC4)c3-c3ccncc3)n2)c1] |
| 27 | 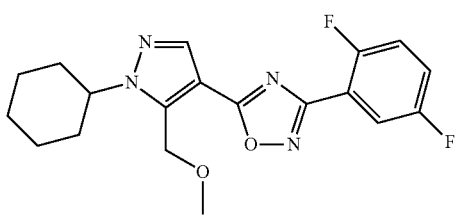 [SMILES: COCc1c(-c2nc(-c3cc(F)ccc3F)no2)cnn1C1CCCCC1] |
| 28 | 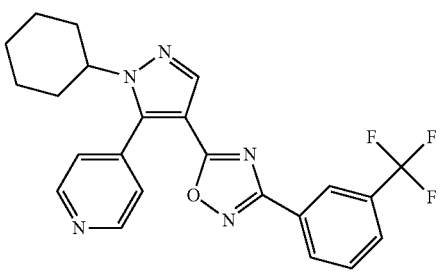 [SMILES: FC(F)(F)c1cccc(-c2noc(-c3cnn(C4CCCCC4)c3-c3ccncc3)n2)c1] |
| 29 | 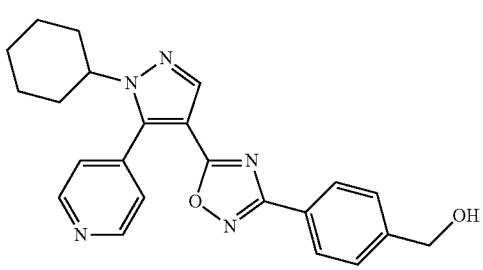 [SMILES: OCc1ccc(-c2noc(-c3cnn(C4CCCCC4)c3-c3ccncc3)n2)cc1] |

-continued
| Example Nb | Formula |
|---|---|
| 30 | 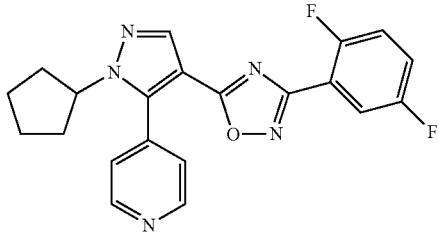 [SMILES: Fc1ccc(F)c(-c2noc(-c3cnn(C4CCCC4)c3-c3ccncc3)n2)c1] |
| 31 | 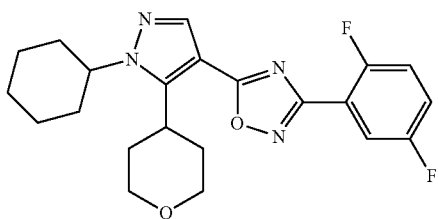 [SMILES: Fc1ccc(F)c(-c2noc(-c3cnn(C4CCCCC4)c3C3CCOCC3)n2)c1] |
| 34 | 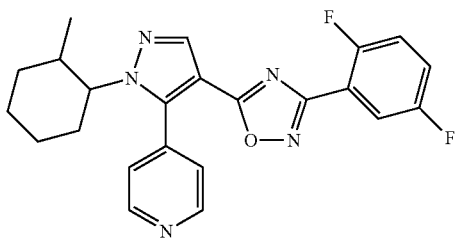 |
| 38 | 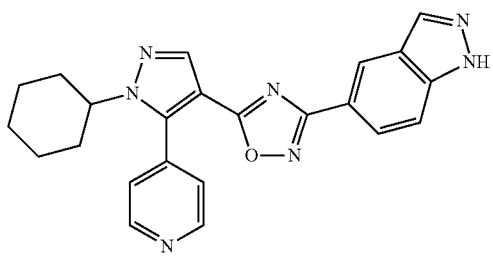 [SMILES: c1cc(-c2c(-c3nc(-c4ccc5[nH]ncc5c4)no3)cnn2C2CCCCC2)ccn1] |
| 39 | 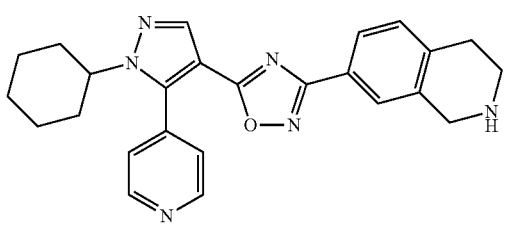 [SMILES: c1cc(-c2c(-c3nc(-c4ccc5c(c4)CNCC5)no3)cnn2C2CCCCC2)ccn1] |
| 41 | 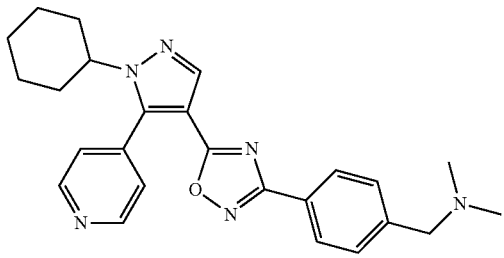 [SMILES: CN(C)Cc1ccc(-c2noc(-c3cnn(C4CCCCC4)c3-c3ccncc3)n2)cc1] |

-continued
| Example Nb | Formula |
|---|---|
| 44 | 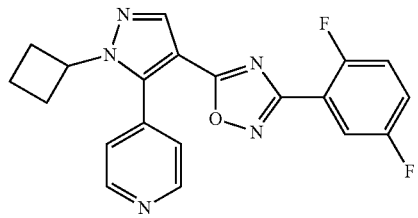 [SMILES: Fc1ccc(F)c(-c2noc(-c3cnn(C4CCC4)c3-c3ccncc3)n2)c1] |
| 46 | 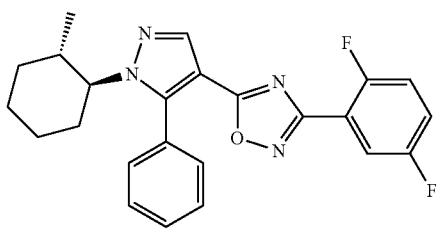 [SMILES: C[C@H]1CCCC[C@@H]1n1ncc(-c2nc(-c3cc(F)ccc3F)no2)c1-c1ccccc1] |
| 47 | 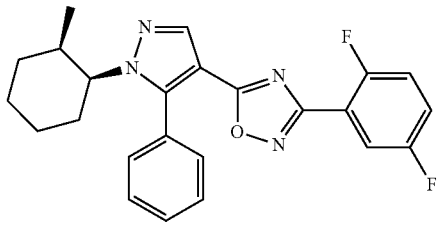 [SMILES: C[C@@H]1CCCC[C@@H]1n1ncc(-c2nc(-c3cc(F)ccc3F)no2)c1-c1ccccc1] |
| 48 | 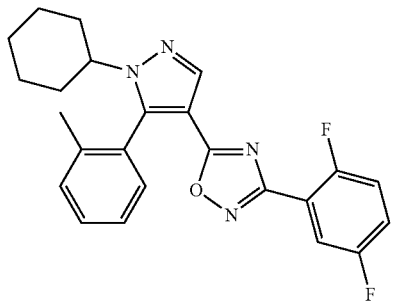 [SMILES: Cc1ccccc1-c1c(-c2nc(-c3cc(F)ccc3F)no2)cnn1C1CCCCC1] |
| 49 | 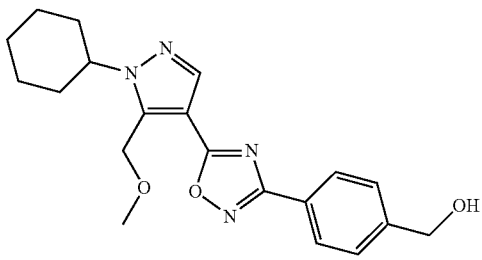 [SMILES: COCc1c(-c2nc(-c3ccc(CO)cc3)no2)cnn1C1CCCCC1] |
| 51 | 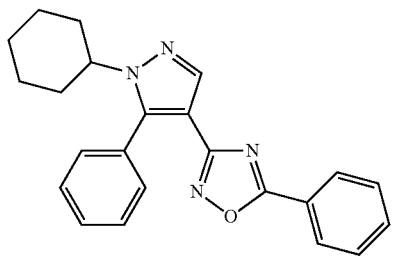 [SMILES: c1ccc(-c2nc(-c3cnn(C4CCCCC4)c3-c3ccccc3)no2)cc1] |

-continued
| Example Nb | Formula |
|---|---|
| 52 | 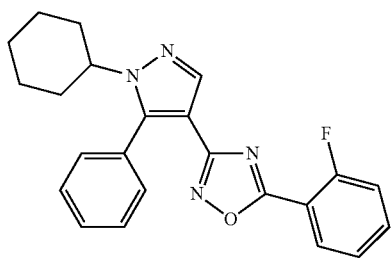 [SMILES: Fc1ccccc1-c1nc(-c2cnn(C3CCCCC3)c2-c2ccccc2)no1] |
| 53 | 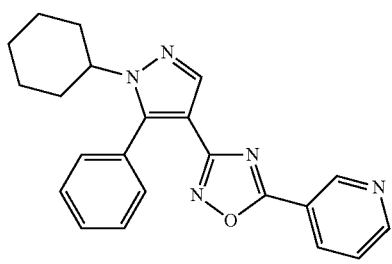 |
| 55 | 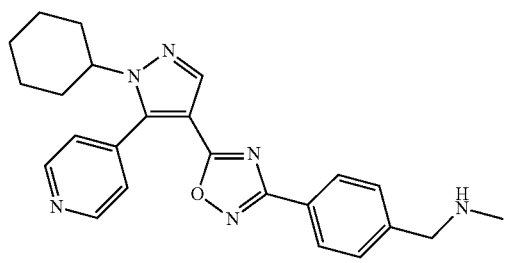 [SMILES: CNCc1ccc(-c2noc(-c3cnn(C4CCCCC4)c3-c3ccncc3)n2)cc1] |
| 56 | 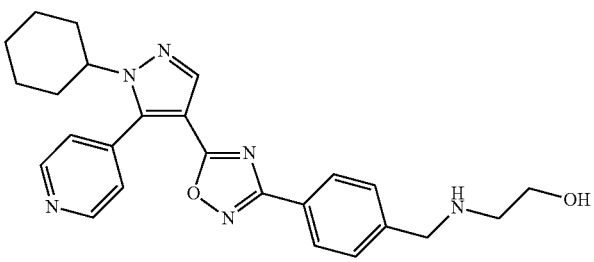 [SMILES: OCCNCc1ccc(-c2noc(-c3cnn(C4CCCCC4)c3-c3ccncc3)n2)cc1] |
| 57 | 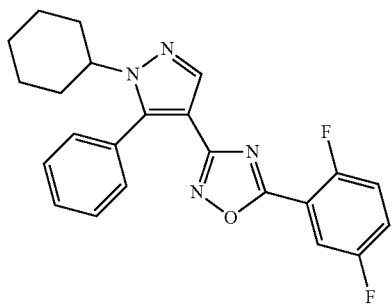 [SMILES: Fc1ccc(F)c(-c2nc(-c3cnn(C4CCCCC4)c3-c3ccccc3)no2)c1] |

-continued
| Example Nb | Formula |
|---|---|
| 58 | 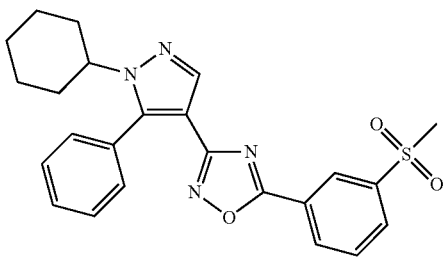 [SMILES: CS(=O)(=O)c1cccc(-c2nc(-c3cnn(C4CCCCC4)c3-c3ccccc3)no2)c1] |
| 59 | 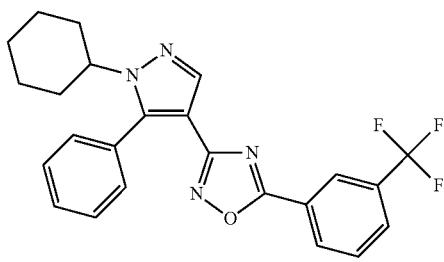 [SMILES: FC(F)(F)c1cccc(-c2nc(-c3cnn(C4CCCCC4)c3-c3ccccc3)no2)c1] |
| 61 | 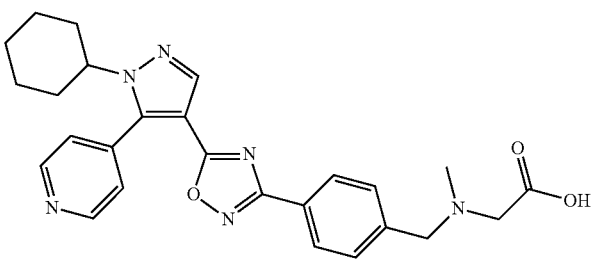 [SMILES: CN(CC(=O)O)Cc1ccc(-c2noc(-c3cnn(C4CCCCC4)c3-c3ccncc3)n2)cc1] |
| 65 | 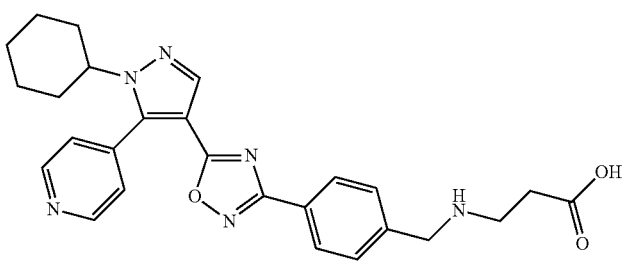 [SMILES: O=C(O)CCNCc1ccc(-c2noc(-c3cnn(C4CCCCC4)c3-c3ccncc3)n2)cc1] |
| 67 | 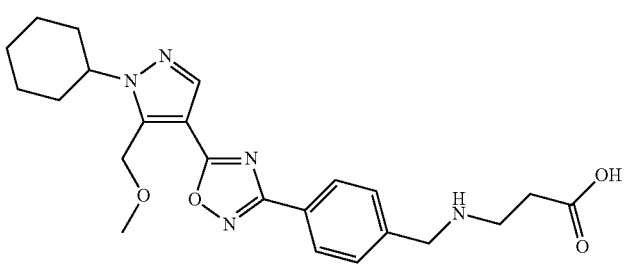 [SMILES: COCc1c(-c2nc(-c3ccc(CNCCC(=O)O)cc3)no2)cnn1C1CCCCC1] |
| 70 | 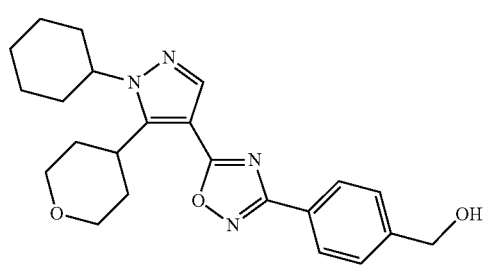 [SMILES: OCc1ccc(-c2noc(-c3cnn(C4CCCCC4)c3C3CCOCC3)n2)cc1] |

| Example Nb | Formula |
|---|---|
| 72 | 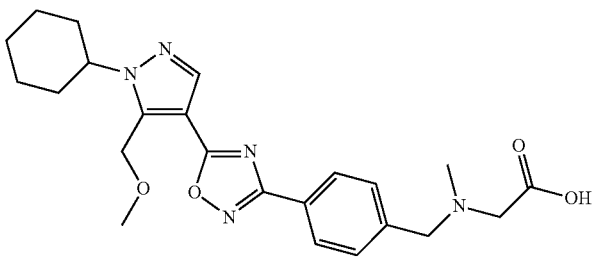 [SMILES: COCc1c(-c2nc(-c3ccc(CN(C)CC(=O)O)cc3)no2)cnn1C1CCCCC1] |
| 75 | 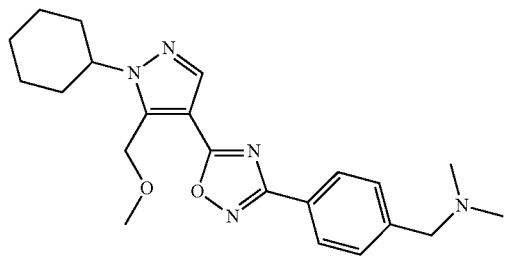 [SMILES: COCc1c(-c2nc(-c3ccc(CN(C)C)cc3)no2)cnn1C1CCCCC1] |
| 78 | 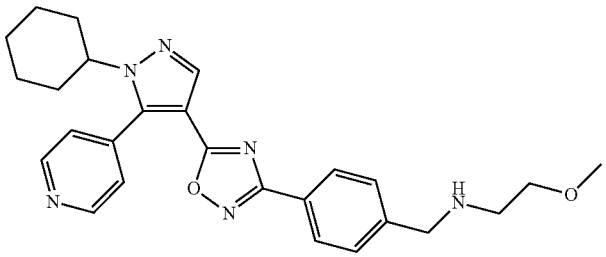 [SMILES: COCCNCc1ccc(-c2noc(-c3cnn(C4CCCCC4)c3-c3ccncc3)n2)cc1] |
| 83 | 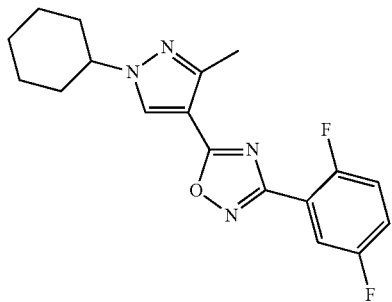 [SMILES: Cc1nn(C2CCCCC2)cc1-c1nc(-c2cc(F)ccc2F)no1] |
| 86 | 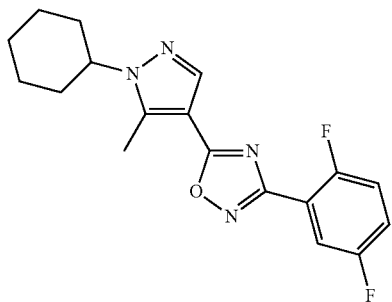 [SMILES: Cc1c(-c2nc(-c3cc(F)ccc3F)no2)cnn1C1CCCCC1] |

-continued
| Example Nb | Formula |
|---|---|
| 87 | 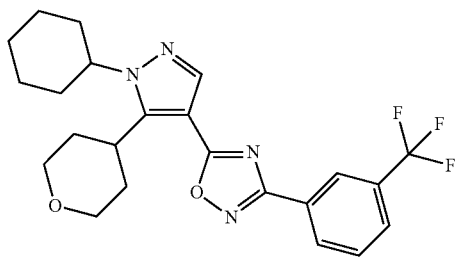 [SMILES: FC(F)(F)c1cccc(-c2noc(-c3cnn(C4CCCCC4)c3C3CCOCC3)n2)c1] |
| 88 | 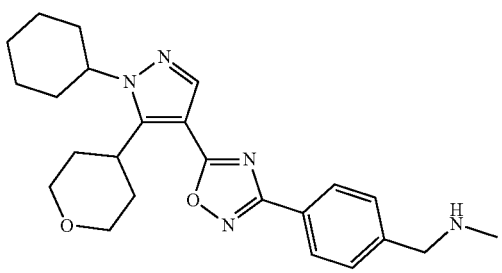 [SMILES: CNCc1ccc(-c2noc(-c3cnn(C4CCCCC4)c3C3CCOCC3)n2)cc1] |
| 91 | 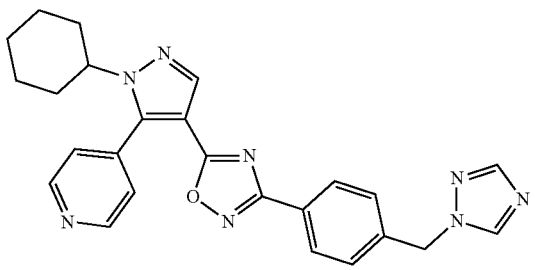 |
| 95 | 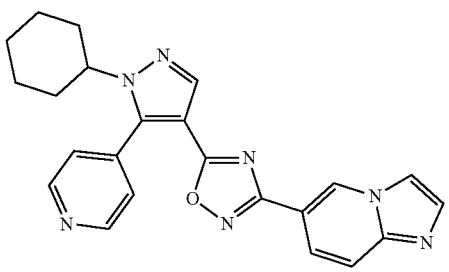 [SMILES: c1cc(-c2c(-c3nc(-c4ccc5nccn5c4)no3)cnn2C2CCCCC2)ccn1] |
| 98 | 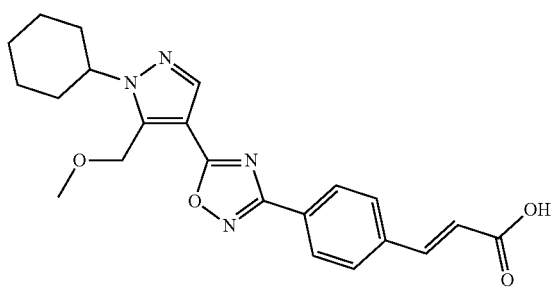 [SMILES: COCc1c(-c2nc(-c3ccc(/C=C/C(=O)O)cc3)no2)cnn1C1CCCCC1] |

| Example Nb | Formula |
|---|---|
| 102 | 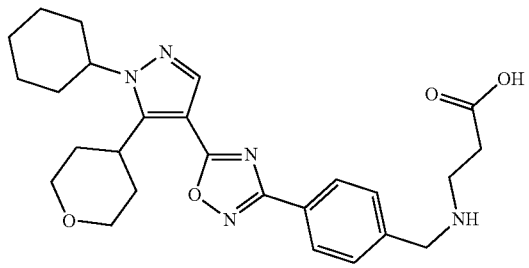 [SMILES: O=C(O)CCNCc1ccc(-c2noc(-c3cnn(C4CCCCC4)c3C3CCOCC3)n2)cc1] |
| 103 | 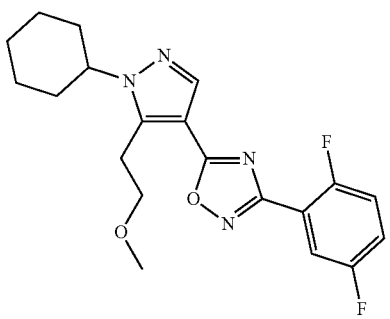 [SMILES: COCCc1c(-c2nc(-c3cc(F)ccc3F)no2)cnn1C1CCCCC1] |
| 107 | 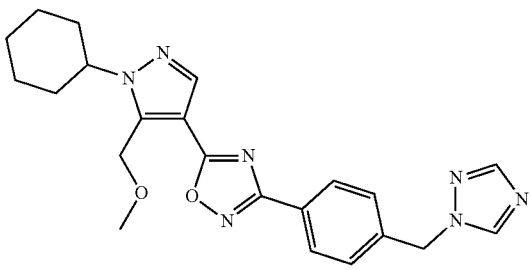 [SMILES: COCc1c(-c2nc(-c3ccc(Cn4cncn4)cc3)no2)cnn1C1CCCCC1] |
| 108 | 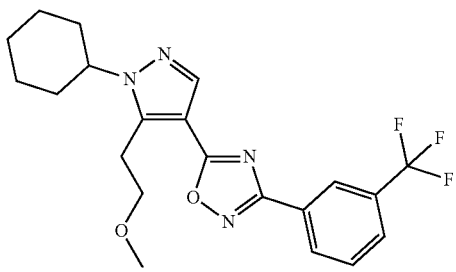 [SMILES: COCCc1c(-c2nc(-c3cccc(C(F)(F)F)c3)no2)cnn1C1CCCCC1] |
| 109 | 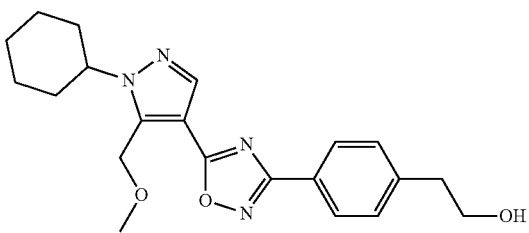 [SMILES: COCc1c(-c2nc(-c3ccc(CCO)cc3)no2)cnn1C1CCCCC1] |

| Example Nb | Formula |
|---|---|
| 111 | 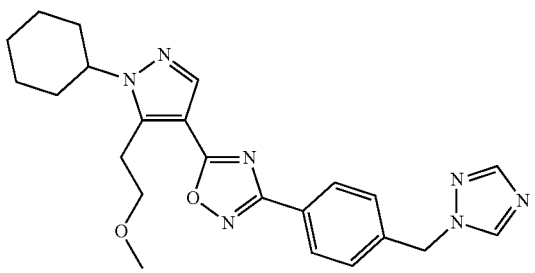 [SMILES: COCCc1c(-c2nc(-c3ccc(Cn4cncn4)cc3)no2)cnn1C1CCCCC1] |
| 114 | 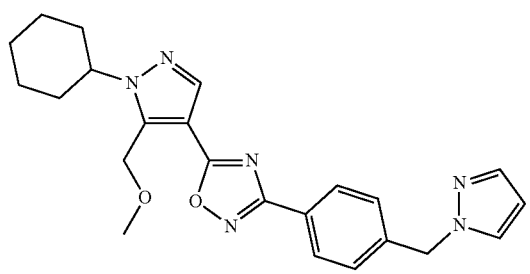 [SMILES: COCc1c(-c2nc(-c3ccc(Cn4cccn4)cc3)no2)cnn1C1CCCCC1] |
| 115 | 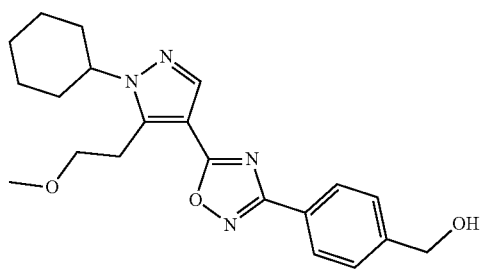 [SMILES: COCCc1c(-c2nc(-c3ccc(CO)cc3)no2)cnn1C1CCCCC1] |
| 116 | 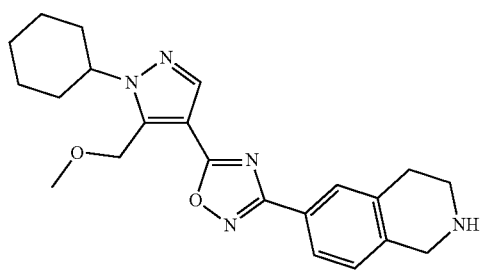 [SMILES: COCc1c(-c2nc(-c3ccc4c(c3)CCNC4)no2)cnn1C1CCCCC1] |
| 117 | 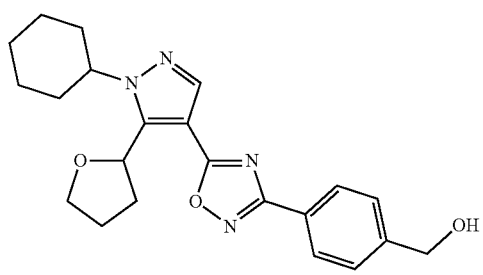 [SMILES: OCc1ccc(-c2noc(-c3cnn(C4CCCCC4)c3C3CCCO3)n2)cc1] |

| Example Nb | Formula |
|---|---|
| 118 | 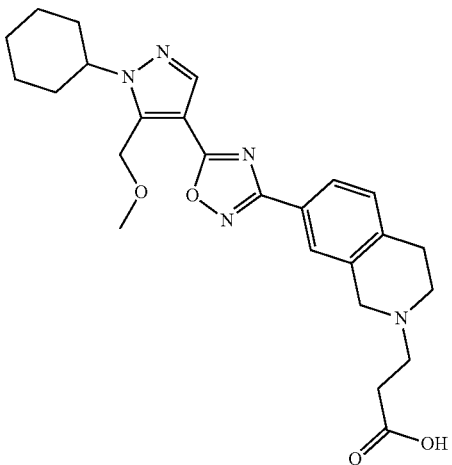 [SMILES: COCc1c(-c2nc(-c3ccc4c(c3)CN(CCC(=O)O)CC4)no2)cnn1C1CCCCC1] |
| 119 | 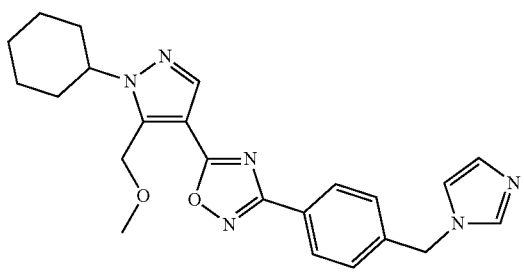 [SMILES: COCc1c(-c2nc(-c3ccc(Cn4ccnc4)cc3)no2)cnn1C1CCCCC1] |
| 121 | 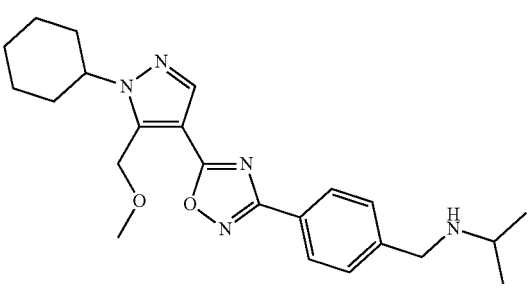 [SMILES: COCc1c(-c2nc(-c3ccc(CNC(C)C)cc3)no2)cnn1C1CCCCC1] |
| 122 | 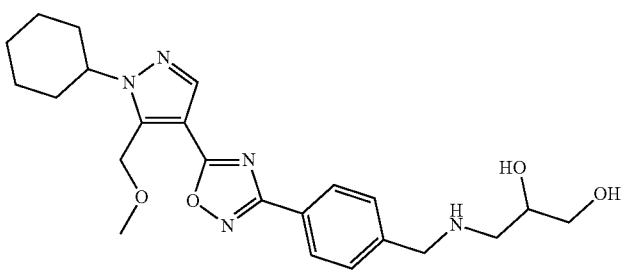 [SMILES: COCc1c(-c2nc(-c3ccc(CNCC(O)CO)cc3)no2)cnn1C1CCCCC1] |
| 123 | 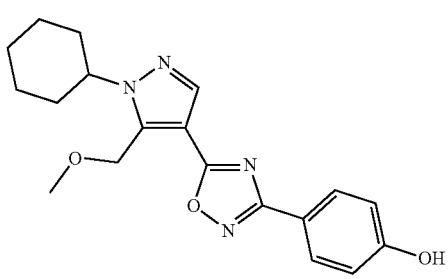 [SMILES: COCc1c(-c2nc(-c3ccc(O)cc3)no2)cnn1C1CCCCC1] |

-continued
| Example Nb | Formula |
|---|---|
| 124 | 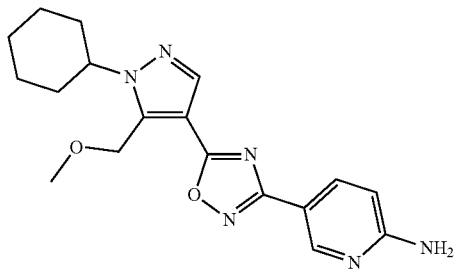 [SMILES: COCc1c(-c2nc(-c3ccc(N)nc3)no2)cnn1C1CCCCC1] |
| 126 | 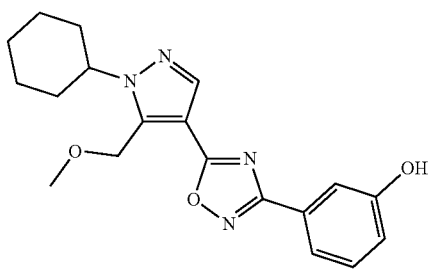 [SMILES: COCc1c(-c2nc(-c3cccc(O)c3)no2)cnn1C1CCCCC1] |
| 127 | 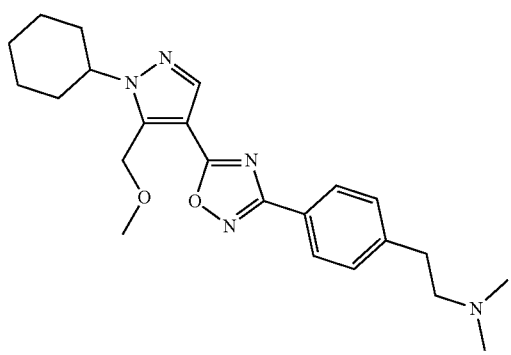 [SMILES: COCc1c(-c2nc(-c3ccc(CCN(C)C)cc3)no2)cnn1C1CCCCC1] |
| 128 | 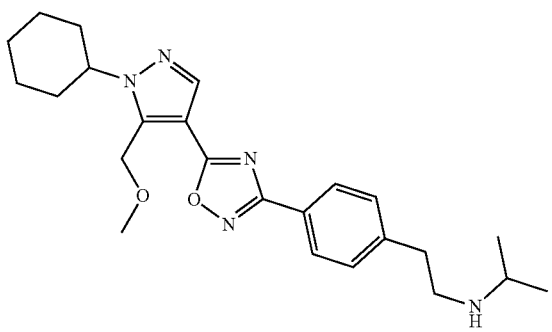 [SMILES: COCc1c(-c2nc(-c3ccc(CCNC(C)C)cc3)no2)cnn1C1CCCCC1] |
| 131 | 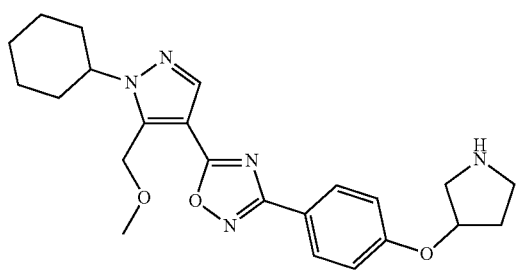 [SMILES: COCc1c(-c2nc(-c3ccc(OC4CCNC4)cc3)no2)cnn1C1CCCCC1] |

-continued
| Example Nb | Formula |
|---|---|
| 133 | 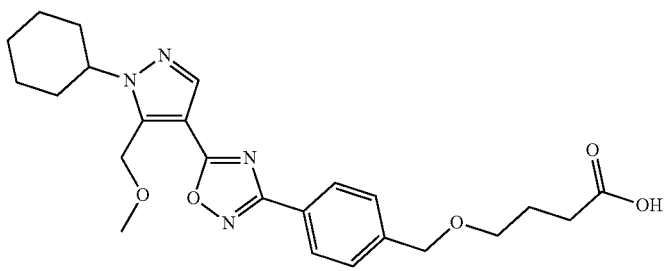 [SMILES: COCc1c(-c2nc(-c3ccc(COCCCC(=O)O)cc3)no2)cnn1C1CCCCC1] |
| 134 | 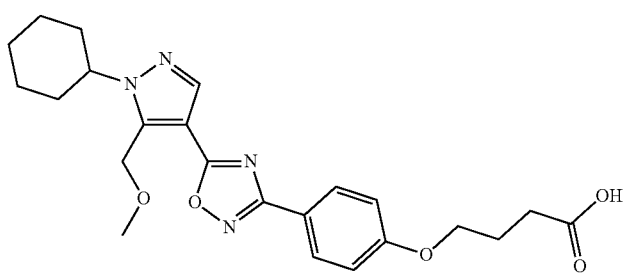 [SMILES: COCc1c(-c2nc(-c3ccc(OCCCC(=O)O)cc3)no2)cnn1C1CCCCC1] |
| 136 | 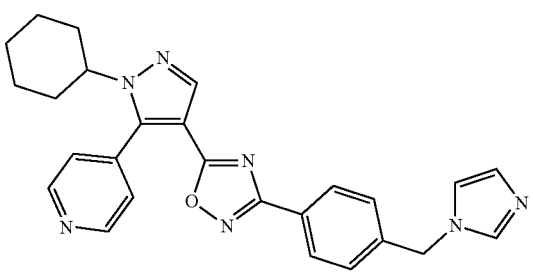 |
| 137 | 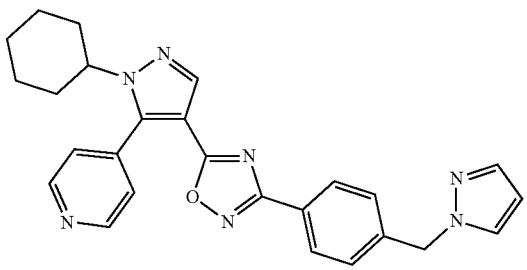 [SMILES: c1cnn(Cc2ccc(-c3noc(-c4cnn(C5CCCCC5)c4-c4ccncc4)n3)cc2)c1] |
| 138 | 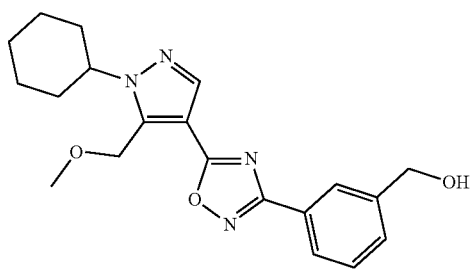 [SMILES: COCc1c(-c2nc(-c3cccc(CO)c3)no2)cnn1C1CCCCC1] |

| Example Nb | Formula |
|---|---|
| 139 | 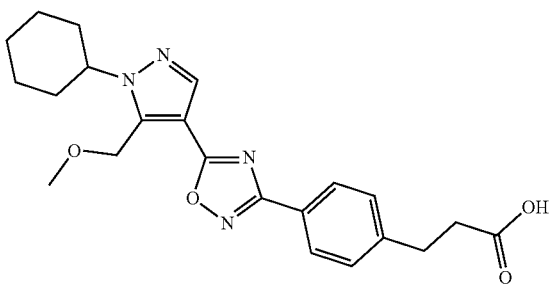 [SMILES: COCc1c(-c2nc(-c3ccc(CCC(=O)O)cc3)no2)cnn1C1CCCCC1] |
| 140 | 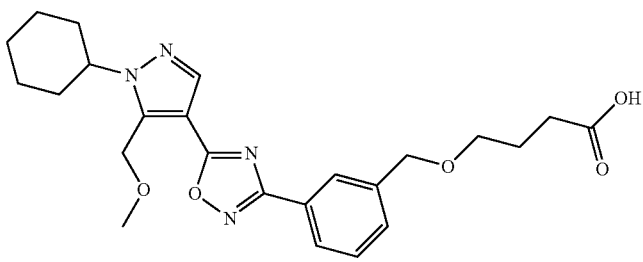 [SMILES: COCc1c(-c2nc(-c3cccc(COCCCC(=O)O)c3)no2)cnn1C1CCCCC1] |
| 141 | 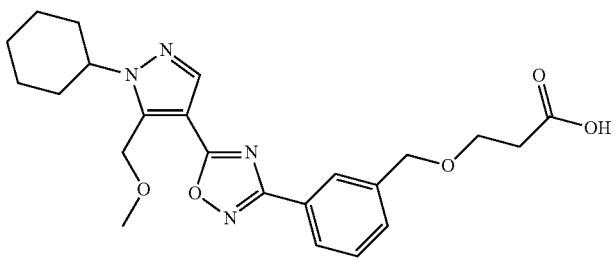 [SMILES: COCc1c(-c2nc(-c3cccc(COCCC(=O)O)c3)no2)cnn1C1CCCCC1] |
| 142 | 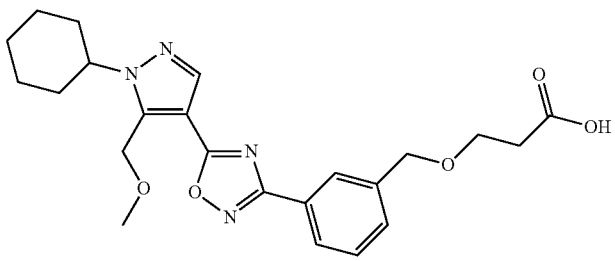 [SMILES: COCc1c(-c2nc(-c3cccc(COCCC(=O)O)c3)no2)cnn1C1CCCCC1] |
| 143 | 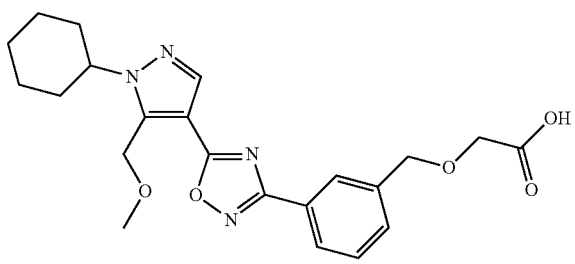 [SMILES: COCc1c(-c2nc(-c3cccc(COCC(=O)O)c3)no2)cnn1C1CCCCC1] |

| Example Nb | Formula |
|---|---|
| 144 | 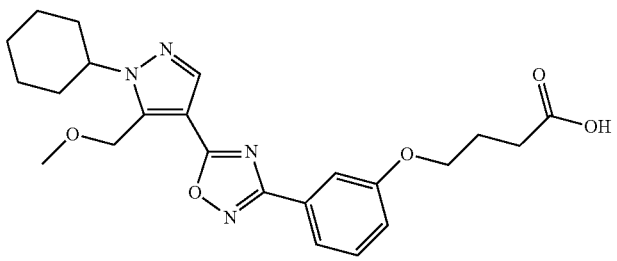 [SMILES: COCc1c(-c2nc(-c3cccc(OCCCC(=O)O)c3)no2)cnn1C1CCCCC1] |
| 145 | 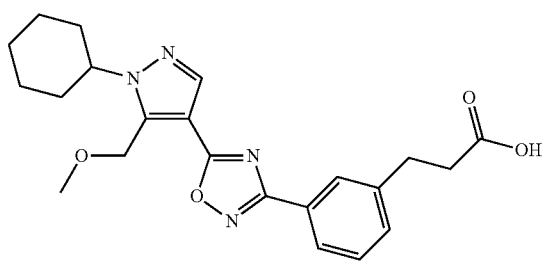 [SMILES: COCc1c(-c2nc(-c3cccc(CCC(=O)O)c3)no2)cnn1C1CCCCC1] |
| 146 | 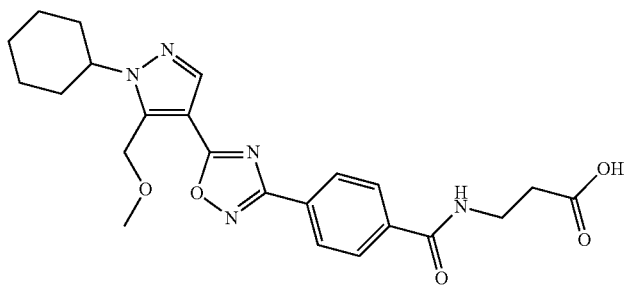 [SMILES: COCc1c(-c2nc(-c3ccc(C(=O)NCCC(=O)O)cc3)no2)cnn1C1CCCCC1] |
| 147 | 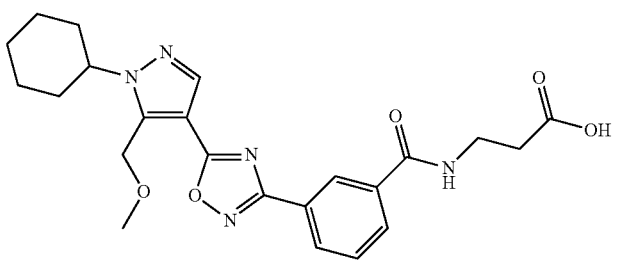 [SMILES: COCc1c(-c2nc(-c3cccc(C(=O)NCCC(=O)O)c3)no2)cnn1C1CCCCC1] |
| 148 | 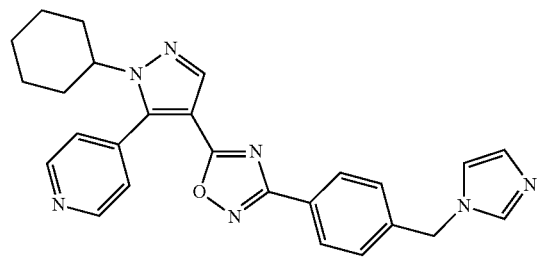 [SMILES: c1cc(-c2c(-c3nc(-c4ccc(Cn5ccnc5)cc4)no3)cnn2C2CCCCC2)ccn1] |

-continued
| Example Nb | Formula |
|---|---|
| 149 | 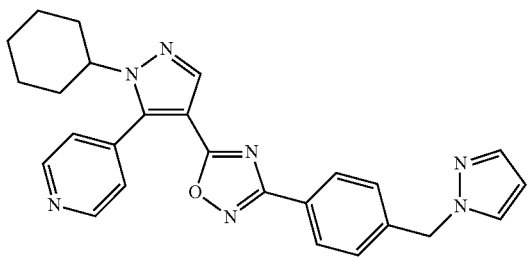 [SMILES: c1cnn(Cc2ccc(-c3noc(-c4cnn(C5CCCCC5)c4-c4ccncc4)n3)cc2)c1] |
| 150 | 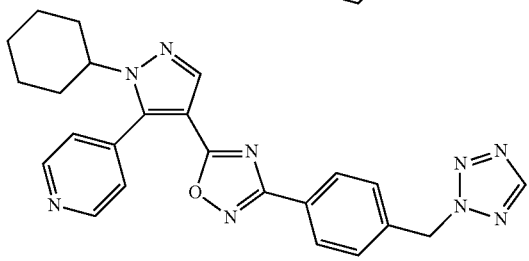 |
| 152 | 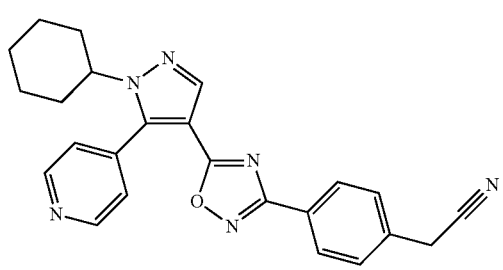 [SMILES: N#CCc1ccc(-c2noc(-c3cnn(C4CCCCC4)c3-c3ccncc3)n2)cc1] |
| 153 | 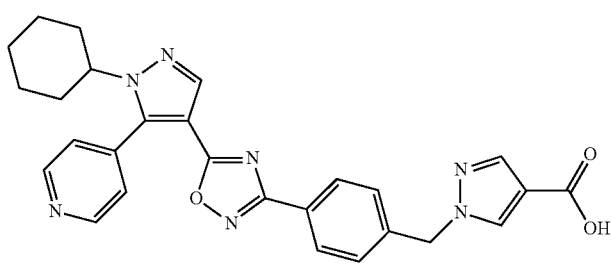 [SMILES: O=C(O)c1cnn(Cc2ccc(-c3noc(-c4cnn(C5CCCCC5)c4-c4ccncc4)n3)cc2)c1] |
| 154 | 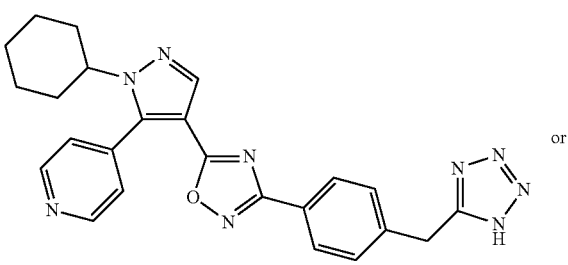 [SMILES: c1cc(-c2c(-c3nc(-c4ccc(Cc5nnn[nH]5)cc4)no3)cnn2C2CCCCC2)ccn1] or |
| 155 | 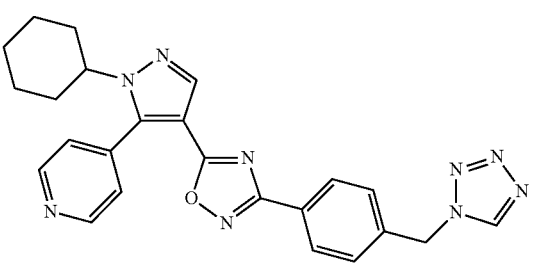 [SMILES: c1cc(-c2c(-c3nc(-c4ccc(Cn5cnnn5)cc4)no3)cnn2C2CCCCC2)ccn1] | and pharmaceutically acceptable solvates, tautomers, salts and stereoisomers thereof.

4. A pharmaceutical composition comprising at least one compound according to claim 1 and/or pharmaceutically acceptable tautomers, salts, solvates and stereoisomers thereof and, optionally, excipients and/or adjuvants.

5. The pharmaceutical composition according to claim 4, said composition further comprising an additional active ingredient.

6. A kit comprising:
(a) a compound according to claim 1 and/or pharmaceutically acceptable, solvates and stereoisomers thereof; and
(b) a second active ingredient;
wherein said compound and said second active ingredient are packaged separately or together in a single container.

7. A process for the preparation of a compound of formula (I):

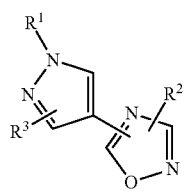

wherein
R¹ is

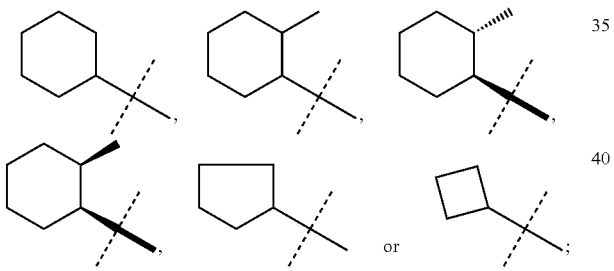

R² is selected from the following groups:

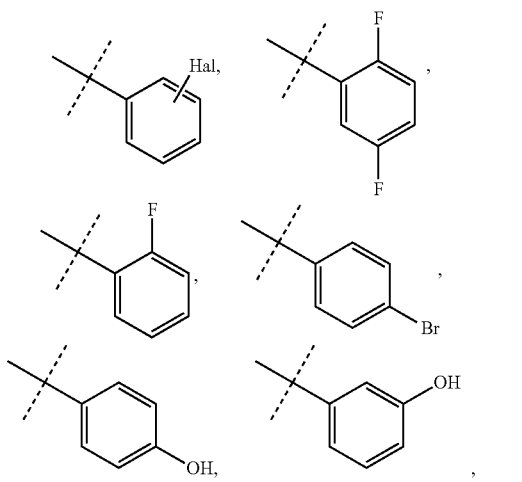

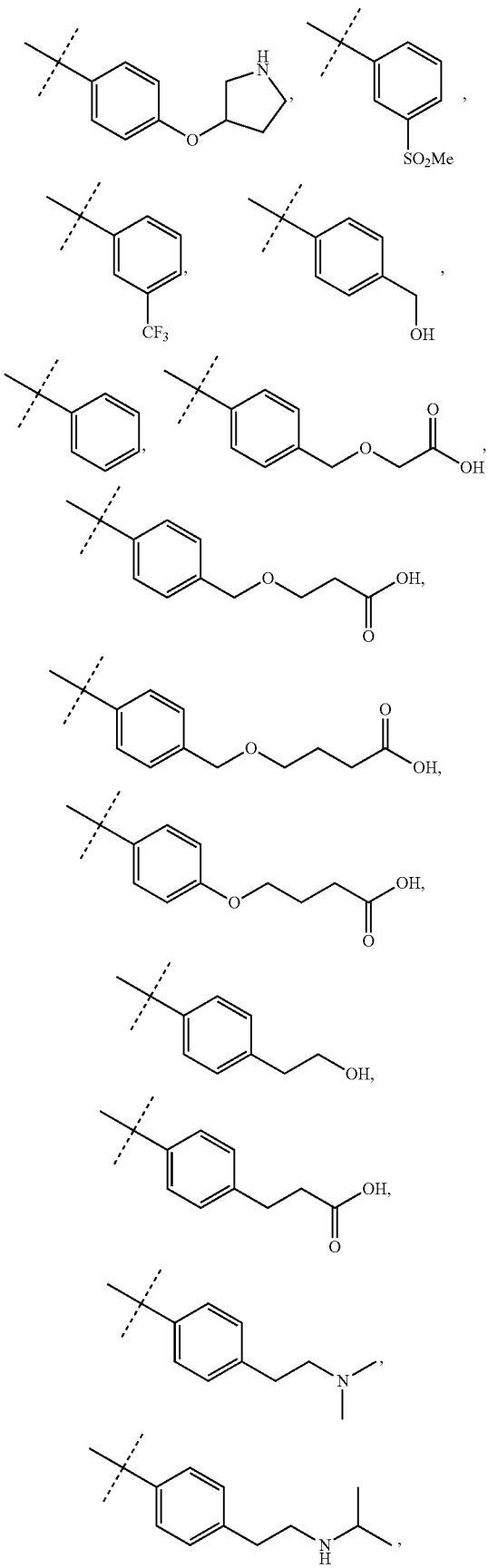

303
-continued
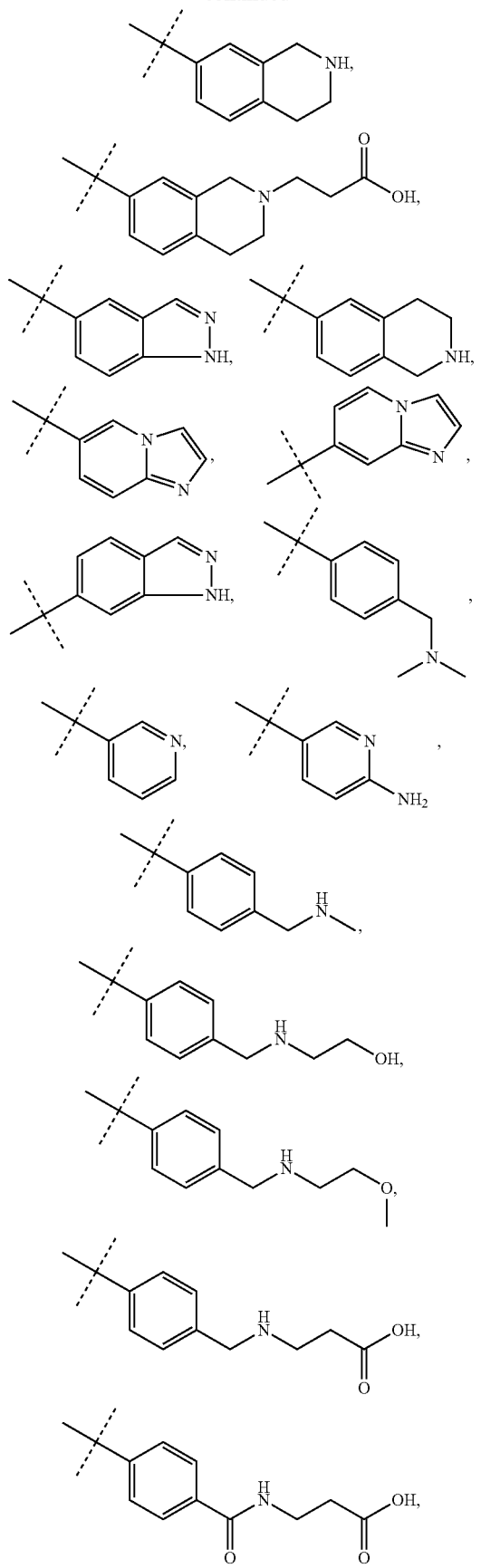
304
-continued
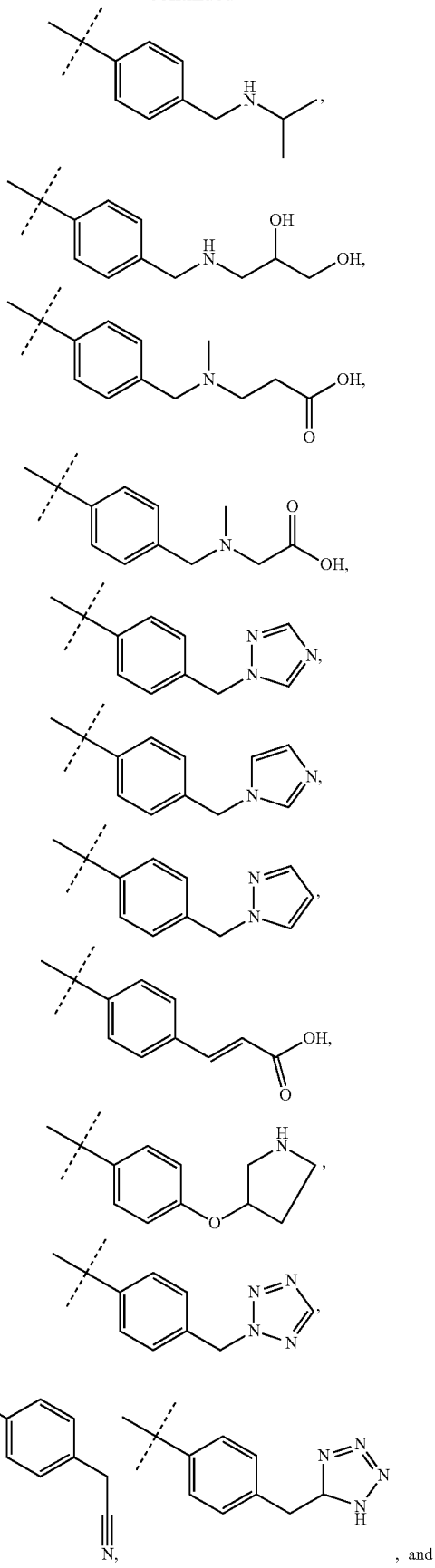
, and

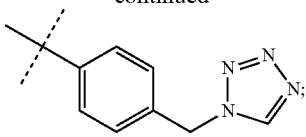

$R^3$ is $Ar^2$, $Het^1$, Cyc, A, $CH_3$, or $S$—$(C_1$-$C_6$-alkyl);

A is a branched or linear alkyl having 2 to 12 C-atoms, wherein one or more H-atoms may be replaced by Hal, $OR^4$, CN, $CO_2R^4$, or $CF_3$; cycloalkyl having 3 to 7 ring carbon atoms; $Ar^2$, or $N(R^4)_2$ and wherein one or more non-adjacent $CH_2$-groups may be replaced by O, $NR^4$, —CO—, $NR^4CO_2$—, —$CO_2$—, —$NR^4CONR^4$—, —CH=CH—, —C≡C—, or A is cycloalkyl or cycloalkylalkylene having 3-7 ring C atoms, or A is $Het^2$;

Z is a branched or linear alkyl having 2 to 12 C-atoms, wherein one or more H-atoms are replaced by Hal, $OR^4$, CN, $CO_2R^4$, $CF_3$, cycloalkyl having 3 to 7 ring carbon atoms, $Ar^2$, $N(R^4)_2$ and/or wherein one or more $CH_2$-groups are replaced by O, $NR^4$, S, —CO—, $NR^4CO_2$—, —$NR^4CONR^4$—, —CH=CH—, —C=O—, or Z is cycloalkyl or cycloalkylalkylene having 3-7 ring C atoms;

Hal is F, Cl, Br or I;

$Ar^2$ is a monocyclic or bicyclic, unsaturated or aromatic carbocyclic ring having 6 to 14 carbon atoms which may be unsubstituted, monosubstituted, disubstituted or trisubstituted by substituents selected from Z, F, Br, I, —$OR^4$, —$(CH_2)OR^4$, —$(CH_2)N(R^4)_2$, Perfluoro-alkoxy, —$SO_2R^4$, —CN, —$NO_2$, —$N(R^4)_2$, —CO$(NR^4)_2$, $(NR^4)COR^4$, —$CO_2R^4$, —$COR^4$, —$SO_2N(R^4)_2$, —$SO_2$alkyl, $NR^4SO_2(C_1$-$C_6)$alkyl, —$(CH_2)_n$ $Het^1$, —$OHet^1$, or $CF_3$;

$Het^1$ is a monocyclic saturated, unsaturated or aromatic heterocyclic ring or a bicyclic, saturated, or unsaturated heterocyclic ring having 1 to 4 N, O and/or S atoms which may be unsubstituted, monosubstituted, disubstituted or trisubstituted by substituents selected from A, Hal, —$OR^4$, —$(CH_2)OR^4$, Perfluoro-alkyl, Perfluoro-alkoxy, —$SO_2(R^4)_2$, CN, $NO_2$, —$N(R^4)_2$, —CO$(NR^4)_2$, $(NR^4)COR^4$, —$CO_2R^4$, —$COR^4$, —$SO_2N(R^4)_2$, —$SO_2$alkyl, $NR^4SO_2$alkyl, $NR^4SO_2$alkyl, or $C_1$-$C_6$ alkyl;

Cyc is a saturated or unsaturated carbocyclic ring containing 3 to 7 carbon atoms which may be substituted by Hal, A, $(C_1$-$C_6)$alkyl, —$[C(R^4)_2]_{n\text{-}cycloalkyl}$, $OR^4$, $CF_3$, $OCF_3$, $N(R^4)_2$, $NR^4CON(R^4)_2$, $NO_2$, CN, —$[C(R^4)_2]_n$—$COOR^4$, —$[C(R^4)_2]_n$—$CON(R^4)_2$, $NR^4COA$, $NR^4SO_2A$, $COR^4$, $SO_2N(R^4)_2$, SOA, and/or $SO_2A$;

$R^4$ is H, A, Cyc or $(C_1$-$C_6)$alkyl; and n is 0, 1, 2, 3 or 4;

said method comprising the step of reacting a compound of formula (V)

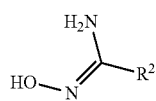

(V)

with a compound of formula (IV)

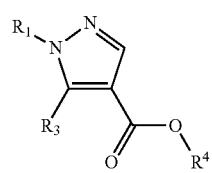

(IV)

or (VI)

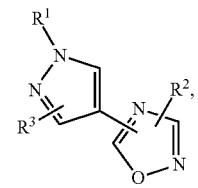

(VI)

wherein $R^1$, $R^2$, $R^3$ and $R^4$ are as defined above.

8. A process for the preparation of compounds of formula (I)

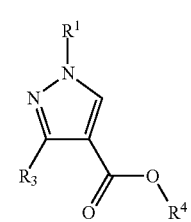

wherein $R^1$ is

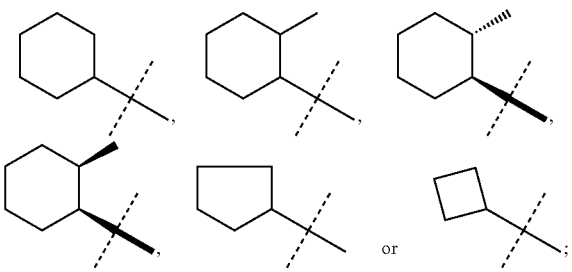

$R^2$ is selected from the following groups:

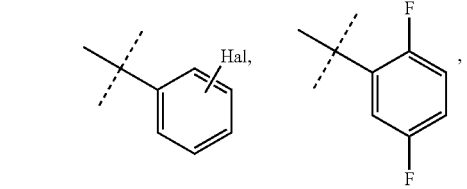

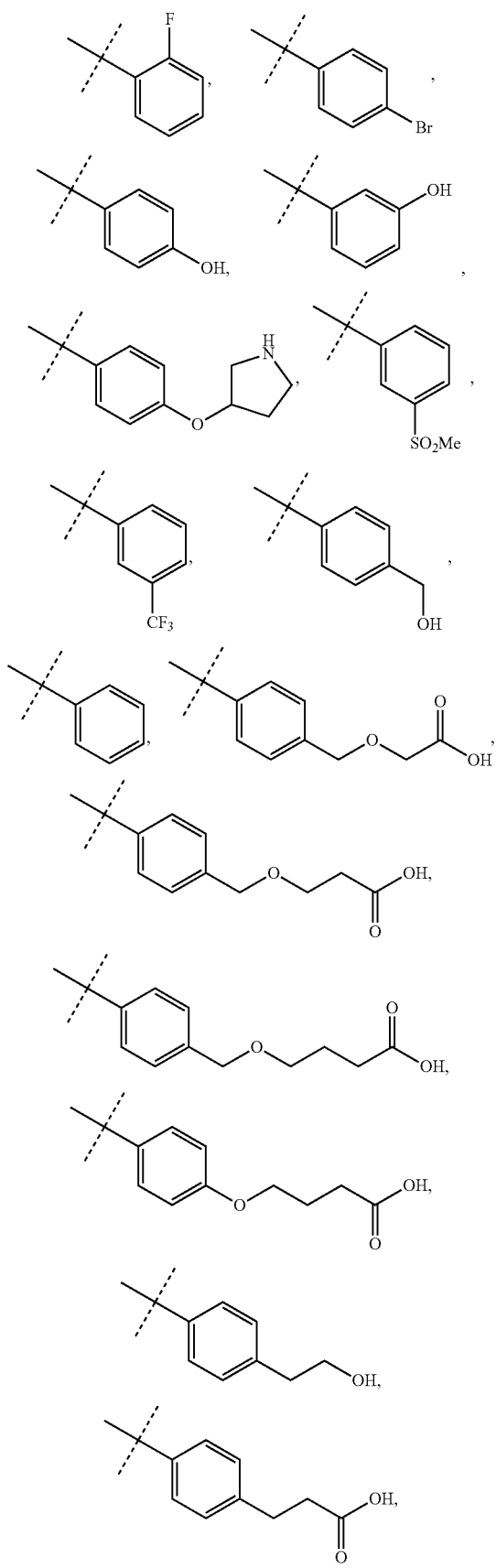
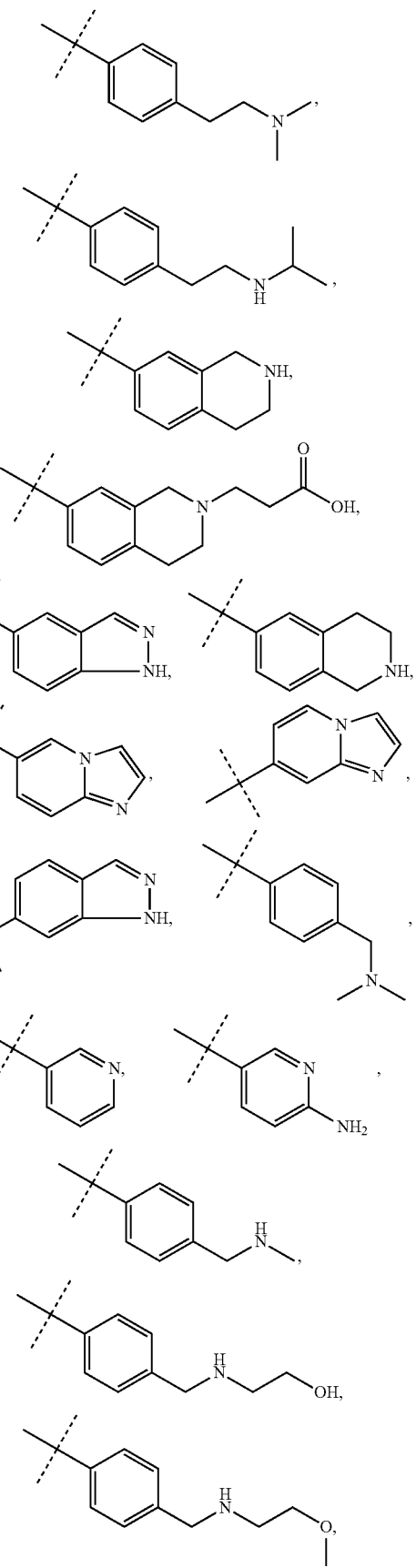

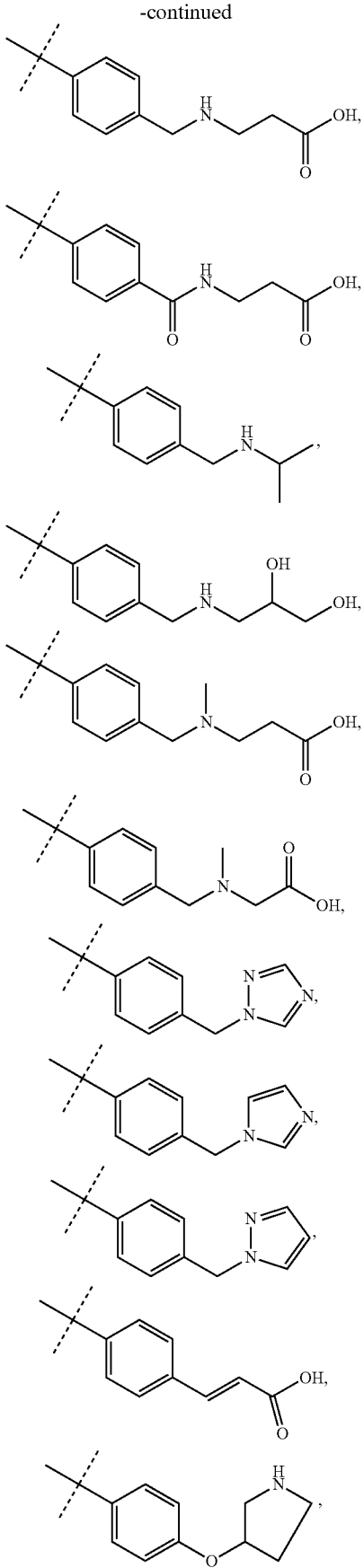
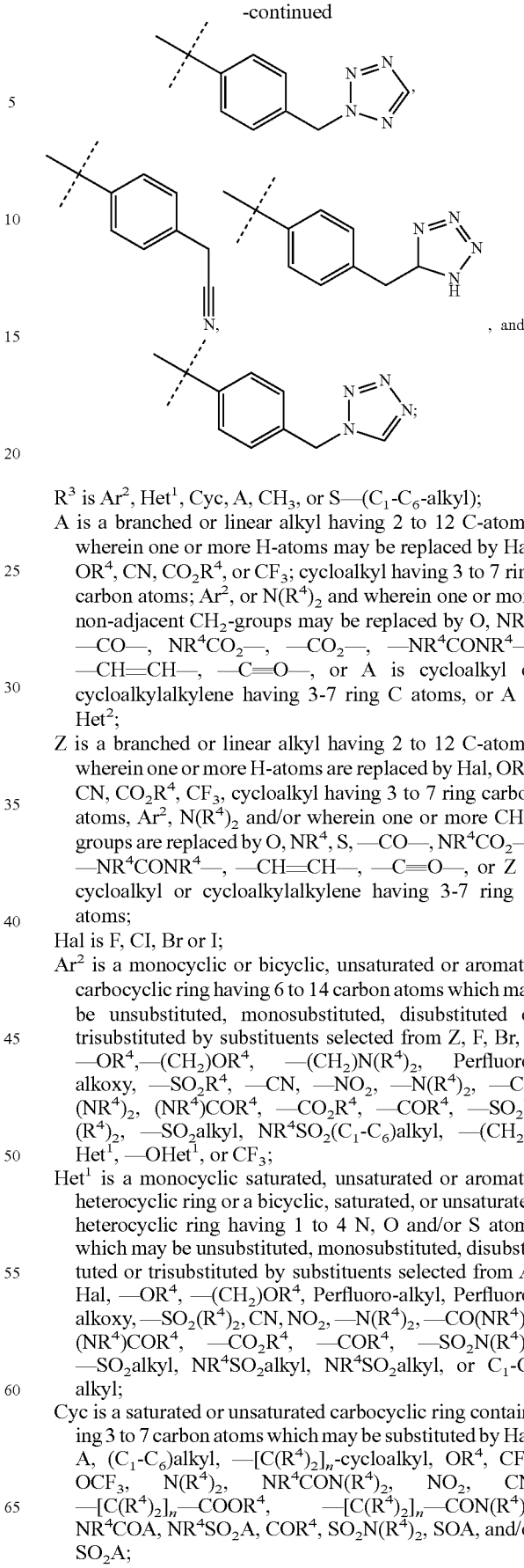

$R^3$ is $Ar^2$, $Het^1$, Cyc, A, $CH_3$, or S—($C_1$-$C_6$-alkyl);

A is a branched or linear alkyl having 2 to 12 C-atoms, wherein one or more H-atoms may be replaced by Hal, $OR^4$, CN, $CO_2R^4$, or $CF_3$; cycloalkyl having 3 to 7 ring carbon atoms; $Ar^2$, or $N(R^4)_2$ and wherein one or more non-adjacent $CH_2$-groups may be replaced by O, $NR^4$, —CO—, $NR^4CO_2$—, —$CO_2$—, —$NR^4CONR^4$—, —CH=CH—, —C≡O—, or A is cycloalkyl or cycloalkylalkylene having 3-7 ring C atoms, or A is $Het^2$;

Z is a branched or linear alkyl having 2 to 12 C-atoms, wherein one or more H-atoms are replaced by Hal, $OR^4$, CN, $CO_2R^4$, $CF_3$, cycloalkyl having 3 to 7 ring carbon atoms, $Ar^2$, $N(R^4)_2$ and/or wherein one or more $CH_2$-groups are replaced by O, $NR^4$, S, —CO—, $NR^4CO_2$—, —$NR^4CONR^4$—, —CH=CH—, —C≡O—, or Z is cycloalkyl or cycloalkylalkylene having 3-7 ring C atoms;

Hal is F, Cl, Br or I;

$Ar^2$ is a monocyclic or bicyclic, unsaturated or aromatic carbocyclic ring having 6 to 14 carbon atoms which may be unsubstituted, monosubstituted, disubstituted or trisubstituted by substituents selected from Z, F, Br, I, —$OR^4$,—($CH_2$)$OR^4$, —($CH_2$)$N(R^4)_2$, Perfluoro-alkoxy, —$SO_2R^4$, —CN, —$NO_2$, —$N(R^4)_2$, —CO($NR^4)_2$, ($NR^4$)$COR^4$, —$CO_2R^4$, —$COR^4$, —$SO_2N(R^4)_2$, —$SO_2$alkyl, $NR^4SO_2(C_1$-$C_6$)alkyl, —($CH_2$)$_n$$Het^1$, —O$Het^1$, or $CF_3$;

$Het^1$ is a monocyclic saturated, unsaturated or aromatic heterocyclic ring or a bicyclic, saturated, or unsaturated heterocyclic ring having 1 to 4 N, O and/or S atoms which may be unsubstituted, monosubstituted, disubstituted or trisubstituted by substituents selected from A, Hal, —$OR^4$, —($CH_2$)$OR^4$, Perfluoro-alkyl, Perfluoro-alkoxy,—$SO_2(R^4)_2$, CN, $NO_2$,—$N(R^4)_2$,—$CO(NR^4)_2$, ($NR^4$)$COR^4$, —$CO_2R^4$, —$COR^4$, —$SO_2N(R^4)_2$, —$SO_2$alkyl, $NR^4SO_2$alkyl, $NR^4SO_2$alkyl, or $C_1$-$C_6$ alkyl;

Cyc is a saturated or unsaturated carbocyclic ring containing 3 to 7 carbon atoms which may be substituted by Hal, A, ($C_1$-$C_6$)alkyl, —[C($R^4$)$_2$]$_n$-cycloalkyl, $OR^4$, $CF_3$, $OCF_3$, $N(R^4)_2$, $NR^4CON(R^4)_2$, $NO_2$, CN, —[C($R^4$)$_2$]$_n$—$COOR^4$, —[C($R^4$)$_2$]$_n$—$CON(R^4)_2$, $NR^4COA$, $NR^4SO_2A$, $COR^4$, $SO_2N(R^4)_2$, SOA, and/or $SO_2A$;

$R^4$ is H, A, Cyc or $(C_1-C_6)$alkyl; and
n is 0, 1, 2, 3 or 4;
said method comprising the step of reacting a compound of formula (XI)
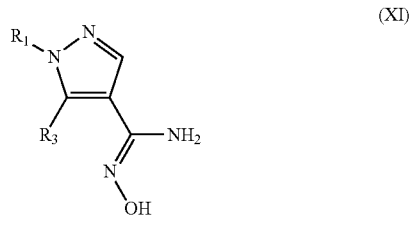
(XI)
with a compound of Formula (XII)
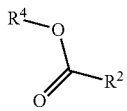
(XII)
wherein $R^1$, $R^2$, $R^3$ and $R^4$ are as defined above.
* * * * *

UNITED STATES PATENT AND TRADEMARK OFFICE
CERTIFICATE OF CORRECTION

PATENT NO. : 8,802,663 B2
APPLICATION NO. : 13/322939
DATED : August 12, 2014
INVENTOR(S) : Anna Quattropani et al.

Page 1 of 4

It is certified that error appears in the above-identified patent and that said Letters Patent is hereby corrected as shown below:

In the Specification

Column 3,
Line 2, "Oyster JG" should read --Cyster JG--.

Column 23,
Line 50, "areas" should read --are as--.

Column 86,
Line 67, "areas" should read --are as--.

Column 98,
Line 38, "immunorgulatory" should read --immunoregulatory--.

Column 122,
Line 54, "(40 ▢L)" should read --(40 µL)--.

Column 132,
Lines 41-42, "{4-[5(1-cyclohexyl-5-pyridin-4-yl-1H-pyrazol-4-yl)-1,2,4-oxadiazol-3-yl]phenyl}methanol" should read
--{4-[5-(1-cyclohexyl-5-pyridin-4-yl-1H-pyrazol-4-yl)-1,2,4-oxadiazol-3-yl]phenyl}methanol--.

Column 133,
Lines 13-14, "4-{1-cyclopentyl-4-[3-(2,5-difluorophenyl)-1,2,4-oxadiazol-5-yl]-1H-pyrazol-5-yl}Pyridine" should read
--4-{1-cyclopentyl-4-[3-(2,5-difluorophenyl)-1,2,4-oxadiazol-5-yl]-1H-pyrazol-5-yl}pyridine--.

Signed and Sealed this
Thirtieth Day of June, 2015

Michelle K. Lee
*Director of the United States Patent and Trademark Office*

Column 152,
Lines 3-4, "(4-{5-[1-isobutyl-54tetrahydro-2H-pyran-4-yl)-1H-pyrazol-4-yl]-1,2,4-
       oxadiazol-3-yl}phenyl)methanol" should read
    --(4-{5-[1-isobutyl-5-(tetrahydro-2H-pyran-4-yl)-1H-pyrazol-4-yl]-1,2,4-
       oxadiazol-3-yl}phenyl)methanol--.

Column 176,
Lines 42-44, "1-(4-(5-(1-(cyclopropylmethyl)-5-(pyridin-4-yl)-1H-pyrazol-4-yl)-1,2,4-
       oxadiazol-3-yl)benzyl)azetidine3-carboxylic acid, formate" should read
    --1-(4-(5-(1-(cyclopropylmethyl)-5-(pyridin-4-yl)-1H-pyrazol-4-yl)-1,2,4-
       oxadiazol-3-yl)benzyl)azetidine-3-carboxylic acid, formate--.

Column 178,
Line 5, "R-alanine" should read --β-alanine--.

Column 204,
Line 66, "355-GTPγS" should read --35S-GTPγS--.

Column 257,
Example Nb 140,

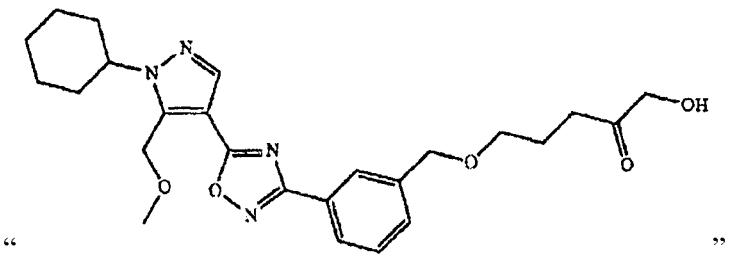

"                                                                                                "

should read

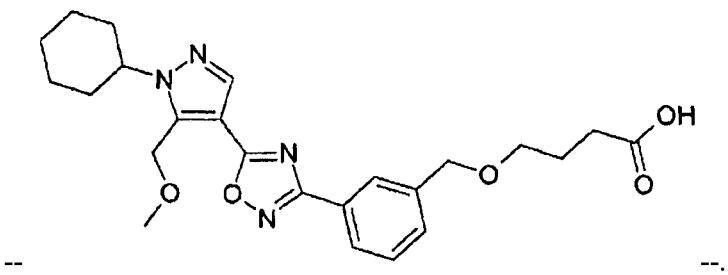

--                                                                                                --.

In the Claims

Column 270,
Line 22, Claim 1 "[C(R$^4$)$_2$]$_n$-cycloalkyl" should read -- –[C(R$^4$)$_2$]$_n$-cycloalkyl--.

Column 275,
Example Nb 49, Claim 2
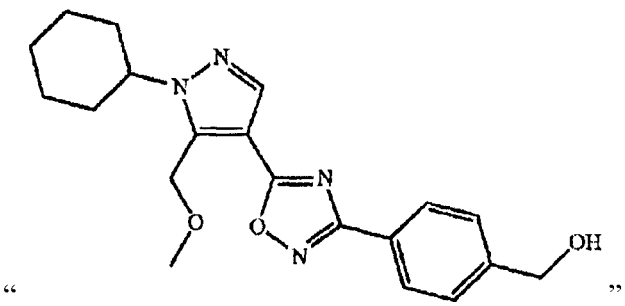
" "
should read
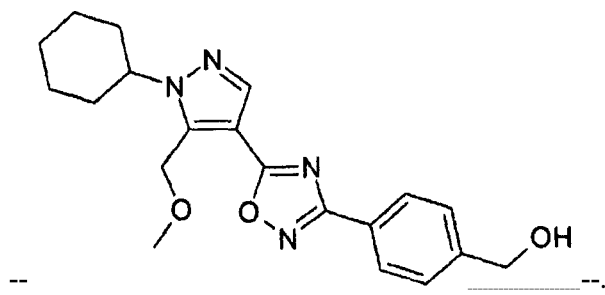
-- --.
Column 283,
Example Nb 88, Claim 2
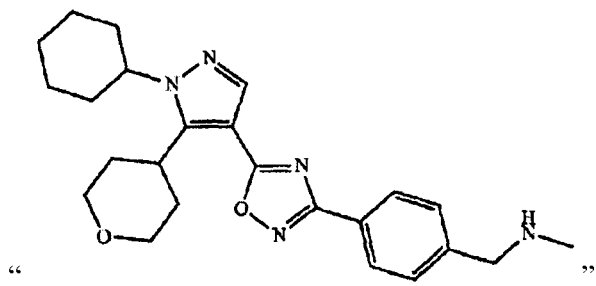
" "
should read
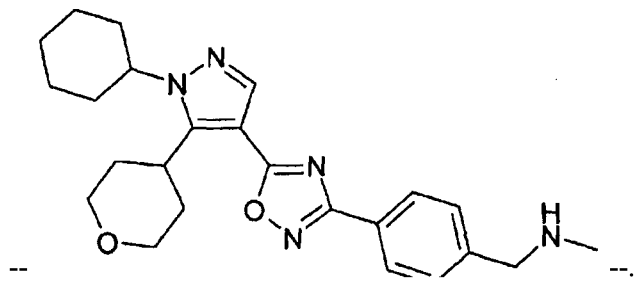
-- --.
Column 305,
Line 25, Claim 7 "–C≡O–" should read -- –C≡C– --.
Line 51, Claim 7 "–[C(R⁴)₂]$_{n\text{-}cycloalkyl}$, O$_R$⁴," should read -- –[C(R⁴)₂]$_n$-cycloalkyl, OR⁴,--.

Column 310,
Line 29, Claim 8 "–C≡O–" should read -- –C≡C– --.
Line 38, Claim 8 "–C≡O–" should read -- –C≡C– --.